(12) United States Patent
Johnson et al.

(10) Patent No.: US 10,654,855 B2
(45) Date of Patent: *May 19, 2020

(54) PROTEIN KINASE B INHIBITORS

(71) Applicant: AstraZeneca AB, Sodertalje (SE)

(72) Inventors: Paul David Johnson, Macclesfield (GB); Andrew Leach, Macclesfield (GB); Richard William Arthur Luke, Macclesfield (GB); Zbigniew Stanley Matusiak, Macclesfield (GB); Jeffrey James Morris, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,979

(22) Filed: Jul. 6, 2018

(65) Prior Publication Data

US 2018/0312516 A1 Nov. 1, 2018

Related U.S. Application Data

(63) Continuation of application No. 15/351,481, filed on Nov. 15, 2016, now Pat. No. 10,059,714, which is a continuation of application No. 14/626,303, filed on Feb. 19, 2015, now Pat. No. 9,492,453, which is a continuation of application No. 13/324,191, filed on Dec. 13, 2011, now abandoned, which is a continuation of application No. 12/249,477, filed on Oct. 10, 2008, now Pat. No. 8,101,623.

(60) Provisional application No. 61/047,862, filed on Apr. 25, 2008, provisional application No. 60/979,192, filed on Oct. 11, 2007.

(51) Int. Cl.
| | |
|---|---|
| A61K 31/519 | (2006.01) |
| A61P 35/04 | (2006.01) |
| C07D 487/04 | (2006.01) |
| C07D 473/34 | (2006.01) |
| A61P 35/00 | (2006.01) |

(52) U.S. Cl.
CPC .......... *C07D 487/04* (2013.01); *A61K 31/519* (2013.01); *A61P 35/04* (2018.01); *C07D 473/34* (2013.01); *A61P 35/00* (2018.01)

(58) Field of Classification Search
CPC .......................... C07D 487/04; A61K 31/519
See application file for complete search history.

(56) References Cited

U.S. PATENT DOCUMENTS

| | | | |
|---|---|---|---|
| 6,162,804 | A | 12/2000 | Bilodeau et al. |
| 6,432,947 | B1 | 8/2002 | Arnaiz et al. |
| 8,101,623 | B2 | 1/2012 | Luke et al. |
| 2002/0094974 | A1 | 7/2002 | Castelhano et al. |
| 2003/0045536 | A1 | 3/2003 | Castelhano et al. |
| 2003/0073708 | A1 | 4/2003 | Castelhano et al. |
| 2003/0139427 | A1 | 7/2003 | Castelhano et al. |
| 2004/0082598 | A1 | 4/2004 | Castelhano et al. |
| 2004/0082599 | A1 | 4/2004 | Castelhano et al. |
| 2006/0111362 | A1 | 5/2006 | Kira et al. |
| 2006/0148844 | A1 | 7/2006 | Nakade et al. |
| 2007/0135402 | A1 | 6/2007 | Habashita et al. |
| 2008/0070936 | A1 | 3/2008 | Castelhano et al. |
| 2012/0190679 | A1 | 7/2012 | Johnson et al. |
| 2015/0182531 | A1 | 7/2015 | Johnson et al. |

FOREIGN PATENT DOCUMENTS

| | | |
|---|---|---|
| EP | 1444982 A1 | 8/2004 |
| GB | 1047935 A1 | 9/1966 |
| WO | 199500516 A1 | 1/1995 |
| WO | 199738665 A2 | 10/1997 |
| WO | 199907703 A1 | 2/1999 |
| WO | 199962908 A2 | 12/1999 |
| WO | 199965909 A1 | 12/1999 |

(Continued)

OTHER PUBLICATIONS

Barnett et al, "The Akt-PKB Family of Protein Kinases: A Review of Small Molecule Inhibitors and Progress Towards Target Validation", Current Topics in Medicinal Chemistry, 2005, pp. 109-125, vol. 5.

(Continued)

*Primary Examiner* — Susanna Moore

(57) ABSTRACT

The invention relates to a novel group of compounds of Formula (I) or salts thereof:

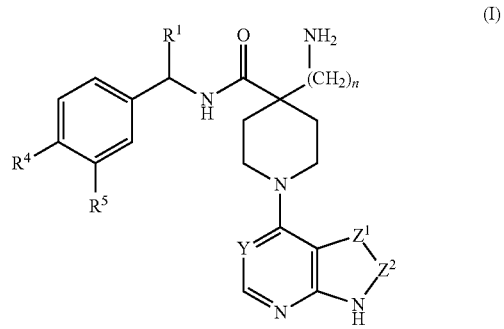

Figure 1:
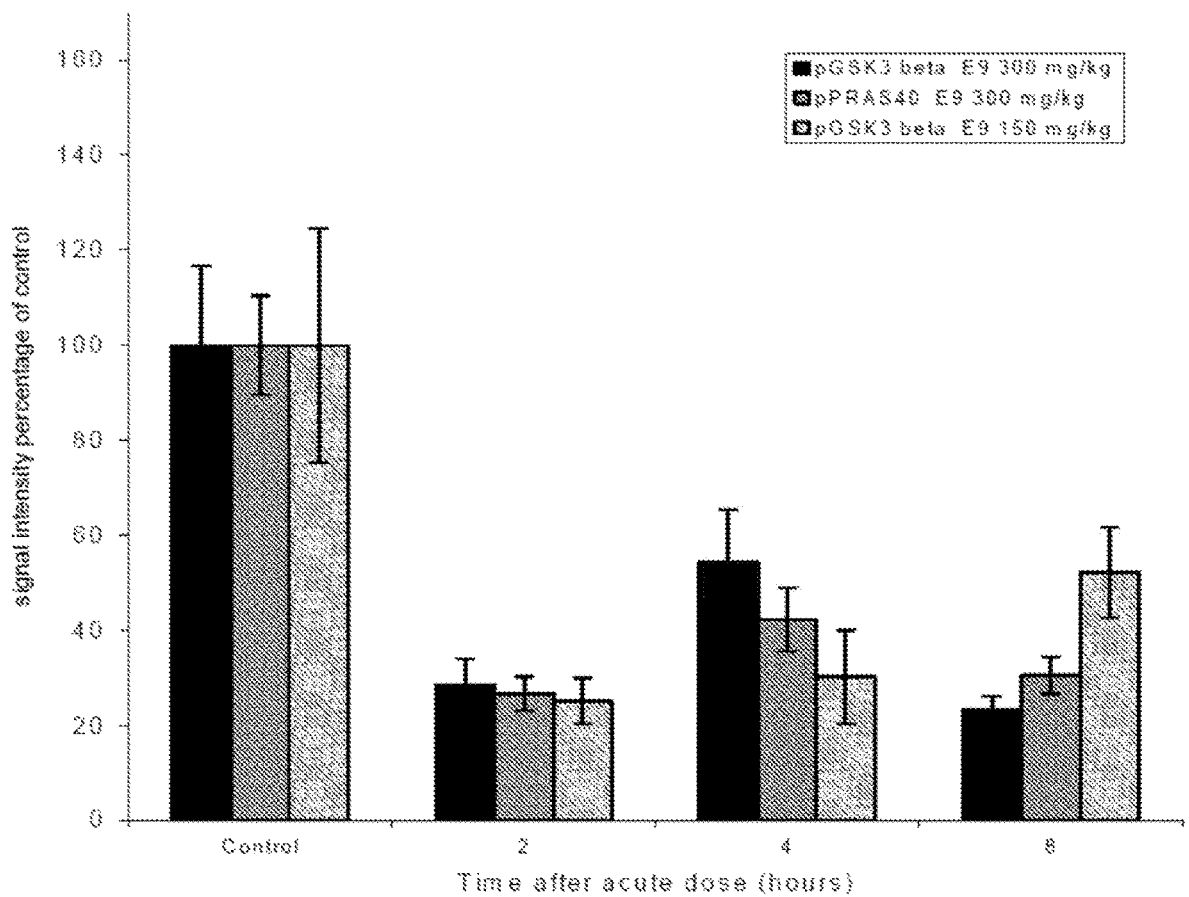

wherein Y, $Z^1$, $Z^2$, $R^1$, $R^4$, $R^5$ and n are as described in the specification, which may be useful in the treatment or prevention of a disease or medical condition mediated through protein kinase B (PKB) such as cancer. The invention also relates to pharmaceutical compositions comprising said compounds, methods of treatment of diseases mediated by PKB using said compounds and methods for preparing compounds of Formula (I).

10 Claims, 2 Drawing Sheets

(56) References Cited

FOREIGN PATENT DOCUMENTS

| WO | 200075145 A1 | 12/2000 |
|---|---|---|
| WO | 200107050 A1 | 2/2001 |
| WO | 2001014371 A1 | 3/2001 |
| WO | 2002000661 A1 | 1/2002 |
| WO | 2002018348 A3 | 3/2002 |
| WO | 2002057267 A1 | 7/2002 |
| WO | 2003057696 A1 | 7/2003 |
| WO | 2003088908 A3 | 10/2003 |
| WO | 2004014850 A3 | 2/2004 |
| WO | 2004021979 A2 | 3/2004 |
| WO | 2004043380 A3 | 5/2004 |
| WO | 2004080463 A1 | 9/2004 |
| WO | 2004094426 A1 | 11/2004 |
| WO | 2005003128 A1 | 1/2005 |
| WO | 2005020921 A3 | 3/2005 |
| WO | 2005026149 A1 | 3/2005 |
| WO | 2005044181 A3 | 5/2005 |
| WO | 2005051304 A3 | 6/2005 |
| WO | 2005117909 A3 | 12/2005 |
| WO | 2006046023 A1 | 5/2006 |
| WO | 2006046024 A1 | 5/2006 |
| WO | 2006071819 A1 | 7/2006 |
| WO | 2006075094 A3 | 7/2006 |
| WO | 2006075095 A3 | 7/2006 |
| WO | 2006091450 A1 | 8/2006 |
| WO | 2006135639 A1 | 12/2006 |
| WO | 2007007919 A2 | 1/2007 |
| WO | 2007025090 A3 | 3/2007 |
| WO | 2007084667 A3 | 7/2007 |
| WO | 2007125310 A3 | 11/2007 |
| WO | 2007125315 A3 | 11/2007 |
| WO | 2007125320 A1 | 11/2007 |
| WO | 2007125321 A3 | 11/2007 |
| WO | 2007125325 A3 | 11/2007 |
| WO | 2008075109 A1 | 6/2008 |
| WO | 2008075110 A1 | 6/2008 |
| WO | 2008079346 A1 | 7/2008 |
| WO | 2009047563 A1 | 4/2009 |

OTHER PUBLICATIONS

Quintela et al, "Pyrazolopyrimidines: synthesis, effect on histamine release from rat peritoneal mast cells and cytotoxic activity", Eur J Med Chem, 2001, pp. 321-332, vol. 36.

IPRP for corresponding PCT application. Application No. PCT/GB2008/050925 dated Apr. 22, 2010.

Opposition filed against corresponding application in Dominican Republic, Patent Application No. P2010-0103 dated Aug. 20, 2010.

Opposition filed against corresponding application in Ecuador, Patent Application No. SP-10-10093 dated Oct. 13, 2010.

Opposition filed against corresponding application in Costa Rica, Patent Application No. 11.359 dated Nov. 1, 2010.

Bales et al, Use of F-FDG PET as a biomarker to demonstrate activity of the novel AKT inhibitor AZD5363 in a xenograft model, AACR Apr. 4, 2011, p. 1030.

Davies et al, Characterization of AZD5363, an orally bioavailable, potent ATP-competitive inhibitor of AKT kinases with pharmacodynamic and antitumor activity in preclinical models, AACR Apr. 4, 2011, p. 4477.

Greenwood et al, In vitro mechanism of action of AZD5363, a novel AKT inhibitor, in breast and prostate cancer cell lines, AACR Apr. 4, 2011, p. 1052.

Lamoureux et al, AZD5363 a novel Akt inhibitor delays prostate cancer progression by inhibiting androgen-receptor activity, The Vancouver Prostate Centre and AstraZeneca, Apr. 4, 2011.

Luke et al, Discovery of AZD5363 in orally bioavailable potent ATP-competitive inhibitor of AKT kinases, AACR, Apr. 4, 2011, p. 4478.

Mackay, Transforming Drug Discovery Innovative Platforms, Pfizer, Nov. 30, 2006.

Bohl et al. (PNAS, 2005, vol. 102(17), pp. 6201-6206.

Drugs.com ( available Feb. 2007, https://www.drugs.com/clinical_trials/medivation-s-mdv3100-shown-effective-preclinical-model-hormone-refractory-prostate-cancer-215.html , downloaded Oct. 30, 2017).

Eniu et al. (The Oncologist, 2005, vol. 10, pp. 665-685).

PROTEIN KINASE B INHIBITORS

This application is a Continuation of U.S. application Ser. No. 15/351,481 filed on 15 Nov. 2016, which is a Continuation of U.S. application Ser. No. 14/626,303, filed on 19 Feb. 2015 (now granted as U.S. Pat. No. 9,492,453 on Nov. 15, 2016), which is a Continuation of U.S. application Ser. No. 13/324,191, filed on 13 Dec. 2011, which is a Continuation of U.S. application Ser. No. 12/249,477, filed on 10 Oct. 2008 (now granted as U.S. Pat. No. 8,101,623 on 24 Jan. 2012), which claims the benefit under 35 U.S.C. § 119(e) of Application No. 60/979,192 (US) filed on 11 Oct. 2007 and Application No. 61/047,862 (US) filed on 25 Apr. 2008, each of which is hereby incorporated herein by reference in their entireties.

The present invention relates to a novel group of bicyclic heterocycles which may be useful in the treatment or prevention of a disease or medical condition mediated through protein kinase B (PKB, also known as AKT). Such compounds may therefore be useful in the treatment or prevention of a number of different cancers. The invention also relates to pharmaceutical compositions comprising said compounds, to processes for the manufacture of said compounds and to methods of treatment of diseases mediated by PKB using said compounds.

PKB is a component of the phosphatidyl 3-kinase (PI3K) signalling pathway which plays an important part in cell proliferation and survival, including cellular responses to growth factors. Upon binding of a growth factor, for example epidermal growth factor (EGF), to its cell surface receptor tyrosine kinase, for example EGF receptor (EGFR), the receptor dimerises and undergoes autophosphorylation. This autophosphorylation event allows the 85 kDa regulatory subunit of PI3K (p85) to interact with the receptor either directly or via an adaptor protein, for example growth factor receptor-bound protein 2 (GRB2), and thereby activate the 110 kDa catalytic subunit of PI3K (p110). Upon activation, p110 catalyses the phosphorylation of phosphatidylinositol-4,5-bisphosphate ($PIP_2$) to produce phosphatidylinositol-3,4,5-triphosphate ($PIP_3$), a second messenger molecule that recruits both phosphatidylinositol-dependent kinase 1 (PDK1) and PKB to the plasma membrane where PDK1 phosphorylates and activates PKB.

There are three known isoforms of PKB (PKBα/AKT1, PKBβ/AKT2 and PKBγ/AKT3), derived from three distinct genes. Activation of PKBα is associated with cell signalling events that mediate cell proliferation and survival, whereas activation of PKBβ is associated with invasion, motility and insulin-mediated metabolic processes. Activated PKB protects cells from apoptosis by inactivating proapoptotic factors, for example the BAD, procaspase-9 and forkhead (FKHR) transcription factors, and activating transcription factors that upregulate antiapoptotic genes, for example cyclic-AMP response element binding protein (CREB). PKB can also contribute to cell survival by inactivation of p53 via phosphorylation of MDM2. Similarly, activated PKB induces cell proliferation by activating proteins involved in cell growth and metabolism, for example by a pathway leading to activation of the mammalian target of rapamycin (mTOR) and via glycogen synthase kinase-3 (GSK3).

PKB-mediated stimulation of cell proliferation and protection from apoptosis therefore favour tumourigenesis and genetic disturbances of components within the PI3K pathway are commonly found in cancer. For example, mutation or amplification of the genes encoding the p110 isoforms of PI3K are found in breast cancers, bowel cancer, ovarian cancer, head and neck and cervical squamous cancers, gastric and lung cancers, angioplastic oligodendrogliomas, amaplastic astrocytomas, glioblastoma multiforme and medulloblastomas. Similarly, mutation amplification and/or overexpression of the genes encoding the PKB isoforms are found in pancreatic, breast and ovarian tumours. Furthermore, the gene encoding for PTEN (a phosphatase which has a reverse role to PI3K, catalysing the conversion of $PIP_3$ to $PIP_2$) is inactivated in many tumour types, including ovarian, colorectal, breast, glioma, melanoma, lung, leukaemias and lymphomas; this results in activation of PKB/AKT.

In view of the importance of the PI3K signalling pathway in tumour cell proliferation and survival, any compound that disrupted this pathway, including PKB inhibitors, may be useful in the treatment of cancer. Detailed reviews of the PI3K signalling pathway and its involvement in tumourigenisis are provided by Hennessy et al., Nature Reviews/Drug Discovery (December 2005) Vol. 4, 988-1004. and Cully et al., Nature reviews/Cancer (March 2006) Vol. 6, 184-192.

The voltage-dependent potassium channel encoded by the human ether-a-go-go-related gene (hERG) is believed to play a key role in repolarisation of the ventricular cardiac action potential. Changes in its activity, caused either by inherited mutations of the gene sequence or pharmacological modification, can lead to prolongation of action potential duration. This can lead to prolongation of the QT interval recorded in man on an electrocardiogram and to a potentially fatal cardiac arrhythmia known as Torsades de Pointes (Vandenberg et al. (2001). Trends Pharmacol. Sci. 22, 240-246). Recent regulatory guidelines (CPMP/ICH/539/00) recommend that an in vitro assay investigating the effects of test compounds at the hERG channel could be one element of a pre-clinical strategy aiming to predict the likelihood that new chemical entities will prolong the QT interval recorded in man on an electrocardiogram. As such, the elimination of hERG blocking activity remains an important consideration in the development of any new drug.

A number of compounds have been described that target the PI3K pathway. For example WO2006/046023 and WO2006/046024 (Astex Therapeutics Limited) describe purine, purinone and deazapurinone compounds that inhibit or modulate the activity of protein kinase B (PKB) and protein kinase A (PKA). However, there still exists the need for further improved agents having superior potency against PKB and/or advantageous physical properties (for example, higher aqueous solubility, higher permeability, and/or lower plasma protein binding) and/or favourable toxicity profiles (for example a decreased hERG blocking liability) and/or favourable metabolic profiles in comparison with other known PKB inhibitors.

The applicants have surprisingly found that certain bicyclic heterocycle derivatives are particularly effective at inhibiting PKB activity and may therefore be useful in the treatment of disease states in which PKB activity is implicated, for example cancer.

According to a first aspect of the invention, there is therefore provided a compound of Formula (I), or a pharmaceutically acceptable salt thereof:

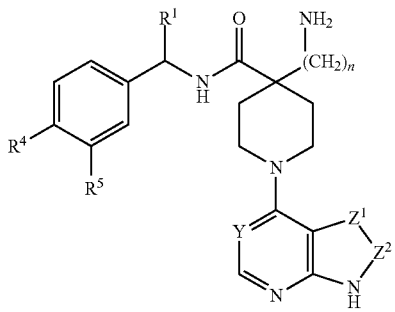

wherein:
Y represents CH or N;
$Z^1$-$Z^2$ represents a group selected from C($R^6$)=CH, N=CH and C($R^6$)=N; where
  $R^6$ represents hydrogen, fluoro, chloro, bromo, cyano, methyl, ethyl, difluoromethyl, trifluoromethyl or cyclopropyl;
n is 0, 1 or 2;
$R^1$ represents $C_{1-4}$alkyl, $C_{2-4}$alkenyl, $C_{2-4}$alkynyl, $C_{1-4}$alkoxy, $C_{1-4}$alkoxy$C_{1-4}$alkyl, fluoro$C_{1-4}$alkyl, amino$C_{1-4}$ alkyl, hydroxy$C_{1-4}$alkyl, cyano, cyano$C_{1-4}$alkyl, $C_{3-6}$cycloalkyl, —$(CH_2)_p$NHCOCH$_3$, —$(CH_2)_p$NHSO$_2$CH$_3$, —$(CH_2)_p$NHCONH$_2$, —$(CH_2)_p$NHCONR$^2$R$^3$, —$(CH_2)_p$NR$^2$R$^3$, —$(CH_2)_p$SO$_2$NH$_2$, —$(CH_2)_p$SO$_2$NR$^2$R$^3$, —$(CH_2)_p$CONH$_2$, —$(CH_2)_p$CONR$^2$R$^3$ or —$(CH_2)_p$—$R^7$; where
  p is 0, 1, 2 or 3;
  $R^2$ represents hydrogen or $C_{1-3}$ alkyl;
  $R^3$ represents $C_{1-3}$ alkyl; and
  $R^7$ represents phenyl;
  $R^7$ represents a 5 or 6 membered monocyclic heteroaryl ring which comprises 1, 2 or 3 heteroatoms selected from O, N or S; or
  $R^7$ represents a monocyclic 4, 5, or 6 membered heterocyclic ring which comprises 1, 2 or 3 heteroatoms selected from O, N or S;
  wherein $R^7$ is optionally substituted by 1 or 2 substituents selected from $C_{1-4}$alkyl, trifluoromethyl, $C_{1-4}$alkoxy, fluoro, chloro, bromo, and cyano;
$R^4$ represents hydrogen, fluoro, chloro, bromo, cyano or trifluoromethyl; and
$R^5$ represents hydrogen, fluoro, chloro or bromo.

In one embodiment of the invention, there is provided a compound of Formula (I), or a pharmaceutically acceptable salt thereof:

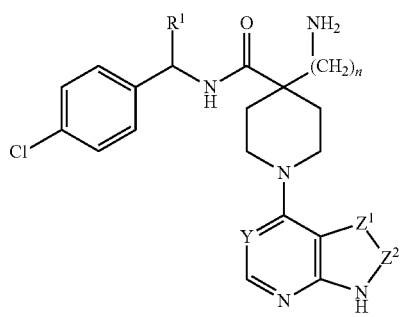

wherein:
Y represents CH or N;
$Z^1$-$Z^2$ represents a group selected from CH=CH, N=CH and CH=N;
n is 0, 1 or 2; and
$R^1$ represents $C_{1-4}$ alkyl, amino$C_{1-4}$alkyl, hydroxy$C_{1-4}$ alkyl, —$(CH_2)_p$NHCOCH$_3$, —$(CH_2)_q$NR$^2$R$^3$ or $C_{3-6}$cycloalkyl;
where
  $R^2$ represents hydrogen or $C_{1-3}$ alkyl;
  $R^3$ represents $C_{1-3}$ alkyl; and
  p and q independently represent 2 or 3.

In a further embodiment of the invention, there is therefore provided a compound of Formula (I), or a pharmaceutically acceptable salt thereof:

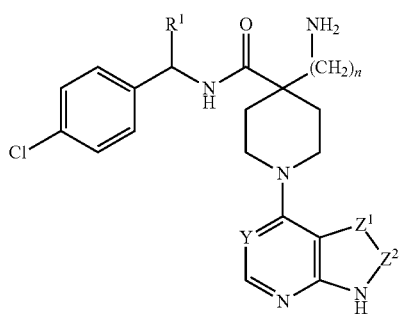

wherein:
Y represents CH or N;
$Z^1$-$Z^2$ represents a group selected from CH=CH, N=CH and CH=N;
$R^1$ represents $C_{1-4}$alkyl, amino$C_{1-4}$alkyl or $C_{3-6}$cycloalkyl; and
n is 0, 1 or 2.

The term "$C_{1-4}$ alkyl" is intended to mean a saturated carbon chain of 1 to 4 carbon atoms in length which may be straight-chained or branched. However references to individual alkyl groups such as "propyl" are specific for the straight chain version only and references to individual branched-chain alkyl groups such as t-butyl are specific for the branched chain version only. For example, "$C_{1-4}$alkyl" includes methyl, ethyl, propyl, isopropyl and t-butyl.

The term "$C_{2-4}$alkenyl" is intended to mean an unsaturated carbon chain of 2 to 4 carbon atoms in length, which may be straight-chained or branched, containing at least one carbon to carbon double bond. However references to individual alkenyl groups such as "propenyl" are specific for the straight chain version only and references to individual branched-chain alkyl groups such as tert-butenyl are specific for the branched chain version only. For example, "$C_{2-4}$ alkenyl" includes, but is not limited to, ethenyl, propenyl, isopropenyl, butenyl and tert-butenyl.

The term "$C_{2-4}$alkynyl" is intended to mean an unsaturated carbon chain of 2 to 4 carbon atoms in length, which may be straight-chained or branched, containing at least one carbon to carbon triple bond. However references to individual alkynyl groups such as "propynyl" are specific for the straight chain version only and references to individual branched-chain alkyl groups such as tert-butynyl are specific for the branched chain version only. For example, "$C_{2-4}$ alkynyl" includes, but is not limited to, ethynyl, propynyl, isopropynyl, butynyl and tert-butynyl.

The term "$C_{1-4}$ alkoxy" is intended to mean a saturated carbon chain of 1 to 4 carbon atoms in length, which may be straight-chained or branched, linked to oxygen. For example, "$C_{1-6}$ alkoxy" includes, but is not limited to, methoxy, ethoxy, propoxy and butoxy.

The term "$C_{1-4}$ alkoxy$C_{1-4}$ alkyl" is intended to mean a saturated carbon chain of 1 to 4 carbon atoms in length, which may be straight-chained or branched, linked via oxygen to another saturated carbon chain of 1 to 4 carbon atoms in length, which may be straight-chained or branched. For example, "$C_{1-4}$alkoxy$C_{1-4}$alkyl" includes, but is not limited to, methoxyethyl, methoxypropyl, ethoxypropyl, propoxyethyl and butoxypropyl.

The term "fluoro$C_{1-4}$alkyl" is intended to mean a saturated carbon chain of 1 to 4 carbon atoms in length which may be straight-chained or branched wherein at least one of the hydrogen atoms have been replaced by fluorine. For example, "fluoro$C_{1-4}$alkyl" includes, but is not limited to, fluoromethyl, fluoroethyl, fluoropropyl, fluoroisopropyl, fluorobutyl, fluoroisobutyl, fluoro-tert-butyl, trifluoromethyl, pentafluoroethyl, heptafluoropropyl and nonafluorobutyl.

The term "amino$C_{1-4}$ alkyl" is intended to mean a saturated carbon chain of 1 to 4 carbon atoms in length, which may be straight-chained or branched, comprising one primary amino group. For example "amino$C_{1-4}$alkyl" includes aminomethyl, aminoethyl, 2-aminopropyl, 3-aminopropyl, 1-aminoisopropyl and 4-aminobutyl.

The term "hydroxy$C_{1-4}$alkyl" is intended to mean a saturated carbon chain of 1 to 4 carbon atoms in length, which may be straight-chained or branched, comprising a hydroxyl group. For example "hydroxy$C_{1-4}$alkyl" includes hydroxymethyl, hydroxyethyl, 2-hydroxypropyl, 3-hydroxypropyl, 1-hydroxyisopropyl and 4-hydroxybutyl.

The term "$C_{3-6}$cycloalkyl" is intended to mean a saturated 3 to 6 membered monocyclic carbon ring. For example "$C_{3-6}$cycloalkyl" includes cyclopropyl, cyclobutyl, cyclopentyl and cyclohexyl.

The term "heteroaryl ring" is intended to mean a 5 or 6 membered, totally unsaturated, aromatic monocyclic ring which comprises 1, 2 or 3 heteroatoms independently selected from nitrogen, oxygen or sulphur, linked via a ring carbon atom or a ring nitrogen atom where a bond from a nitrogen is possible, for example no bond is possible to the nitrogen of a pyridine ring, but a bond is possible through the 1-nitrogen of a pyrazole ring. Examples of 5 or 6 membered heteroaryl rings include, but are not limited to, pyrrole, furan, imidazole, triazole, tetrazole, pyrazine, pyrimidine, pyridazine, pyridine, pyrazole, isoxazole, oxazole, 1,2,4 oxadiazole, isothiazole, thiazole, 1,2,4-triazole and thiophene.

The term "heterocyclic ring" is intended to mean a 4, 5 or 6 membered fully saturated or partially saturated monocyclic ring which comprises 1, 2 or 3 heteroatoms selected from nitrogen, oxygen or sulphur linked via a ring carbon atom or a ring nitrogen atom. Examples of 4, 5 or 6 membered heterocyclic rings include azetidine, tetrahydrofuran, tetrahydropyran, pyrroline, pyrrolidine, thiazolidine, morpholine, piperidine, piperazine, dihydropyridine, dihydropyrimidine and azepane.

In further embodiments of the invention, each of the following definitions of Y, $Z^1$-$Z^2$, $R^1$, $R^4$, $R^5$, $R^6$, n and p in paragraphs (1) to (26) hereinafter may be used individually or in combination with one of the other following definitions to limit the broadest definition of Formulae (I), (IA) or (IB) as appropriate.

(1) Y represents N;
(2) $Z^1$-$Z^2$ represents CH=CH;
(3) $Z^1$-$Z^2$ represents C(Cl)=CH;
(4) $Z^1$-$Z^2$ represents C(Br)=CH;
(5) $R^1$ represents $C_{1-4}$ alkyl;
(6) $R^1$ represents amino$C_{1-4}$alkyl;
(7) $R^1$ represents hydroxy$C_{1-4}$alkyl;
(8) $R^1$ represents $C_{3-6}$cycloalkyl;
(9) $R^1$ represents $C_{1-4}$ alkoxy$C_{1-4}$ alkyl, fluoro$C_{1-4}$alkyl, amino$C_{1-4}$alkyl, hydroxy$C_{1-4}$alkyl, cyano$C_{1-4}$alkyl, $C_{3-6}$ cycloalkyl, —$(CH_2)_p$NHCOCH$_3$, —$(CH_2)_p$NHSO$_2$CH$_3$, —$(CH_2)_p$NHCONH$_2$, —$(CH_2)_p$NHCONR$^2$R$^3$, —$(CH_2)_p$NR$^2$R$^3$, —$(CH_2)_p$SO$_2$NH$_2$,
(6.1) —$(CH_2)_p$CONH$_2$, —$(CH_2)_p$CONR$^2$R$^3$ or —$(CH_2)_p$—R$^7$;
(10) $R^1$ represents —$(CH_2)_p$—R$^7$ wherein R$^7$ is selected from phenyl, piperidinyl, piperazinyl, pyrrolidinyl, morpholinyl, imidazolyl, isoxazolyl, pyrazolyl and thiazolyl and R$^7$ is optionally substituted by a single methyl group;
(11) $R^1$ represents hydroxyethyl;
(12) n is 0;
(13) n is 1;
(14) n is 1 or 2;
(15) n is 0 or 1;
(16) p is 1, 2 or 3;
(17) $R^4$ represents chloro, bromo or cyano;
(18) $R^4$ represents chloro, bromo;
(19) $R^4$ represents chloro;
(20) $R^4$ represents bromo;
(21) $R^5$ represents hydrogen;
(22) $R^5$ represents chloro;
(23) $R^6$ represents hydrogen;
(24) $R^6$ represents methyl;
(25) $R^6$ represents difluoromethyl;
(26) $R^6$ represents trifluoromethyl.

According to another embodiment of the invention, there is provided a compound of Formula (I), or a pharmaceutically acceptable salt thereof, which is:

4-amino-N-(1-(4-chlorophenyl)ethyl)-1-(7H-pyrrolo[2,3-d]pyrimidin-4-yl)piperidine-4-carboxamide;

(S)-4-amino-N-(1-(4-chlorophenyl)ethyl)-1-(7H-pyrrolo[2,3-d]pyrimidin-4-yl)piperidine-4-carboxamide;

4-amino-N-(1-(4-chlorophenyl)propyl)-1-(7H-pyrrolo[2,3-d]pyrimidin-4-yl)piperidine-4-carboxamide;

(S)-4-amino-N-(1-(4-chlorophenyl)propyl)-1-(7H-pyrrolo[2,3-d]pyrimidin-4-yl)piperidine-4-carboxamide;

(R)-4-amino-N-(1-(4-chlorophenyl)propyl)-1-(7H-pyrrolo[2,3-d]pyrimidin-4-yl)piperidine-4-carboxamide;

4-amino-N-((4-chlorophenyl)(cyclopropyl)methyl)-1-(7H-pyrrolo[2,3-d]pyrimidin-4-yl)piperidine-4-carboxamide;

4-amino-N-(2-amino-1-(4-chlorophenyl)ethyl)-1-(7H-pyrrolo[2,3-d]pyrimidin-4-yl)piperidine-4-carboxamide;

(S)-4-(aminomethyl)-N-(1-(4-chlorophenyl)ethyl)-1-(7H-pyrrolo[2,3-d]pyrimidin-4-yl)piperidine-4-carboxamide;

4-amino-N-(1-(4-chlorophenyl)-4-hydroxybutyl)-1-(7H-pyrrolo[2,3-d]pyrimidin-4-yl)piperidine-4-carboxamide;

(S)-4-amino-N-(1-(4-chlorophenyl)-4-hydroxybutyl)-1-(7H-pyrrolo[2,3-d]pyrimidin-4-yl)piperidine-4-carboxamide;

(R)-4-amino-N-(1-(4-chlorophenyl)-4-hydroxybutyl)-1-(7H-pyrrolo[2,3-d]pyrimidin-4-yl)piperidine-4-carboxamide;

4-amino-N-(1-(4-chlorophenyl)-2-hydroxyethyl)-1-(7H-pyrrolo[2,3-d]pyrimidin-4-yl)piperidine-4-carboxamide;

(S)-4-amino-N-(1-(4-chlorophenyl)-3-hydroxypropyl)-1-(7H-pyrrolo[2,3-d]pyrimidin-4-yl)piperidine-4-carboxamide;

N-(3-acetamido-1-(4-chlorophenyl)propyl)-4-amino-1-(7H-pyrrolo[2,3-d]pyrimidin-4-yl)piperidine-4-carboxamide;

4-amino-N-(1-(4-chlorophenyl)-3-(dimethylamino)propyl)-1-(7H-pyrrolo[2,3-d]pyrimidin-4-yl)piperidine-4-carboxamide;

(S)-4-amino-N-(1-(4-chlorophenyl)-3-(dimethylamino)propyl)-1-(7H-pyrrolo[2,3-d]pyrimidin-4-yl)piperidine-4-carboxamide;

(R)-4-amino-N-(1-(4-chlorophenyl)-3-(dimethylamino)propyl)-1-(7H-pyrrolo[2,3-d]pyrimidin-4-yl)piperidine-4-carboxamide;

4-(aminomethyl)-N-(1-(4-chlorophenyl)-3-hydroxypropyl)-1-(7H-pyrrolo[2,3-d]pyrimidin-4-yl)piperidine-4-carboxamide;

4-amino-N-(1-(4-chlorophenyl)-3-hydroxypropyl)-1-(7H-pyrrolo[2,3-d]pyrimidin-4-yl)piperidine-4-carboxamide;

4-amino-N-(3-amino-1-(4-chlorophenyl)propyl)-1-(7H-pyrrolo[2,3-d]pyrimidin-4-yl)piperidine-4-carboxamide;

(R)-4-amino-N-(1-(4-chlorophenyl)-3-hydroxypropyl)-1-(7H-pyrrolo[2,3-d]pyrimidin-4-yl)piperidine-4-carboxamide;

(R)-4-amino-N-(1-(4-chlorophenyl)ethyl)-1-(7H-pyrrolo[2,3-d]pyrimidin-4-yl)piperidine-4-carboxamide;

(R)-4-(aminomethyl)-N-(1-(4-chlorophenyl)ethyl)-1-(7H-pyrrolo[2,3-d]pyrimidin-4-yl)piperidine-4-carboxamide;

(S)-4-amino-N-(1-(4-cyanophenyl)-3-hydroxypropyl)-1-(7H-pyrrolo[2,3-d]pyrimidin-4-yl)piperidine-4-carboxamide;

(S)-4-amino-1-(5-bromo-7H-pyrrolo[2,3-d]pyrimidin-4-yl)-N-(1-(4-chlorophenyl)-3-hydroxypropyl)piperidine-4-carboxamide;

(S)-4-amino-N-(1-(4-chlorophenyl)-3-hydroxypropyl)-1-(1H-pyrazolo[3,4-d]pyrimidin-4-yl)piperidine-4-carboxamide;

(S)-4-amino-N-(3-hydroxy-1-phenylpropyl)-1-(7H-pyrrolo[2,3-d]pyrimidin-4-yl)piperidine-4-carboxamide;

(S)-4-amino-N-(1-(4-chlorophenyl)-3-hydroxypropyl)-1-(9H-purin-6-yl)piperidine-4-carboxamide;

(S)-4-(aminomethyl)-N-(1-(4-chlorophenyl)-3-hydroxypropyl)-1-(7H-pyrrolo[2,3-d]pyrimidin-4-yl)piperidine-4-carboxamide;

(S)-4-amino-N-(1-(4-bromophenyl)-3-hydroxypropyl)-1-(7H-pyrrolo[2,3-d]pyrimidin-4-yl)piperidine-4-carboxamide;

4-amino-N-(1-(4-chlorophenyl)-4-(dimethylamino)butyl)-1-(7H-pyrrolo[2,3-d]pyrimidin-4-yl)piperidine-4-carboxamide;

(S)-4-amino-N-(1-(4-chlorophenyl)-3-(diethylamino)propyl)-1-(7H-pyrrolo[2,3-d]pyrimidin-4-yl)piperidine-4-carboxamide;

(S)-4-amino-N-(1-(4-chlorophenyl)-3-hydroxypropyl)-1-(5-cyclopropyl-7H-pyrrolo[2,3-d]pyrimidin-4-yl)piperidine-4-carboxamide;

4-amino-N-(1-(4-chlorophenyl)-3-(methylamino)propyl)-1-(7H-pyrrolo[2,3-d]pyrimidin-4-yl)piperidine-4-carboxamide;

4-amino-N-[(4-chlorophenyl)(phenyl)methyl]-1-(7H-pyrrolo[2,3-d]pyrimidin-4-yl)piperidine-4-carboxamide;

4-amino-N-[2-amino-1-(4-chlorophenyl)-2-oxoethyl]-1-(7H-pyrrolo[2,3-d]pyrimidin-4-yl)piperidine-4-carboxamide;

4-amino-1-(3-bromo-1H-pyrazolo[3,4-d]pyrimidin-4-yl)-N-[(1S)-1-(4-chlorophenyl)ethyl]piperidine-4-carboxamide;

4-amino-N-[(1S)-1-(4-chlorophenyl)ethyl]-1-(5-chloro-7H-pyrrolo[2,3-d]pyrimidin-4-yl)piperidine-4-carboxamide;

4-amino-1-(3-bromo-1H-pyrazolo[3,4-d]pyrimidin-4-yl)-N-[(1S)-1-(4-chlorophenyl)-3-hydroxypropyl]piperidine-4-carboxamide;

4-amino-N-[(1S)-1-(4-chlorophenyl)-3-hydroxypropyl]-1-(5-chloro-7H-pyrrolo[2,3-d]pyrimidin-4-yl)piperidine-4-carboxamide;

4-amino-1-(5-bromo-7H-pyrrolo[2,3-d]pyrimidin-4-yl)-N-[(1S)-1-(4-chlorophenyl)ethyl]piperidine-4-carboxamide;

4-amino-N-[(1S)-1-(4-chlorophenyl)-3-hydroxypropyl]-1-(5-methyl-7H-pyrrolo[2,3-d]pyrimidin-4-yl)piperidine-4-carboxamide;

4-amino-N-[(1S)-1-(4-chlorophenyl)ethyl]-1-(5-methyl-7H-pyrrolo[2,3-d]pyrimidin-4-yl)piperidine-4-carboxamide;

4-amino-N-[(1S)-1-(4-chlorophenyl)-3-hydroxy-3-methylbutyl]-1-(7H-pyrrolo[2,3-d]pyrimidin-4-yl)piperidine-4-carboxamide;

4-amino-N-[(1S)-1-(4-cyanophenyl)ethyl]-1-(7H-pyrrolo[2,3-d]pyrimidin-4-yl)piperidine-4-carboxamide;

4-amino-N-[(1S)-1-(3-chlorophenyl)-3-hydroxypropyl]-1-(7H-pyrrolo[2,3-d]pyrimidin-4-yl)piperidine-4-carboxamide;

4-amino-1-(7H-pyrrolo[2,3-d]pyrimidin-4-yl)-N-{(1S)-1-[4-(trifluoromethyl)phenyl]ethyl}piperidine-4-carboxamide;

4-amino-N-[(1R)-1-(4-bromophenyl)ethyl]-1-(7H-pyrrolo[2,3-d]pyrimidin-4-yl)piperidine-4-carboxamide;

4-amino-N-[1-(4-chlorophenyl)-2-phenylethyl]-1-(7H-pyrrolo[2,3-d]pyrimidin-4-yl)piperidine-4-carboxamide;

4-amino-N-[1-(4-fluorophenyl)ethyl]-1-(7H-pyrrolo[2,3-d]pyrimidin-4-yl)piperidine-4-carboxamide;

4-amino-N-[(4-chlorophenyl)(cyano)methyl]-1-(7H-pyrrolo[2,3-d]pyrimidin-4-yl)piperidine-4-carboxamide;

4-amino-N-(1-phenylethyl)-1-(7H-pyrrolo[2,3-d]pyrimidin-4-yl)piperidine-4-carboxamide;

4-amino-N-[1-(4-chlorophenyl)-4-pyrrolidin-1-ylbutyl]-1-(7H-pyrrolo[2,3-d]pyrimidin-4-yl)piperidine-4-carboxamide;

4-amino-N-[1-(4-chlorophenyl)-4-morpholin-4-ylbutyl]-1-(7H-pyrrolo[2,3-d]pyrimidin-4-yl)piperidine-4-carboxamide;

4-amino-N-[1-(4-chlorophenyl)-4-piperidin-1-ylbutyl]-1-(7H-pyrrolo[2,3-d]pyrimidin-4-yl)piperidine-4-carboxamide;

4-amino-N-[(1S)-1-(4-chlorophenyl)-4-piperidin-1-ylbutyl]-1-(7H-pyrrolo[2,3-c]pyrimidin-4-yl)piperidine-4-carboxamide;

4-amino-N-[(1R)-1-(4-chlorophenyl)-4-piperidin-1-ylbutyl]-1-(7H-pyrrolo[2,3-c]pyrimidin-4-yl)piperidine-4-carboxamide;

4-amino-N-[(1S)-1-(4-chlorophenyl)-3-(4-methylpiperazin-1-yl)propyl]-1-(7H-pyrrolo[2,3-d]pyrimidin-4-yl)piperidine-4-carboxamide;

4-amino-N-[(1S)-1-(4-chlorophenyl)-3-morpholin-4-ylpropyl]-1-(7H-pyrrolo[2,3-d]pyrimidin-4-yl)piperidine-4-carboxamide;

4-amino-N-[(1S)-1-(4-chlorophenyl)-3-piperidin-1-ylpropyl]-1-(7H-pyrrolo[2,3-d]pyrimidin-4-yl)piperidine-4-carboxamide;

4-amino-N-[(1S)-1-(4-chlorophenyl)-3-piperazin-1-ylpropyl]-1-(7H-pyrrolo[2,3-d]pyrimidin-4-yl)piperidine-4-carboxamide;

4-amino-N-[(1S)-1-(4-chlorophenyl)-3-(1H-imidazol-1-yl)propyl]-1-(7H-pyrrolo[2,3-d]pyrimidin-4-yl)piperidine-4-carboxamide;

4-amino-N-[(1S)-1-(4-chlorophenyl)-3-pyrrolidin-1-ylpropyl]-1-(7H-pyrrolo[2,3-d]pyrimidin-4-yl)piperidine-4-carboxamide;

4-amino-N-(1-(4-chlorophenyl)-2-sulfamoylethyl)-1-(7H-pyrrolo[2,3-d]pyrimidin-4-yl)piperidine-4-carboxamide;

4-amino-N-(1-(4-chlorophenyl)-2-sulfamoylethyl)-1-(7H-pyrrolo[2,3-d]pyrimidin-4-yl)piperidine-4-carboxamide;

N-(2-acetamido-1-(4-chlorophenyl)ethyl)-4-amino-1-(7H-pyrrolo[2,3-d]pyrimidin-4-yl)piperidine-4-carboxamide;

4-amino-N-(1-(4-chlorophenyl)-2-(1H-imidazol-2-yl)ethyl)-1-(7H-pyrrolo[2,3-d]pyrimidin-4-yl)piperidine-4-carboxamide;

4-Amino-N-[1-(4-chlorophenyl)-2-(1H-pyrazol-1-yl)ethyl]-1-(7H-pyrrolo[2,3-d]pyrimidin-4-yl)piperidine-4-carboxamide;

4-amino-N-[1-(4-chlorophenyl)-2-(3-methylisoxazol-5-yl)ethyl]-1-(7H-pyrrolo[2,3-d]pyrimidin-4-yl)piperidine-4-carboxamide;

4-amino-N-(1-(4-chlorophenyl)-2-(thiazol-2-yl)ethyl)-1-(7H-pyrrolo[2,3-d]pyrimidin-4-yl)piperidine-4-carboxamide;

4-amino-N-(1-(4-chlorophenyl)-3-(dimethylamino)-3-oxopropyl)-1-(7H-pyrrolo[2,3-c]pyrimidin-4-yl)piperidine-4-carboxamide;

4-amino-N-(1-(4-chlorophenyl)-3-methoxypropyl)-1-(7H-pyrrolo[2,3-d]pyrimidin-4-yl)piperidine-4-carboxamide;

4-amino-N-(1-(4-chlorophenyl)-3-sulfamoylpropyl)-1-(7H-pyrrolo[2,3-d]pyrimidin-4-yl)piperidine-4-carboxamide;

4-amino-N-(3-amino-1-(4-chlorophenyl)-3-oxopropyl)-1-(7H-pyrrolo[2,3-d]pyrimidin-4-yl)piperidine-4-carboxamide;

4-amino-N-(1-(4-chlorophenyl)-3-ureidopropyl)-1-(7H-pyrrolo[2,3-d]pyrimidin-4-yl)piperidine-4-carboxamide;

4-amino-N-(1-(4-chlorophenyl)-2-cyanoethyl)-1-(7H-pyrrolo[2,3-d]pyrimidin-4-yl)piperidine-4-carboxamide; or 4-amino-N-(1-(4-chlorophenyl)-3-(methylsulfonamido)propyl)-1-(7H-pyrrolo[2,3-c]pyrimidin-4-yl)piperidine-4-carboxamide.

It is to be understood that, insofar as compounds of Formula (I) defined above exist in optically active or racemic forms by virtue of the asymmetric carbon atom, the invention includes in its definition any such optically active or racemic form which possesses the property of inhibiting PKB activity. The synthesis of optically active forms may be carried out by standard techniques of organic chemistry well known in the art, for example by synthesis from optically active starting materials or by resolution of a racemic form. Racemic compounds and racemic intermediates thereof are drawn herein as flat structures whereas stereospecific compounds and stereospecific intermediates thereof are drawn with the appropriate stereochemistry indicated.

The invention also relates to any and all tautomeric forms of the compounds of Formula (I) which are inhibitors of PKB activity.

In one embodiment of the invention, the compound of Formula (I) has the configuration shown in Formula (IA):

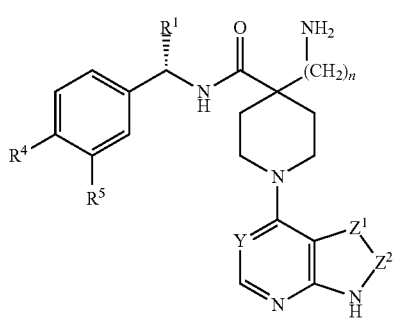

(IA)

wherein Y, $Z^1$, $Z^2$, $R^1$, $R^4$, $R^5$ and n are as defined hereinbefore.

In another embodiment of the invention, the compound of Formula (I) has the configuration shown in Formula (IB):

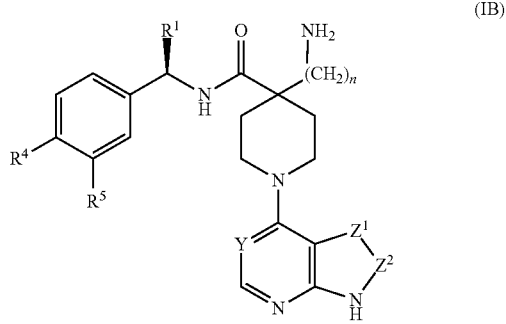

(IB)

wherein Y, $Z^1$, $Z^2$, $R^1$, $R^4$, $R^5$ and n are as defined hereinbefore.

Reference herein to a compound of Formula (I) should be understood to refer equally to a compound of Formula (I), (IA) or (IB).

In one embodiment of the invention, there is provided a compound of Formula (IA), or a pharmaceutically acceptable salt thereof:

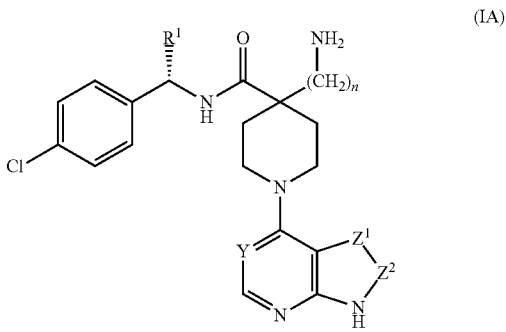

(IA)

wherein:

Y represents CH or N;

$Z^1$-$Z^2$ represents a group selected from CH=CH, N=CH and CH=N;

n is 0, 1 or 2; and $R^1$ represents $C_{1-4}$ alkyl, amino$C_{1-4}$ alkyl, hydroxy$C_{1-4}$ alkyl, —$(CH_2)_p$NHCOCH$_3$, —$(CH_2)_q$NR$^2$R$^3$ or $C_{3-6}$ cycloalkyl; where $R^2$ represents hydrogen or $C_{1-3}$ alkyl;

$R^3$ represents $C_{1-3}$ alkyl; and p and q independently represent 2 or 3.

In a further embodiment of the invention, there is therefore provided a compound of Formula (IA) or a pharmaceutically acceptable salt thereof:

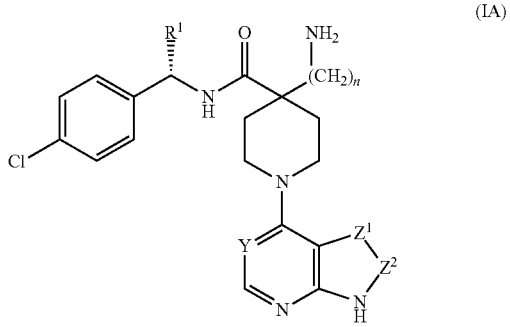

wherein:
Y represents CH or N;
$Z^1$-$Z^2$ represents a group selected from CH=CH, N=CH and CH=N;
$R^1$ represents $C_{1-4}$ alkyl, amino$C_{1-4}$ alkyl or $C_{3-6}$ cycloalkyl; and
n is 0, 1 or 2.

In one embodiment of the invention, there is provided a compound of Formula (I), (IA) or (IB) as defined hereinbefore, or a pharmaceutically acceptable salt thereof, wherein the compound of Formula (I), (IA) or (IB) is other than (S)-4-amino-N-(1-(4-chlorophenyl)-3-hydroxypropyl)-1-(7H-pyrrolo[2,3-d]pyrimidin-4-yl)piperidine-4-carboxamide.

A suitable pharmaceutically acceptable salt of a compound of Formula (I) is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid.

It will be understood that certain compounds of the present invention may exist in solvated, for example hydrated, as well as unsolvated forms. It is to be understood that the present invention encompasses all such solvated forms which are inhibitors of PKB activity.

The compounds of the Formula (I) may be administered in the form of a prodrug which is broken down in the human or animal body to give a compound of the Formula (I). Examples of prodrugs include in vivo hydrolysable esters of a compound of the formula (I). Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
N. Kakeya, et al., Chem Pharm Bull, 32, 692 (1984).

According to a further aspect of the invention there is provided a pharmaceutical composition, which comprises a compound of the Formula (I), or a pharmaceutically acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The compound of Formula (I) will normally be administered to a warm-blooded animal at a unit dose within the range 5-5000 mg/m² body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed, for example 4-7 mg/kg twice daily. However the daily dose will necessarily be varied depending upon the host treated, the particular route of administration, and the severity of the illness being treated. Accordingly the practitioner who is treating any particular patient may determine the optimum dosage.

For example, a pharmaceutical composition of the present invention suitable for oral administration could comprise 1-200 mg/ml of a compound of Formula (I), or a pharmaceutically-acceptable salt thereof, (such as (S)-4-amino-N-(1-(4-chlorophenyl)-3-hydroxypropyl)-1-(7H-pyrrolo[2,3-d]pyrimidin-4-yl)piperidine-4-carboxamide) in 0.5% hydroxypropylmethylcellulose (HPMC).

In the context of the present specification, the term "therapy" also includes "prophylaxis" unless there are specific indications to the contrary. The terms "therapeutic" and "therapeutically" should be construed accordingly.

As used herein, the term "treatment" is intended to have its normal everyday meaning of dealing with a disease in order to entirely or partially relieve one, some or all of its symptoms, or to correct or compensate for the underlying pathology.

As used herein, the term "prophylaxis" is intended to have its normal everyday meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

As a result of their PKB inhibitory activity, the compounds of Formula (I) of the present invention are expected to be useful in the treatment of diseases or medical conditions mediated alone or in part by PKB activity, for example cancer. The types of cancers which may be susceptible to treatment using compounds of Formula (I) of the present invention include, but are not limited to, ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma.

Breast cancer, and more specifically luminal breast cancer, may be particularly susceptible to treatment using compounds of the present invention.

It is envisaged that for the methods of treatment of cancer mentioned herein, the compound of Formula (I) will be administered to a mammal, more particularly a human being. Similarly, for the uses of a compound of Formula (I) for the treatment of cancer mentioned herein, it is envisaged that the compound of Formula (I) will be administered to a mammal, more particularly a human being.

According to a another aspect of the invention, there is therefore provided a compound of Formula (I) as defined hereinbefore, or a pharmaceutically acceptable salt thereof, for use as a medicament.

According to a further aspect of the invention, there is provided a compound of Formula (I) as defined hereinbefore, or a pharmaceutically acceptable salt thereof for use in the treatment of a disease mediated through PKB. In one embodiment of the invention, said disease mediated through PKB is cancer. In a further embodiment of the invention, said cancer is selected from ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. In one embodiment of the invention, said cancer is selected from breast cancer, Non-Hodgkins lymphoma, pancreatic cancer, hepatocellular cancer, gastric cancer, prostate cancer and lung cancer. In one particular embodiment, said cancer is breast cancer, more particularly luminal breast cancer.

According to a further aspect of the invention, there is provided the use of a compound of Formula (I) as defined hereinbefore, or a pharmaceutically acceptable salt thereof for the preparation of a medicament for the treatment of a disease mediated through PKB. In one embodiment of the invention, said disease mediated through PKB is cancer. In a further embodiment of the invention, said cancer is selected from ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. In one embodiment of the invention, said cancer is selected from breast cancer, Non-Hodgkins lymphoma, pancreatic cancer, hepatocellular cancer, gastric cancer, prostate cancer and lung cancer. In one particular embodiment, said cancer is breast cancer, more particularly luminal breast cancer.

According to a further aspect of the invention, there is provided the use of a compound of Formula (I) as defined hereinbefore, or a pharmaceutically acceptable salt thereof, for the preparation of a medicament for the treatment of cancer. In one embodiment of the invention, said cancer is selected from ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. In one embodiment of the invention, said cancer is selected from breast cancer, Non-Hodgkins lymphoma, pancreatic cancer, hepatocellular cancer, gastric cancer, prostate cancer and lung cancer. In one particular embodiment, said cancer is breast cancer, more particularly luminal breast cancer.

According to a further aspect of the invention, there is provided a method of using a compound of Formula (I) as defined hereinbefore, or a pharmaceutically acceptable salt thereof, for the treatment of cancer. In one embodiment of the invention, said cancer is selected from ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. In one embodiment of the invention, said cancer is selected from breast cancer, Non-Hodgkins lymphoma, pancreatic cancer, hepatocellular cancer, gastric cancer, prostate cancer and lung cancer. In one particular embodiment, said cancer is breast cancer, more particularly luminal breast cancer.

According to a further aspect of the invention, there is provided a method of treating a human suffering from a disease in which inhibition of PKB is beneficial, comprising the steps of administering to a person in need thereof of a therapeutically effective amount of a compound of Formula (I) as defined hereinbefore, or a pharmaceutically acceptable salt thereof. In one embodiment of the invention, the disease in which inhibition of PKB is beneficial is cancer. In a further embodiment of the invention, said cancer is selected from ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. In one embodiment of the invention, said cancer is selected from breast cancer, Non-Hodgkins lymphoma, pancreatic cancer, hepatocellular cancer, gastric cancer, prostate cancer and lung cancer. In one particular embodiment, said cancer is breast cancer, more particularly luminal breast cancer.

The cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Certain processes for the synthesis of compounds of Formula (I) are provided as a further feature of the invention. Thus, according to a further aspect of the invention there is provided a process for the preparation of a compound of Formula (I) or a pharmaceutically acceptable salt thereof, which comprises a process (a), (b), (c) or (d) (wherein the variables are as defined hereinbefore for compounds of Formula (I) unless otherwise defined):

(a) reaction of an acid of Formula (II) with an amine of Formula (III):

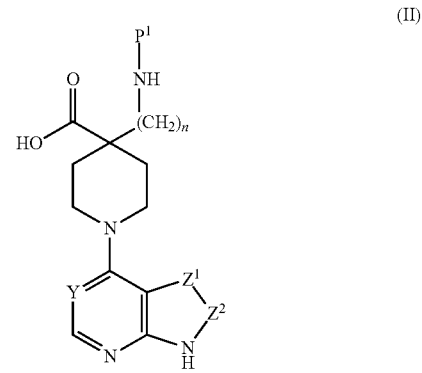

(II)

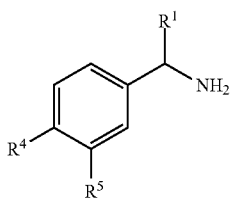

(III)

wherein P¹ represents a suitable protecting group, for example tert-butoxycarbonyl;

(b) reaction of a carboxamide of Formula (IV) with a bicyclic heterocycle of Formula (V):

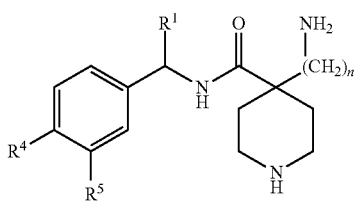

(IV)

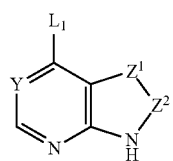

(V)

wherein L₁ represents a suitable leaving group, for example chlorine;

(c) when n is 1, hydrogenation of a compound of Formula (VI): or

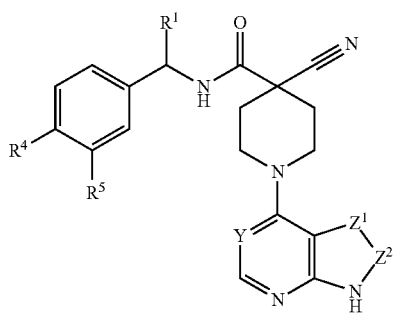

(VI)

(d) when R¹ represents aminomethyl, hydrogenation of a compound of Formula (VII):

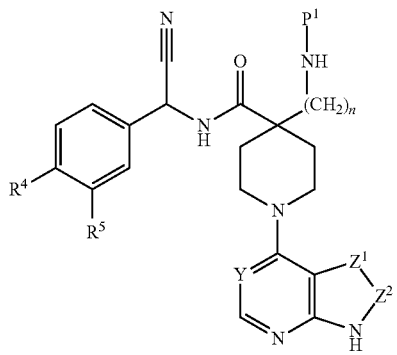

(VII)

wherein P¹ represents a suitable protecting group, for example tert-butoxycarbonyl;
and thereafter, if necessary:
(i) converting a compound of Formula (I) into another compound of Formula (I);
(ii) removing any protecting groups; and/or
(iii) forming a pharmaceutically acceptable salt thereof.

Examples of conversions of a compound of Formula (I) into another compound of Formula (I), are well known to those skilled in the art, and include functional group interconversions such as hydrolysis, hydrogenation, hydrogenolysis, oxidation or reduction, and/or further functionalisation by standard reactions such as amide or metal-catalysed coupling, or nucleophilic displacement reactions.

Specific reaction conditions for processes (a), (b), (c) and (d) above are as follows:

Process (a)—acids of Formula (II) and amines of Formula (III) may be reacted together in the presence of a suitable coupling reagent, for example O-(7-azabenzotriazol-1-yl)-N,N,N',N'-tetramethyluronium hexafluorophosphate (HATU), and a suitable base, for example N,N'-diisopropylethylamine (DIPEA), in a suitable solvent, for example dimethylacetamide (DMA), and at a suitable temperature, for example 50 to 70° C., more suitably about 60° C.;

Process (b)—carboxamides of Formula (IV) and heterocycles of Formula (V) may be reacted together in the presence of a suitable base, for example N,N'-diisopropylethylamine (DIPEA), in a suitable solvent, for example butan-1-ol, and at a suitable temperature, for example 50 to 70° C., more suitably about 60° C.;

Processes (c) and (d)—compounds of Formula (VI) or (VII) dissolved in a suitable solvent, for example ethanol, may be hydrogenated under an atmosphere of hydrogen in the presence of a suitable catalyst, for example Raney™ nickel, and a suitable base, for example ammonium hydroxide.

Compounds of Formula (II) may be prepared according to Scheme 1:

Scheme 1

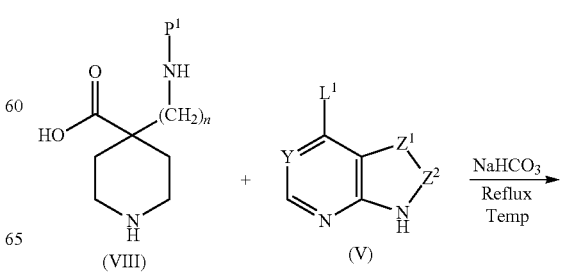

(VIII)   (V)

-continued

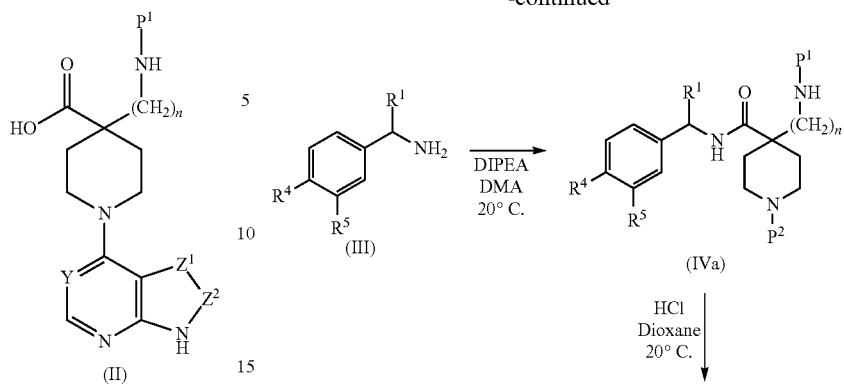

wherein $P^1$ is a suitable protecting group, for example tert-butoxycarbonyl, $L^1$ is a suitable leaving group, for example chlorine, and all other variables are as defined hereinbefore.

Compounds of Formula (IV) may be prepared according to Scheme 2:

Scheme 2

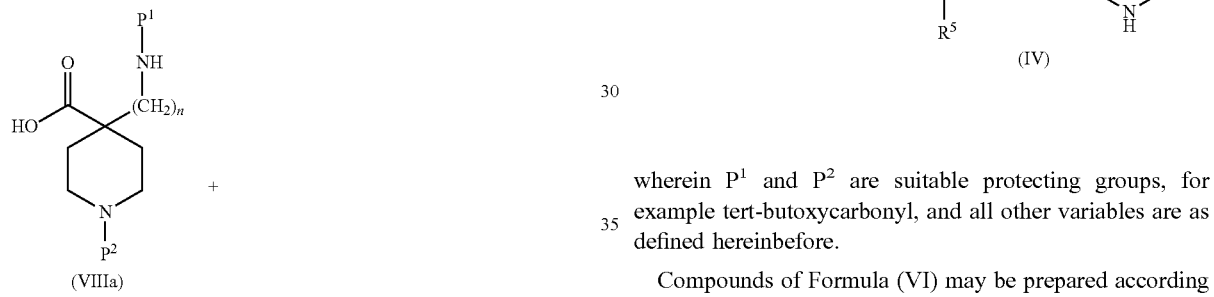

wherein $P^1$ and $P^2$ are suitable protecting groups, for example tert-butoxycarbonyl, and all other variables are as defined hereinbefore.

Compounds of Formula (VI) may be prepared according to Scheme 3:

Scheme 3

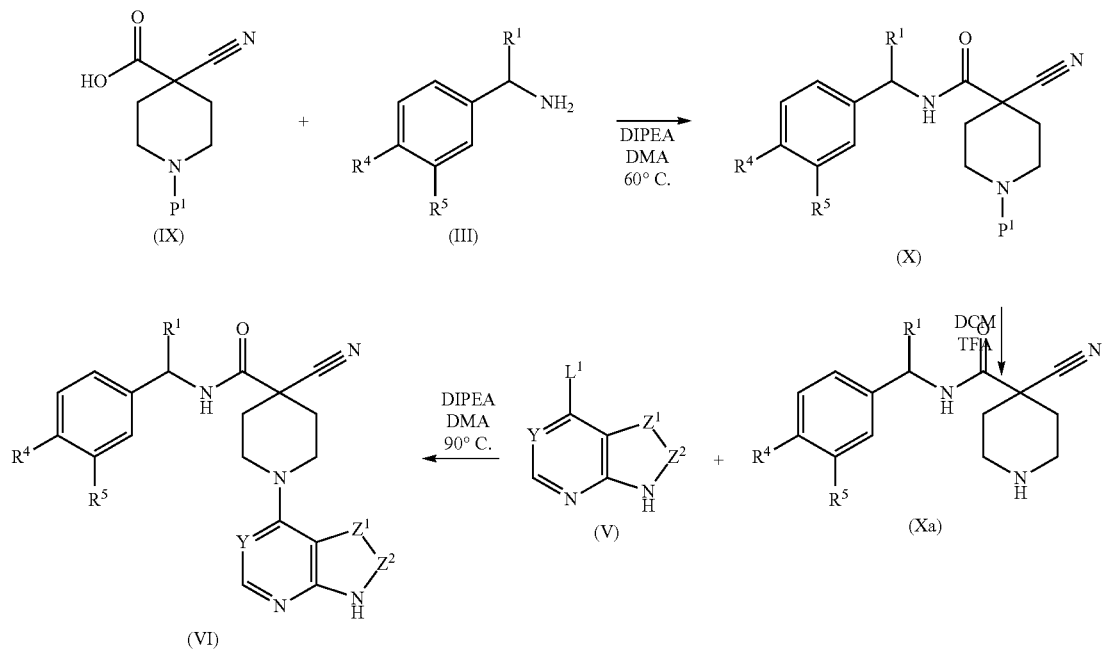

wherein P¹ is a suitable protecting group, for example tert-butoxycarbonyl, and all other variables are as defined hereinbefore.

Compounds of Formula (VII) may be prepared according to Scheme 4:

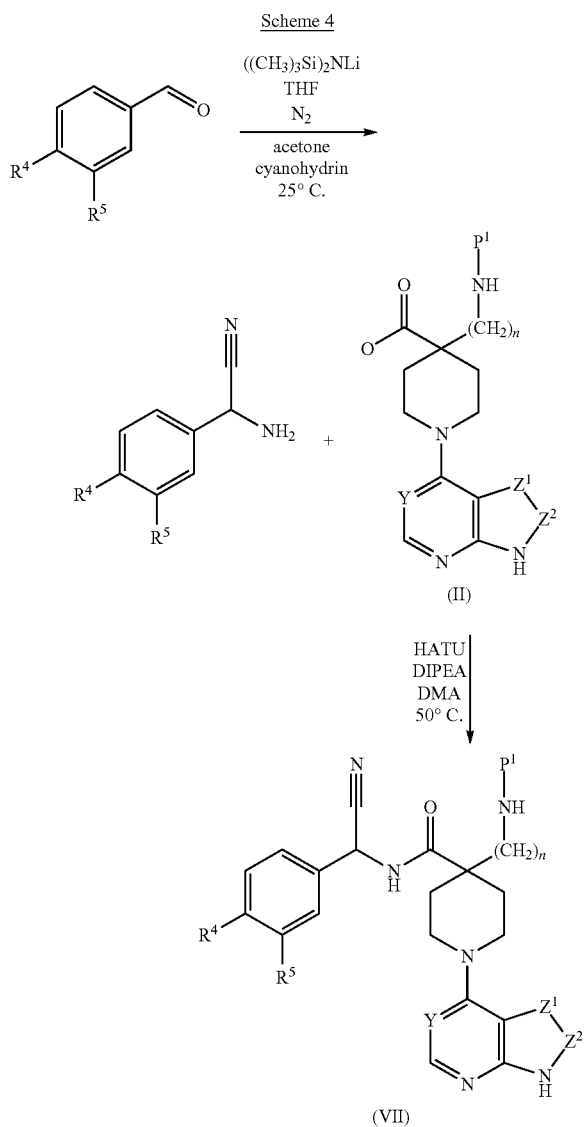

wherein P¹ represents a suitable protecting group, for example tert-butoxycarbonyl, and all other variables are as defined hereinbefore.

Compounds of Formulas (III), (V), (VIII) and (IX) are commercially available, known in the literature, prepared by standard processes known in the art, or may be prepared according to the processes described herein.

The following examples are for illustration purposes and are not intended to limit the scope of this application. Each exemplified compound represents a particular and independent aspect of the invention. All starting materials are commercially available compounds, or they are known in the literature, or they are prepared by standard processes known in the art.

Generally, with respect to the following Examples:
(i) temperatures are given in degrees Celsius (° C.); operations were carried out at room or ambient temperature, that is, at a temperature in the range of 18 to 25° C.;
(ii) organic solutions were dried over anhydrous magnesium sulfate or anhydrous sodium sulfate; evaporation of solvent was carried out using a rotary evaporator under reduced pressure (600 to 4000 Pascals; 4.5 to 30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and/or analytical LC-MS, and reaction times where given are for illustration only.
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; bs, broad singlet;
(viii) chemical symbols have their usual meanings; SI units and symbols are used;
(ix) Mass spectra (MS) and LC-MS data were generated on an LC-MS system where the HPLC component comprised generally either an Agilent 1100, Waters Alliance HT (2790 & 2795) equipment or an HP1100 pump and Diode Array with CTC autosampler and was run on a Phenomenex Gemini C18 5 μm, 50×2 mm column (or similar) eluting with either acidic eluent (for example, using a gradient between 0-95% water/acetonitrile with 5% of a 1% formic acid in 50:50 water:acetonitrile (v/v) mixture), or basic eluent (for example, using a gradient between 0-95% water/acetonitrile with 5% of a 0.1% 880 Ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the (M+H)+ for positive ion mode and (M−H)− for negative ion mode;
(x) unless stated otherwise compounds containing an asymmetrically substituted carbon and/or sulfur atom have not been resolved;
(xi) any microwave reactions were carried out in either a Biotage Optimizer EXP, or a CEM Explorer microwave;
(xii) preparative high performance liquid chromatography (HPLC) was performed on a Gilson instrument using the following conditions:
Column: C18 reversed-phase silica, for example, Waters 'Xbridge', 5 μm silica, 19×100 mm, or 30×100 mm, using decreasingly polar solvent mixtures as eluent (decreasing ratio of Solvent A to Solvent B)
Solvent A: Water with 1% ammonium hydroxide
Solvent B: Acetonitrile
Flow rate: 28 ml/min or 61 ml/min
Gradient: Tailored to suit each compound—generally 7-10 min in length
Wavelength: 254 nm

Abbreviations

Boc Tert-butoxycarbonyl
CAS™ Chemical Abstracts Service
DCM dichloromethane
DIPEA N,N'-diisopropylethylamine
DEA diethylamine
DMA dimethylacetamide
DMF dimethylformamide
HATU O-(7-Azabenzotriazol-1-yl)-N,N,N',N'-tetramethyluronium hexafluorophosphate
LCMS liquid chromatography mass spectroscopy
LDA lithium diisopropylamide
MPLC medium pressure liquid chromatography
NMP N-methylpyrrolidinone
OBD optimum bed density
PTFE polytetrafluoroethylene
SCX strong cation exchange
SFC supercritical flow chromatography
TBME t-butyl methyl ether
TEA triethylamine
TFA trifluoroacetic acid
THF tetrahydrofuran

EXAMPLE 1: 4-AMINO-N-(1-(4-CHLOROPHENYL)ETHYL)-1-(7H-PYRROLO[2,3-D]PYRIMIDIN-4-YL)PIPERIDINE-4-CARBOXAMIDE

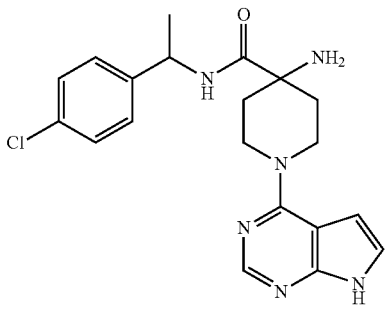 [SMILES: CC(NC(=O)C1(N)CCN(c2ncnc3[nH]ccc23)CC1)c1ccc(Cl)cc1]

4-(tert-Butoxycarbonylamino)-1-(7H-pyrrolo[2,3-d]pyrimidin-4-yl)piperidine-4-carboxylic acid (Intermediate 1) (362 mg), 1-(4-chlorophenyl)ethanamine (172 mg), N-(3-dimethylaminopropyl)-3-ethylcarbodiimide (231 mg) and 1-hydroxybenzotriazole (163 mg) were stirred together in DMF (2 mL) under nitrogen for 16 hours. The reaction mixture was partitioned between EtOAc (20 mL) and brine (4×20 mL). The organics were combined, dried over MgSO4 and evaporated in vacuo. The resultant white solid was dissolved in 1,4-dioxane (5 mL) and a 4M solution of HCl in 1,4-dioxane (5 mL) was added. The resulting mixture was stirred for 16 hours, then diluted with diethyl ether (50 mL). The crude product was isolated by filtration as the HCl salt which was purified by ion exchange chromatography, using an SCX column. The desired product was eluted from the column using 7M ammonia/MeOH and pure fractions were evaporated to dryness. This material was purified by preparative LCMS using decreasingly polar mixtures of water (containing 1% NH$_3$) and MeCN as eluents. Fractions containing the desired compound were evaporated to dryness to afford 4-amino-N-(1-(4-chlorophenyl)ethyl)-1-(7H-pyrrolo[2,3-d]pyrimidin-4-yl)piperidine-4-carboxamide as a white solid (168 mg, 42%).

1H NMR (d6-dmso, 400 MHz) 1.33-1.49 (m, 5H), 1.84-2.04 (m, 2H), 2.12-2.22 (br s, 2H), 3.54 (t, 2H), 4.39 (t, 2H), 4.81-4.92 (m, 1H), 6.55-6.59 (m, 1H), 7.13-7.18 (m, 1H), 7.31-7.39 (m, 4H), 8.12 (s, 1H), 8.30 (d, 1H), 11.62 (s, 1H).

MS m/e MH+ 399.

EXAMPLE 2: (S)-4-AMINO-N-(1-(4-CHLOROPHENYL)ETHYL)-1-(7H-PYRROLO[2,3-D]PYRIMIDIN-4-YL)PIPERIDINE-4-CARBOXAMIDE

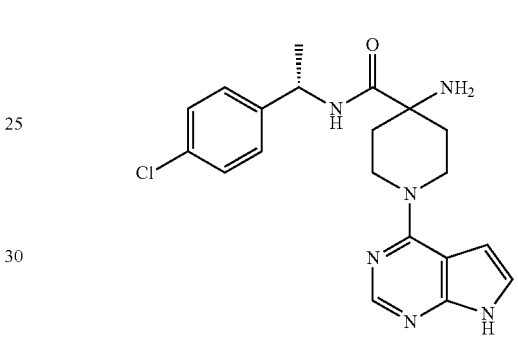

O-(7-Azabenzotriazol-1-yl)-N,N,N',N'-tetramethyluronium hexafluorophosphate (0.418 g) was added in one portion to 4-(tert-butoxycarbonylamino)-1-(7H-pyrrolo[2,3-d]pyrimidin-4-yl)piperidine-4-carboxylic acid (Intermediate 1) (0.361 g), (S)-1-(4-chlorophenyl)ethanamine (0.140 mL) and DIPEA (0.524 mL) in DMA (10 mL) at 25° C. under nitrogen. The resulting solution was stirred at 60° C. for 4 hours. The crude product was purified by ion exchange chromatography, using an SCX column. The desired product was eluted from the column using 7M NH$_3$/MeOH and pure fractions were evaporated to dryness. This crude material was then treated with a 20% solution of TFA in DCM (10 mL) and stirred at room temperature. The crude product was purified by ion exchange chromatography, using an SCX column. The desired product was eluted from the column using 7M ammonia/MeOH and pure fractions were evaporated to dryness. This material was purified by preparative LCMS using decreasingly polar mixtures of water (containing 1% NH$_3$) and MeCN as eluents. Fractions containing the desired compound were evaporated to dryness to afford (S)-4-amino-N-(1-(4-chlorophenyl)ethyl)-1-(7H-pyrrolo[2,3-d]pyrimidin-4-yl)piperidine-4-carboxamide as a white solid (0.281 g, 70.4%).

1H NMR (400.13 MHz, DMSO-d6) δ 1.37 (3H, d), 1.42-1.45 (2H, m), 1.88-2.01 (2H, m), 2.27 (2H, s), 3.49-3.59 (2H, m), 4.34-4.44 (2H, m), 4.83-4.90 (1H, m), 6.57-6.58 (1H, m), 7.14-7.16 (1H, m), 7.32-7.38 (4H, m), 8.12 (1H, s), 8.30 (1H, d), 11.62 (1H, s).

MS m/e MH+ 399.

EXAMPLE 3: 4-AMINO-N-(1-(4-CHLOROPHENYL)PROPYL)-1-(7H-PYRROLO[2,3-D]PYRIMIDIN-4-YL)PIPERIDINE-4-CARBOXAMIDE

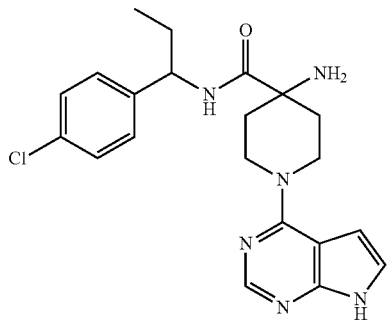 [SMILES: CCC(NC(=O)C1(N)CCN(c2ncnc3[nH]ccc23)CC1)c1ccc(Cl)cc1]

O-(7-Azabenzotriazol-1-yl)-N,N,N',N'-tetramethyluronium hexafluorophosphate (0.209 g) was added in one portion to 4-(tert-butoxycarbonylamino)-1-(7H-pyrrolo[2,3-d]pyrimidin-4-yl)piperidine-4-carboxylic acid (Intermediate 1) (0.181 g), 1-(4-chlorophenyl)propan-1-amine (0.085 g) and DIPEA (0.262 mL) in DMA (10 mL) at 25° C. under nitrogen. The resulting solution was stirred at 60° C. for 4 hours. The crude product was purified by ion exchange chromatography, using an SCX column. The desired product was eluted from the column using 7N ammonia/MeOH and pure fractions were evaporated to dryness. This crude material was then treated with a 20% solution of TFA in DCM (10 mL) and stirred at room temperature for 2 hours. The crude product was purified by ion exchange chromatography, using an SCX column. The desired product was eluted from the column using 7N ammonia/MeOH and pure fractions were evaporated to dryness. This material was purified by preparative LCMS using decreasingly polar mixtures of water (containing 1% ammonia) and MeCN as eluents. Fractions containing the desired compound were evaporated to dryness to afford 4-amino-N-(1-(4-chlorophenyl)propyl)-1-(7H-pyrrolo[2,3-d]pyrimidin-4-yl)piperidine-4-carboxamide as a white solid (0.138 g, 66.8%).

$^1$H NMR (400.13 MHz, DMSO-d6) δ 0.87 (3H, t), 1.42-1.55 (2H, m), 1.72-1.79 (2H, m), 1.91-2.05 (2H, m), 2.21 (2H, s), 3.54-3.62 (2H, m), 4.38-4.45 (2H, m), 4.65-4.70 (1H, m), 6.61 (1H, dd), 7.18 (1H, dd), 7.32-7.37 (4H, m), 8.31 (1H, d), 8.12 (1H, s).

MS m/e MH$^+$ 413.

EXAMPLES 3A AND 3B: (S)-4-AMINO-N-(1-(4-CHLOROPHENYL)PROPYL)-1-(7H-PYRROLO[2,3-D]PYRIMIDIN-4-YL)PIPERIDINE-4-CARBOXAMIDE AND (R)-4-AMINO-N-(1-(4-CHLOROPHENYL)PROPYL)-1-(7H-PYRROLO[2,3-D]PYRIMIDIN-4-YL)PIPERIDINE-4-CARBOXAMIDE

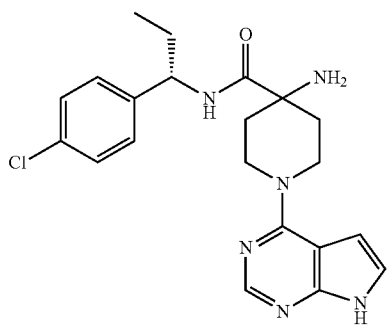

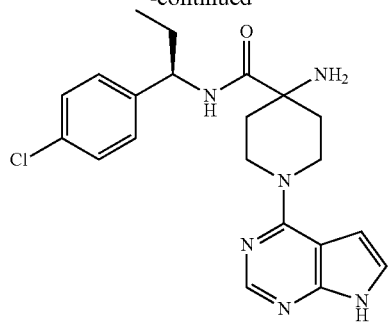

Racemic 4-amino-N-(1-(4-chlorophenyl)propyl)-1-(7H-pyrrolo[2,3-d]pyrimidin-4-yl)piperidine-4-carboxamide (Example 3) was purified by preparative chiral-HPLC. The fractions containing the desired compound were evaporated to dryness to afford Isomer 1 (first to elute, 41 mg) as a white solid, and Isomer 2 (second to elute, 41 mg) as a white solid. Analytical data was identical to the original sample. Chiral analytical HPLC analysis (using a 20 μm Chiralpak AS (250 mm×4.6 mm) column, with an eluent mixture of iso-hexane/(EtOH/MeOH 50/50)/TEA 90/10/0.1, 1 mL/min at 25° C., injecting 10 μl of a 1 mg/mL solution in EtOH) showed each enantiomer to be distinct from each other and enantiomerically pure (e.e.=100%).

EXAMPLE 4: 4-AMINO-N-((4-CHLOROPHENYL)(CYCLOPROPYL)METHYL)-1-(7H-PYRROLO[2,3-D]PYRIMIDIN-4-YL)PIPERIDINE-4-CARBOXAMIDE

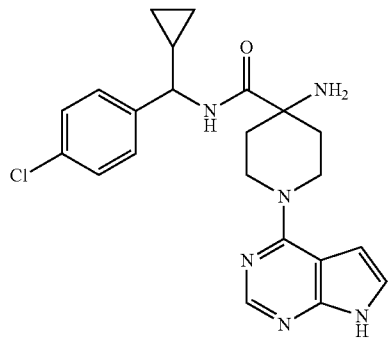 [SMILES: NC1(C(=O)NC(c2ccc(Cl)cc2)C2CC2)CCN(c2ncnc3[nH]ccc23)CC1]

O-(7-Azabenzotriazol-1-yl)-N,N,N',N'-tetramethyluronium hexafluorophosphate (0.228 g) was added to 4-(tert-butoxycarbonylamino)-1-(7H-pyrrolo[2,3-d]pyrimidin-4-yl)piperidine-4-carboxylic acid (Intermediate 1) (0.181 g), (4-chlorophenyl)(cyclopropyl)methanamine (Intermediate 3) (0.091 g) and DIPEA (0.261 mL) in DMA (5 mL) at 25° C. The resulting solution was stirred at 50° C. for 1 hour. The crude product was purified by ion exchange chromatography, using an SCX column. The desired product was eluted from the column using 7N ammonia/MeOH and pure fractions were evaporated to dryness. This crude material was suspended in dichloromethane (25 mL), and TFA (5 mL) was added. The reaction mixture was stirred for 1 hour, then the crude product was purified by ion exchange chromatography, using an SCX column. The desired product was eluted from the column using 7N ammonia/MeOH and pure fractions were evaporated to dryness to afford the crude EXAMPLE 5: 4-AMINO-N-(2-AMINO-1-(4-CHLOROPHENYL)ETHYL)-1-(7H-PYRROLO[2,3-D]PYRIMIDIN-4-YL)PIPERIDINE-4-CARBOXAMIDE

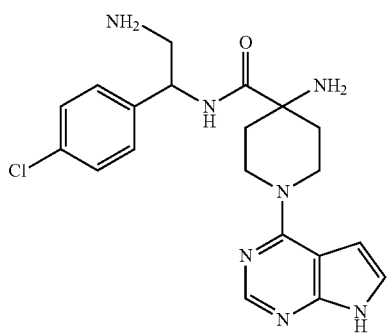 [SMILES: NCC(NC(=O)C1(N)CCN(c2ncnc3[nH]ccc23)CC1)c1ccc(Cl)cc1]

Trifluoroacetic acid (3 mL) was added to tert-butyl 4-(2-amino-1-(4-chlorophenyl)ethylcarbamoyl)-1-(7H-pyrrolo[2,3-d]pyrimidin-4-yl)piperidin-4-ylcarbamate (Intermediate 6) (0.514 g) in DCM (100 mL) at 25° C. The resulting solution was stirred at 25° C. for 3 hours. The crude product was purified by ion exchange chromatography, using an SCX column. The desired product was eluted from the column using 7M $NH_3$/MeOH and pure fractions were evaporated to dryness. The crude product was purified by preparative HPLC (Waters XBridge Prep C18 OBD column, 5μ silica, 19 mm diameter, 100 mm length), using decreasingly polar mixtures of water (containing 1% NH3) and MeCN as eluents. Fractions containing the desired compound were evaporated to dryness. This material was then further purified by flash silica chromatography, elution gradient 0 to 10% methanolic ammonia (7N) in DCM. Pure fractions were evaporated to dryness to afford 4-amino-N-(2-amino-1-(4-chlorophenyl)ethyl)-1-(7H-pyrrolo[2,3-d]pyrimidin-4-yl)piperidine-4-carboxamide as a colourless gum (0.047 g, 11.4%).

1H NMR (400.13 MHz, DMSO-$d_6$) δ 1.41-1.51 (2H, m), 1.86-1.94 (2H, m), 1.97-2.05 (2H, m), 2.77-2.86 (2H, m), 3.18 (2H, s), 3.51-3.59 (2H, m), 4.35-4.44 (2H, m), 4.70 (1H, t), 6.58 (1H, d), 7.15 (1H, d), 7.30-7.32 (2H, m), 7.35-7.37 (2H, m), 8.12 (1H, s), 8.41 (1H, s), 11.62 (1H, s).

MS m/e MH$^+$ 414.

EXAMPLE 6: (S)-4-(AMINOMETHYL)-N-(1-(4-CHLOROPHENYL)ETHYL)-1-(7H-PYRROLO[2,3-D]PYRIMIDIN-4-YL)PIPERIDINE-4-CARBOXAMIDE

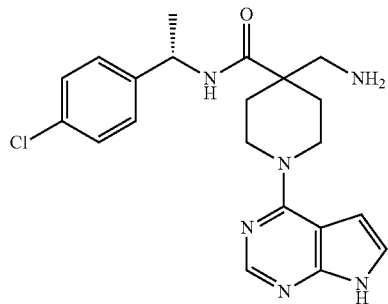 [SMILES: C[C@H](NC(=O)C1(CN)CCN(c2ncnc3[nH]ccc23)CC1)c1ccc(Cl)cc1]

Trifluoroacetic acid (2 mL, 25.96 mmol) was added to (S)-tert-butyl (4-(1-(4-chlorophenyl)ethylcarbamoyl)-1-(7H-pyrrolo[2,3-d]pyrimidin-4-yl)piperidin-4-yl)methylcarbamate (Intermediate 13) (0.257 g, 0.5 mmol) in DCM (20 mL) at 25° C. The resulting solution was stirred at 25° C. for 1 hour. The crude product was purified by ion exchange chromatography, using an SCX column. The desired product was eluted from the column using 7M $NH_3$/MeOH and pure fractions were evaporated to dryness. The crude product was purified by flash silica chromatography, elution gradient 0 to 10% 7N ammonia/MeOH in DCM. Pure fractions were evaporated to dryness to afford (S)-4-(aminomethyl)-N-(1-(4-chlorophenyl)ethyl)-1-(7H-pyrrolo[2,3-d]pyrimidin-4-yl)piperidine-4-carboxamide (0.095 g, 46.0%) as a white solid.

1H NMR (400.13 MHz, DMSO-d6) δ 1.39 (3H, d), 1.43-1.50 (4H, m), 2.05-2.14 (2H, m), 2.69 (2H, s), 3.37-3.47 (2H, m), 4.20-4.25 (2H, m), 4.96-5.04 (1H, t), 6.55 (1H, d), 7.15 (1H, d), 7.37 (4H, s), 8.11 (1H, s), 8.49 (1H, d), 11.61 (1H, s).

MS m/e MH$^+$ 413.

EXAMPLE 7: 4-AMINO-N-(1-(4-CHLOROPHENYL)-4-HYDROXYBUTYL)-1-(7H-PYRROLO[2,3-D]PYRIMIDIN-4-YL)PIPERIDINE-4-CARBOXAMIDE

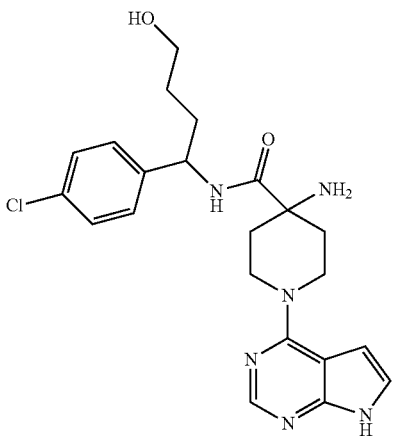 [SMILES: NC1(C(=O)NC(CCCO)c2ccc(Cl)cc2)CCN(c2ncnc3[nH]ccc23)CC1]

Trifluoroacetic acid (2 ml, 25.96 mmol) was added to tert-butyl 4-(1-(4-chlorophenyl)-4-hydroxybutylcarbamoyl)-1-(7H-pyrrolo[2,3-d]pyrimidin-4-yl)piperidin-4-ylcarbamate (Intermediate 17) (140 mg, 0.26 mmol) at 20° C. and the resulting solution stirred for 1 hour. The solution was then diluted with methanol, applied to a 10 g SCX column and eluted with methanol followed by 2N NH$_3$/MeOH. Fractions containing product were combined, concentrated by evaporation and purified by preparative HPLC (Waters XBridge Prep C18 OBD column, 5 μm silica, 19 mm diameter, 100 mm length), using decreasingly polar mixtures of water (containing 1% NH$_3$) and MeCN as eluents. Fractions containing the desired compound were evaporated to dryness to afford 4-amino-N-(1-(4-chlorophenyl)-4-hydroxybutyl)-1-(7H-pyrrolo[2,3-d]pyrimidin-4-yl)piperidine-4-carboxamide (58.0 mg, 50.8%) as a colourless solid.

1H NMR (399.902 MHz, DMSO) δ 1.28-1.51 (4H, m), 1.69-1.80 (2H, m), 1.90-2.03 (2H, m), 3.37-3.41 (2H, m), 3.50-3.58 (2H, m), 4.37-4.43 (3H, m), 4.71-4.76 (1H, m), 6.59 (1H, m), 7.16 (1H, m), 7.36 (4H, m), 8.13 (1H, s), 8.33 (1H, d), 11.64 (1H, s).

MS m/e MH$^+$ 443.

EXAMPLES 7A AND 7B: (S)-4-AMINO-N-(1-(4-CHLOROPHENYL)-4-HYDROXYBUTYL)-1-(7H-PYRROLO[2,3-D]PYRIMIDIN-4-YL)PIPERIDINE-4-CARBOXAMIDE AND (R)-4-AMINO-N-(1-(4-CHLOROPHENYL)-4-HYDROXYBUTYL)-1-(7H-PYRROLO[2,3-D]PYRIMIDIN-4-YL) PIPERIDINE-4-CARBOXAMIDE

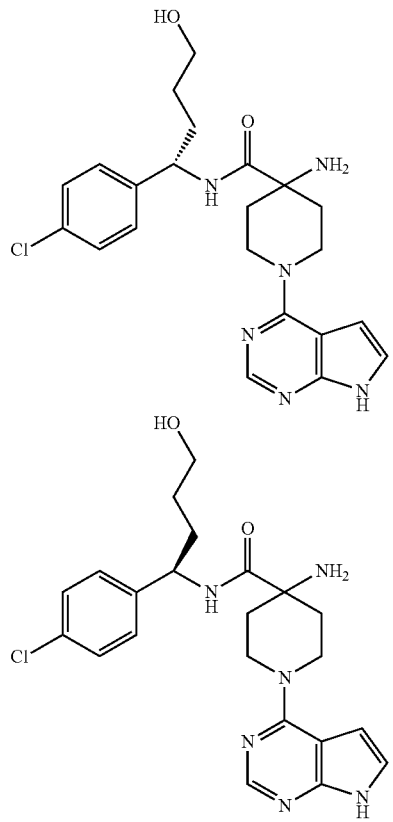

DIPEA (2.85 mL, 16.0 mmol) was added to 4-amino-N-(1-(4-chlorophenyl)-4-hydroxybutyl)piperidine-4-carboxamide (Intermediate 72) (1.04 g, 3.19 mmol) and 4-chloro-7H-pyrrolo[2,3-d]pyrimidine (0.490 g, 3.19 mmol) in ethanol (15.96 mL) at 25° C. The resulting solution was stirred at 65° C. overnight. The crude product was analysed by LCMS and evaporated to dryness. The crude solid was then purified by ion exchange chromatography, using an SCX-2 column. The product was eluted from the column using 20% 7N ammonia in methanol/DCM. The crude mixture was then re-purified by flash silica chromatography (eluent 0-10% 7N ammonia/MeOH in DCM) and pure fractions evaporated to dryness to afford 4-amino-N-(1-(4-chlorophenyl)-4-hydroxybutyl)-1-(7H-pyrrolo[2,3-d]pyrimidin-4-yl)piperidine-4-carboxamide (63.9%) (racemate) as a fine white solid. The racemate was chirally resolved by supercritical flow chromatography (SFC) to afford the pure enantiomers in yields of 272 mg (19%) and 245 mg (17%) respectively. The NMR spectra for both enantiomers were identical.

$^1$H NMR (400.13 MHz, DMSO) δ 1.38-1.42 (2H, m), 1.46-1.49 (2H, d), 1.74 (2H, s), 1.92-2.03 (2H, m), 2.19 (2H, s), 3.55-3.58 (2H, d), 4.38 (1H, s), 4.41 (2H, s), 4.75-4.76 (1H, d), 6.59 (1H, s), 7.17 (1H, s), 7.36 (4H, s), 8.15 (1H, s), 8.32-8.34 (1H, d), 11.65 (1H, s, exchange);

MS m/e MH$^+$ 443; HPLC $t_R$=1.66 min.

EXAMPLE 8: 4-AMINO-N-(1-(4-CHLOROPHENYL)-2-HYDROXYETHYL)-1-(7H-PYRROLO[2,3-D]PYRIMIDIN-4-YL)PIPERIDINE-4-CARBOXAMIDE

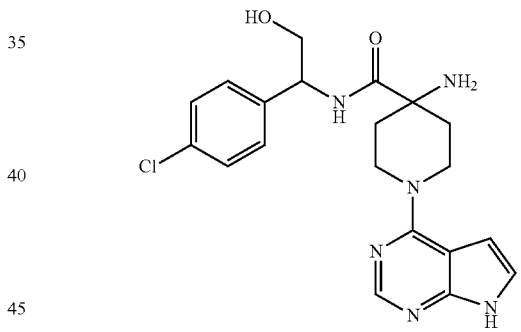

tert-Butyl 4-(1-(4-chlorophenyl)-2-hydroxyethylcarbamoyl)-1-(7H-pyrrolo[2,3-d]pyrimidin-4-yl)piperidin-4-ylcarbamate (Intermediate 18) (137 mg, 0.27 mmol) was treated with trifluoroacetic acid (2 mL). The solution was stirred for 1 hour at room temperature. The mixture was concentrated under reduced pressure. The crude product was purified by ion exchange chromatography, using a SCX column. The residue was loaded onto the column in methanol and washed with methanol. The desired product was eluted from the column using 2M ammonia in methanol and pure fractions were evaporated to dryness to afford 4-amino-N-(1-(4-chlorophenyl)-2-hydroxyethyl)-1-(7H-pyrrolo[2,3-d]pyrimidin-4-yl)piperidine-4-carboxamide (111 mg, quant.) as a colourless crystalline solid.

$^1$H NMR (399.9 MHz, DMSO-d$_6$) δ 1.40-1.49 (2H, m), 1.85-2.09 (2H, m), 3.48-3.69 (4H, m), 4.35-4.48 (2H, m), 4.72-4.81 (1H, m), 4.90-4.96 (1H, m), 6.58 (1H, br, s), 7.12-7.18 (1H, m), 7.30-7.40 (4H, m), 8.13 (1H, s), 8.45-8.53 (1H, m), 11.64 (1H, s)

m/z (ESI+) (M+H)+=415; HPLC $t_R$=1.57 min.

EXAMPLE 9: (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE (E9)

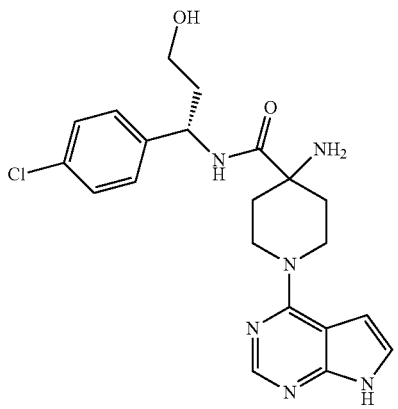 [SMILES: NC1(C(=O)N[C@@H](CCO)c2ccc(Cl)cc2)CCN(c2ncnc3[nH]ccc23)CC1]

HCl (4M in Dioxane) (3.00 mL, 12.00 mmol) was added to (S)-tert-butyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 22) (1.27 g, 2.40 mmol) in dichloromethane (20 mL). The resulting suspension was stirred at 20° C. for 16 hours. The reaction mixture was filtered through a PTFE filter cup and the crude solid was purified by preparative HPLC (Waters XTerra C18 column, 5 µm silica, 19 mm diameter, 100 mm length), using decreasingly polar mixtures of water (containing 1% TFA) and MeCN as eluents. Fractions containing the desired compound were purified by ion exchange chromatography, using an SCX column. The desired product was eluted from the column using 7M NH$_3$/MeOH and pure fractions were evaporated to dryness to afford (S)-4-amino-N-(1-(4-chlorophenyl)-3-hydroxypropyl)-1-(7H-pyrrolo[2,3-d]pyrimidin-4-yl)piperidine-4-carboxamide (0.200 g, 19.4%) as a white solid. 1H NMR (399.9 MHz, DMSO-d6) δ 1.45 (2H, d), 1.86 (1H, d), 1.90-1.93 (1H, m), 2.19 (2H, s), 3.38 (2H, q), 3.51-3.58 (2H, m), 4.35-4.38 (2H, m), 4.53 (1H, t), 4.88 (1H, d), 6.58 (1H, t), 7.16 (1H, t), 7.32-7.38 (4H, m), 8.12 (1H, s), 8.43 (1H, d), 11.63 (1H, s), m/z (ESI+) (M+H)+= 429; HPLC tR=1.46 min.

EXAMPLE 9 ALTERNATIVE ROUTE 1: (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

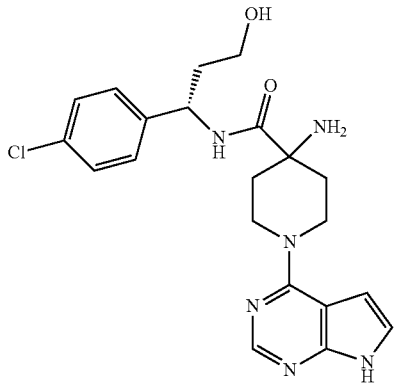

N-Ethyldiisopropylamine (1.676 ml, 9.62 mmol) was added to (S)-4-amino-N-(1-(4-chlorophenyl)-3-hydroxypropyl)piperidine-4-carboxamide (Intermediate 49) (1 g, 3.21 mmol) and 4-chloro-7H-pyrrolo[2,3-d]pyrimidine (0.493 g, 3.21 mmol) in butan-1-ol (15 ml). The resulting solution was stirred at 60° C. for 18 hours. The reaction mixture was diluted with EtOAc (50 mL), and washed sequentially with water (25 mL) and saturated brine (25 mL). The organic layer was dried over MgSO$_4$, filtered and evaporated to afford crude product. The crude product was purified by flash silica chromatography, elution gradient 0 to 6% MeOH with ammonia in DCM. Pure fractions were evaporated to dryness to afford (S)-4-amino-N-(1-(4-chlorophenyl)-3-hydroxypropyl)-1-(7H-pyrrolo[2,3-d]pyrimidin-4-yl)piperidine-4-carboxamide (842 mg) as a white foam. (S)-4-amino-N-(1-(4-chlorophenyl)-3-hydroxypropyl)-1-(7H-pyrrolo[2,3-d]pyrimidin-4-yl)piperidine-4-carboxamide was stirred in ethyl acetate (7 mL) for 18 hours. The solid was collected by filtration, washed with a small amount of ethyl acetate and vacuum oven dried at 55° C. for 18 hours to afford (S)-4-amino-N-(1-(4-chlorophenyl)-3-hydroxypropyl)-1-(7H-pyrrolo[2,3-d]pyrimidin-4-yl)piperidine-4-carboxamide (0.585 g, 42.5%) as a white solid.

m/z (ES+) (M+H)+=429; HPLC tR=1.60 min.

1H NMR (400.13 MHz, DMSO-d$_6$) δ 1.39-1.47 (2H, m), 1.80-2.02 (4H, m), 2.17 (2H, s), 3.35-3.40 (2H, m), 3.50-3.59 (2H, m), 4.34-4.41 (2H, m), 4.53 (1H, t), 4.88 (1H, d), 6.57 (1H, m), 7.14-7.16 (1H, m), 7.31-7.37 (4H, m), 8.12 (1H, s), 8.42 (1H, d), 11.62 (1H, s)

EXAMPLE 9 ALTERNATIVE ROUTE 2: (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

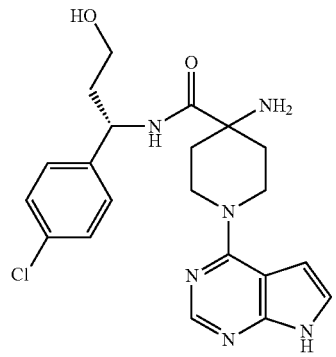 [SMILES: NC1(C(=O)N[C@@H](CCO)c2ccc(Cl)cc2)CCN(c2ncnc3[nH]ccc23)CC1]

(S)-3-Amino-3-(4-chlorophenyl)propan-1-ol (Intermediate 47) (2.055 g, 11.07 mmol) was added in one portion to 4-(tert-butoxycarbonylamino)-1-(7H-pyrrolo[2,3-d]pyrimidin-4-yl)piperidine-4-carboxylic acid (Intermediate 1) (4 g, 11.07 mmol) and DIPEA (5.80 ml, 33.20 mmol) in DMA (40 ml). HATU (4.63 g, 12.18 mmol) was added and the resulting solution was stirred at 20° C. for 24 hours. The reaction mixture was evaporated to dryness then diluted with EtOAc (300 mL), and washed sequentially with water (50 mL) and saturated brine (50 mL). The organic layer was dried over MgSO$_4$, filtered and evaporated to afford crude product. The crude product was purified by flash silica chromatography, elution gradient 2 to 6% MeOH with ammonia in DCM. Pure fractions were evaporated to dryness and triturated with dioxane (40 ml) to afford (S)-tertbutyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 22) (4.82 g, 82%) as a white solid. (S)-tert-butyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 22) (4.82 g, 82%) was suspended in dioxane (40.0 ml) and 4M hydrogen chloride in dioxane (7.69 ml, 221.36 mmol) added. The reaction was stirred at ambient temperature for 2 hours. The crude product was purified by ion exchange chromatography, using an SCX column. The desired product was eluted from the column using 3.5M $NH_3$/MeOH and pure fractions were evaporated to dryness. The crude product was purified by preparative HPLC (Waters XBridge Prep C18 OBD column, 5 μm silica, 19 mm diameter, 100 mm length), using decreasingly polar mixtures of water (containing 1% $NH_3$) and MeCN as eluents. Fractions containing the desired compound were evaporated to dryness to afford (S)-4-amino-N-(1-(4-chlorophenyl)-3-hydroxypropyl)-1-(7H-pyrrolo[2,3-d]pyrimidin-4-yl)piperidine-4-carboxamide (1.200 g, 25.3%) as a white solid.

m/z (ES+) (M+H)+=429; HPLC tR=1.67 min.

$^1$H NMR matches previous.

EXAMPLE 10: N-(3-ACETAMIDO-1-(4-CHLOROPHENYL)PROPYL)-4-AMINO-1-(7H-PYRROLO[2,3-D]PYRIMIDIN-4-YL)PIPERIDINE-4-CARBOXAMIDE

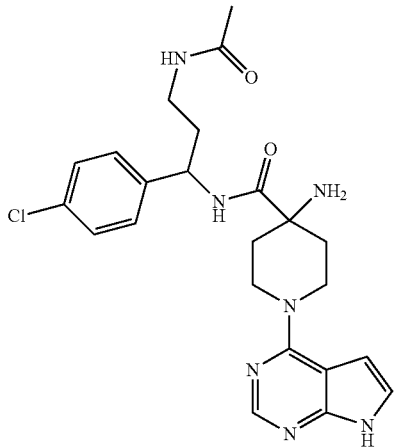 [SMILES: CC(=O)NCCC(NC(=O)C1(N)CCN(c2ncnc3[nH]ccc23)CC1)c1ccc(Cl)cc1]

Hydrogen chloride (4M) in 1,4-Dioxane (0.430 mL, 1.72 mmol) was added to tert-butyl 4-(3-acetamido-1-(4-chlorophenyl)propylcarbamoyl)-1-(7H-pyrrolo[2,3-d]pyrimidin-4-yl)piperidin-4-ylcarbamate (Intermediate 28) (98 mg, 0.17 mmol) in DCM (4 mL) at 20° C. The resulting suspension was stirred at 20° C. for 70 hours. The reaction mixture was evaporated to dryness. The crude product was purified by preparative HPLC (Waters XTerra C18 column, 5μ silica, 19 mm diameter, 100 mm length), using decreasingly polar mixtures of water (containing 1% $NH_3$) and MeCN as eluents. Fractions containing the desired compound were evaporated to dryness to afford N-(3-acetamido-1-(4-chlorophenyl)propyl)-4-amino-1-(7H-pyrrolo[2,3-d]pyrimidin-4-yl)piperidine-4-carboxamide (15.00 mg, 18.5%) as a white dry film. 1H NMR (399.9 MHz, DMSO-d6) δ 1.42-1.47 (2H, m), 1.79 (3H, s), 1.85 (1H, t), 1.89-1.93 (1H, m), 2.10 (2H, s), 3.00 (2H, t), 3.55 (2H, d), 4.36-4.40 (2H, m), 4.80 (1H, d), 6.58-6.60 (1H, m), 7.16 (1H, t), 7.34-7.39 (4H, m), 7.80 (1H, t), 8.13 (1H, s), 8.39 (1H, s), 11.64 (1H, s) No visible NH2. m/z (ESI+) (M+H)+=470; HPLC tR=1.56 min.

EXAMPLE 11: 4-AMINO-N-(1-(4-CHLOROPHENYL)-3-(DIMETHYLAMINO)PROPYL)-1-(7H-PYRROLO[2,3-D]PYRIMIDIN-4-YL)PIPERIDINE-4-CARBOXAMIDE

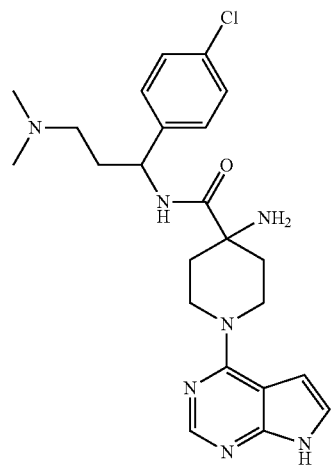 [SMILES: CN(C)CCC(NC(=O)C1(N)CCN(c2ncnc3[nH]ccc23)CC1)c1ccc(Cl)cc1]

Hydrogen chloride (4M in 1,4-dioxane, 1.01 mL, 4.05 mmol) was added to tert-butyl 4-(1-(4-chlorophenyl)-3-(dimethylamino)propylcarbamoyl)-1-(7H-pyrrolo[2,3-d]pyrimidin-4-yl)piperidin-4-ylcarbamate (Intermediate 34) (0.045 g, 0.08 mmol) in a mixture of DCM (5 mL) and methanol (2 mL) at 22° C. The resulting solution was stirred at 22° C. for 16 hours. The mixture was evaporated and the residue was purified by ion exchange chromatography, using an SCX column. The desired product was eluted from the column using 2M $NH_3$/MeOH and pure fractions were evaporated to dryness to afford 4-amino-N-(1-(4-chlorophenyl)-3-(dimethylamino)propyl)-1-(7H-pyrrolo[2,3-d]pyrimidin-4-yl)piperidine-4-carboxamide (0.034 g, 92%) as a colourless gum.

1H NMR (399.902 MHz, CDCl3) δ 1.57 (2H, m), 1.66 (2H, br.s), 1.81 (1H, m), 2.02 (1H, m), 2.18 (6H, s), 2.18-2.36 (4H, m), 3.67 (3H, m), 4.50 (2H, m), 5.00 (1H, dt), 6.52 (1H, d), 7.05 (1H, d), 7.18 (2H, d), 7.29 (2H, d), 8.33 (1H, s), 9.07 (1H, d), 9.61 (1H, s).

MS m/e MH+ 456

EXAMPLES 11A AND 11B: (S)-4-AMINO-N-(1-(4-CHLOROPHENYL)-3-(DIMETHYLAMINO)PROPYL)-1-(7H-PYRROLO[2,3-D]PYRIMIDIN-4-YL)PIPERIDINE-4-CARBOXAMIDE AND (R)-4-AMINO-N-(1-(4-CHLOROPHENYL)-3-(DIMETHYLAMINO)PROPYL)-1-(7H-PYRROLO[2,3-D]PYRIMIDIN-4-YL)PIPERIDINE-4-CARBOXAMIDE

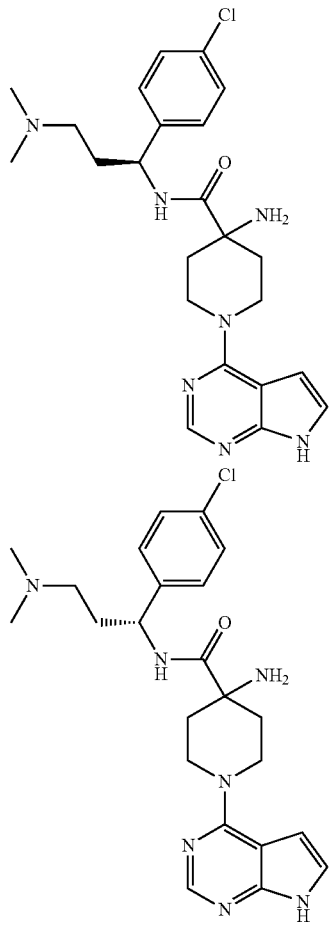

Racemic 4-amino-N-(1-(4-chlorophenyl)-3-(dimethylamino)propyl)-1-(7H-pyrrolo[2,3-d]pyrimidin-4-yl)piperidine-4-carboxamide (Example 11) (231 mg, 0.51 mmol) was chirally separated on a Chiralpak AD-H SFC (250 mm×20 mm) column, using supercritical fluid chromatography, elution solvent 7:3 $CO_2$/(EtOH+0.1% DEA). The appropriate fractions for the first eluted isomer were evaporated and the residue triturated with diethyl ether to give 4-amino-N-(1-(4-chlorophenyl)-3-(dimethylamino)propyl)-1-(7H-pyrrolo[2,3-d]pyrimidin-4-yl)piperidine-4-carboxamide (59 mg, 25%) as a white solid.

1H NMR (399.902 MHz, DMSO) δ 1.43 (2H, ddd), 1.83 (2H, dt), 1.86-2.01 (2H, m), 2.11 (6H, s), 2.14 (2H, t), 3.56 (2H, ddd), 4.39 (2H, ddd), 4.83 (1H, dt), 6.58 (1H, dd), 7.16 (1H, dd), 7.33 (2H, d), 7.37 (2H, d), 8.13 (1H, s), 8.61 (1H, d), 11.63 (1H, s).

MS m/e MH$^+$ 456.5.

The appropriate fractions for the second eluted isomer were evaporated and the residue triturated with diethyl ether to give 4-amino-N-(1-(4-chlorophenyl)-3-(dimethylamino)propyl)-1-(7H-pyrrolo[2,3-d]pyrimidin-4-yl)piperidine-4-carboxamide (43 mg, 19%) as a white solid.

1H NMR (399.902 MHz, DMSO) δ 1.43 (2H, ddd), 1.83 (2H, dt), 1.86-2.01 (2H, m), 2.11 (6H, s), 2.14 (2H, t), 3.56 (2H, ddd), 4.39 (2H, ddd), 4.83 (1H, q), 6.58 (1H, dd), 7.16 (1H, dd), 7.33 (2H, d), 7.37 (2H, d), 8.13 (1H, s), 8.61 (1H, d), 11.63 (1H, s).

MS m/e MH$^+$ 456.4, 458.4

EXAMPLE 12: 4-(AMINOMETHYL)-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

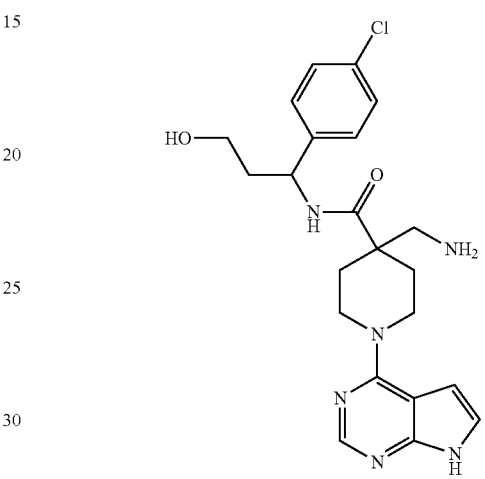

O-(7-Azabenzotriazol-1-yl)-N,N,N',N'-tetramethyluronium hexafluorophosphate (106 mg, 0.28 mmol) was added to 4-((tert-butoxycarbonylamino)methyl)-1-(7H-pyrrolo[2,3-d]pyrimidin-4-yl)piperidine-4-carboxylic acid (Intermediate 12) (100 mg, 0.27 mmol) and N,N-diisopropylethylamine (0.055 mL, 0.32 mmol) in NMP (5 mL) at 22° C. The resulting solution was stirred at 50° C. for 10 minutes then cooled to ambient temperature. 3-Amino-3-(4-chlorophenyl)propan-1-ol (Intermediate 29) (49.5 mg, 0.27 mmol) was added as a solution in NMP (2 mL) and the mixture was stirred at 22° C. for 16 hours. 4M HCl in dioxane (1 mL) was added and the mixture was stirred at 22° C. for a further 24 hours. The mixture was concentrated and the residue was purified by ion exchange chromatography, using an SCX column. The desired product was eluted from the column using 30% (2M $NH_3$ in MeOH) in DCM and pure fractions were evaporated to dryness to afford crude product. The crude product was purified by preparative HPLC (Waters XBridge Prep C18 OBD column, 5μ silica, 19 mm diameter, 100 mm length), using decreasingly polar mixtures of water (containing 1% $NH_3$) and MeCN as eluents. Fractions containing the desired compound were evaporated to dryness to afford 4-(aminomethyl)-N-(1-(4-chlorophenyl)-3-hydroxypropyl)-1-(7H-pyrrolo[2,3-d]pyrimidin-4-yl)piperidine-4-carboxamide (0.095 g, 81%) as a white solid.

1H NMR (399.902 MHz, DMSO) δ 1.47 (2H, m), 1.80-1.96 (2H, m), 2.09 (2H, m), 2.69 (1H, s), 3.27-3.45 (4H, m), 4.26 (2H, ddd), 5.02 (1H, dd), 6.56 (1H, d), 7.15 (1H, d), 7.33-7.39 (4H, m), 8.12 (1H, s), 8.44 (1H, d), 11.63 (1H, s).

MS m/e MH$^+$ 556

EXAMPLE 13: 4-AMINO-N-(1-(4-CHLOROPHE-NYL)-3-HYDROXYPROPYL)-1-(7H-PYRROLO[2,3-D]PYRIMIDIN-4-YL)PIPERIDINE-4-CARBOXAMIDE

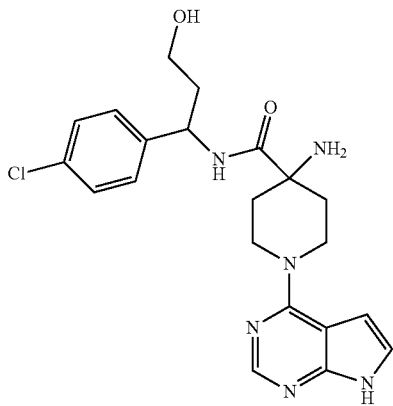 [SMILES: NC1(C(=O)NC(CCO)c2ccc(Cl)cc2)CCN(c2ncnc3[nH]ccc23)CC1]

TFA (0.7 mL) was added to a suspension of tert-butyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 36) (175 mg, 0.33 mmol) in dichloromethane (7 mL) under argon. The resulting solution was stirred at 20° C. for 16 hours. The solvents were removed in vacuo and the reaction mixture was purified by preparative HPLC using a Waters X-Bridge reverse-phase column (C-18, 5 microns silica, 19 mm diameter, 100 mm length) with decreasingly polar mixtures of water (containing 0.2% ammonium carbonate) and acetonitrile as eluent. The pure fractions were evaporated to dryness to afford 4-amino-N-(1-(4-chlorophenyl)-3-hydroxypropyl)-1-(7H-pyrrolo[2,3-d]pyrimidin-4-yl)piperidine-4-carboxamide (99 mg, 69.8%) as a white powder.

1H NMR (500 MHz, DMSO-d6) δ 1.38-1.46 (2H, m), 1.81-1.91 (4H, m), 2.25 (2H, br s), 3.48 (2H, m), 3.35-3.54 (2H, m), 4.35-4.41 (2H, m), 4.57 (1H, t), 4.87 (1H, m), 6.58 (1H, d), 7.16 (1H, d), 7.31-7.37 (4H, m), 8.11 (1H, s), 8.45 (1H, d), 11.65 (1H, s). m/z (ESI+) (M+H)+=429; HPLC tR=1.58 min.

EXAMPLE 14: 4-AMINO-N-(3-AMINO-1-(4-CHLOROPHENYL)PROPYL)-1-(7H-PYRROLO[2,3-D]PYRIMIDIN-4-YL)PIPERIDINE-4-CARBOXAMIDE

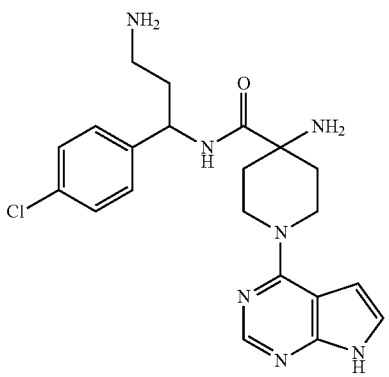 [SMILES: NCCC(NC(=O)C1(N)CCN(c2ncnc3[nH]ccc23)CC1)c1ccc(Cl)cc1]

Trifluoroacetic acid (0.05 mL) was added to a stirred suspension of tert-butyl 4-(3-amino-1-(4-chlorophenyl)propylcarbamoyl)-1-(7H-pyrrolo[2,3-d]pyrimidin-4-yl)piperidin-4-ylcarbamate (Intermediate 38) (7.0 mg) in DCM (1 mL) under argon at 25° C. The resulting suspension was stirred at 25° C. for 2 days. The reaction mixture was evaporated to dryness to afford the di-TFA salt of 4-amino-N-(3-amino-1-(4-chlorophenyl)propyl)-1-(7H-pyrrolo[2,3-d]pyrimidin-4-yl)piperidine-4-carboxamide as a partially solid oil (13.0 mg).

$^1$H NMR (500 MHz, DMSO-$d_6$) δ 1.86 (1H, d), 2.01 (2H, m), 2.08 (1H, m) 2.41 (2H, m), 2.69 (2H, m), 2.85 (1H, m), 3.61 (2H, t), 4.63 (2H, t), 5.02 (1H, q), 6.82 (1H, s), 7.36 (1H, t), 7.41 (2H, d), 7.49 (2H, d), 7.93 (3H, s br), 8.32 (1H, s), 8.59 (3H, s br), 8.96 (1H, d).

MS m/e MH+ 428.

EXAMPLE 15: (R)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

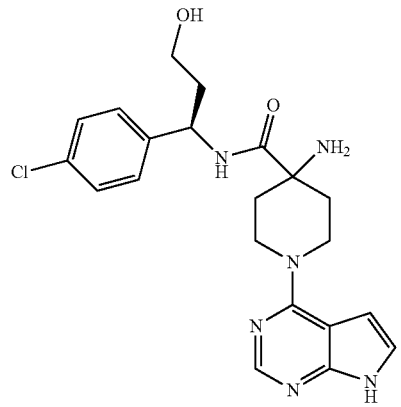 [SMILES: NC1(C(=O)N[C@H](CCO)c2ccc(Cl)cc2)CCN(c2ncnc3[nH]ccc23)CC1]

HCl (4M in dioxane) (0.378 mL, 1.51 mmol) was added to (R)-tert-butyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 42) (0.160 g, 0.30 mmol) in DCM (3 mL). The resulting suspension was stirred at 20° C. for 3 hours. The reaction mixture was evaporated. The crude product was purified by preparative HPLC (Waters XTerra C18 column, 5 μm silica, 19 mm diameter, 100 mm length), using decreasingly polar mixtures of water (containing 1% ammonia) and MeCN as eluents. Fractions containing the desired compound were evaporated to dryness to afford (R)-4-amino-N-(1-(4-chlorophenyl)-3-hydroxypropyl)-1-(7H-pyrrolo[2,3-d]pyrimidin-4-yl)piperidine-4-carboxamide (0.051 g, 39.3%) as a white solid.

$^1$H NMR (399.9 MHz, DMSO-d6) δ 1.46 (2H, d), 1.86 (1H, d), 1.90-1.93 (1H, m), 2.10 (2H, m), 3.37 (1H, t), 3.55 (2H, d), 4.40 (2H, d), 4.53 (2H, m), 4.88 (1H, d), 6.58 (1H, t), 7.16 (1H, t), 7.32-7.38 (4H, m), 8.14 (1H, d), 8.43 (1H, d), 11.63 (1H, s) no visible NH2.

MS m/e MH+ 429; HPLC tR=1.46 min.

EXAMPLE 16: (R)-4-AMINO-N-(1-(4-CHLOROPHENYL)ETHYL)-1-(7H-PYRROLO[2,3-D]PYRIMIDIN-4-YL)PIPERIDINE-4-CARBOXAMIDE

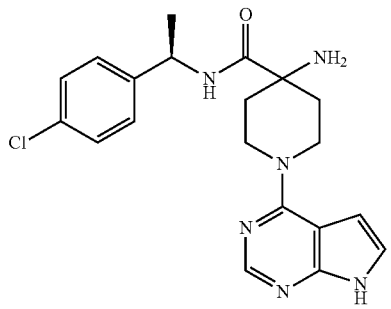 [SMILES: C[C@@H](NC(=O)C1(N)CCN(c2ncnc3[nH]ccc23)CC1)c1ccc(Cl)cc1]

O-(7-azabenzotriazol-1-yl)-N,N,N',N'-tetramethyluronium hexafluorophosphate (0.418 g, 1.10 mmol) was added in one portion to 4-(tert-butoxycarbonylamino)-1-(7H-pyrrolo[2,3-d]pyrimidin-4-yl)piperidine-4-carboxylic acid (Intermediate 1) (0.361 g, 1 mmol), (R)-1-(4-chlorophenyl)ethanamine (0.156 g, 1.00 mmol) and DIPEA (0.524 mL, 3.00 mmol) in DMA (10 mL) at 25° C. under nitrogen. The resulting solution was stirred at 60° C. for 4 hours. The crude product was purified by ion exchange chromatography, using an SCX column. The desired product was eluted from the column using 7N ammonia/MeOH and pure fractions were evaporated to dryness. The crude material was treated with a 10% solution of TFA in DCM (5 mL) and stirred at room temperature. The crude product was purified by ion exchange chromatography, using an SCX column. The desired product was eluted from the column using 7N ammonia/MeOH and pure fractions were evaporated to dryness. The crude product was purified by preparative LCMS using decreasingly polar mixtures of water (containing 1% ammonia) and MeCN as eluents. Fractions containing the desired compound were evaporated to dryness to afford (R)-4-amino-N-(1-(4-chlorophenyl)ethyl)-1-(7H-pyrrolo[2,3-d]pyrimidin-4-yl)piperidine-4-carboxamide (0.211 g, 52.9%) as a white solid.

$^1$H NMR (400 MHz, DMSO) δ 1.37 (3H, d), 1.39-1.48 (2H, m), 1.86-2.02 (2H, m), 2.19 (2H, s), 3.49-3.58 (2H, m), 4.34-4.43 (2H, m), 4.83-4.91 (1H, m), 6.56-6.59 (1H, m), 7.14-7.16 (1H, m), 7.32-7.38 (4H, m), 8.12 (1H, s), 8.30 (1H, d), 11.62 (1H, s).

MS m/e MH$^+$ 399.

EXAMPLE 17: (R)-4-(AMINOMETHYL)-N-(1-(4-CHLOROPHENYL)ETHYL)-1-(7H-PYRROLO[2,3-D]PYRIMIDIN-4-YL)PIPERIDINE-4-CARBOXAMIDE

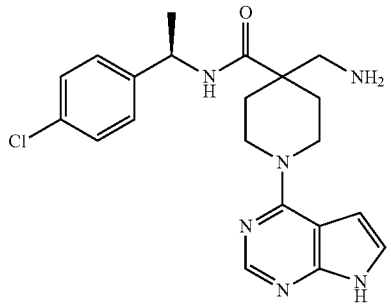 [SMILES: C[C@@H](NC(=O)C1(CN)CCN(c2ncnc3[nH]ccc23)CC1)c1ccc(Cl)cc1]

Raney® nickel (293 mg, 1.71 mmol) was added to a solution of (R)—N-(1-(4-chlorophenyl)ethyl)-4-cyano-1-(7H-pyrrolo[2,3-d]pyrimidin-4-yl)piperidine-4-carboxamide (Intermediate 45) (466 mg, 1.14 mmol), in ethanol (30 mL). Ammonium hydroxide (10 mL) was added. This mixture was first purged with nitrogen, then placed under a balloon of hydrogen and stirred for 36 hours. The reaction mixture was filtered through celite and the solvent evaporated to dryness. The crude product was purified by flash silica chromatography, elution gradient 0 to 10% 7N ammonia/MeOH in DCM. Pure fractions were evaporated to dryness to afford (R)-4-(aminomethyl)-N-(1-(4-chlorophenyl)ethyl)-1-(7H-pyrrolo[2,3-d]pyrimidin-4-yl)piperidine-4-carboxamide (276 mg, 58.6%) as a white solid.

$^1$H NMR (400 MHz, DMSO) δ 1.38 (3H, d), 1.41-1.51 (2H, m), 1.61 (2H, s), 2.09 (2H, d), 2.68 (2H, s), 3.37-3.50 (2H, m), 4.18-4.28 (2H, m), 4.95-5.04 (1H, m), 6.56 (1H, d), 7.15 (1H, d), 7.26-7.50 (4H, m), 8.11 (1H, s), 8.52 (1H, d), 11.66 (1H, s).

MS m/e MH$^+$ 413.

EXAMPLE 18: (S)-4-AMINO-N-(1-(4-CYANOPHENYL)-3-HYDROXYPROPYL)-1-(7H-PYRROLO[2,3-D]PYRIMIDIN-4-YL)PIPERIDINE-4-CARBOXAMIDE

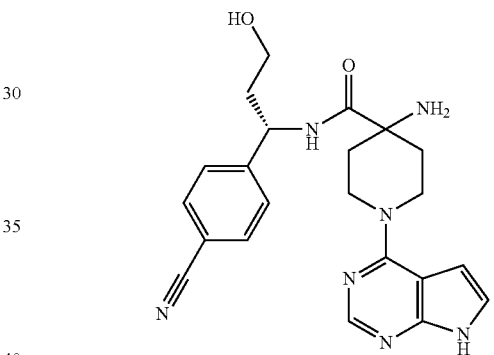

(S)-4-(1-amino-3-hydroxypropyl)benzonitrile (Intermediate 46) (195 mg, 1.11 mmol) was added in one portion to 4-(tert-butoxycarbonylamino)-1-(7H-pyrrolo[2,3-d]pyrimidin-4-yl)piperidine-4-carboxylic acid (Intermediate 1) (400 mg, 1.11 mmol) and DIPEA (0.580 mL, 3.32 mmol) in DMA (5 mL). O-(7-azabenzotriazol-1-yl)-N,N,N',N'-tetramethyluronium hexafluorophosphate (463 mg, 1.22 mmol) was added and the resulting solution was stirred at 20° C. for 24 hours. The reaction mixture was evaporated to dryness then diluted with EtOAc (300 mL), and washed sequentially with water (50 mL) and saturated brine (50 mL). The organic layer was dried over MgSO$_4$, filtered and evaporated to afford crude product. The crude product was purified by flash silica chromatography, elution gradient 2 to 6% MeOH with ammonia in DCM. Pure fractions were evaporated to dryness to afford (S)-tert-butyl 4-(1-(4-cyanophenyl)-3-hydroxypropylcarbamoyl)-1-(7H-pyrrolo[2,3-d]pyrimidin-4-yl)piperidin-4-ylcarbamate (267 mg, 46.4%) as a white solid. (S)-tert-butyl 4-(1-(4-cyanophenyl)-3-hydroxypropylcarbamoyl)-1-(7H-pyrrolo[2,3-d]pyrimidin-4-yl)piperidin-4-ylcarbamate (267 mg, 0.51 mmol) was suspended in dioxane (5.00 mL) and 4M hydrogen chloride in dioxane (0.769 mL, 22.14 mmol) added. The reaction was stirred at ambient temperature for 2 hours. The crude product was purified by ion exchange chromatography, using an SCX column. The desired product was eluted from the column using 3.5N ammonia/MeOH and pure fractions were evaporated to dryness. The product was then purified by preparative HPLC (Waters XBridge Prep C18 OBD column, 5μ silica, 21 mm diameter, 100 mm length), using decreasingly polar mixtures of water (containing 1% ammonia) and MeCN as eluents. Fractions containing the desired compound were evaporated to dryness to afford (S)-4-amino-N-(1-(4-cyanophenyl)-3-hydroxypropyl)-1-(7H-pyrrolo[2,3-d]pyrimidin-4-yl)piperidine-4-carboxamide (70.0 mg, 15.1%) as a white solid.

¹H NMR (400.13 MHz, DMSO-d$_6$) δ 1.36-1.47 (2H, m), 1.80-2.01 (4H, m), 2.17 (2H, s), 3.39 (2H, q), 3.52-3.59 (2H, m), 4.34-4.40 (2H, m), 4.58 (1H, t), 4.94 (1H, s), 6.57 (1H, d), 7.15 (1H, d), 7.50 (2H, d), 7.76-7.79 (2H, d), 8.12 (1H, s), 8.52 (1H, s), 11.61 (1H, s).

MS m/e MH⁺ 420.

EXAMPLE 19: (S)-4-AMINO-1-(5-BROMO-7H-PYRROLO[2,3-D]PYRIMIDIN-4-YL)-N-(1-(4-CHLOROPHENYL)-3-HYDROXYPROPYL)PIPERIDINE-4-CARBOXAMIDE

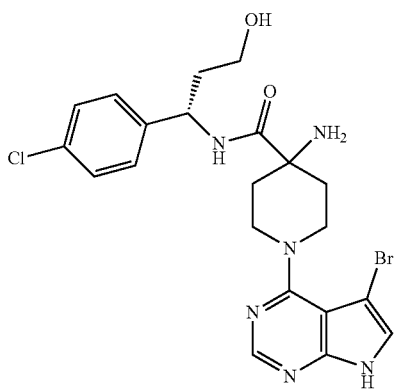 [SMILES: NC1(C(=O)N[C@@H](CCO)c2ccc(Cl)cc2)CCN(c2ncnc3[nH]cc(Br)c23)CC1]

DIPEA (0.670 mL, 3.85 mmol) was added to (S)-4-amino-N-(1-(4-chlorophenyl)-3-hydroxypropyl)piperidine-4-carboxamide (Intermediate 49) (400 mg, 1.28 mmol) and 5-bromo-4-chloro-7H-pyrrolo[2,3-d]pyrimidine (Intermediate 50) (298 mg, 1.28 mmol) in butan-1-ol (6 mL). The resulting solution was stirred at 60° C. for 18 hours. The reaction mixture was diluted with EtOAc (50 mL), and washed sequentially with water (25 mL) and saturated brine (25 mL). The organic layer was dried over MgSO$_4$, filtered and evaporated to afford crude product. The crude product was purified by flash silica chromatography, elution gradient 0 to 6% MeOH with ammonia in DCM. The product was then purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness and triturated with diethyl ether to afford (S)-4-amino-1-(5-bromo-7H-pyrrolo[2,3-d]pyrimidin-4-yl)-N-(1-(4-chlorophenyl)-3-hydroxypropyl)piperidine-4-carboxamide (70 mg, 10.8%) as a white solid.

¹H NMR (400.13 MHz, DMSO-d$_6$) δ 1.41-1.50 (2H, m), 1.81-1.92 (2H, m), 2.04-2.20 (4H, m), 3.37-3.44 (4H, m), 3.91 (2H, t), 4.54 (1H, t), 4.90 (1H, m), 7.33-7.38 (4H, m), 7.50 (1H, s), 8.25 (1H, s), 8.47 (1H, d), 12.18 (1H, s).

MS m/e MH⁺ 510.

EXAMPLE 20: (S)-4-AMINO-N-(1-(4-CHLOROPHENYL)-3-HYDROXYPROPYL)-1-(1H-PYRAZOLO[3,4-D]PYRIMIDIN-4-YL)PIPERIDINE-4-CARBOXAMIDE

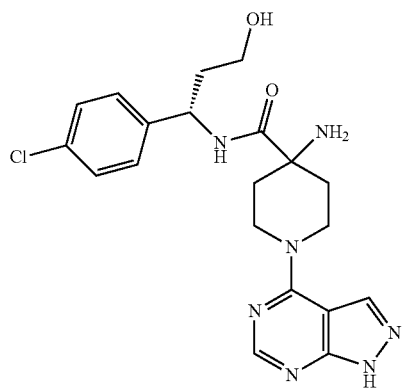 [SMILES: NC1(C(=O)N[C@@H](CCO)c2ccc(Cl)cc2)CCN(c2ncnc3[nH]ncc23)CC1]

DIPEA (0.419 mL, 2.41 mmol) was added to (S)-4-amino-N-(1-(4-chlorophenyl)-3-hydroxypropyl)piperidine-4-carboxamide (Intermediate 49) (250 mg, 0.80 mmol) and 4-chloro-1H-pyrazolo[3,4-d]pyrimidine (124 mg, 0.80 mmol) in butan-1-ol (5 mL). The resulting solution was stirred at 60° C. for 6 hours. The reaction mixture was diluted with EtOAc (50 mL), and washed sequentially with water (25 mL) and saturated brine (25 mL). The organic layer was dried over MgSO$_4$, filtered and evaporated to afford crude product. The crude product was purified by flash silica chromatography, elution gradient 0 to 6% MeOH with ammonia in DCM. Pure fractions were evaporated to dryness and triturated with diethyl ether to afford (S)-4-amino-N-(1-(4-chlorophenyl)-3-hydroxypropyl)-1-(1H-pyrazolo[3,4-d]pyrimidin-4-yl)piperidine-4-carboxamide (112 mg, 32.5%) as a white solid.

1H NMR (399.9 MHz, DMSO-d$_6$) δ 1.49 (2H, t), 1.79-2.01 (4H, m), 3.39 (2H, m), 3.62 (2H, s), 4.40 (2H, s), 4.57 (1H, t), 4.88 (1H, m), 7.32-7.38 (4H, m), 8.22 (1H, d), 8.29 (1H, s), 8.45 (1H, d), 13.52 (1H, s).

MS m/e MH⁺ 430.

EXAMPLE 21: (S)-4-AMINO-N-(3-HYDROXY-1-PHENYLPROPYL)-1-(7H-PYRROLO[2,3-D]PYRIMIDIN-4-YL)PIPERIDINE-4-CARBOXAMIDE

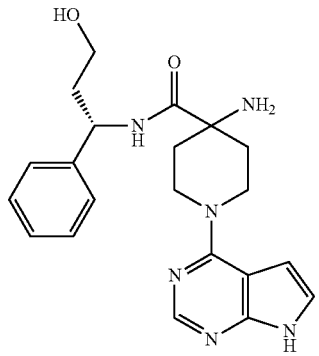 [SMILES: NC1(C(=O)N[C@@H](CCO)c2ccccc2)CCN(c2ncnc3[nH]ccc23)CC1]

(S)-3-Amino-3-phenylpropan-1-ol hydrochloride (260 mg, 1.38 mmol) was added in one portion to 4-(tert-butoxycarbonylamino)-1-(7H-pyrrolo[2,3-d]pyrimidin-4-yl)piperidine-4-carboxylic acid (Intermediate 21) (500 mg, 1.38 mmol) and DIPEA (0.967 mL, 5.53 mmol) in DMA (5 mL). O-(7-azabenzotriazol-1-yl)-N,N,N',N'-tetramethyluronium hexafluorophosphate (579 mg, 1.52 mmol) was added and the resulting solution was stirred at 20° C. for 24 hours. The reaction mixture was evaporated to dryness then diluted with EtOAc (300 mL), and washed sequentially with water (50 mL) and saturated brine (50 mL). The organic layer was dried over MgSO$_4$, filtered and evaporated to afford crude product. The crude product was purified by flash silica chromatography, elution gradient 2 to 6% MeOH with ammonia in DCM. Fractions were evaporated to afford (S)-tert-butyl 4-(3-hydroxy-1-phenylpropylcarbamoyl)-1-(7H-pyrrolo[2,3-d]pyrimidin-4-yl)piperidin-4-ylcarbamate (334 mg, 48.8%) as a white solid. The product (334 mg, 0.67 mmol) was suspended in dioxane (5.00 mL) and 4M hydrogen chloride in dioxane (0.961 mL, 27.67 mmol) added. The reaction was stirred at ambient temperature for 2 hours. The crude product was purified by ion exchange chromatography, using an SCX column. The desired product was eluted from the column using 3.5N ammonia/MeOH and pure fractions were evaporated to dryness. The resulting gum was triturated with EtOAc to give a solid which was collected by filtration and dried under vacuum to give (S)-4-amino-N-(3-hydroxy-1-phenylpropyl)-1-(7H-pyrrolo[2,3-d]pyrimidin-4-yl)piperidine-4-carboxamide (93 mg, 17.0%) as an off white solid.

$^1$H NMR (400.13 MHz, DMSO-d$_6$) δ 1.44 (2H, t), 1.82-2.03 (4H, m), 3.37 (2H, t), 3.50-3.58 (2H, m), 4.40 (2H, t), 4.49 (1H, t), 4.90 (1H, d), 6.58 (1H, s), 7.15 (1H, t), 7.21-7.23 (1H, m), 7.30-7.31 (4H, m), 8.12 (1H, s), 8.41 (1H, d), 11.62 (1H, s).

MS m/e MH$^+$ 395.

EXAMPLE 22: (S)-4-AMINO-N-(1-(4-CHLOROPHENYL)-3-HYDROXYPROPYL)-1-(9H-PURIN-6-YL)PIPERIDINE-4-CARBOXAMIDE

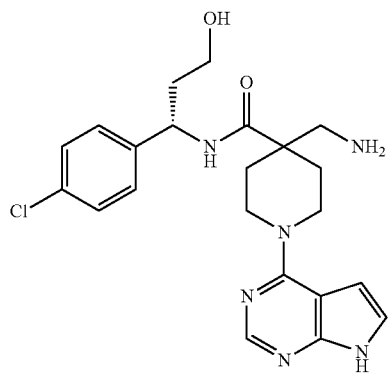

DIPEA (0.335 mL, 1.92 mmol) was added to (S)-4-amino-N-(1-(4-chlorophenyl)-3-hydroxypropyl)piperidine-4-carboxamide (Intermediate 49) (200 mg, 0.64 mmol) and 6-chloro-9H-purine (99 mg, 0.64 mmol) in butan-1-ol (4 mL). The resulting solution was stirred at 60° C. for 18 hours. The reaction mixture was diluted with EtOAc (50 mL), and washed sequentially with water (25 mL) and saturated brine (25 mL). The organic layer was dried over MgSO$_4$, filtered and evaporated to afford crude product. The crude product was purified by flash silica chromatography, elution gradient 0 to 6% MeOH with ammonia in DCM. Pure fractions were evaporated to dryness to afford (S)-4-amino-N-(1-(4-chlorophenyl)-3-hydroxypropyl)-1-(9H-purin-6-yl)piperidine-4-carboxamide (141 mg, 51.1%) as a white solid.

$^1$H NMR (400.13 MHz, DMSO-d$_6$) δ 1.42 (2H, t), 1.78-2.00 (4H, m), 3.34-3.41 (2H, m), 3.61 (2H, s), 4.53 (1H, t), 4.88 (1H, d), 5.02 (2H, s), 7.30-7.39 (4H, m), 8.08 (1H, s), 8.17-8.22 (1H, s), 8.42 (1H, d), 13.02 (1H, s).

MS m/e MH$^+$ 430.

EXAMPLE 23: (S)-4-(AMINOMETHYL)-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

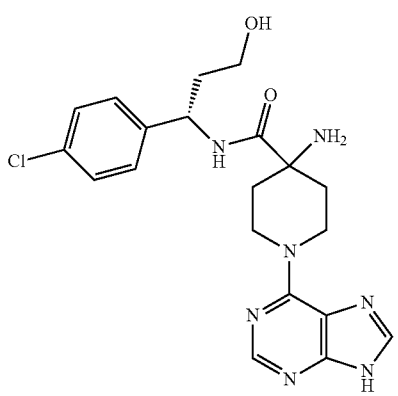 [SMILES: NC1(C(=O)N[C@@H](CCO)c2ccc(Cl)cc2)CCN(c2ncnc3[nH]cnc23)CC1]

(S)-3-Amino-3-(4-chlorophenyl)propan-1-ol (Intermediate 47) (247 mg, 1.33 mmol) was added in one portion to 4-((tert-butoxycarbonylamino)methyl)-1-(7H-pyrrolo[2,3-d]pyrimidin-4-yl)piperidine-4-carboxylic acid (Intermediate 12) (500 mg, 1.33 mmol) and DIPEA (0.698 mL, 4.00 mmol) in DMA (6 mL). O-(7-azabenzotriazol-1-yl)-N,N,N',N'-tetramethyluronium hexafluorophosphate (557 mg, 1.47 mmol) was added and the resulting solution was stirred at 20° C. for 2 hours then 20° C. for 18 hours. The reaction mixture was diluted with EtOAc (50 mL), and washed sequentially with water (20 mL) and saturated brine (20 mL). The organic layer was dried over MgSO$_4$, filtered and evaporated to afford crude product. The crude product was purified by flash silica chromatography, elution gradient 2 to 6% MeOH with ammonia in DCM. Pure fractions were evaporated to dryness to afford (S)-tert-butyl (4-(1-(4-chlorophenyl)-3-hydroxypropylcarbamoyl)-1-(7H-pyrrolo[2,3-d]pyrimidin-4-yl)piperidin-4-yl)methylcarbamate (428 mg, 59.2%) as a colourless gum. The product (428 mg) was dissolved in dioxane (6.00 mL) and 4M hydrogen chloride in dioxane (0.925 mL, 26.64 mmol) added. The reaction was stirred at ambient temperature for 2 hours. The crude product was purified by ion exchange chromatography, using an SCX column. The desired product was eluted from the column using 3.5N ammonia/MeOH and pure fractions were evaporated to dryness. The crude product was purified by preparative HPLC (Waters XBridge Prep C18 OBD column, 5 μm silica, 19 mm diameter, 100 mm length), using decreasingly polar mixtures of water (containing 1% ammonia) and MeCN as eluents. Fractions containing the desired compound were evaporated to dryness to afford (S)-4-(aminomethyl)-N-(1-(4-chlorophenyl)-3-hydroxypropyl)-1-

(7H-pyrrolo[2,3-d]pyrimidin-4-yl)piperidine-4-carboxamide (192 mg, 32.5%) as a white dry film.

¹H NMR (400.13 MHz, DMSO-d6) δ 1.45-1.47 (2H, m), 1.79-1.84 (1H, m), 1.89-1.99 (1H, m), 2.09 (2H, s), 2.67 (2H, s), 3.36-3.42 (4H, m), 4.25 (2H, d), 4.57 (1H, s), 5.01 (1H, d), 6.55 (1H, s), 7.14 (1H, s), 7.33-7.36 (4H, m), 8.11 (1H, s), 8.44 (1H, d), 11.61 (1H, s).

MS m/e MH⁺ 443.

EXAMPLE 24: (S)-4-AMINO-N-(1-(4-BROMOPHENYL)-3-HYDROXYPROPYL)-1-(7H-PYRROLO[2,3-D]PYRIMIDIN-4-YL)PIPERIDINE-4-CARBOXAMIDE

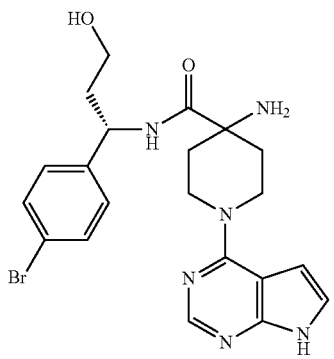

(S)-3-Amino-3-(4-bromophenyl)propan-1-ol (Intermediate 51) (191 mg, 0.83 mmol) was added in one portion to 4-(tert-butoxycarbonylamino)-1-(7H-pyrrolo[2,3-d]pyrimidin-4-yl)piperidine-4-carboxylic acid (Intermediate 1) (300 mg, 0.83 mmol) and DIPEA (0.435 mL, 2.49 mmol) in DMA (5 mL). O-(7-azabenzotriazol-1-yl)-N,N,N',N'-tetramethyluronium hexafluorophosphate (347 mg, 0.91 mmol) was added and the resulting solution was stirred at 20° C. for 24 hours. The reaction mixture was evaporated to dryness then diluted with EtOAc (300 mL), and washed sequentially with water (50 mL) and saturated brine (50 mL). The organic layer was dried over MgSO₄, filtered and evaporated to afford crude product. The crude product was purified by flash silica chromatography, elution gradient 2 to 6% MeOH with ammonia in DCM. Fractions were evaporated to afford (S)-tert-butyl 4-(1-(4-bromophenyl)-3-hydroxypropylcarbamoyl)-1-(7H-pyrrolo[2,3-d]pyrimidin-4-yl)piperidin-4-ylcarbamate (212 mg, 44.5%) as a white solid. The product (212 mg, 0.36 mmol) was suspended in dioxane (5.00 mL) and 4M hydrogen chloride in dioxane (0.577 mL, 16.6 mmol) added. The reaction was stirred at ambient temperature for 2 hours. The crude product was purified by ion exchange chromatography, using an SCX column. The desired product was eluted from the column using 3.5N ammonia/MeOH and pure fractions were evaporated to dryness. The product was then purified by preparative HPLC (Waters XBridge Prep C18 OBD column, 5 nm silica, 19 mm diameter, 100 mm length), using decreasingly polar mixtures of water (containing 1% ammonia) and MeCN as eluents. Fractions containing the desired compound were evaporated to dryness to afford (S)-4-amino-N-(1-(4-bromophenyl)-3-hydroxypropyl)-1-(7H-pyrrolo[2,3-d]pyrimidin-4-yl)piperidine-4-carboxamide (51.0 mg, 13.0%) as a white solid.

¹H NMR (400.13 MHz, DMSO-d₆) δ 1.38-1.46 (2H, m), 1.79-2.01 (4H, m), 2.15 (2H, s), 3.37 (2H, q), 3.51-3.58 (2H, m), 4.37 (2H, t), 4.52 (1H, t), 4.86 (1H, d), 6.57 (1H, d), 7.15 (1H, d), 7.27 (2H, d), 7.48-7.51 (2H, m), 8.12 (1H, s), 8.42 (1H, d), 11.62 (1H, s).

MS m/e MH⁺ 473.

EXAMPLE 25: 4-AMINO-N-(1-(4-CHLOROPHENYL)-4-(DIMETHYLAMINO)BUTYL)-1-(7H-PYRROLO[2,3-D]PYRIMIDIN-4-YL)PIPERIDINE-4-CARBOXAMIDE

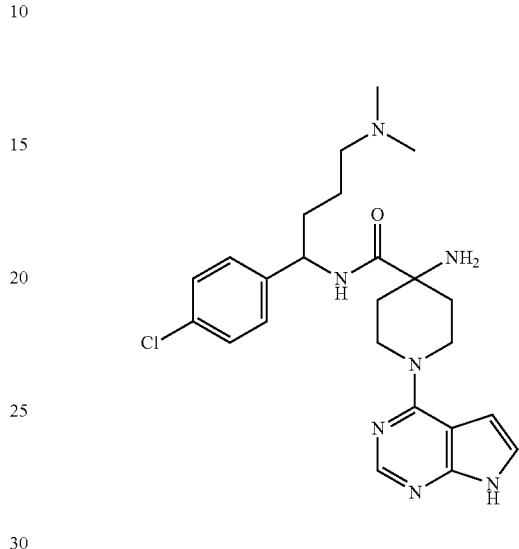

1-(4-Chlorophenyl)-N4,N4-dimethylbutane-1,4-diamine (Intermediate 57) (330 mg, 1.46 mmol) was added in one portion to 4-(tert-butoxycarbonylamino)-1-(7H-pyrrolo[2,3-d]pyrimidin-4-yl)piperidine-4-carboxylic acid (Intermediate 1) (526 mg, 1.46 mmol) and DIPEA (0.763 mL, 4.37 mmol) in DMA (5 mL). O-(7-azabenzotriazol-1-yl)-N,N,N',N'-tetramethyluronium hexafluorophosphate (609 mg, 1.60 mmol) was added and the resulting solution was stirred at 50° C. for 2 hours. The reaction mixture was diluted with EtOAc (25 mL), and washed sequentially with water (20 mL) and saturated brine (20 mL). The organic layer was dried over MgSO₄, filtered and evaporated to afford crude product. The crude product was purified by flash silica chromatography, elution gradient 5 to 10% MeOH with ammonia in isohexane. Pure fractions were evaporated to dryness to afford tert-butyl 4-(1-(4-chlorophenyl)-4-(dimethylamino)butylcarbamoyl)-1-(7H-pyrrolo[2,3-d]pyrimidin-4-yl)piperidin-4-ylcarbamate (423 mg, 51.0%) as a colourless gum. tert-Butyl 4-(1-(4-chlorophenyl)-4-(dimethylamino)butylcarbamoyl)-1-(7H-pyrrolo[2,3-d]pyrimidin-4-yl)piperidin-4-ylcarbamate (423 mg, 0.74 mmol) was dissolved in DCM (5.00 mL) and TFA (1 mL) added. The reaction was stirred at ambient temperature for 2 hours. The crude product was purified by ion exchange chromatography, using an SCX column. The desired product was eluted from the column using 3.5N ammonia/MeOH and pure fractions were evaporated to dryness to afford crude product which was triturated with diethyl ether to afford 4-amino-N-(1-(4-chlorophenyl)-4-(dimethylamino)butyl)-1-(7H-pyrrolo[2,3-d]pyrimidin-4-yl)piperidine-4-carboxamide (245 mg, 35.8%) as a white solid.

¹H NMR (400.13 MHz, DMSO-d6) δ 1.26-1.33 (2H, m), 1.38-1.47 (2H, m), 1.65-1.75 (2H, m), 1.87-2.01 (2H, m), 2.08 (6H, s), 2.18 (2H, t), 3.50-3.58 (2H, m), 4.35-4.41 (2H, m), 4.73 (1H, m), 6.57 (1H, d), 7.14-7.16 (1H, m), 7.32-7.37 (4H, m), 8.12 (1H, s), 8.31 (1H, d), 11.62 (1H, s).

MS m/e MH⁺ 470.

EXAMPLE 26: (S)-4-AMINO-N-(1-(4-CHLOROPHENYL)-3-(DIETHYLAMINO)PROPYL)-1-(7H-PYRROLO[2,3-D]PYRIMIDIN-4-YL)PIPERIDINE-4-CARBOXAMIDE

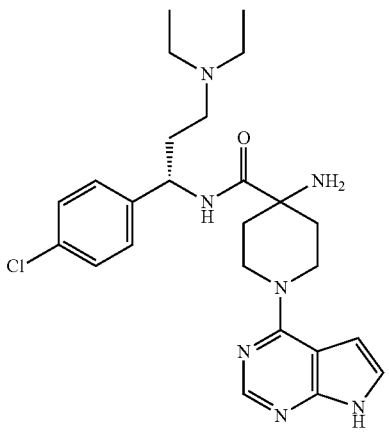 [SMILES: CCN(CC)CC[C@H](NC(=O)C1(N)CCN(c2ncnc3[nH]ccc23)CC1)c1ccc(Cl)cc1]

(S)-1-(4-Chlorophenyl)-N3,N3-diethylpropane-1,3-diamine (Intermediate 60) (119 mg, 0.49 mmol) was added in one portion to 4-(tert-butoxycarbonylamino)-1-(7H-pyrrolo[2,3-d]pyrimidin-4-yl)piperidine-4-carboxylic acid (Intermediate 1) (179 mg, 0.49 mmol) and DIPEA (0.259 mL, 1.48 mmol) in DMA (5 mL). O-(7-azabenzotriazol-1-yl)-N,N,N',N'-tetramethyluronium hexafluorophosphate (207 mg, 0.54 mmol) was added and the resulting solution was stirred at 50° C. for 2 hours. The reaction mixture was diluted with EtOAc (25 mL), and washed sequentially with water (20 mL) and saturated brine (20 mL). The organic layer was dried over MgSO$_4$, filtered and evaporated to afford crude product. The crude product was purified by flash silica chromatography, elution gradient 5 to 10% MeOH with ammonia in DCM. Pure fractions were evaporated to dryness to afford (S)-tert-butyl 4-(1-(4-chlorophenyl)-3-(diethylamino)propylcarbamoyl)-1-(7H-pyrrolo[2,3-d]pyrimidin-4-yl)piperidin-4-ylcarbamate (189 mg, 65.5%) as a colourless gum. (S)-tert-butyl 4-(1-(4-chlorophenyl)-3-(diethylamino)propylcarbamoyl)-1-(7H-pyrrolo[2,3-d]pyrimidin-4-yl)piperidin-4-ylcarbamate (189 mg, 0.33 mmol) was dissolved in DCM (5.00 mL) and TFA (1 mL) added. The reaction was stirred at ambient temperature for 2 hours. The crude product was purified by ion exchange chromatography, using an SCX column. The desired product was eluted from the column using 7N ammonia/MeOH and pure fractions were evaporated to dryness to afford crude product which was triturated with diethyl ether to afford (S)-4-amino-N-(1-(4-chlorophenyl)-3-(diethylamino)propyl)-1-(7H-pyrrolo[2,3-d]pyrimidin-4-yl)piperidine-4-carboxamide (70.0 mg, 29.3%) as a white foam.

$^1$H NMR (400.13 MHz, DMSO-d6) δ 0.94 (6H, d), 1.42-1.49 (2H, m), 1.86-2.01 (4H, m), 2.43 (2H, m), 3.51-3.59 (2H, m), 4.37-4.43 (2H, m), 4.84 (1H, t), 6.58 (1H, d), 7.15-7.16 (1H, d), 7.32-7.38 (4H, m), 8.12 (1H, s), 8.59 (1H, s), 11.63 (1H, s).

MS m/e MH$^+$ 484.

EXAMPLE 27: (S)-4-AMINO-N-(1-(4-CHLOROPHENYL)-3-HYDROXYPROPYL)-1-(5-CYCLOPROPYL-7H-PYRROLO[2,3-D]PYRIMIDIN-4-YL)PIPERIDINE-4-CARBOXAMIDE

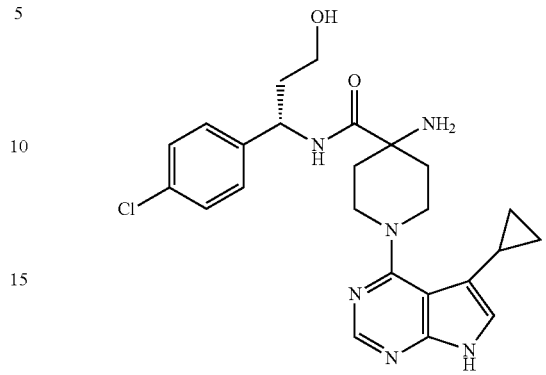

Hydrogen chloride 4M in dioxane (0.923 mL, 3.69 mmol) was added to (S)-tert-butyl 4-(1-(4-chlorophenyl)-3-hydroxypropylcarbamoyl)-1-(5-cyclopropyl-7H-pyrrolo[2,3-d]pyrimidin-4-yl)piperidin-4-ylcarbamate (Intermediate 65) (420 mg, 0.74 mmol) in dioxane (25 mL). The resulting solution was stirred at ambient temperature for 2 hours. The reaction mixture was dissolved in methanol and purified by ion exchange chromatography, using an SCX column. The desired product was eluted from the column using 3.5N ammonia/MeOH and pure fractions were evaporated to dryness. The product was then purified by preparative LCMS (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to afford (S)-4-amino-N-(1-(4-chlorophenyl)-3-hydroxypropyl)-1-(5-cyclopropyl-7H-pyrrolo[2,3-d]pyrimidin-4-yl)piperidine-4-carboxamide (25.0 mg, 7.2%) as a white solid.

$^1$H NMR (400.13 MHz, DMSO-d$_6$) δ 0.66-0.70 (2H, m), 0.86-0.91 (2H, m), 1.41-1.50 (2H, m), 1.81-2.13 (5H, m), 3.35-3.43 (4H, m), 3.99-4.07 (2H, m), 4.54 (1H, t), 4.90 (1H, d), 6.90 (1H, s), 7.32-7.38 (4H, m), 8.18 (1H, s), 8.47 (1H, d), 11.46 (1H, s).

MS m/e MH$^+$ 470.

EXAMPLE 28: 4-AMINO-N-(1-(4-CHLOROPHENYL)-3-(METHYLAMINO)PROPYL)-1-(7H-PYRROLO[2,3-D]PYRIMIDIN-4-YL)PIPERIDINE-4-CARBOXAMIDE

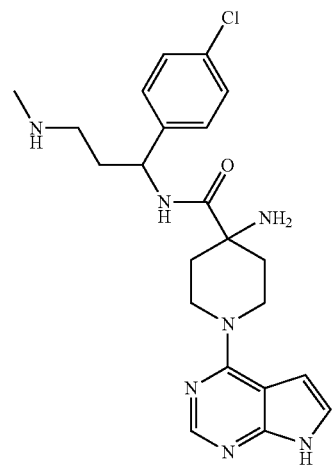 [SMILES: CNCCC(NC(=O)C1(N)CCN(c2ncnc3[nH]ccc23)CC1)c1ccc(Cl)cc1]

Hydrogen chloride (4M in dioxane, 0.461 mL, 1.84 mmol) was added to tert-butyl 4-(1-(4-chlorophenyl)-3-(methylamino)propylcarbamoyl)-1-(7H-pyrrolo[2,3-d]pyrimidin-4-yl)piperidin-4-ylcarbamate (Intermediate 68) (10 mg, 0.02 mmol) in a mixture of DCM (3 mL) and methanol (1 mL) at 22° C. The resulting solution was stirred at 22° C. for 2 hours. The mixture was evaporated and the residue was purified by ion exchange chromatography, using an SCX column. The desired product was eluted from the column using 30% (2M NH$_3$ in MeOH) in DCM and pure fractions were evaporated to dryness to afford 4-amino-N-(1-(4-chlorophenyl)-3-(methylamino)propyl)-1-(7H-pyrrolo[2,3-d]pyrimidin-4-yl)piperidine-4-carboxamide (7 mg, 86%) as a colourless gum.

$^1$H NMR (399.902 MHz, DMSO) δ 1.44 (2H, m), 1.83 (2H, dt), 1.87-2.01 (2H, m), 2.15 (2H, m), 2.25 (2H, br.s), 2.42 (2H, m), 3.56 (2H, m), 4.38 (2H, m), 4.84 (1H, br.s), 6.58 (1H, d), 7.16 (1H, d), 7.32-7.38 (4H, m), 8.13 (1H, s), 8.57 (1H, s), 11.63 (1H, s).

MS m/e MH$^+$ 442.4.

The compounds of the invention listed in Table A below were made from the appropriate starting materials using a process analogous to that described in Example 2.

TABLE A

| Compound No. | Name | Structure | NMR/MS |
|---|---|---|---|
| 29 | 4-amino-N-[(4-chlorophenyl)phenyl)methyl]-1-(7H-pyrrolo[2,3-d]pyrimidin-4-yl)piperidine-4-carboxamide | 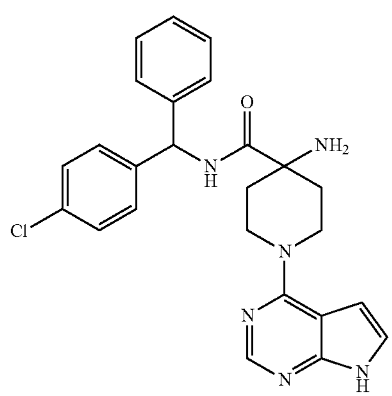 [SMILES: NC1(C(=O)NC(c2ccccc2)c2ccc(Cl)cc2)CCN(c2ncnc3[nH]ccc23)CC1] | 1H NMR (399.902 MHz, DMSO) δ 11.65 (1H, s), 8.76 (1H, s), 8.13 (1H, s), 7.42-7.25 (9H, m), 7.17-7.15 (1H, m), 6.60-6.58 (1H, m), 6.07 (1H, s), 4.45-4.39 (2H, m), 3.59-3.51 (2H, m), 2.34-2.27 (2H, m), 2.02-1.93 (2H, m), 1.52-1.46 (2H, m) m/z (ESI+) (M + H)+ = 461; HPLC t$_R$ = 2.21 min. |
| 30 | 4-amino-N-[2-amino-1-(4-chlorophenyl)-2-oxoethyl]-1-(7H-pyrrolo[2,3-d]pyrimidin-4-yl)piperidine-4-carboxamide | 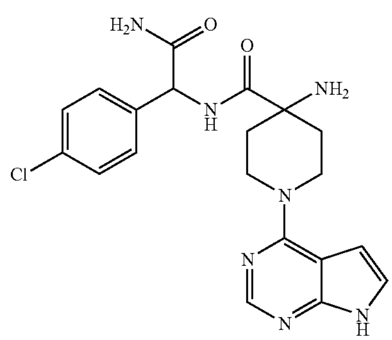 [SMILES: NC(=O)C(NC(=O)C1(N)CCN(c2ncnc3[nH]ccc23)CC1)c1ccc(Cl)cc1] | 1H NMR (399.902 MHz, DMSO) δ 11.65 (1H, s), 8.92 (1H, s), 8.13 (1H, s), 7.80 (1H, s), 7.45-7.39 (4H, m), 7.29 (1H, s), 7.17-7.15 (1H, m), 6.58-6.57 (1H, m), 5.30 (1H, s), 4.48-4.38 (2H, m), 3.55-3.46 (2H, m), 2.43 (2H, s), 2.03-1.94 (1H, m), 1.90-1.82 (1H, m), 1.49-1.39 (2H, m) m/z (ESI+) (M + H)+ = 428; HPLC t$_R$ = 1.45 min. |

The compounds of the invention listed in Table B below were made from the appropriate starting materials using a process analogous to that described in Example 9 alternative route 1.

TABLE B

| No. | Compound Name | Structure | NMR/MS |
|---|---|---|---|
| 31 | 4-amino-1-(3-bromo-1H-pyrazolo[3,4-d]pyrimidin-4-yl)-N-[(1S)-1-(4-chlorophenyl)ethyl]piperidine-4-carboxamide | 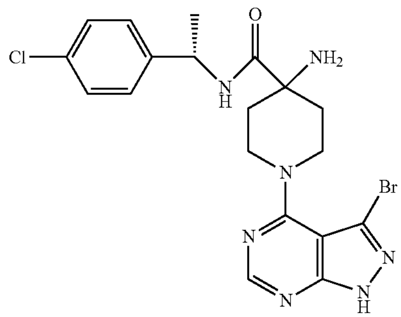 [SMILES: C[C@H](NC(=O)C1(N)CCN(c2ncnc3[nH]nc(Br)c23)CC1)c1ccc(Cl)cc1] | MS: m/z (ESI+) (M + H)+ = 480; HPLC tR = 1.34 min. |
| 32 | 4-amino-N-[(1S)-1-(4-chlorophenyl)ethyl]-1-(5-chloro-7H-pyrrolo[2,3-d]pyrimidin-4-yl)piperidine-4-carboxamide | 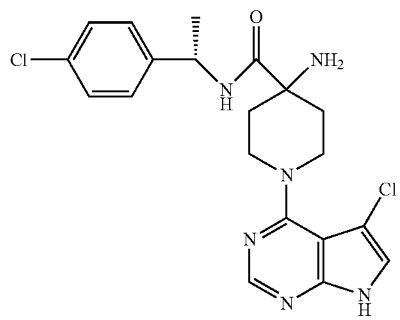 [SMILES: C[C@H](NC(=O)C1(N)CCN(c2ncnc3[nH]cc(Cl)c23)CC1)c1ccc(Cl)cc1] | $^1$H NMR (400 MHz, DMSO) δ 1.39 (3H, d), 1.42-1.51 (2H, m), 1.98-2.18 (4H, m), 3.36-3.48 (2H, m), 3.90-4.03 (2H, m), 4.82-4.96 (1H, m), 7.31-7.41 (4H, m), 7.45 (1H, s), 8.23 (1H, s), 8.34 (1H, d), 11.98-12.18 (1H, m). MS: m/z (ESI+) (M + H)+ = 433; HPLC tR = 1.96 min. |
| 33 | 4-amino-1-(3-bromo-1H-pyrazolo[3,4-d]pyrimidin-4-yl)-N-[(1S)-1-(4-chlorophenyl)-3-hydroxypropyl]piperidine-4-carboxamide | 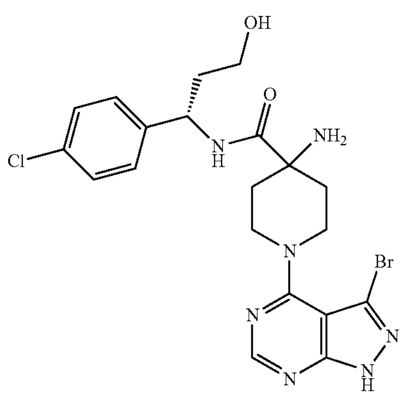 [SMILES: NC1(C(=O)N[C@@H](CCO)c2ccc(Cl)cc2)CCN(c2ncnc3[nH]nc(Br)c23)CC1] | 1H NMR (400.13 MHz, DMSO-d6) δ 1.45-1.53 (2H, m), 1.81-1.94 (2H, m), 1.98-2.14 (2H, m), 3.38 (2H, m), 3.55-3.62 (2H, m), 4.17-4.23 (2H, m), 4.54 (1H, t), 4.90 (1H, d), 7.32-7.38 (4H, m), 8.29 (1H, s), 8.46 (1H, d) MS m/e MH+ 510 |
| 34 | 4-amino-N-[(1S)-1-(4-chlorophenyl)-3-hydroxypropyl]-1-(5-chloro-7H-pyrrolo[2,3-d]pyrimidin-4-yl)piperidine-4-carboxamide | 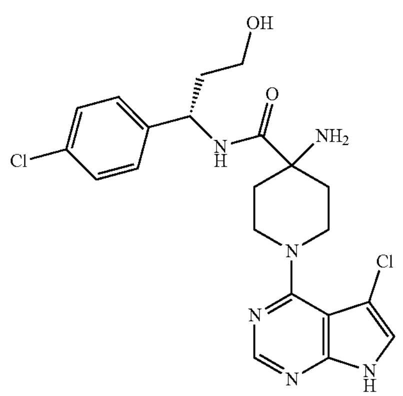 [SMILES: NC1(C(=O)N[C@@H](CCO)c2ccc(Cl)cc2)CCN(c2ncnc3[nH]cc(Cl)c23)CC1] | 1H NMR (399.9 MHz, DMSO-d6) δ 1.42-1.50 (2H, m), 1.82-1.92 (2H, m), 2.01-2.15 (2H, m), 3.39-3.46 (4H, m), 3.93-3.99 (2H, m), 4.59 (1H, t), 4.90 (1H, m), 7.33-7.39 (4H, m), 7.47 (1H, s), 8.25 (1H, s), 8.52 (1H, d), 12.14 (1H, s) MS m/e MH+ 463 |

TABLE B-continued

| No. | Compound Name | Structure | NMR/MS |
|---|---|---|---|
| 35 | 4-amino-1-(5-bromo-7H-pyrrolo[2,3-d]pyrimidin-4-yl)-N-[(1S)-1-(4-chlorophenyl)ethyl]piperidine-4-carboxamide | 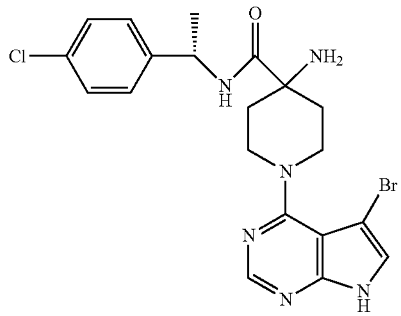 [SMILES: C[C@H](NC(=O)C1(N)CCN(c2ncnc3[nH]cc(Br)c23)CC1)c1ccc(Cl)cc1] | ¹H NMR (400 MHz, DMSO) δ 1.38 (3H, d), 1.42-1.52 (2H, m), 2.02-2.23 (4H, m), 3.40-3.45 (2H, m), 3.85-3.99 (2H, m), 4.80-4.97 (1H, m), 7.33-7.40 (4H, m), 7.51 (1H, s), 8.26 (1H, s), 8.33 (1H, d), 12.11-12.28 (1H, m). MS: m/z (ESI+) (M + H)+ = 479; HPLC tR = 2.08 min. |
| 36 | 4-amino-N-[(1S)-1-(4-chlorophenyl)-3-hydroxypropyl]-1-(5-methyl-7H-pyrrolo[2,3-d]pyrimidin-4-yl)piperidine-4-carboxamide | 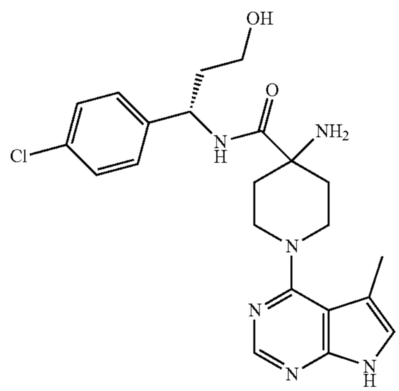 [SMILES: Cc1c[nH]c2ncnc(N3CCC(N)(C(=O)N[C@@H](CCO)c4ccc(Cl)cc4)CC3)c12] | 1H NMR (399.9 MHz, DMSO-d6) δ 1.41-1.49 (2H, m), 1.79-2.13 (6H, m), 2.34 (3H, s), 3.38-3.42 (2H, m), 3.73 (2H, t), 4.59 (1H, t), 4.90-4.93 (1H, m), 7.05 (1H, s), 7.31-7.41 (4H, m), 8.19 (1H, s), 8.50 (1H, d), 11.50 (1H, s) MS m/e MH+ 443 |
| 37 | 4-amino-N-[(1S)-1-(4-chlorophenyl)ethyl]-1-(5-methyl-7H-pyrrolo[2,3-d]pyrimidin-4-yl)piperidine-4-carboxamide | 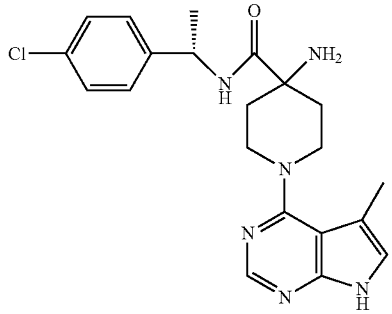 [SMILES: Cc1c[nH]c2ncnc(N3CCC(N)(C(=O)N[C@@H](C)c4ccc(Cl)cc4)CC3)c12] | ¹H NMR (400 MHz, DMSO) δ 1.39 (3H, d), 1.41-1.54 (2H, m), 1.96-2.17 (4H, m), 2.34 (3H, s), 3.31-3.43 (2H, m), 3.65-3.84 (2H, m), 4.81-4.97 (1H, m), 7.03 (1H, s), 7.30-7.44 (4H, m), 8.18 (1H, s), 8.34 (1H, d), 11.45 (1H, s). MS: m/z (ESI+) (M + H)+ = 413; HPLC tR = 1.41 min. |

The compounds of the invention listed in Table C below were made from the appropriate starting materials using a process analogous to that described in Example 9 alternative route 2.

TABLE C

| No. | Compound Name | Structure | NMR/MS |
|---|---|---|---|
| 38* | 4-amino-N-[(1S)-1-(4-chlorophenyl)-3-hydroxy-3-methylbutyl]-1-(7H-pyrrolo[2,3-d]pyrimidin-4-yl)piperidine-4-carboxamide | 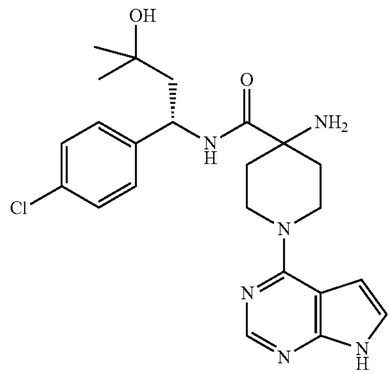 [SMILES: CC(C)(O)C[C@H](NC(=O)C1(N)CCN(c2ncnc3[nH]ccc23)CC1)c1ccc(Cl)cc1] | 1H NMR (399.902 MHz, DMSO-d6) δ 1.10 (s, 3H), 1.12 (s, 3H), 1.54-1.63 (m, 2H), 1.66-1.71 (m, 1H), 1.92-1.99 (m, 1H), 2.05-2.16 (m, 2H), 3.49-3.60 (m, 2H), 4.41-4.49 (m, 2H), 4.96 (dd, 1H), 6.61 (d, 1H), 7.18 (d, 1H), 7.29-7.35 (m, 4H), 8.15 (s, 1H), 8.62 (d, 1H), 11.64 (s, 1H) m/z (ES+) (M + H)+ = 457.22 |
| 39 | 4-amino-N-[(1S)-1-(4-cyanophenyl)ethyl]-1-(7H-pyrrolo[2,3-d]pyrimidin-4-yl)piperidine-4-carboxamide | 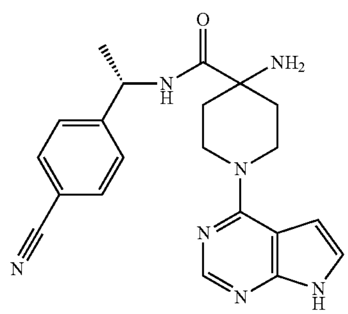 [SMILES: C[C@H](NC(=O)C1(N)CCN(c2ncnc3[nH]ccc23)CC1)c1ccc(C#N)cc1] | 1H NMR (400.13 MHz, DMSO-d6) δ 1.40 (3H, d), 1.51 (2H, d), 1.93-2.08 (2H, m), 3.52-3.58 (2H, m), 4.39-4.45 (2H, m), 4.94 (1H, t), 6.59 (1H, d), 7.16-7.17 (1H, d), 7.51 (2H, d), 7.78 (2H, d), 8.13 (1H, s), 8.47 (1H, d), 11.64 (1H, s) MS m/e MH+ 390 |
| 40 | 4-amino-N-[(1S)-1-(3-chlorophenyl)-3-hydroxypropyl]-1-(7H-pyrrolo[2,3-d]pyrimidin-4-yl)piperidine-4-carboxamide | 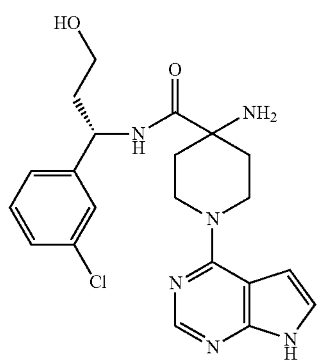 [SMILES: NC1(C(=O)N[C@@H](CCO)c2cccc(Cl)c2)CCN(c2ncnc3[nH]ccc23)CC1] | 1H NMR (400.13 MHz, DMSO-d6) δ 1.44 (2H, t), 1.81-2.03 (4H, m), 3.35-3.40 (2H, m), 3.50-3.58 (2H, m), 4.35-4.42 (2H, m), 4.54 (1H, t), 4.89 (1H, d), 6.58 (1H, m), 7.14-7.16 (1H, m), 7.26-7.28 (2H, m), 8.12 (1H, s), 8.46 (1H, d), 11.62 (1H, s) MS m/e MH+ 429 |
| 41 | 4-amino-1-(7H-pyrrolo[2,3-d]pyrimidin-4-yl)-N-{(1S)-1-[4-(trifluoromethyl)phenyl]ethyl} piperidine-4-carboxamide | 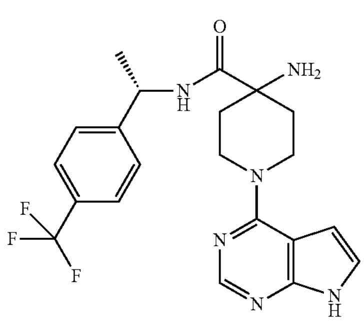 [SMILES: C[C@H](NC(=O)C1(N)CCN(c2ncnc3[nH]ccc23)CC1)c1ccc(C(F)(F)F)cc1] | 1H NMR (400.13 MHz, DMSO-d6) δ 1.41 (3H, d), 1.50 (2H, d), 1.93-2.06 (2H, m), 3.52-3.58 (2H, m), 4.39-4.44 (2H, m), 4.95 (1H, t), 6.59 (1H, d), 7.15-7.17 (1H, d), 7.54 (2H, d), 7.67 (2H, d), 8.13 (1H, s), 8.46 (1H, d), 11.64 (1H, s) MS m/e MH+ 433 |

*Made by the same HATU coupling methodology as that described in Example 9 alternative route 2 and deprotected with TFA using the same methodology as described for Example 8.

The compounds of the invention listed in Table D below were made from the appropriate starting materials using a process analogous to that described in Example 16.

TABLE D

| No. | Compound Name | Structure | NMR/MS |
|---|---|---|---|
| 42 | 4-amino-N-[(1R)-1-(4-bromophenyl)ethyl]-1-(7H-pyrrolo[2,3-d]pyrimidin-4-yl)piperidine-4-carboxamide | 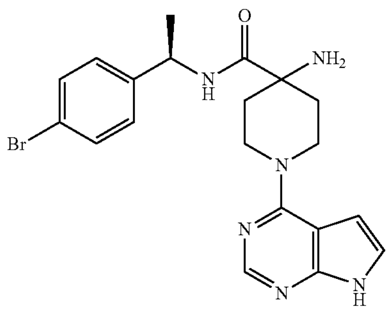 | 1H NMR (400.13 MHz, DMSO-d6) δ 1.37 (3H, d), 1.39-1.47 (2H, m), 1.85-2.02 (2H, m), 2.18 (2H, s), 3.50-3.58 (2H, m), 4.33-4.43 (2H, m), 4.80-4.88 (1H, s), 6.57-6.59 (1H, m), 7.14-7.16 (1H, m), 7.27-7.29 (2H, m), 7.48-7.51 (2H, m), 8.12 (1H, s), 8.30 (1H, d), 11.62 (1H, s)<br>MH+ = 443<br>RT = 1.69 min |
| 43 | 4-amino-N-[1-(4-chlorophenyl)-2-phenylethyl]-1-(7H-pyrrolo[2,3-d]pyrimidin-4-yl)piperidine-4-carboxamide | 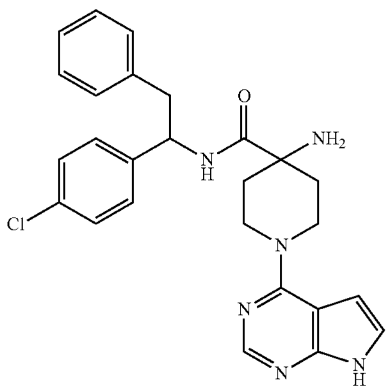 [SMILES: NC1(C(=O)NC(Cc2ccccc2)c2ccc(Cl)cc2)CCN(c2ncnc3[nH]ccc23)CC1] | 1H NMR (400 MHz, DMSO) δ 1.21-1.42 (2H, m), 1.72-1.94 (2H, m), 2.98-3.10 (2H, m), 3.44-3.62 (2H, m), 4.13-4.23 (1H, m), 4.24-4.35 (1H, m), 4.98-5.12 (1H, m), 6.54 (1H, d), 7.12-7.29 (6H, m), 7.32-7.44 (4H, m), 8.12 (1H, s), 8.44 (1H, d), 11.63 (1H, s)<br>MH+ = 475<br>RT = 2.31 min |
| 44 | 4-amino-N-[1-(4-fluorophenyl)ethyl]-1-(7H-pyrrolo[2,3-d]pyrimidin-4-yl)piperidine-4-carboxamide | 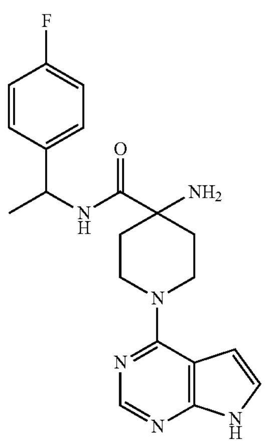 [SMILES: CC(NC(=O)C1(N)CCN(c2ncnc3[nH]ccc23)CC1)c1ccc(F)cc1] | 1H NMR (400.13 MHz, DMSO-d6) δ 1.38 (3H, d), 1.40-1.46 (2H, m), 1.87-1.91 (1H, m), 1.96-2.01 (1H, m), 2.16 (2H, s), 3.50-3.58 (2H, m), 4.35-4.43 (2H, m), 4.84-4.92 (1H, m), 6.57-6.58 (1H, m), 7.10-7.15 (3H, m), 7.34-7.37 (2H, m), 8.12 (1H, s), 8.28 (1H, d), 11.62 (1H, s)<br>MH+ = 383<br>RT = 1.47 min, |
| 45 | 4-amino-N-[(4-chlorophenyl)(cyano)methyl]-1-(7H-pyrrolo[2,3-d]pyrimidin-4-yl)piperidine-4-carboxamide | 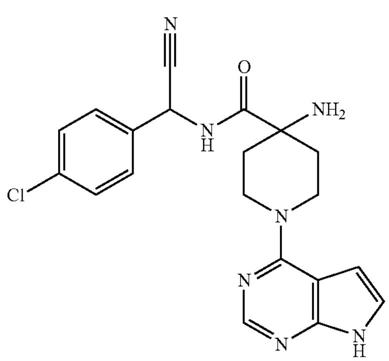 [SMILES: N#CC(NC(=O)C1(N)CCN(c2ncnc3[nH]ccc23)CC1)c1ccc(Cl)cc1] | 1H NMR (400 MHz, DMSO) δ 1.42-1.58 (3H, m), 1.84-2.04 (2H, m), 3.49-3.64 (2H, m), 4.30-4.44 (2H, m), 6.16 (1H, s), 6.57-6.63 (1H, m), 7.13-7.19 (1H, m), 7.46-7.55 (4H, m), 8.13 (1H, s), 11.64 (1H, s)<br>MH+ = 410<br>RT = 1.79 min |

TABLE D-continued

| No. | Compound Name | Structure | NMR/MS |
|---|---|---|---|
| 46 | 4-amino-N-(1-phenylethyl)-1-(7H-pyrrolo[2,3-d]pyrimidin-4-yl)piperidine-4-carboxamide | 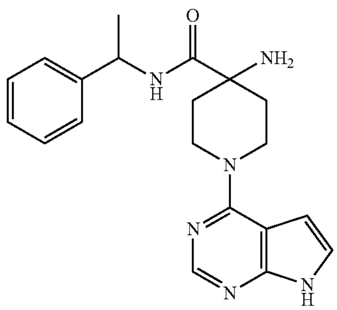 [SMILES: CC(NC(=O)C1(N)CCN(c2ncnc3[nH]ccc23)CC1)c1ccccc1] | 1H NMR (400.13 MHz, DMSO-d6) δ 1.38 (3H, d), 1.89-2.03 (2H, m), 2.17 (2H, s), 3.50-3.57 (2H, m), 4.37-4.43 (2H, m), 4.84-4.92 (1H, m), 6.57-6.58 (1H, m), 7.15 (1H, dd), 7.19-7.26 (1H, m), 7.31-7.32 (4H, m), 8.12 (1H, s), 8.28 (1H, d), 11.62 (1H, s) MH+ = 365 RT = 1.40 min, |

The compounds of the invention listed in Table E below were made from the appropriate starting materials using a process analogous to that described in Example 25.

TABLE E

| No. | Compound Name | Structure | NMR/MS |
|---|---|---|---|
| 47 | 4-amino-N-[1-(4-chlorophenyl)-4-pyrrolidin-1-ylbutyl]-1-(7H-pyrrolo[2,3-d]pyrimidin-4-yl)piperidine-4-carboxamide | 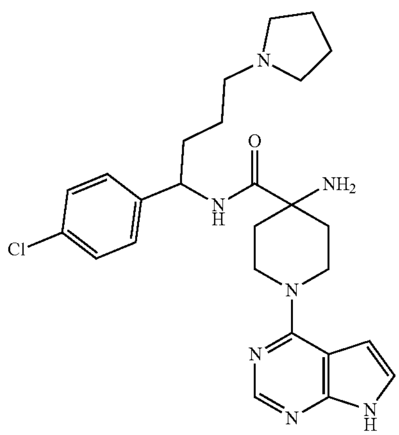 [SMILES: NC1(C(=O)NC(CCCN2CCCC2)c2ccc(Cl)cc2)CCN(c2ncnc3[nH]ccc23)CC1] | 1H NMR (400.13 MHz, DMSO-d6) δ 1.31-1.49 (4H, m), 1.65 (4H, s), 1.69-1.77 (2H, m), 1.88-1.98 (2H, m), 2.15 (2H, s), 2.34 (4H, s), 2.36 (2H, s), 3.53-3.58 (2H, m), 4.34-4.41 (2H, m), 4.73 (1H, m), 6.57 (1H, d), 7.14-7.15 (1H, d), 7.32-7.37 (4H, m), 8.12 (1H, s), 8.30 (1H, d), 11.62 (1H, s) MS m/e MH+ 496 |
| 48 | 4-amino-N-[1-(4-chlorophenyl)-4-morpholin-4-ylbutyl]-1-(7H-pyrrolo[2,3-d]pyrimidin-4-yl)piperidine-4-carboxamide | 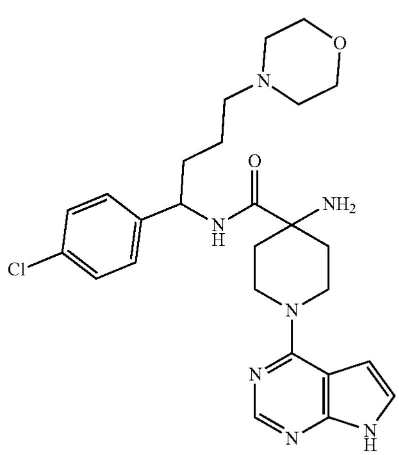 [SMILES: NC1(C(=O)NC(CCCN2CCOCC2)c2ccc(Cl)cc2)CCN(c2ncnc3[nH]ccc23)CC1] | 1H NMR (399.9 MHz, DMSO-d6) δ 1.32-1.37 (1H, m), 1.44-1.51 (1H, m), 1.57-1.76 (4H, m), 2.10-2.17 (2H, m), 2.26-2.35 (6H, m), 3.47-3.56 (6H, m), 4.51 (2H, d), 4.79 (1H, m), 6.62-6.64 (1H, m), 7.19 (1H, t), 7.32-7.34 (2H, d), 7.37-7.39 (2H, d), 8.16 (1H, s), 8.49 (1H, s), 11.68 (1H, s) MS m/e MH+ 512 |

| No. | Compound Name | Structure | NMR/MS |
|---|---|---|---|
| 49 | 4-amino-N-[1-(4-chlorophenyl)-4-piperidin-1-ylbutyl]-1-(7H-pyrrolo[2,3-d]pyrimidin-4-yl)piperidine-4-carboxamide | 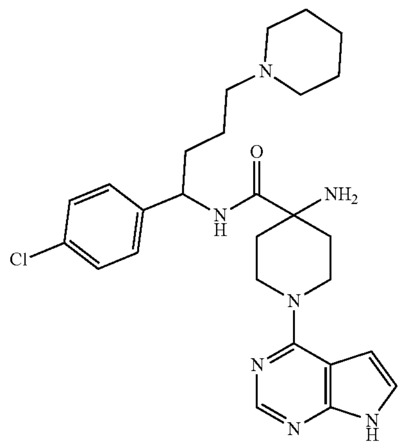 [SMILES: NC1(C(=O)NC(CCCN2CCCCC2)c2ccc(Cl)cc2)CCN(c2ncnc3[nH]ccc23)CC1] | 1H NMR (400.13 MHz, DMSO-d6) δ 1.31-1.37 (3H, m), 1.41-1.47 (6H, m), 1.66-1.73 (2H, m), 1.86-2.00 (2H, m), 2.16-2.24 (7H, m), 3.50-3.58 (2H, m), 4.34-4.40 (2H, m), 4.73 (1H, m), 6.57 (1H, d), 7.15 (1H, d), 7.31-7.37 (4H, m), 8.12 (1H, s), 8.29 (1H, d), 11.62 (1H, s) MS m/e MH+ 510 |

EXAMPLE 49A AND 49B: 4-AMINO-N-[(1S)-1-(4-CHLOROPHENYL)-4-PIPERIDIN-1-YLBUTYL]-1-(7H-PYRROLO[2,3-D]PYRIMIDIN-4-YL)PIPERIDINE-4-CARBOXAMIDE AND 4-AMINO-N-[(1R)-1-(4-CHLOROPHENYL)-4-PIPERIDIN-1-YLBUTYL]-1-(7H-PYRROLO[2,3-D]PYRIMIDIN-4-YL)PIPERIDINE-4-CARBOXAMIDE

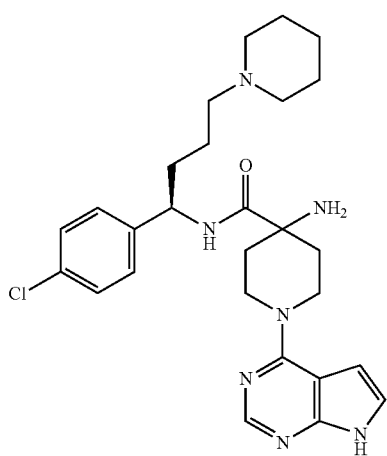

-continued

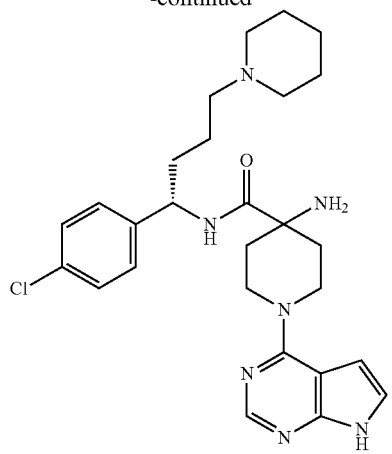

The individual stereoisomers of the racemate of Example 49 were separated using the same methodology as that described for Examples 11A and 11B.

1H NMR (500.13 MHz, DMSO-d6) δ 1.31-1.41 (4H, m), 1.44-1.48 (6H, m), 1.68-1.71 (2H, m), 1.90-1.98 (4H, m), 2.21 (6H, m), 3.54-3.56 (2H, m), 4.38 (2H, t), 4.73 (1H, d), 6.58 (1H, q), 7.15 (1H, q), 7.32-7.37 (4H, m), 8.12 (1H, s), 8.29 (1H, s), 11.63 (1H, s)

MS m/e MH+ 510

1H NMR (500.13 MHz, DMSO-d6) δ 1.31-1.41 (4H, m), 1.44-1.48 (7H, m), 1.68-1.71 (2H, m), 1.90-1.98 (2H, m), 2.21 (6H, m), 3.54-3.56 (2H, m), 4.38 (2H, t), 4.73 (1H, d), 6.58 (1H, q), 7.15 (1H, q), 7.32-7.37 (4H, m), 8.12 (1H, s), 8.29 (1H, s), 11.63 (1H, s)

MS m/e MH+ 510

The compounds of the invention listed in Table F below were made from the appropriate starting materials using a process analogous to that described in Example 26.

TABLE F

| No. | Compound Name | Structure | NMR/MS |
|---|---|---|---|
| 50 | 4-amino-N-[(1S)-1-(4-chlorophenyl)-3-(4-methylpiperazin-1-yl)propyl]-1-(7H-pyrrolo[2,3-d]pyrimidin-4-yl)piperidine-4-carboxamide | 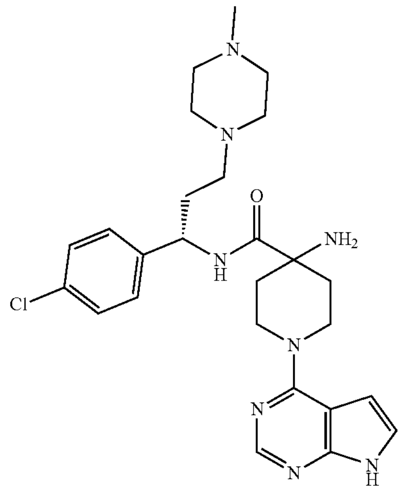 [SMILES: CN1CCN(CC[C@H](NC(=O)C2(N)CCN(c3ncnc4[nH]ccc34)CC2)c2ccc(Cl)cc2)CC1] | 1H NMR (400.13 MHz, DMSO-d6) δ 1.39-1.47 (2H, m), 1.84-1.97 (4H, m), 2.13 (4H, s), 2.19 (2H, t), 2.31-2.34 (7H, m), 3.54-3.57 (2H, m), 4.38 (2H, m), 4.82 (1H, m), 6.57 (1H, d), 7.14-7.16 (1H, d), 7.31-7.37 (4H, m), 8.12 (1H, s), 8.55 (1H, d), 11.62 (1H, s)<br>MS m/e MH+ 511 |
| 51 | 4-amino-N-[(1S)-1-(4-chlorophenyl)-3-morpholin-4-ylpropyl]-1-(7H-pyrrolo[2,3-d]pyrimidin-4-yl)piperidine-4-carboxamide | 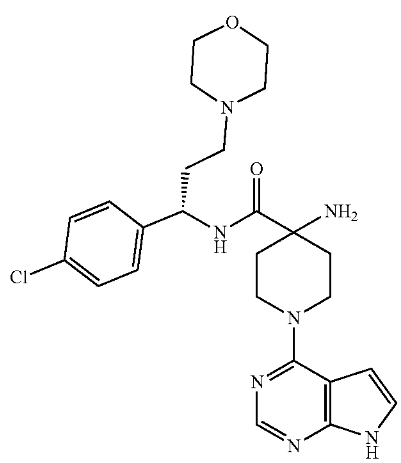 [SMILES: NC1(C(=O)N[C@@H](CCN2CCOCC2)c2ccc(Cl)cc2)CCN(c2ncnc3[nH]ccc23)CC1] | 1H NMR (400.13 MHz, DMSO-d6) δ 1.43 (2H, m), 1.83-2.00 (4H, m), 2.20 (2H, t), 2.27-2.37 (4H, m), 3.51-3.63 (6H, m), 4.35-4.41 (2H, m), 4.85 (1H, m), 6.57 (1H, d), 7.15 (1H, d), 7.32-7.37 (4H, m), 8.12 (1H, s), 8.65 (1H, d), 11.62 (1H, s)<br>MS m/e MH+ 498 |
| 52 | 4-amino-N-[(1S)-1-(4-chlorophenyl)-3-piperidin-1-ylpropyl]-1-(7H-pyrrolo[2,3-d]pyrimidin-4-yl)piperidine-4-carboxamide | 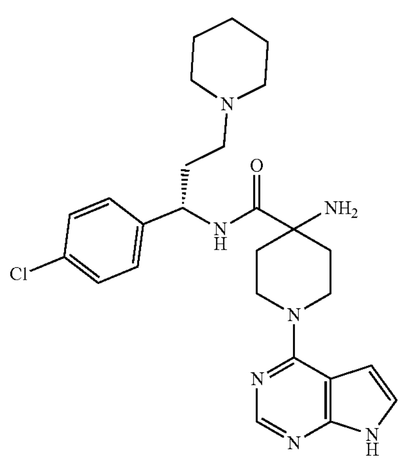 [SMILES: NC1(C(=O)N[C@@H](CCN2CCCCC2)c2ccc(Cl)cc2)CCN(c2ncnc3[nH]ccc23)CC1] | 1H NMR (400.13 MHz, DMSO-d6) δ 1.33-1.50 (8H, m), 1.82-1.90 (4H, m), 2.15 (2H, t), 2.25-2.34 (4H, m), 3.53-3.57 (2H, m), 4.39 (2H, m), 4.82 (1H, m), 6.57 (1H, d), 7.14-7.16 (1H, d), 7.30-7.37 (4H, m), 8.12 (1H, s), 8.64-8.66 (1H, d), 11.62 (1H, s)<br>MS m/e MH+ 496 |

TABLE F-continued

| No. | Compound Name | Structure | NMR/MS |
|---|---|---|---|
| 53* | 4-amino-N-[(1S)-1-(4-chlorophenyl)-3-piperazin-1-ylpropyl]-1-(7H-pyrrolo[2,3-d]pyrimidin-4-yl)piperidine-4-carboxamide | 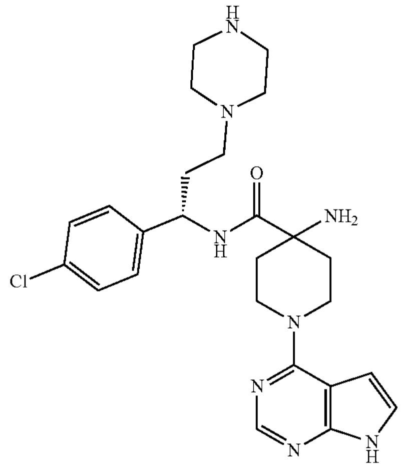 [SMILES: NC1(C(=O)N[C@@H](CCN2CCNCC2)c2ccc(Cl)cc2)CCN(c2ncnc3[nH]ccc23)CC1] | 1H NMR (400.13 MHz, DMSO-d6) δ 1.40-1.47 (2H, m), 1.82-1.99 (4H, m), 2.11-2.25 (6H, m), 2.67-2.69 (4H, m), 3.54-3.57 (2H, m), 4.35-4.41 (2H, m), 4.83 (1H, m), 6.57 (1H, d), 7.15 (1H, d), 7.31-7.37 (4H, m), 8.12 (1H, s), 8.61 (1H, d), 11.62 (1H, s)<br>MS m/e MH+ 497 |
| 54 | 4-amino-N-[(1S)-1-(4-chlorophenyl)-3-(1H-imidazol-1-yl)propyl]-1-(7H-pyrrolo[2,3-d]pyrimidin-4-yl)piperidine-4-carboxamide | 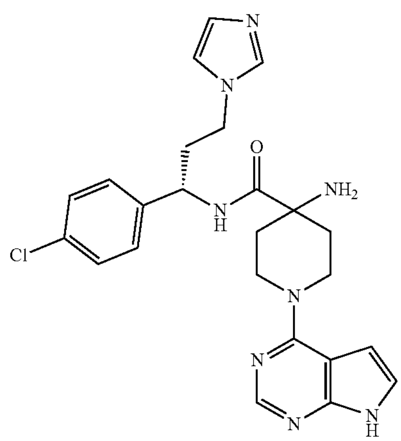 [SMILES: NC1(C(=O)N[C@@H](CCn2ccnc2)c2ccc(Cl)cc2)CCN(c2ncnc3[nH]ccc23)CC1] | 1H NMR (400.13 MHz, DMSO-d6) δ 1.41-1.53 (2H, m), 1.86-2.04 (2H, m), 2.13-2.25 (4H, m), 3.52-3.61 (2H, m), 3.96-4.00 (2H, m), 4.34-4.42 (2H, m), 4.69 (1H, m), 6.58 (1H, d), 6.89 (1H, s), 7.15 (2H, t), 7.31 (2H, d), 7.36-7.38 (2H, d), 7.56 (1H, s), 8.12 (1H, s), 8.44 (1H, d), 11.62 (1H, s)<br>MS m/e MH+ 479 |
| 55 | 4-amino-N-[(1S)-1-(4-chlorophenyl)-3-pyrrolidin-1-ylpropyl]-1-(7H-pyrrolo[2,3-d]pyrimidin-4-yl)piperidine-4-carboxamide | 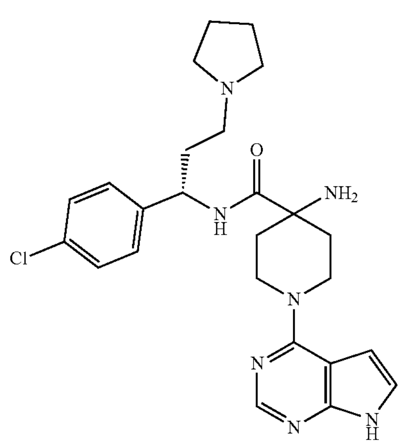 [SMILES: NC1(C(=O)N[C@@H](CCN2CCCC2)c2ccc(Cl)cc2)CCN(c2ncnc3[nH]ccc23)CC1] | 1H NMR (400.13 MHz, DMSO-d6) δ 1.42-1.58 (2H, m), 1.71 (5H, s), 1.84-2.02 (5H, m), 2.33 (2H, m), 2.55 (2H, m), 3.51-3.59 (2H, m), 4.36-4.43 (2H, m), 4.86 (1H, t), 6.58 (1H, d), 7.16 (1H, d), 7.30-7.38 (5H, m), 8.12 (1H, s), 11.63 (1H, s)<br>MS m/e MH+ 482 |

*Made by the same methodology as that described for Example 26 starting from 1-(2,4-dimethoxybenzyl)piperazine. The TFA deprotection in the final step was heated at 80° C. to remove Boc and dimethoxybenzyl groups.

EXAMPLE 56: 4-AMINO-N-(1-(4-CHLOROPHE-NYL)-2-SULFAMOYLETHYL)-1-(7H-PYRROLO[2,3-D]PYRIMIDIN-4-YL)PIPERIDINE-4-CARBOXAMIDE

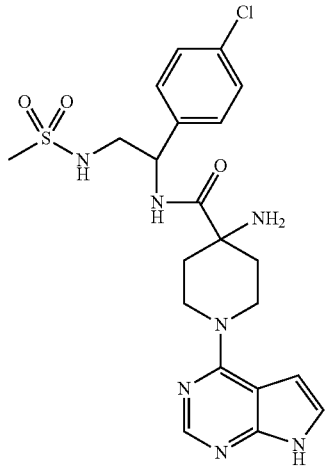 [SMILES: CS(=O)(=O)NCC(NC(=O)C1(N)CCN(c2ncnc3[nH]ccc23)CC1)c1ccc(Cl)cc1]

Tert-butyl 4-(1-(4-chlorophenyl)-2-(methylsulfonamido)ethylcarbamoyl)-1-(7H-pyrrolo[2,3-d]pyrimidin-4-yl)piperidin-4-ylcarbamate (Intermediate 76) (100 mg, 0.17 mmol) was treated with trifluoroacetic acid (2 mL). The solution was stirred for 1 hour at room temperature. The mixture was concentrated under reduced pressure. The crude product was purified by ion exchange chromatography, using an SCX column. The residue was loaded onto the column in methanol and washed with methanol. The desired product was eluted from the column using 2M ammonia in methanol and pure fractions were evaporated to dryness to afford 4-amino-N-(1-(4-chlorophenyl)-2-(methylsulfonamido)ethyl)-1-(7H-pyrrolo[2,3-d]pyrimidin-4-yl)piperidine-4-carboxamide (79 mg, 95%) as a colourless solid.

$^1$H NMR (399.9 MHz, DMSO-d6) δ 1.38-1.53 (2H, m), 1.85-2.07 (2H, m), 2.20 (2H, br, s), 2.85 (3H, s), 3.57 (2H, m), 4.34-4.46 (2H, m), 4.87-4.94 (1H, m), 6.57-6.60 (1H, m), 7.12-7.19 (2H, m), 7.35-7.43 (4H, m), 8.13 (1H, s), 8.46 (1H, br, s), 11.64 (1H, s)

MS m/e MH$^+$=492

EXAMPLE 57: 4-AMINO-N-(1-(4-CHLOROPHE-NYL)-2-SULFAMOYLETHYL)-1-(7H-PYRROLO[2,3-D]PYRIMIDIN-4-YL)PIPERIDINE-4-CARBOXAMIDE

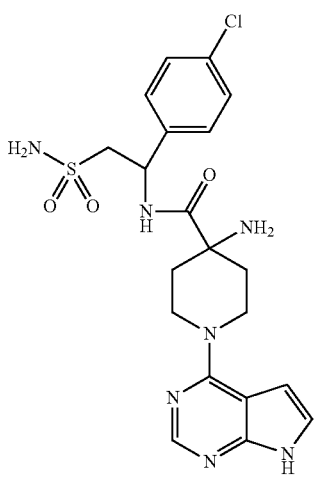 [SMILES: NC1(C(=O)NC(CS(N)(=O)=O)c2ccc(Cl)cc2)CCN(c2ncnc3[nH]ccc23)CC1]

Tert-butyl 4-(1-(4-chlorophenyl)-2-sulfamoylethylcarbamoyl)-1-(7H-pyrrolo[2,3-d]pyrimidin-4-yl)piperidin-4-ylcarbamate (Intermediate 81) (153 mg, 0.26 mmol) was treated with trifluoroacetic acid (4 mL). The solution was stirred for 30 minutes at room temperature. The mixture was concentrated under reduced pressure and the residue was purified by ion exchange chromatography, using an SCX column. The desired product was eluted from the column using ammonia in methanol (2M) and pure fractions were evaporated to dryness to afford 4-amino-N-(1-(4-chlorophenyl)-2-sulfamoylethyl)-1-(7H-pyrrolo[2,3-d]pyrimidin-4-yl)piperidine-4-carboxamide (125 mg, 99%) as a colourless solid.

$^1$H NMR (399.9 MHz, DMSO-d6) δ 1.35-1.53 (2H, m), 1.86-2.04 (2H, m), 3.35-3.40 (1H, m), 3.52-3.62 (2H, m), 3.68 (1H, dd), 4.33-4.41 (2H, m), 5.24-5.29 (1H, m), 6.56-6.60 (1H, m), 6.88 (2H, s), 7.13-7.17 (1H, m), 7.39 (4H, s), 8.13 (1H, s), 8.68 (1H, br, s), 11.63 (1H, s)

MS m/e MH$^+$=478

EXAMPLE 58: N-(2-ACETAMIDO-1-(4-CHLOROPHENYL)ETHYL)-4-AMINO-1-(7H-PYRROLO[2,3-D]PYRIMIDIN-4-YL)PIPERIDINE-4-CARBOXAMIDE

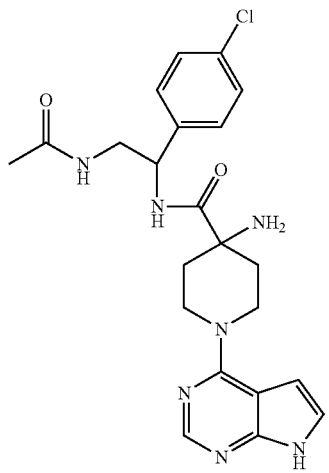 [SMILES: CC(=O)NCC(NC(=O)C1(N)CCN(c2ncnc3[nH]ccc23)CC1)c1ccc(Cl)cc1]

Tert-butyl 4-(2-acetamido-1-(4-chlorophenyl)ethylcarbamoyl)-1-(7H-pyrrolo[2,3-d]pyrimidin-4-yl)piperidin-4-ylcarbamate (Intermediate 84) (97 mg, 0.17 mmol) was treated with trifluoroacetic acid (2 mL). The solution was stirred for 1 hours at room temperature. The mixture was concentrated under reduced pressure. The crude product was purified by ion exchange chromatography, using an SCX column. The residue was loaded onto the column in methanol and washed with methanol. The desired product was eluted from the column using 2M ammonia in methanol and pure fractions were evaporated to dryness to afford N-(2-acetamido-1-(4-chlorophenyl)ethyl)-4-amino-1-(7H-pyrrolo[2,3-d]pyrimidin-4-yl)piperidine-4-carboxamide (80 mg, quant.) as a cream dry film.

$^1$H NMR (399.9 MHz, DMSO-d$_6$) δ 1.43 (2H, t), 1.79 (3H, s), 1.83-2.04 (2H, m), 2.20 (2H, br, s), 3.32-3.38 (2H, m), 3.58 (2H, q), 4.32-4.42 (2H, m), 4.82-4.88 (1H, m), 6.56-6.60 (1H, m), 7.14-7.18 (1H, m), 7.33 (2H, d), 7.38 (2H, d), 7.94 (1H, t), 8.13 (1H, s), 8.42-8.50 (1H, m), 11.63 (1H, s)

MS m/e MH+=456

EXAMPLE 59: 4-AMINO-N-(1-(4-CHLOROPHENYL)-2-(1H-IMIDAZOL-2-YL)ETHYL)-1-(7H-PYRROLO[2,3-D]PYRIMIDIN-4-YL)PIPERIDINE-4-CARBOXAMIDE

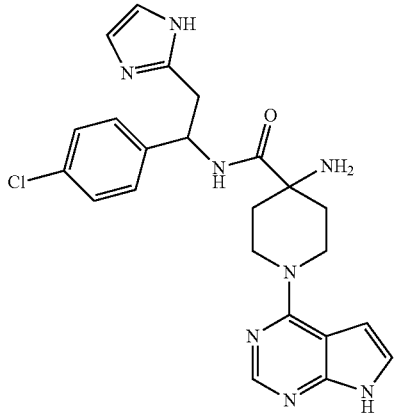 [SMILES: NC1(C(=O)NC(Cc2ncc[nH]2)c2ccc(Cl)cc2)CCN(c2ncnc3[nH]ccc23)CC1]

Trifluoroacetic acid (5 mL, 64.90 mmol) was added to tert-butyl 4-(1-(4-chlorophenyl)-2-(1-trityl-1H-imidazol-2-yl)ethylcarbamoyl)-1-(7H-pyrrolo[2,3-d]pyrimidin-4-yl)piperidin-4-ylcarbamate (Intermediate 89) (310 mg, 0.38 mmol) at room temperature and the resulting solution stirred for 30 minutes. Water (5-6 drops) was then added and stirring continued for a further 30 minutes. The resulting solution was diluted with methanol and applied to a 10 g SCX column which was then eluted with MeOH followed by 2N NH₃ (in MeOH). Product-containing fractions were combined and concentrated by evaporation then triturated with MeCN/DMF (1:1) to give a pale yellow ppt. The precipitate was collected by filtration, washed with MeCN and dried under vacuum to afford 4-amino-N-(1-(4-chlorophenyl)-2-(1H-imidazol-2-yl)ethyl)-1-(7H-pyrrolo[2,3-d]pyrimidin-4-yl)piperidine-4-carboxamide (130 mg, 72.8%) as a cream solid.

1H NMR (399.902 MHz, DMSO) δ 1.36-1.40 (2H, m), 1.85-1.93 (2H, m), 3.08 (2H, d), 3.55 (2H, m), 4.29-4.35 (2H, m), 5.18 (1H, q), 6.57 (1H, d), 6.85 (2H, s), 7.16 (1H, d), 7.25 (2H, d), 7.31 (2H, d), 8.12 (1H, s), 8.89 (1H, d), 11.63 (1H, br s)

m/z (ESI+) (M+H)+=465; HPLC tR=1.62 min.

EXAMPLE 60: 4-AMINO-N-[1-(4-CHLOROPHENYL)-2-(1H-PYRAZOL-1-YL)ETHYL]-1-(7H-PYRROLO[2,3-D]PYRIMIDIN-4-YL)PIPERIDINE-4-CARBOXAMIDE

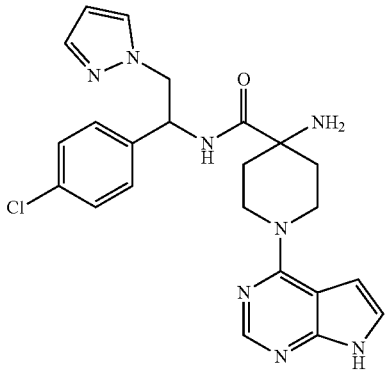 [SMILES: NC1(C(=O)NC(Cn2cccn2)c2ccc(Cl)cc2)CCN(c2ncnc3[nH]ccc23)CC1]

TFA (0.7 mL) was added to a suspension of tert-butyl 4-(1-(4-chlorophenyl)-2-(1H-pyrazol-1-yl)ethylcarbamoyl)-1-(7H-pyrrolo[2,3-d]pyrimidin-4-yl)piperidin-4-ylcarbamate (180 mg, 0.32 mmol) in dichloromethane (Intermediate 93) (7 mL) under argon. The resulting solution was stirred at room temperature overnight. The solvents were removed in vacuo and the reaction mixture was purified by preparative HPLC using a Waters X-Bridge reverse-phase column (C-18, 5 microns silica, 19 mm diameter, 100 mm length) and decreasingly polar mixtures of water (containing 0.2% ammonium carbonate) and acetonitrile as eluent. The fractions were evaporated to dryness to afford 4-amino-N-[1-(4-chlorophenyl)-2-(1H-pyrazol-1-yl)ethyl]-1-(7H-pyrrolo[2,3-d]pyrimidin-4-yl)piperidine-4-carboxamide as a white powder.

1H NMR (500 MHz, DMSO-d6) δ 1.33 (2H, m), 1.83 (2H, m), 2.14 (2H, s), 3.53 (2H, m), 4.28 (2H, m), 4.43 (2H, m), 5.22 (1H, d), 6.15 (1H, t), 6.56 (1H, q), 7.15 (1H, t), 7.30 (2H, d), 7.36 (2H d), 7.44 (1H, d), 7.55 (1H, d), 8.11 (1H, s), 8.81 (1H, br d), 11.64 (1H, s);

m/z (ESI+) (M+H)+=465.

EXAMPLE 61: 4-AMINO-N-[1-(4-CHLOROPHENYL)-2-(3-METHYLISOXAZOL-5-YL)ETHYL]-1-(7H-PYRROLO[2,3-D]PYRIMIDIN-4-YL)PIPERIDINE-4-CARBOXAMIDE

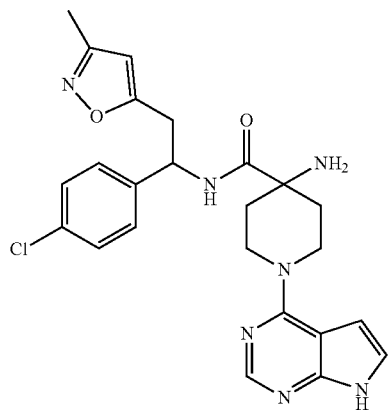 [SMILES: Cc1cc(CC(NC(=O)C2(N)CCN(c3ncnc4[nH]ccc34)CC2)c2ccc(Cl)cc2)on1]

4-Amino-N-[1-(4-chlorophenyl)-2-(3-methylisoxazol-5-yl)ethyl]-1-(7H-pyrrolo[2,3-d]pyrimidin-4-yl)piperidine-4-carboxamide was made from the appropriate starting materials using a process analogous to that described for Example 60.

1H NMR (500 MHz, DMSO-d6) δ 1.35 (2H, d), 1.87 (2H, m), 2.14 (2H, s), 2.15 (3H, s), 3.17-3.33 (2H, m), 3.53 (2H, m), 4.31 (2H, m), 5.15 (1H, d), 6.06 (1H, s), 6.56 (1H, d), 7.16 (1H, t), 7.39 (4H, m), 8.12 (1H, s), 8.60 (1H, br d), 11.65 (1H, s).

m/z (ESI+) (M+H)+=480

EXAMPLE 62: 4-AMINO-N-(1-(4-CHLOROPHENYL)-2-(THIAZOL-2-YL)ETHYL)-1-(7H-PYRROLO[2,3-D]PYRIMIDIN-4-YL)PIPERIDINE-4-CARBOXAMIDE

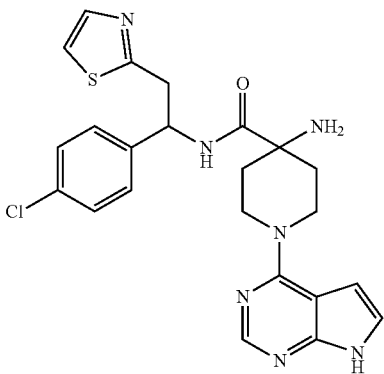 [SMILES: NC1(C(=O)NC(Cc2nccs2)c2ccc(Cl)cc2)CCN(c2ncnc3[nH]ccc23)CC1]

TFA (2.0 mL) was added to a suspension of tert-butyl 4-(1-(4-chlorophenyl)-2-(thiazol-2-yl)ethylcarbamoyl)-1-(7H-pyrrolo[2,3-d]pyrimidin-4-yl)piperidin-4-ylcarbamate (Intermediate 96) (918 mg, 0.95 mmol) in dichloromethane (20 mL) under argon. The resulting solution was stirred at room temperature for one night. The solvents were removed in vacuo and the reaction mixture was purified by preparative HPLC using a Waters X-Bridge reverse-phase column (C-18, 5 microns silica, 19 mm diameter, 100 mm length) and decreasingly polar mixtures of water (containing 0.2% ammonium carbonate) and acetonitrile as eluent. The fractions were evaporated to dryness to afford 4-amino-N-(1-(4-chlorophenyl)-2-(thiazol-2-yl)ethyl)-1-(7H-pyrrolo[2,3-d]pyrimidin-4-yl)piperidine-4-carboxamide (259 mg, 56.8%) as a white powder.

1H NMR (500 MHz, DMSO-d6) δ 1.35 (2H, d), 1.85 (2H, m), 2.07 (2H, br s), 3.41-3.56 (4H, m), 4.30 (2H, m), 5.20 (1H, d), 6.56 (1H, d), 7.15 (1H, t), 7.36 (4H, m), 7.54 (1H, d), 7.70 (1H, d), 8.11 (1H, s), 8.75 (1H, br d), 11.70 (1H, br s);

m/z (ESI+) (M+H)+=482

EXAMPLE 63: 4-AMINO-N-(1-(4-CHLOROPHENYL)-3-(DIMETHYLAMINO)-3-OXOPROPYL)-1-(7H-PYRROLO[2,3-D]PYRIMIDIN-4-YL)PIPERIDINE-4-CARBOXAMIDE

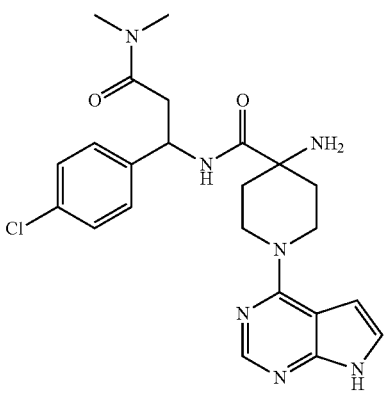 [SMILES: CN(C)C(=O)CC(NC(=O)C1(N)CCN(c2ncnc3[nH]ccc23)CC1)c1ccc(Cl)cc1]

TFA (1.0 mL) was added to a suspension of tert-butyl 4-(1-(4-chlorophenyl)-3-(dimethylamino)-3-oxopropylcarbamoyl)-1-(7H-pyrrolo[2,3-d]pyrimidin-4-yl)piperidin-4-ylcarbamate (Intermediate 98) (770 mg, 0.24 mmol) in dichloromethane (10 mL) under argon. The resulting solution was stirred at room temperature for one night. The solvents were removed in vacuo and the reaction mixture was purified by preparative HPLC using a Waters X-Bridge reverse-phase column (C-18, 5 microns silica, 19 mm diameter, 100 mm length) and decreasingly polar mixtures of water (containing 0.2% ammonium carbonate) and acetonitrile as eluent. The fractions were evaporated to dryness to afford 4-amino-N-(1-(4-chlorophenyl)-3-(dimethylamino)-3-oxopropyl)-1-(7H-pyrrolo[2,3-d]pyrimidin-4-yl)piperidine-4-carboxamide (74.0 mg, 64.8%) as a white powder.

1H NMR (500 MHz, DMSO-d6) δ 1.43 (2H, m), 1.94 (2H, m), 2.75 (3H, s), 2.8 (2H, m), 2.89 (3H, s), 3.52 (2H, m), 4.40 (2H, m), 5.15 (1H, d), 6.58 (1H, d), 7.16 (1H, t), 7.35 (4H, s), 8.12 (1H, s), 8.76 (1H, br d), 11.66 (1H, br s);

m/z (ESI+) (M+H)+=470

EXAMPLE 64: 4-AMINO-N-(1-(4-CHLOROPHENYL)-3-METHOXYPROPYL)-1-(7H-PYRROLO[2,3-D]PYRIMIDIN-4-YL)PIPERIDINE-4-CARBOXAMIDE

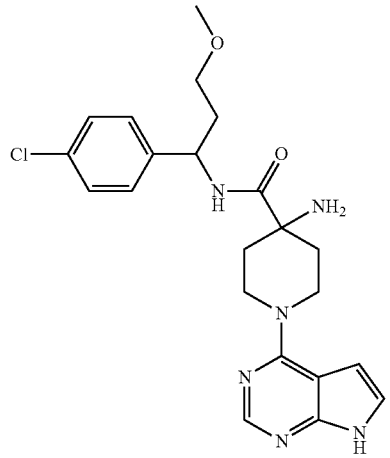 [SMILES: COCCC(NC(=O)C1(N)CCN(c2ncnc3[nH]ccc23)CC1)c1ccc(Cl)cc1]

Hydrogen chloride (4M in 1,4-dioxane, 1.151 mL, 4.60 mmol) was added to tert-butyl 4-(1-(4-chlorophenyl)-3-methoxypropylcarbamoyl)-1-(7H-pyrrolo[2,3-d]pyrimidin-4-yl)piperidin-4-ylcarbamate (Intermediate 101) (50 mg, 0.09 mmol) in a mixture of DCM (5 mL) and methanol (2 mL) at 22° C. The resulting solution was stirred at 22° C. for 2 days. The mixture was evaporated and the residue was purified by ion exchange chromatography, using an SCX column. The desired product was eluted from the column using 2M NH3/MeOH; pure fractions were evaporated to dryness and the residue was triturated with diethyl ether to afford 4-amino-N-(1-(4-chlorophenyl)-3-methoxypropyl)-1-(7H-pyrrolo[2,3-d]pyrimidin-4-yl)piperidine-4-carboxamide (39.0 mg, 96%) as a white solid.

1H NMR (399.902 MHz, DMSO) δ 1.44 (2H, m), 1.88-2.02 (5H, m), 2.46 (2H, s), 3.21 (3H, s), 3.28 (2H, t), 3.55 (2H, m), 4.39 (2H, m), 4.87 (1H, dt), 6.59 (1H, dd), 7.16 (1H, dd), 7.33 (2H, d), 7.37 (2H, d), 8.13 (1H, s), 8.45 (1H, d), 11.63 (1H, s);

m/z (ESI+) (M+H)+=443.4; HPLC tR=1.87 min.

EXAMPLE 65: 4-AMINO-N-(1-(4-CHLOROPHENYL)-3-SULFAMOYLPROPYL)-1-(7H-PYRROLO[2,3-D]PYRIMIDIN-4-YL)PIPERIDINE-4-CARBOXAMIDE

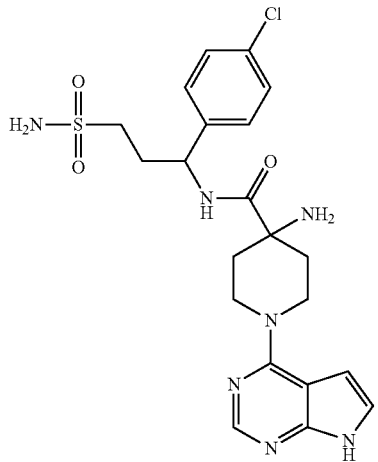 [SMILES: NC1(C(=O)NC(CCS(N)(=O)=O)c2ccc(Cl)cc2)CCN(c2ncnc3[nH]ccc23)CC1]

Hydrogen chloride (4M in dioxane, 0.676 mL, 2.70 mmol) was added to tert-butyl 4-(1-(4-chlorophenyl)-3-sulfamoylpropylcarbamoyl)-1-(7H-pyrrolo[2,3-d]pyrimidin-4-yl)piperidin-4-ylcarbamate (Intermediate 105) (16 mg, 0.03 mmol) in a mixture of DCM (5 mL) and methanol (5 mL) at 22° C. The resulting solution was stirred at 22° C. for 20 hours. The mixture was evaporated and the residue was purified by ion exchange chromatography, using an SCX column. The desired product was eluted from the column using 30% (2M NH$_3$ in MeOH) in DCM and pure fractions were evaporated to dryness to afford 4-amino-N-(1-(4-chlorophenyl)-3-sulfamoylpropyl)-1-(7H-pyrrolo[2,3-d]pyrimidin-4-yl)piperidine-4-carboxamide (12.00 mg, 90%) as a colourless gum.

1H NMR (399.902 MHz, DMSO) δ 1.48 (2H, m), 1.90-2.06 (2H, m), 2.09-2.24 (2H, m), 2.87 (1H, ddd), 3.02 (1H, ddd), 3.56 (2H, m), 3.56 (2H, d), 4.41 (2H, m), 4.91 (1H, br.s), 6.59 (1H, dd), 6.80 (2H, s), 7.16 (1H, dd), 7.38-7.43 (4H, m), 8.13 (1H, s), 8.46 (1H, s), 11.64 (1H, s);

m/z (ESI+) (M+H)+=492.4, 494.3; HPLC tR=1.60 min.

EXAMPLE 66: 4-AMINO-N-(3-AMINO-1-(4-CHLOROPHENYL)-3-OXOPROPYL)-1-(7H-PYRROLO[2,3-D]PYRIMIDIN-4-YL)PIPERIDINE-4-CARBOXAMIDE

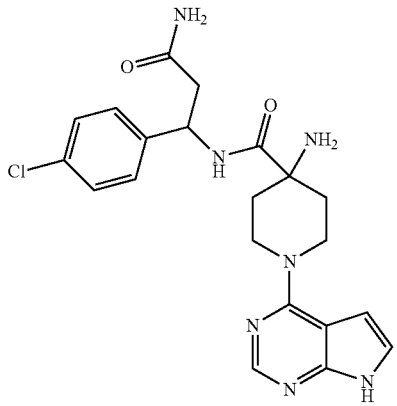 [SMILES: NC(=O)CC(NC(=O)C1(N)CCN(c2ncnc3[nH]ccc23)CC1)c1ccc(Cl)cc1]

HCl in 1,4-dioxane (4M) (0.228 mL, 0.91 mmol) was added to tert-butyl 4-(3-amino-1-(4-chlorophenyl)-3-oxopropylcarbamoyl)-1-(7H-pyrrolo[2,3-d]pyrimidin-4-yl)piperidin-4-ylcarbamate (Intermediate 108) (99 mg, 0.18 mmol) in DCM (4 mL) at 20° C. The resulting solution was stirred at 20° C. for 3 hours. The reaction mixture was filtered through a PTFE cup and the collected solid was purified by preparative HPLC (Waters XTerra C18 column, 5µ silica, 30 mm diameter, 100 mm length), using decreasingly polar mixtures of water (containing 1% NH$_3$) and MeCN as eluents. Fractions containing the desired compound were evaporated to dryness to afford 4-amino-N-(3-amino-1-(4-chlorophenyl)-3-oxopropyl)-1-(7H-pyrrolo[2,3-d]pyrimidin-4-yl)piperidine-4-carboxamide (9.00 mg, 11.1%) as a cream solid.

1H NMR (399.9 MHz, DMSO-d6) δ 1.40-1.43 (2H, m), 1.93-1.96 (2H, m), 2.18 (2H, s), 3.54-3.56 (2H, m), 4.36-4.40 (2H, m), 5.12 (1H, d), 6.58 (1H, d), 6.81 (1H, s), 7.15-7.16 (1H, m), 7.32-7.37 (5H, m), 8.13 (1H, s), 8.76 (1H, d), 11.63 (1H, s), (no NH2 visible).

m/z (ESI+) (M+H)+=442; HPLC tR=1.47 min.

EXAMPLE 67: 4-AMINO-N-(1-(4-CHLOROPHENYL)-3-UREIDOPROPYL)-1-(7H-PYRROLO[2,3-D]PYRIMIDIN-4-YL)PIPERIDINE-4-CARBOXAMIDE

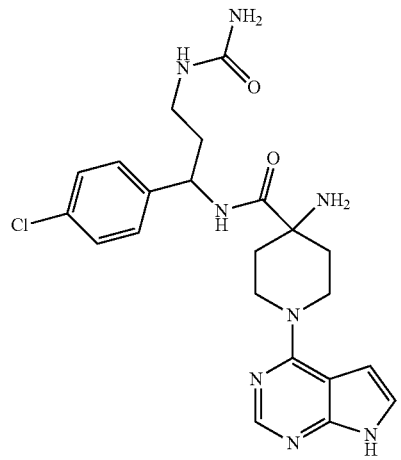 [SMILES: NC(=O)NCCC(NC(=O)C1(N)CCN(c2ncnc3[nH]ccc23)CC1)c1ccc(Cl)cc1]

TFA (3 mL) was added to tert-butyl 4-(1-(4-chlorophenyl)-3-ureidopropylcarbamoyl)-1-(7H-pyrrolo[2,3-d]pyrimidin-4-yl)piperidin-4-ylcarbamate (Intermediate 112) (379 mg, 0.66 mmol). The reaction was left to stir at 20° C. for 4 hours and then vacuumed to dryness. The crude product was purified by ion exchange chromatography, using an SCX column. The desired product was eluted from the column using 0.35M NH$_3$/MeOH and pure fractions were evaporated to dryness to afford crude material. The crude product was purified by preparative HPLC (Waters XBridge Prep C18 OBD column, 5µ silica, 19 mm diameter, 100 mm length), using decreasingly polar mixtures of water (containing 1% NH3) and MeCN as eluents. Fractions containing the desired compound were evaporated to dryness to afford 4-amino-N-(1-(4-chlorophenyl)-3-ureidopropyl)-1-(7H-pyrrolo[2,3-d]pyrimidin-4-yl)piperidine-4-carboxamide (14.00 mg, 5.60%) as a white solid.

1H NMR (399.9 MHz, DMSO-d6) δ 1.41-1.49 (2H, m), 1.78-1.88 (2H, m), 2.01 (1H, d), 2.91 (1H, t), 2.97 (2H, t), 3.55 (2H, d), 4.37 (2H, d), 4.78 (1H, d), 5.40 (2H, s), 5.95 (1H, t), 6.58-6.59 (1H, m), 7.15-7.16 (1H, m), 7.33-7.39 (4H, m), 8.13 (1H, s), 8.36 (1H, d), 11.63 (1H, s);

m/z (ESI+) (M+H)+=471; HPLC tR=1.50 min.

EXAMPLE 68: 4-AMINO-N-(1-(4-CHLOROPHENYL)-2-CYANOETHYL)-1-(7H-PYRROLO[2,3-D]PYRIMIDIN-4-YL)PIPERIDINE-4-CARBOXAMIDE

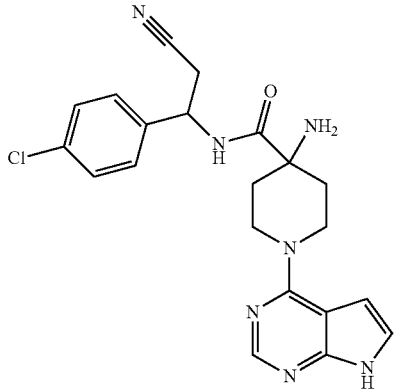 [SMILES: N#CCC(NC(=O)C1(N)CCN(c2ncnc3[nH]ccc23)CC1)c1ccc(Cl)cc1]

HCl (4M) in 1,4-dioxane (2.011 mL, 8.04 mmol) was added to tert-butyl 4-(1-(4-chlorophenyl)-2-cyanoethylcarbamoyl)-1-(7H-pyrrolo[2,3-d]pyrimidin-4-yl)piperidin-4-ylcarbamate (Intermediate 114) (0.281 g, 0.54 mmol) in DCM (8 mL) at 20° C. The resulting solution was stirred at 20° C. for 18 hours. The reaction was vacuumed to dryness and was purified by preparative HPLC (Waters XTerra C18 column, 5μ silica, 19 mm diameter, 100 mm length), using decreasingly polar mixtures of water (containing 1% $NH_3$) and MeCN as eluents. Fractions containing the desired compound were evaporated to dryness to afford 4-amino-N-(1-(4-chlorophenyl)-2-cyanoethyl)-1-(7H-pyrrolo[2,3-d]pyrimidin-4-yl)piperidine-4-carboxamide (0.096 g, 42.2%) as a white solid.

1H NMR (399.9 MHz, DMSO-d6) δ 1.42-1.46 (2H, m), 1.52 (2H, d), 1.95 (1H, d), 1.98-2.01 (1H, m), 3.08 (1H, t), 3.56-3.59 (2H, m), 4.38-4.42 (2H, m), 5.18 (1H, s), 6.59-6.60 (1H, m), 7.16 (1H, t), 7.44 (4H, m), 8.13 (1H, s), 11.65 (1H, s), (no Visible NH2), m/z (ESI+) (M+H)+=424; HPLC tR=1.82 min.

EXAMPLE 69: 4-AMINO-N-(1-(4-CHLOROPHENYL)-3-(METHYLSULFONAMIDO)PROPYL)-1-(7H-PYRROLO[2,3-D]PYRIMIDIN-4-YL)PIPERIDINE-4-CARBOXAMIDE

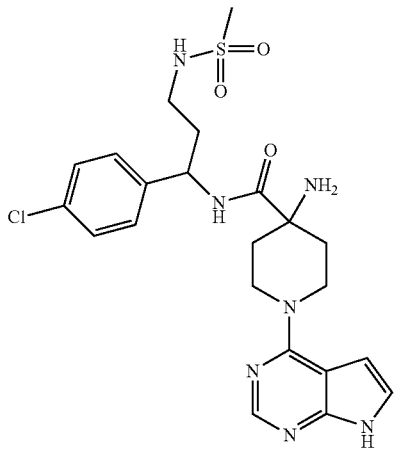 [SMILES: CS(=O)(=O)NCCC(NC(=O)C1(N)CCN(c2ncnc3[nH]ccc23)CC1)c1ccc(Cl)cc1]

HCl (4M) in 1,4-Dioxane (1.615 mL, 6.46 mmol) was added to tert-butyl 4-(1-(4-chlorophenyl)-3-(methylsulfonamido)propylcarbamoyl)-1-(7H-pyrrolo[2,3-d]pyrimidin-4-yl)piperidin-4-ylcarbamate (Intermediate 117) (261 mg, 0.43 mmol), The resulting suspension was stirred at 20° C. for 1 hour. No reaction. TFA (1 mL) was then added to the reaction and stirred for 16 hours. The reaction was vacuumed to dryness and was purified by ion exchange chromatography, using an SCX column. The desired product was eluted from the column using 0.35M $NH_3$/MeOH and pure fractions were evaporated to dryness to afford crude material. The crude product was purified by preparative HPLC (Waters XBridge Prep C18 OBD column, 5μ silica, 19 mm diameter, 100 mm length), using decreasingly polar mixtures of water (containing [AP-HPLC Buffer]) and MeCN as eluents. Fractions containing the desired compound were evaporated to dryness to afford 4-amino-N-(1-(4-chlorophenyl)-3-(methylsulfonamido)propyl)-1-(7H-pyrrolo[2,3-d]pyrimidin-4-yl)piperidine-4-carboxamide (142 mg, 65.2%) as a white solid.

1H NMR (399.9 MHz, DMSO-d6) δ 1.40-1.48 (2H, m), 1.86-1.90 (2H, m), 1.93-1.97 (2H, m), 2.17 (2H, s), 2.88 (3H, s), 2.93-2.97 (2H, m), 3.53-3.60 (2H, m), 4.37 (2H, t), 4.87 (1H, d), 6.57-6.59 (1H, m), 7.00 (1H, t), 7.15-7.16 (1H, m), 7.35-7.40 (4H, m), 8.13 (1H, s), 8.38 (1H, d), 11.63 (1H, s), m/z (ESI+) (M+H)+=506; HPLC tR=1.62 min.

Intermediate 1: 4-(tert-butoxycarbonylamino)-1-(7H-pyrrolo[2,3-d]pyrimidin-4-yl)piperidine-4-carboxylic Acid

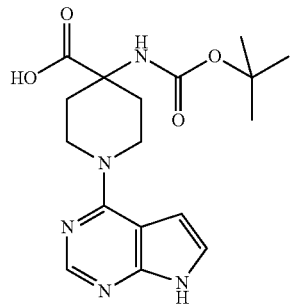 [SMILES: CC(C)(C)OC(=O)NC1(C(=O)O)CCN(c2ncnc3[nH]ccc23)CC1]

To a mixture of 4-[(2-methylpropan-2-yl)oxycarbonylamino]piperidine-4-carboxylic acid (115.6 g) in $CH_3CN-H_2O$ (6 L) was added to $NaHCO_3$ (181 g), followed by 4-chloro 7H-pyrrole[2,3-d]pyrimidine (72.7 g). The mixture was heated to reflux overnight under nitrogen for 24 hrs and then extracted with EtOAc (1 L×4). The aqueous layer was concentrated and MeOH (1.5 L) was added. The mixture was shaken for 30 min at 45° C. and filtered. The filtrate was concentrated again and dissolved in $H_2O$ (300 mL). 6N HCl was added until the pH reached 4.5 (ca. 80 mL). The mixture was filtered and the cake was dried under vacuum to afford the crude product, which was further purified by silica gel chromatography (eluting with MeOH:DCM=1:3) to yield 4-[(2-methylpropan-2-yl)oxycarbonylamino]-1-(3,5,7-triazabicyclo[4.3.0]nona-2,4,8,10-tetraen-2-yl)piperidine-4-carboxylic acid as pale grey solid (105 g, 63%).

1H NMR (400.13 MHz, DMSO-$d_6$) δ 1.40 (9H, s), 1.88-1.95 (2H, m), 2.02-2.06 (2H, m), 3.44-3.51 (2H, m), 4.30 (2H, d), 6.60-6.61 (1H, m), 7.16-7.18 (1H, m), 7.29 (1H, s), 8.14 (1H, s), 11.68 (1H, s).

MS m/e MH+ 362.

Intermediate 2: (4-chlorophenyl)(cyclopropyl)methanone O-methyl Oxime

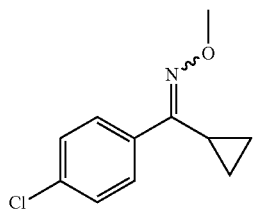

Methoxylamine hydrochloride (2.004 g) was added to (4-chlorophenyl)(cyclopropyl)methanone (2.71 g) in pyridine (60 mL) at 25° C. The resulting solution was stirred at 25° C. for 24 hours. The pyridine was removed in vacuo, and the residual solid extracted with ether. Filtration and evaporation of the solvent gave the crude (4-chlorophenyl)(cyclopropyl)methanone O-methyl oxime (2.75 g, 87%) as a yellow oil. This material was used directly in the next step without further purification.

MS m/e MH+ 210.

Intermediate 3: (4-chlorophenyl)(cyclopropyl)methanamine

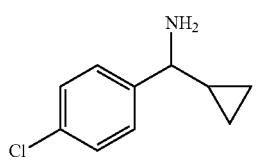 [SMILES: NC(c1ccc(Cl)cc1)C1CC1]

Borane tetrahydrofuran complex (1N in THF, 65.6 mL) was added to (4-O-methyl oxime (Intermediate 2) (2.75 g) in THF (100 mL) at 25° C. under nitrogen. The resulting solution was stirred at reflux for 3 hours, then cooled to 0° C. Water was carefully added, followed by aqueous NaOH (20%, 100 mL). The resulting mixture was stirred at reflux overnight, then allowed to cool to room temperature. The product was extracted into hexane, then dried over sodium sulfate, filtered and evaporated to afford (4-chlorophenyl)(cyclopropyl)methanamine as a clear oil (2.205 g, 93%).

$^1$H NMR (400.13 MHz, CDCl3) δ 0.24-0.29 (1H, m), 0.30-0.13 (1H, m), 0.45-0.50 (1H, m), 0.58-0.64 (1H, m), 1.01-1.09 (1H, m), 1.77 (2H, s), 3.20 (1H, d), 7.28-7.32 (2H, m), 7.33-7.36 (2H, m).

Intermediate 4: 2-amino-2-(4-chlorophenyl)acetonitrile

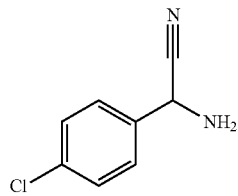 [SMILES: N#CC(N)c1ccc(Cl)cc1]

Lithium bis(trimethylsilyl)amide (42.7 mL) was added to 4-chlorobenzaldehyde (5 g) in THF (100 mL) at −40° C. under nitrogen. The resulting solution was warmed to room temperature and stirred for 4 hours. α-Hydroxyisobutyronitrile (acetone cyanohydrin, 6.50 mL) was then added, and the reaction mixture was stirred at 25° C. for a further 12 hours, then quenched with saturated NaHCO$_3$ (50 mL), extracted with EtOAc (3×100 mL), the organic layer was dried over MgSO$_4$, filtered and evaporated. The crude material was then purified by flash silica chromatography, elution gradient 0 to 100% EtOAc in isohexane. Pure fractions were evaporated to dryness to afford 2-amino-2-(4-chlorophenyl)acetonitrile as a colourless oil, which solidified on standing to give a white solid (3.40 g, 57.4%).

1H NMR (400.13 MHz, CDCl$_3$) δ 1.85 (2H, s), 4.82 (1H, s), 7.30-7.34 (2H, m), 7.39-7.43 (2H, m).

Intermediate 5: Tert-butyl 4-((4-chlorophenyl)(cyano)methylcarbamoyl)-1-(7H-pyrrolo[2,3-d]pyrimidin-4-yl)piperidin-4-ylcarbamate

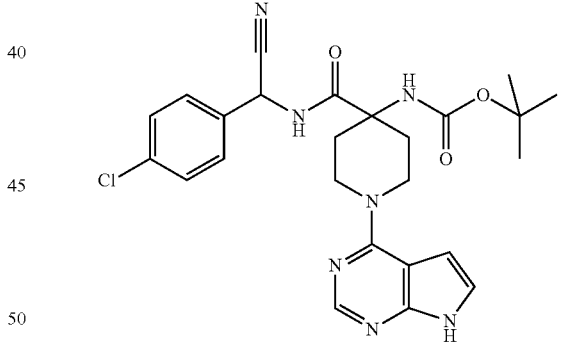

O-(7-Azabenzotriazol-1-yl)-N,N,N',N'-tetramethyluronium hexafluorophosphate (HATU, 0.456 g) was added to 4-(tert-butoxycarbonylamino)-1-(7H-pyrrolo[2,3-d]pyrimidin-4-yl)piperidine-4-carboxylic acid (Intermediate 1) (0.361 g), 2-amino-2-(4-chlorophenyl)acetonitrile (Intermediate 4) (0.167 g) and N-ethyldiisopropylamine (0.523 mL, 3.00 mmol) in DMA (5 mL) at 25° C. The resulting solution was stirred at 50° C. for 1 hour. The crude product was purified by ion exchange chromatography, using an SCX column. The desired product was eluted from the column using 7M NH$_3$/MeOH and pure fractions were evaporated to dryness to afford tert-butyl 4-((4-chlorophenyl)(cyano)methylcarbamoyl)-1-(7H-pyrrolo[2,3-d]pyrimidin-4-yl)piperidin-4-ylcarbamate as a white solid (0.343 g, 67.3%).

MS m/e MH+ 510.

Intermediate 6: Tert-butyl 4-(2-amino-1-(4-chlorophenyl)ethylcarbamoyl)-1-(7H-pyrrolo[2,3-d]pyrimidin-4-yl)piperidin-4-ylcarbamate

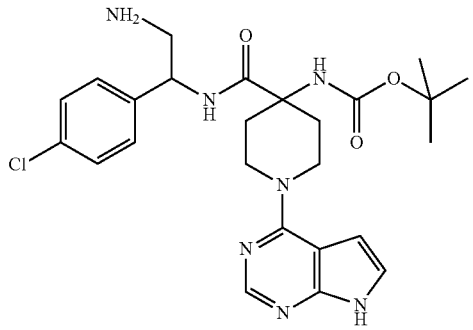 [SMILES: CC(C)(C)OC(=O)NC1(C(=O)NC(CN)c2ccc(Cl)cc2)CCN(c2ncnc3[nH]ccc23)CC1]

Raney™ nickel (0.257 g), was added to tert-butyl 4-((4-chlorophenyl)(cyano)methylcarbamoyl)-1-(7H-pyrrolo[2,3-d]pyrimidin-4-yl)piperidin-4-ylcarbamate (Intermediate 5) (0.510 g) in ethanol (30 mL). Ammonium hydroxide (0.039 mL) was added. This mixture was placed under a balloon of hydrogen and stirred for 48 hours. The reaction mixture was filtered through celite and the solvent evaporated to dryness. The reaction mixture was evaporated to dryness and redissolved in DCM (200 mL), and washed with water (125 mL). The organic layer was dried over MgSO$_4$, filtered and evaporated to afford crude product, tert-butyl 4-(2-amino-1-(4-chlorophenyl)ethylcarbamoyl)-1-(7H-pyrrolo[2,3-d]pyrimidin-4-yl)piperidin-4-ylcarbamate as a colourless gum (0.514 g, 100%). This material was used crude in the next step without further purification.

MS m/e MH$^+$ 514.

Intermediate 7: 1-tert-butyl 4-ethyl 4-cyanopiperidine-1,4-dicarboxylate

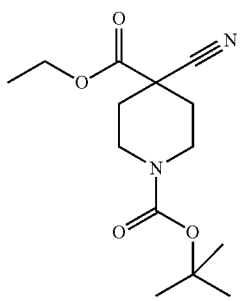 [SMILES: CCOC(=O)C1(C#N)CCN(C(=O)OC(C)(C)C)CC1]

A solution of LDA (107 ml, 214.01 mmol) was added to a stirred solution of tert-butyl 4-cyanopiperidine-1-carboxylate (30 g, 143 mmol) in THF (250 ml) at −78° C., under nitrogen. The resulting solution was stirred at −78° C. for 30 minutes. Ethyl chloroformate (16.37 ml, 171.2 mmol) was added. The resulting solution was stirred and allowed to warm to room temperature. The reaction mixture was quenched with saturated NaHCO$_3$ (250 ml), extracted with DCM, and the organic layer was washed with saturated brine (100 ml) then dried over MgSO$_4$, filtered and evaporated to afford the crude material as a orange oil. This material was purified by flash silica chromatography, elution gradient 10% EtOAc in isohexane. Pure fractions were evaporated to dryness to afford 1-tert-butyl 4-ethyl 4-cyanopiperidine-1,4-dicarboxylate (20.8 g, 51.6%) as a yellow oil.

1H NMR (400.13 MHz, CDCl$_3$) δ 1.33 (3H, t), 1.46 (9H, s), 1.96-2.00 (2H, m), 2.04-2.08 (2H, m), 3.12 (2H, s), 4.09-4.14 (2H, m), 4.29 (2H, q).

Intermediate 8: 1-tert-butyl 4-ethyl 4-(aminomethyl)piperidine-1,4-dicarboxylate

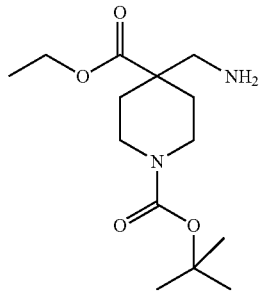 [SMILES: CCOC(=O)C1(CN)CCN(C(=O)OC(C)(C)C)CC1]

Platinum(IV) oxide (0.724 g, 3.19 mmol) and 1-tert-butyl 4-ethyl 4-cyanopiperidine-1,4-dicarboxylate (Intermediate 7) (9 g, 31.9 mmol) in acetic acid (100 ml) were stirred under an atmosphere of hydrogen at 5 bar and 25° C. for 1 day. The crude product was filtered through celite and the filtrate purified by ion exchange chromatography, using an SCX column. The desired product was eluted from the column using 7M NH$_3$/MeOH and pure fractions were evaporated to dryness to afford 1-tert-butyl 4-ethyl 4-(aminomethyl)piperidine-1,4-dicarboxylate (7.59 g, 83%) as a colourless oil.

1H NMR (400.13 MHz, CDCl3) δ 1.27-1.28 (3H, m), 1.30-1.37 (2H, m), 1.41 (2H, s), 1.45 (9H, s), 2.10 (2H, d), 2.78 (2H, s), 2.91-2.97 (2H, m), 3.89 (2H, s), 4.21 (2H, q).

Intermediate 9: Ethyl 4-(aminomethyl)piperidine-4-carboxylate

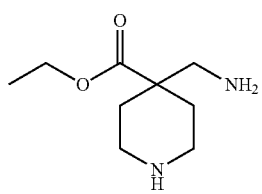

Hydrogen chloride 4M in dioxane (33.2 ml, 132.7 mmol) was added to 1-tert-butyl 4-ethyl 4-(aminomethyl)piperidine-1,4-dicarboxylate (Intermediate 8) (7.6 g, 26.5 mmol) in dioxane (35 ml). The resulting solution was stirred at 20° C. for 3 hours. The crude product was purified by ion exchange chromatography, using an SCX column. The desired product was eluted from the column using 7M NH$_3$/MeOH and pure fractions were evaporated to dryness to afford ethyl 4-(aminomethyl)piperidine-4-carboxylate (3.34 g, 67.6%) as a yellow liquid.

1H NMR (400.13 MHz, CDCl3) δ 1.23-1.30 (3H, m), 1.26-1.37 (2H, m), 2.12 (2H, d), 2.65-2.72 (2H, m), 2.77 (2H, s), 2.94-2.99 (2H, m), 4.21 (2H, q).

Intermediate 10: Ethyl 4-(aminomethyl)-1-(7H-pyrrolo[2,3-d]pyrimidin-4-yl)piperidine-4-carboxylate

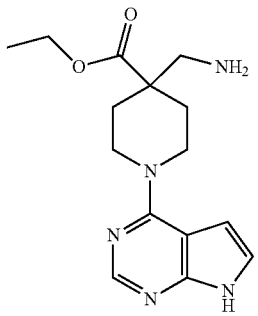 [SMILES: CCOC(=O)C1(CN)CCN(c2ncnc3[nH]ccc23)CC1]

N-Ethyldiisopropylamine (3.70 ml, 21.26 mmol) was added to ethyl 4-(aminomethyl)piperidine-4-carboxylate (Intermediate 9) (3.3 g, 17.7 mmol) and 4-chloro-7H-pyrrolo[2,3-d]pyrimidine (2.72 g, 17.72 mmol) in DMA (35 ml). The resulting solution was stirred at 60° C. for 18 hours. The crude product was purified by ion exchange chromatography, using an SCX column. The desired product was eluted from the column using 7M $NH_3$/MeOH and pure fractions were evaporated to dryness to afford ethyl 4-(aminomethyl)-1-(7H-pyrrolo[2,3-d]pyrimidin-4-yl)piperidine-4-carboxylate (5.08 g, 95%) as a beige solid.

1H NMR (400.13 MHz, DMSO-$d_6$) δ 1.22 (3H, t), 1.44-1.51 (2H, m), 2.04-2.07 (2H, m), 2.67 (2H, d), 3.23-3.30 (2H, m), 4.15 (2H, q), 4.39-4.44 (2H, m), 6.59 (1H, t), 7.16-7.17 (1H, m), 8.12 (1H, s), 11.67 (1H, s)

MS m/e MH+ 304.

Intermediate 11: Ethyl 4-((tert-butoxycarbonylamino)methyl)-1-(7H-pyrrolo[2,3-d]pyrimidin-4-yl)piperidine-4-carboxylate

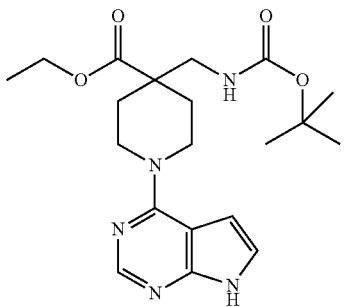 [SMILES: CCOC(=O)C1(CNC(=O)OC(C)(C)C)CCN(c2ncnc3[nH]ccc23)CC1]

Di-tert-butyl dicarbonate (470 mg, 2.15 mmol) was added to ethyl 4-(aminomethyl)-1-(7H-pyrrolo[2,3-d]pyrimidin-4-yl)piperidine-4-carboxylate (Intermediate 10) (653 mg, 2.15 mmol) and triethylamine (0.300 ml, 2.15 mmol) in DCM (10 ml). The resulting suspension was stirred at ambient temperature for 2 hours. The reaction mixture was diluted with DCM (50 mL), and washed sequentially with water (50 mL) and saturated brine (50 mL). The organic layer was dried over MgSO4, filtered and evaporated. The crude product was purified by flash silica chromatography, elution gradient 20 to 100% EtOAc in isohexane. Pure fractions were evaporated to dryness to afford ethyl 4-((tert-butoxycarbonylamino)methyl)-1-(7H-pyrrolo[2,3-d]pyrimidin-4-yl)piperidine-4-carboxylate (468 mg, 53.9%) as a colourless oil which solidified on standing.

1H NMR (400.13 MHz, DMSO-d6) δ 1.22 (3H, t), 1.36-1.38 (9H, m), 1.42-1.49 (2H, m), 2.05 (2H, d), 3.13 (2H, d), 3.20 (2H, t), 4.09-4.14 (2H, m), 4.45 (2H, d), 6.58 (1H, d), 6.94 (1H, t), 7.16 (1H, d), 8.13 (1H, d), 11.65 (1H, s).

MS m/e MH+ 404.

Intermediate 12: 4-((tert-butoxycarbonylamino)methyl)-1-(7H-pyrrolo[2,3-d]pyrimidin-4-yl)piperidine-4-carboxylic acid

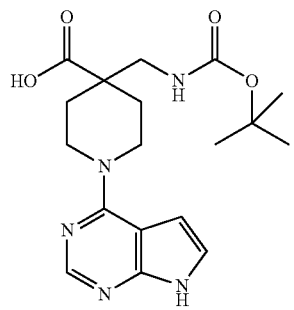 [SMILES: CC(C)(C)OC(=O)NCC1(C(=O)O)CCN(c2ncnc3[nH]ccc23)CC1]

Lithium hydroxide monohydrate (0.556 g, 13.26 mmol) was added to ethyl 4-((tert-butoxycarbonylamino)methyl)-1-(7H-pyrrolo[2,3-d]pyrimidin-4-yl)piperidine-4-carboxylate (Intermediate 11) (1.07 g, 2.65 mmol) in water (6.25 ml), THF (25 ml) and ethanol (25.00 ml). The resulting solution was stirred at 20° C. for 1 day. The reaction mixture was diluted with EtOAc (20 mL) and washed with water (20 mL). The aqueous was adjusted to pH5 with 1M citric acid solution then extracted with EtOAc (3×50 mL). The organic extracts were washed with saturated brine (25 mL) then dried over MgSO4, filtered and evaporated to afford desired product 4-((tert-butoxycarbonylamino)methyl)-1-(7H-pyrrolo[2,3-d]pyrimidin-4-yl)piperidine-4-carboxylic acid (0.628 g, 63.1%) as a white foam.

1H NMR (400.13 MHz, DMSO-d6) δ 1.36 (9H, s), 1.44-1.51 (2H, m), 1.99-2.04 (2H, m), 3.14 (2H, d), 3.25 (2H, s), 4.43-4.46 (2H, m), 6.64 (1H, s), 6.84 (1H, t), 7.21 (1H, s), 8.16 (1H, s), 11.82 (1H, s)

MS m/e MH+ 376.

Intermediate 13: (s)-tert-butyl (4-(1-(4-chlorophenyl)ethylcarbamoyl)-1-(7H-pyrrolo[2,3-d]pyrimidin-4-yl)piperidin-4-yl)methylcarbamate

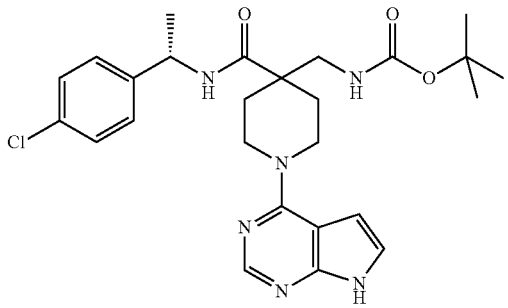 [SMILES: C[C@H](NC(=O)C1(CNC(=O)OC(C)(C)C)CCN(c2ncnc3[nH]ccc23)CC1)c1ccc(Cl)cc1]

HATU (0.251 g, 0.66 mmol) was added in one portion to 4-((tert-butoxycarbonylamino)methyl)-1-(7H-pyrrolo[2,3-d]pyrimidin-4-yl)piperidine-4-carboxylic acid (Intermediate 12) (0.225 g, 0.6 mmol), (S)-1-(4-chlorophenyl)ethanamine (0.093 g, 0.60 mmol) and DIPEA (0.314 mL, 1.80 mmol) in DMA (10 mL) at 25° C. under nitrogen. The resulting solution was stirred at 60° C. for 4 hours. The crude product was purified by ion exchange chromatography, using an SCX column. The desired product was eluted from the column using methanol. Residual HATU was removed by passing the methanol solution through a silica-supported carbonate column. The crude product thus obtained was evaporated to dryness to afford (S)-tert-butyl (4-(1-(4-chlorophenyl)ethylcarbamoyl)-1-(7H-pyrrolo[2,3-d]pyrimidin-4-yl)piperidin-4-yl)methylcarbamate (0.257 g, 83%) as a colourless gum. This material was used directly in the next step without further purification.

1H NMR (400.13 MHz, DMSO-d6) δ 1.37 (9H, s), 1.38 (3H, d), 1.48-1.55 (2H, m), 2.17 (2H, d), 3.12-3.36 (4H, m), 4.28-4.34 (2H, m), 4.95-5.03 (1H, m), 6.65 (2H, s), 7.23-7.24 (1H, m), 7.35 (4H, s), 8.10 (1H, d), 8.18 (1H, s), 11.94 (1H, s).

MS m/e MH+ 513.

Intermediate 14: Ethyl 4-(4-chlorophenyl)-4-(methoxyimino)butanoate

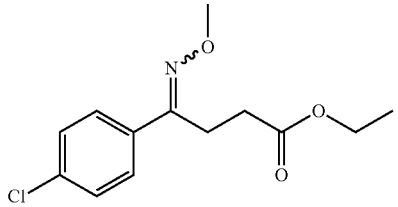 [SMILES: CCOC(=O)CCC(=NOC)c1ccc(Cl)cc1]

4-(4-Chlorophenyl)-4-oxobutanoic acid (2.0 g, 9.41 mmol), methoxylamine hydrochloride (0.982 g, 11.76 mmol) and sodium carbonate (0.472 ml, 11.29 mmol) in ethanol (30 ml) were stirred and heated at 80° C. for 4 hours. The resulting mixture was allowed to cool to room temperature and filtered. The filtrate was concentrated by evaporation then purified by flash silica chromatography, eluting with 15% TBME in isohexane. Pure fractions were evaporated to dryness to afford ethyl 4-(4-chlorophenyl)-4-(methoxyimino)butanoate (1.790 g, 70.6%) as a colourless oil.

1H NMR (399.902 MHz, CDCl3) δ 1.23 (3H, t), 2.53 (2H, t), 3.01 (2H, t), 3.98 (3H, s), 4.11 (2H, q), 7.33 (2H, d), 7.58 (2H, d).

MS m/e MH+ 270.

Intermediate 15: 4-(4-chlorophenyl)-4-(methoxyimino)butanoic acid

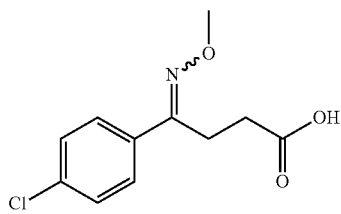 [SMILES: CON=C(CCC(=O)O)c1ccc(Cl)cc1]

Lithium hydroxide (0.632 g, 26.40 mmol) was added in one portion at 20° C. to a solution of ethyl 4-(4-chlorophenyl)-4-(methoxyimino)butanoate (Intermediate 14) (1.78 g, 6.60 mmol) in THF (30 ml) and water (20 ml). The resulting solution was stirred at room temperature for 6 hours then acidified with dilute HCl and extracted with TBME (2×). The combined extracts were washed with brine, dried over MgSO4 and evaporated to give 4-(4-chlorophenyl)-4-(methoxyimino)butanoic acid (1.520 g, 95%) as a colourless solid.

1H NMR (399.902 MHz, CDCl3) δ 2.61 (2H, t), 3.01 (2H, t), 3.99 (3H, s), 7.34 (2H, d), 7.58 (2H, d).

Intermediate 16: 4-amino-4-(4-chlorophenyl)butan-1-ol

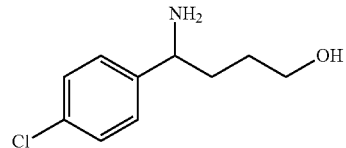 [SMILES: NC(CCCO)c1ccc(Cl)cc1]

4-(4-Chlorophenyl)-4-(methoxyimino)butanoic acid (Intermediate 15) (6.28 g, 26.00 mmol) in tetrahydrofuran (8 ml) was cooled, under an atmosphere of N2, in an ice-methanol bath then treated dropwise with borane-tetrahydrofuran complex (1.0M in THF) (26 ml, 26.00 mmol) over a period of 20 minutes. The resulting solution was allowed to warm to room temperature, stirred for 1 hour then heated at reflux for a further 6 hours. After cooling in ice-water the mixture was treated with water (6 ml) dropwise with stirring over 10 minutes. The mixture was again allowed to warm to room temperature and stirred for 2 hours before evaporating the bulk of the solvent. The residue was then cooled in ice-water and 50% NaOH(aq.) (6 ml) added dropwise with stirring. The resulting mixture was stirred and heated at 90° C. for 4 hours then cooled to room temperature and extracted with Et2O (3×). The combined extracts were washed with water followed by brine, dried over MgSO4 and evaporated to give 4-amino-4-(4-chlorophenyl)butan-1-ol (1.100 g, 21.2%) as a colourless, viscous oil which was used without further purification.

1H NMR (399.902 MHz, CDCl3) δ 1.58-1.84 (4H, m), 2.39 (3H, br. s), 3.57-3.67 (2H, m), 3.88-3.91 (1H, m), 7.23 (2H, d), 7.30 (2H, d).

MS m/e MH+ 200.

Intermediate 17: Tert-butyl 4-(1-(4-chlorophenyl)-4-hydroxybutylcarbamoyl)-1-(7H-pyrrolo[2,3-d]pyrimidin-4-yl)piperidin-4-ylcarbamate

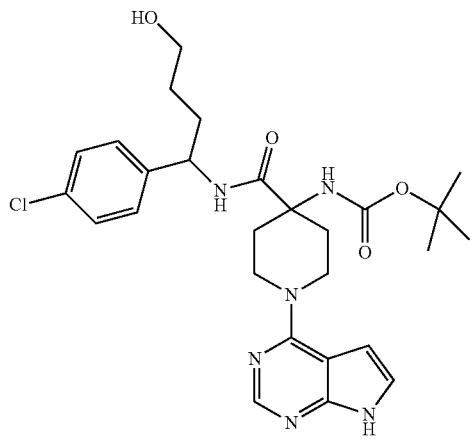 [SMILES: CC(C)(C)OC(=O)NC1(C(=O)NC(CCCO)c2ccc(Cl)cc2)CCN(c2ncnc3[nH]ccc23)CC1]

O-(7-Azabenzotriazol-1-yl)-N,N,N',N'-tetramethyluronium hexafluorophosphate (166 mg, 0.44 mmol) was added portionwise to 4-(tert-butoxycarbonylamino)-1-(7H-pyrrolo[2,3-d]pyrimidin-4-yl)piperidine-4-carboxylic acid (Intermediate 1) (150 mg, 0.42 mmol), 4-amino-4-(4-chlorophenyl)butan-1-ol (Intermediate 16) (83 mg, 0.42 mmol) and N-ethyldiisopropylamine (0.087 ml, 0.50 mmol) in DMF (2.0 mL) at 20° C. The resulting solution was stirred at 20° C. for 3 hours then quenched in water (10 ml) to give a pale yellow ppt. The precipitate was collected by filtration, washed with water and dried under vacuum to afford tert-butyl 4-(1-(4-chlorophenyl)-4-hydroxybutylcarbamoyl)-1-(7H-pyrrolo[2,3-d]pyrimidin-4-yl)piperidin-4-ylcarbamate (152 mg, 67.4%) as a cream solid, which was used without further purification.

1H NMR (399.902 MHz, DMSO) δ 1.40 (11H, s), 1.69-1.74 (2H, m), 1.93-2.09 (4H, m), 3.38-3.43 (2H, m), 3.51-3.61 (2H, m), 4.19-4.27 (2H, m), 4.38 (1H, br s), 4.76 (1H, q), 6.65 (1H, m), 6.95 (1H, s), 7.20 (1H, m), 7.33 (4H, s), 7.89 (1H, d), 11.78 (1H, s).

MS m/e MH+ 543.

Intermediate 18: Tert-butyl 4-(1-(4-chlorophenyl)-2-hydroxyethylcarbamoyl)-1-(7H-pyrrolo[2,3-d]pyrimidin-4-yl)piperidin-4-ylcarbamate

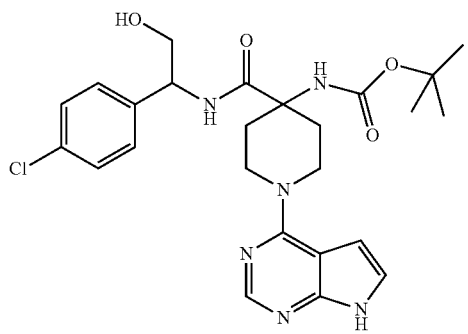 [SMILES: CC(C)(C)OC(=O)NC1(C(=O)NC(CO)c2ccc(Cl)cc2)CCN(c2ncnc3[nH]ccc23)CC1]

O-(7-Azabenzotriazol-1-yl)-N,N,N',N'-tetramethyluronium hexafluorophosphate (148 mg, 0.39 mmol) was added in one portion to a stirred solution of 4-(tert-butoxycarbonylamino)-1-(7H-pyrrolo[2,3-d]pyrimidin-4-yl)piperidine-4-carboxylic acid (Intermediate 1) (134 mg, 0.37 mmol) and N-ethyldiisopropylamine (0.077 mL, 0.44 mmol) in NMP (3 mL). The mixture was treated with 2-amino-2-(4-chlorophenyl)ethanol (70 mg, 0.41 mmol) (CAS™ no. 179811-64-4, see US2006/0004045 for preparation). The dark solution was stirred for 16 hours at room temperature. The mixture was partitioned between ethyl acetate and aqueous sodium bicarbonate solution. The organic layer was washed twice with water and then brine. The organic solution was dried over magnesium sulfate, filtered and evaporated. The residue was purified by flash silica chromatography on silica using gradient elution (1% methanol/DCM to 15% methanol/DCM). Product containing fractions were combined to give tert-butyl 4-(1-(4-chlorophenyl)-2-hydroxyethylcarbamoyl)-1-(7H-pyrrolo[2,3-d]pyrimidin-4-yl)piperidin-4-ylcarbamate (152 mg, 80%) as colourless solid.

1H NMR (399.9 MHz, DMSO-d6) δ 1.42 (9H, s), 1.93-2.12 (4H, m), 3.45-3.63 (4H, m), 4.22-4.33 (2H, m), 4.75-4.88 (2H, m), 6.59-6.61 (1H, m), 7.14-7.24 (2H, m), 7.33 (4H, s), 7.76 (1H, d), 8.14 (1H, s), 11.65 (1H, br, s) m/z (ESI+) (M+H)+=515; HPLC $t_R$=1.99 min.

Intermediate 19: (s)-methyl 3-(tert-butoxycarbonylamino)-3-(4-chlorophenyl)propanoate

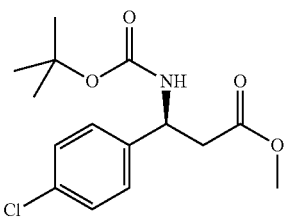 [SMILES: COC(=O)C[C@H](NC(=O)OC(C)(C)C)c1ccc(Cl)cc1]

Iodomethane (1.038 mL, 16.68 mmol) was added in one portion to (S)-3-(tert-butoxycarbonylamino)-3-(4-chlorophenyl)propanoic acid (1 g, 3.34 mmol) and potassium carbonate (0.922 g, 6.67 mmol) in DMF (15 mL). The resulting suspension was stirred at 80° C. for 24 hours. The reaction mixture was concentrated and diluted with EtOAc (50 mL) with water (50 mL). The organic layer was dried over MgSO4, filtered and evaporated to afford (S)-methyl 3-(tert-butoxycarbonylamino)-3-(4-chlorophenyl)propanoate (1.340 g, 128%) as a orange solid. 1H NMR (399.9 MHz, DMSO-d6) δ 1.36 (9H, s), 2.71-2.74 (1H, m), 2.74-2.80 (1H, m), 3.57 (3H, s), 4.91 (1H, d), 7.33 (2H, d), 7.39 (2H, d), 7.49 (1H, d). m/z (ESI–) (M–H)–=312; HPLC tR=2.57 min.

Intermediate 20: (s)-methyl 3-amino-3-(4-chlorophenyl)propanoate (hydrochloride)

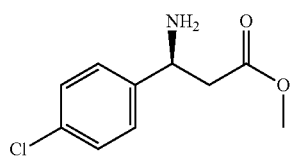

Hydrochloric acid (4.0M in 1,4 Dioxane) (4.18 mL, 16.73 mmol) was added in one portion to (S)-methyl 3-(tert-butoxycarbonylamino)-3-(4-chlorophenyl)propanoate (Intermediate 19) (1.05 g, 3.35 mmol) in DCM (20 mL) at 20° C. The resulting solution was stirred at 20° C. for 5 hours. The reaction mixture was evaporated to give (S)-methyl 3-amino-3-(4-chlorophenyl)propanoate (hydrochloride) (0.850 g, 102%) as a white solid. 1H NMR (399.9 MHz, DMSO-d6) δ 2.98-3.04 (1H, m), 3.16-3.21 (1H, m), 3.58 (3H, s), 4.62-4.66 (1H, m), 7.50-7.52 (2H, m), 7.57-7.59 (2H, m), 8.66 (3H, s). m/z (ESI+) (M+H)+=214; HPLC tR=1.71 min.

Intermediate 21: (s)-methyl 3-(4-(tert-butoxycarbonylamino)-1-(7H-pyrrolo[2,3-d]pyrimidin-4-yl)piperidine-4-carboxamido)-3-(4-chlorophenyl)propanoate

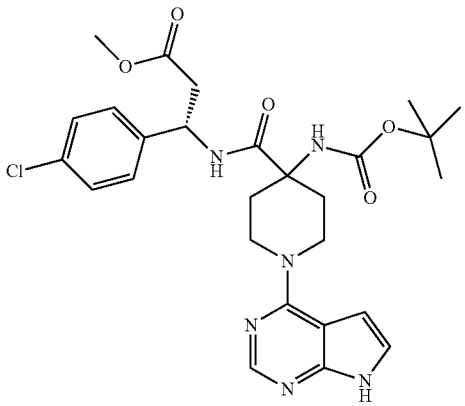 [SMILES: COC(=O)C[C@H](NC(=O)C1(NC(=O)OC(C)(C)C)CCN(c2ncnc3[nH]ccc23)CC1)c1ccc(Cl)cc1]

O-(7-azabenzotriazol-1-yl)-N,N,N',N'-tetramethyluronium hexafluoro-phosphate (1.157 g, 3.04 mmol) was added in one portion to 4-(tert-butoxycarbonylamino)-1-(7H-pyrrolo[2,3-d]pyrimidin-4-yl)piperidine-4-carboxylic acid (Intermediate 1) (1 g, 2.77 mmol) and N,N-diisopropylethylamine (1.006 mL, 6.09 mmol) in NMP (10 mL) at 20° C. The resulting solution was stirred at 20° C. for 5 minutes. (S)-methyl 3-amino-3-(4-chlorophenyl)propanoate (hydrochloride) (Intermediate 20) (0.692 g, 2.77 mmol) was then added to the solution and stirred at room temperature for 3 hours. The reaction mixture was diluted with EtOAc (100 mL), and washed sequentially with water (2×50 mL) and brine (50 mL). The organic layer was dried over MgSO$_4$, filtered and evaporated to afford crude product. The crude product was purified by flash silica chromatography, elution gradient 0 to 5% MeOH in DCM. Pure fractions were evaporated to dryness to afford (S)-methyl 3-(4-(tert-butoxycarbonylamino)-1-(7H-pyrrolo[2,3-d]pyrimidin-4-yl)piperidine-4-carboxamido)-3-(4-chlorophenyl)propanoate (1.27 g, 82%) as a white solid. 1H NMR (399.9 MHz, DMSO-d6) δ 1.40 (9H, s), 1.99 (2H, s), 2.04-2.07 (2H, m), 2.79-2.84 (2H, m), 3.56 (3H, s), 3.60-3.66 (1H, m), 3.67-3.70 (1H, m), 4.20 (2H, t), 5.20-5.26 (1H, m), 6.73 (1H, d), 7.13 (1H, s), 7.27 (1H, t), 7.35 (4H, q), 8.14 (1H, d), 8.21 (1H, s), 11.98 (1H, s). m/z (ESI+) (M+H)+=557; HPLC tR=2.12 min.

Intermediate 22: (s)-tert-butyl 4-(1-(4-chlorophenyl)-3-hydroxypropylcarbamoyl)-1-(7H-pyrrolo[2,3-d]pyrimidin-4-yl)piperidin-4-ylcarbamate

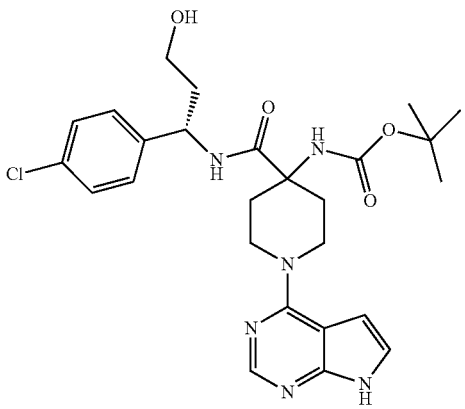 [SMILES: CC(C)(C)OC(=O)NC1(C(=O)N[C@@H](CCO)c2ccc(Cl)cc2)CCN(c2ncnc3[nH]ccc23)CC1]

LiAlH$_4$ (2.280 mL, 2.28 mmol) was added dropwise to (S)-methyl 3-(4-(tert-butoxycarbonylamino)-1-(7H-pyrrolo[2,3-d]pyrimidin-4-yl)piperidine-4-carboxamido)-3-(4-chlorophenyl)propanoate (Intermediate 21) (1.27 g, 2.28 mmol) in THF (70 mL) cooled to 0° C. under nitrogen. The resulting solution was stirred at 20° C. for 1 hour. The reaction mixture was quenched with sodium hydroxide (2M) (2 mL) and water (1 mL). The solution was filtered and was diluted with EtOAc (200 mL), and washed sequentially with water (100 mL), water (100 mL), and saturated brine (100 mL). The organic layer was dried over MgSO$_4$, filtered and evaporated to afford (S)-tert-butyl 4-(1-(4-chlorophenyl)-3-hydroxypropylcarbamoyl)-1-(7H-pyrrolo[2,3-d]pyrimidin-4-yl)piperidin-4-ylcarbamate (1.04 g, 86%) as a white solid. M/z (ESI+) (M+H)+=529; HPLC tR=2.00 min.

Intermediate 23: 2-(tert-butoxycarbonylamino)-2-(4-chlorophenyl)ethyl methanesulfonate

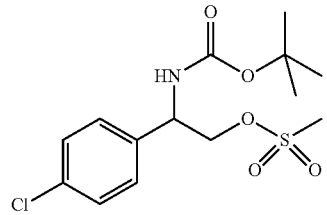 [SMILES: CC(C)(C)OC(=O)NC(COS(C)(=O)=O)c1ccc(Cl)cc1]

Methanesulfonyl chloride (1.451 mL, 18.74 mmol) was added to tert-butyl 1-(4-chlorophenyl)-2-hydroxyethylcarbamate (4.63 g, 17.04 mmol) and N,N-diisopropylethylamine (6.23 mL, 35.78 mmol) in DCM (40 mL) cooled to 0° C. over a period of 5 minutes under nitrogen. The resulting solution was stirred at 20° C. for 2 hours. The reaction mixture was diluted with DCM (100 mL) and washed sequentially with water (100 mL). The organic layer was dried over MgSO$_4$, filtered and evaporated to afford crude product. The crude product was purified by flash silica chromatography, elution gradient 0 to 10% EtOAc in DCM. Pure fractions were evaporated to dryness to afford 2-(tert-butoxycarbonylamino)-2-(4-chlorophenyl)ethyl methanesulfonate (3.12 g, 52.3%) as a white solid. 1H NMR (399.9 MHz, DMSO-d6) δ 1.39 (9H, s), 3.17 (3H, s), 4.22-4.28 (2H, m), 4.90 (1H, d), 7.40-7.46 (4H, m), 7.68 (1H, d). m/z (ESI+) (M−H)−=348; HPLC tR=2.32 min.

The tert-butyl 1-(4-chlorophenyl)-2-hydroxyethylcarbamate used in the above reaction was prepared as follows. 2-Amino-2-(4-chlorophenyl)acetic acid (12 g, 64.65 mmol) was stirred in THF (200 mL) and sodium borohydride (5.82 g, 153.87 mmol) was added in portions to the stirred mixture under nitrogen. A solution of iodine (16.41 g, 64.65 mmol) in THF (20 mL) was added dropwise maintaining the temperature below 15° C. using an ice bath. The resulting mixture was warmed to room temperature and stirred at reflux overnight. The reaction was quenched by the addition of methanol (40 mL). A portion of this solution was removed (50 mL) and partitioned between ethyl acetate and water. The organic layer was concentrated under reduced pressure. The residue was purified by MPLC on silica using gradient elution (0 to 10% methanol/DCM). The desired product, 2-amino-2-(4-chlorophenyl)ethanol (1.318 g, 11.88%), was thus isolated as a colourless solid.

1H NMR (399.9 MHz, CDCl3) δ 2.00 (3H, br, s), 3.48-3.58 (1H, m), 3.68-3.76 (1H, m), 4.02-4.08 (1H, m), 7.23-7.39 (4H, m). m/z (ESI−) (M−H)−=284, 286; HPLC tR=2.20 min.

The remainder of the solution was treated with triethylamine (18.02 mL, 129.31 mmol) and di-tert-butyl dicarbonate (14.11 g, 64.65 mmol). The mixture was stirred for 2 hours at room temperature before being partitioned between ethyl acetate and water. The organic layer was dried with magnesium sulfate, filtered, and concentrated under reduced pressure. The residue was purified by MPLC on silica using gradient elution (10% ethyl acetate/DCM to 50% ethyl acetate/DCM). The desired product, tert-butyl 1-(4-chlorophenyl)-2-hydroxyethylcarbamate (7.91 g, 45.0%), was thus isolated as a colourless solid. Impure fractions were repurified by MPLC to give a second crop (2.41 g, 14%).

1H NMR (399.9 MHz, DMSO-d6) δ 1.37 (9H, s), 3.41-3.52 (2H, m), 4.42-4.58 (1H, m), 4.79 (1H, t), 7.23 (1H, d), 7.31 (2H, d), 7.37 (2H, d).

Intermediate 24: Tert-butyl 1-(4-chlorophenyl)-2-cyanoethylcarbamate

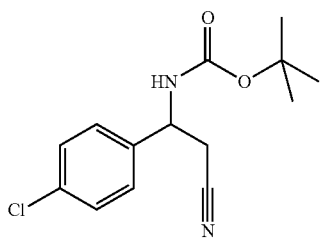 [SMILES: CC(C)(C)OC(=O)NC(CC#N)c1ccc(Cl)cc1]

Sodium cyanide (105 mg, 2.14 mmol) was added to 2-(tert-butoxycarbonylamino)-2-(4-chlorophenyl)ethyl methanesulfonate (Intermediate 23) (300 mg, 0.86 mmol) in DMF (5 mL) at 20° C. The resulting suspension was stirred at 80° C. for 3 hours. The reaction mixture was evaporated to dryness and redissolved in water (10 mL), and washed sequentially with DCM 3× (10 mL). The organic layer was dried over MgSO$_4$, filtered and evaporated to afford crude product. The crude product was purified by flash silica chromatography, elution gradient 0 to 25% EtOAc in isohexane. Pure fractions were evaporated to dryness to afford tert-butyl 1-(4-chlorophenyl)-2-cyanoethylcarbamate (209 mg, 87%) as a white solid. 1H NMR (399.9 MHz, DMSO-d6) δ1.38-1.42 (9H, s), 2.82-2.89 (2H, m), 4.89 (1H, d), 7.38-7.45 (4H, m), 7.76 (1H, d). m/z (ESI+) (M−H)−=279; HPLC tR=2.42 min.

Intermediate 25: Tert-butyl 3-amino-1-(4-chlorophenyl)propylcarbamate

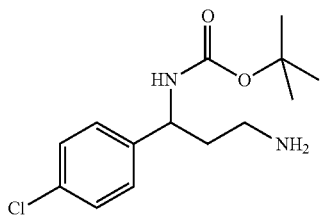 [SMILES: CC(C)(C)OC(=O)NC(CCN)c1ccc(Cl)cc1]

Lithium aluminium hydride (0.712 mL, 0.71 mmol) was added dropwise to tert-butyl 1-(4-chlorophenyl)-2-cyanoethylcarbamate (Intermediate 24) (200 mg, 0.71 mmol) in THF (4 mL) at 20° C. under nitrogen. The resulting solution was stirred at 20° C. for 2 hours. The reaction mixture was quenched with NaOH (1M) (1 mL) and the solution was filtered. The solution was diluted with EtOAc (20 mL), and washed with water 2× (10 mL). The organic layer was dried over MgSO$_4$, filtered and evaporated to afford tert-butyl 3-amino-1-(4-chlorophenyl)propylcarbamate (203 mg, 100%) as a gum. m/z (ESI+) (M+H)+=285; HPLC tR=2.33 min.

Intermediate 26: Tert-butyl 3-acetamido-1-(4-chlorophenyl)propylcarbamate

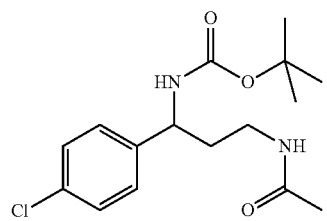 [SMILES: CC(=O)NCCC(NC(=O)OC(C)(C)C)c1ccc(Cl)cc1]

Acetic anhydride (0.084 mL, 0.89 mmol) was added dropwise to tert-butyl 3-amino-1-(4-chlorophenyl)propylcarbamate (Intermediate 25) (203 mg, 0.71 mmol) and N,N-diisopropylethylamine (0.248 mL, 1.43 mmol) in DCM (5 mL) at 20° C. The resulting solution was stirred at 20° C. for 16 hours. The reaction mixture was quenched with NaHCO$_3$ (2M) (10 mL) and water (10 mL) and extracted with DCM (20 mL). The organic layer was dried over MgSO$_4$, filtered and evaporated to afford crude product. The crude product was purified by flash silica chromatography, elution gradient 0 to 2.5% MeOH in DCM. Pure fractions were evaporated to dryness to afford tert-butyl 3-acetamido-1-(4-chlorophenyl)propylcarbamate (142 mg, 61.0%) as a white solid. 1H NMR (399.9 MHz, DMSO-d6) δ1.36 (9H, s), 1.67-1.82 (2H, m), 1.79 (3H, s), 2.97 (2H, q), 4.50 (1H, d), 7.32 (2H, d), 7.38 (2H, d), 7.43-7.45 (1H, m), 7.79 (1H, s). m/z (ESI+) (M+H)+=327; HPLC tR=2.03 min.

Intermediate 27: N-(3-amino-3-(4-chlorophenyl)propyl)acetamide

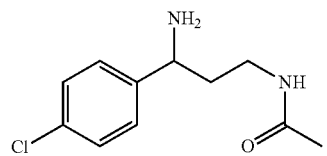

tert-Butyl 3-acetamido-1-(4-chlorophenyl)propylcarbamate (Intermediate 26) (142 mg, 0.43 mmol) was added to TFA (2 mL) at 20° C. The resulting solution was stirred at 20° C. for 40 minutes. The reaction mixture was evaporated and purified by ion exchange chromatography using an SCX column. The desired product was eluted from the column using 7M NH$_3$/MeOH and pure fractions were evaporated to dryness to afford N-(3-amino-3-(4-chlorophenyl)propyl)acetamide (39.0 mg, 39.6%) as a colourless gum. m/z (ESI+) (M+H)+=227; HPLC tR=1.32 min.

Intermediate 28: Tert-butyl 4-(3-acetamido-1-(4-chlorophenyl)propylcarbamoyl)-1-(7H-pyrrolo[2,3-d]pyrimidin-4-yl)piperidin-4-ylcarbamate

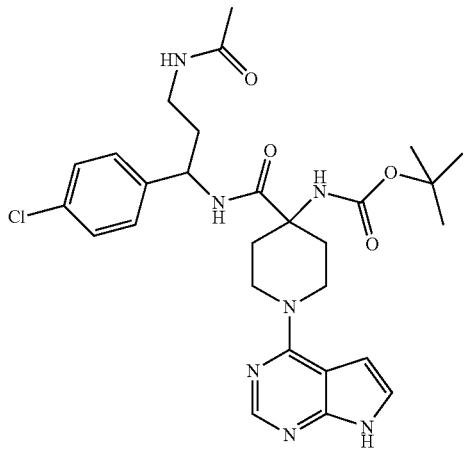 [SMILES: CC(=O)NCCC(NC(=O)C1(NC(=O)OC(C)(C)C)CCN(c2ncnc3[nH]ccc23)CC1)c1ccc(Cl)cc1]

O-(7-azabenzotriazol-1-yl)-N,N,N',N'-tetramethyluronium hexafluoro-phosphate (98 mg, 0.26 mmol) was added in one portion to 4-(tert-butoxycarbonylamino)-1-(7H-pyrrolo[2,3-d]pyrimidin-4-yl)piperidine-4-carboxylic acid (Intermediate 1) (62.2 mg, 0.17 mmol) and N,N-diisopropylethylamine (0.085 mL, 0.52 mmol) in NMP (2 mL) at 20° C. under nitrogen. The resulting solution was stirred at 20° C. for 5 minutes. N-(3-amino-3-(4-chlorophenyl)propyl)acetamide (Intermediate 27) (39 mg, 0.17 mmol) in NMP (2 mL) was then added to the reaction and stirred for 1 hour. The reaction mixture was concentrated and diluted with EtOAc (20 mL) and washed with water (20 mL). The organic layer was dried over MgSO₄, filtered and evaporated to afford tert-butyl 4-(3-acetamido-1-(4-chlorophenyl)propylcarbamoyl)-1-(7H-pyrrolo[2,3-d]pyrimidin-4-yl)piperidin-4-ylcarbamate (1.04 g, 86%) as a white solid. m/z (ESI+) (M+H)+= 570; HPLC tR=1.95 min.

Intermediate 29:
3-amino-3-(4-chlorophenyl)propan-1-ol

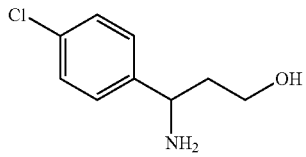 [SMILES: NC(CCO)c1ccc(Cl)cc1]

Borane-tetrahydrofuran complex (94.0 mL, 93.92 mmol) was added dropwise to a stirred suspension of 3-amino-3-(4-chlorophenyl)propionic acid (2.50 g, 12.52 mmol) in THF (75 mL) at 0° C. over a period of 20 minutes under nitrogen. The resulting suspension was stirred at 0° C. for 30 minutes then at 22° C. for 5 hours. The reaction mixture was added portionwise to methanol (500 mL). The mixture was concentrated, redissolved in methanol (250 mL) and reconcentrated (this process was repeated three times). The residue was dissolved in DCM (200 mL) and washed with 1N NaOH (150 mL). The aqueous layer was extracted with DCM (5×100 mL) and the extracts combined with the organic layer. The combined organics were washed with saturated brine (2×150 mL), dried over MgSO₄ and concentrated to afford a white semi-solid. The crude product was purified by flash silica chromatography, elution gradient 5 to 7% (10:1 MeOH/conc. NH₃ (aq)) in DCM. Pure fractions were evaporated to dryness to afford 3-amino-3-(4-chlorophenyl)propan-1-ol (1.320 g, 56.8%) as a white solid.

1H NMR (399.902 MHz, CDCl3) δ 1.87 (2H, m), 2.34 (2H, br.s), 3.79 (2H, m), 4.13 (1H, t), 7.24 (2H, d), 7.32 (2H, d).

MS m/e MH+ 169

Intermediate 30: Tert-butyl 1-(4-chlorophenyl)-3-hydroxypropylcarbamate

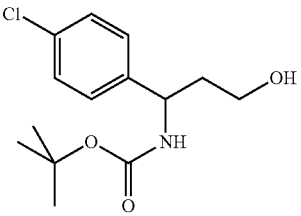 [SMILES: CC(C)(C)OC(=O)NC(CCO)c1ccc(Cl)cc1]

Di-tert-butyl dicarbonate (0.705 g, 3.23 mmol) was added to 3-amino-3-(4-chlorophenyl)propan-1-ol (Intermediate 29) (0.500 g, 2.69 mmol) in DCM (30 mL) at 22° C. The resulting solution was stirred at 22° C. for 2 hours. The mixture was concentrated and the residue was purified by flash silica chromatography, elution gradient 0 to 4% (10:1 MeOH/conc. NH₃(aq)) in DCM. Pure fractions were evaporated to dryness to afford tert-butyl 1-(4-chlorophenyl)-3-hydroxypropylcarbamate (0.759 g, 99%) as a white solid.

1H NMR (399.902 MHz, CDCl3) δ 1.43 (9H, s), 1.81 (1H, m), 2.04 (1H, m), 2.74 (1H, br.s), 3.69 (2H, m), 4.88 (1H, br.s), 5.04 (1H, d), 7.23 (2H, d), 7.32 (2H, d).

MS m/e MH⁻ 284, 286

Intermediate 31: 3-(tert-butoxycarbonylamino)-3-(4-chlorophenyl)propyl methanesulfonate

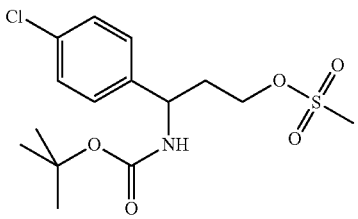 [SMILES: CC(C)(C)OC(=O)NC(CCOS(C)(=O)=O)c1ccc(Cl)cc1]

Methanesulfonyl chloride (0.097 mL, 1.25 mmol) was added dropwise to tert-butyl 1-(4-chlorophenyl)-3-hydroxypropylcarbamate (Intermediate 30) (0.326 g, 1.14 mmol) and triethylamine (0.191 mL, 1.37 mmol) in DCM (15 mL) at 22° C. The resulting solution was stirred at 22° C. for 2 hours. The mixture was concentrated and the residue was purified by flash silica chromatography, elution gradient 20 to 40% EtOAc in isohexane. Pure fractions were evaporated to dryness to afford 3-(tert-butoxycarbonylamino)-3-(4-methanesulfonate (0.366 g, 88%) as a white solid.

1H NMR (399.902 MHz, CDCl3) δ 1.42 (9H, s), 2.19 (2H, m), 3.01 (3H, s), 4.24 (2H, m), 4.82 (2H, m), 7.22 (2H, d), 7.33 (2H, d).

MS m/e MH⁻ 362, 364

Intermediate 32: Tert-butyl 1-(4-chlorophenyl)-3-(dimethylamino)propylcarbamate

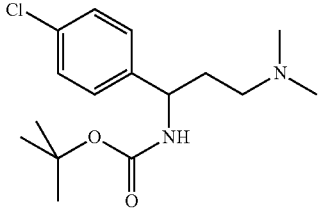 [SMILES: CN(C)CCC(NC(=O)OC(C)(C)C)c1ccc(Cl)cc1]

3-(tert-Butoxycarbonylamino)-3-(4-chlorophenyl)propyl methanesulfonate (Intermediate 31) (0.075 g, 0.21 mmol) and tetrabutylammonium iodide (0.015 g, 0.04 mmol) were dissolved in a solution of dimethylamine in THF (2M, 5.153 mL, 10.31 mmol) and sealed into a microwave tube. The reaction was heated to 150° C. for 30 minutes in the microwave reactor and cooled to ambient temperature. The reaction mixture was concentrated, diluted with DCM (25 mL) and washed with water (25 mL). The organic layer was filtered through a phase-separating filter paper and evaporated. The crude product was purified by flash silica chromatography, elution gradient 4 to 8% (10:1 MeOH/conc. $NH_{3(aq)}$) in DCM. Pure fractions were evaporated to dryness to afford tert-butyl 1-(4-chlorophenyl)-3-(dimethylamino)propylcarbamate (0.054 mg, 84%) as a colourless oil.

1H NMR (399.902 MHz, CDCl3) δ 1.40 (9H, s), 1.80 (1H, br.s), 1.94 (1H, m), 2.23 (6H, s), 2.26 (2H, m), 4.71 (1H, br.s), 6.16 (1H, br.s), 7.21 (2H, d), 7.29 (2H, d).

MS m/e MH+ 313

Intermediate 33: 1-(4-chlorophenyl)-N3,N3-dimethylpropane-1,3-diamine

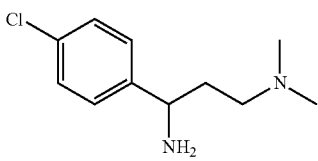

Hydrogen chloride (4M in dioxane, 1.132 mL, 32.61 mmol) was added to tert-butyl 1-(4-(Intermediate 32) (0.051 g, 0.16 mmol) in a mixture of DCM (5 mL) and methanol (2 mL) at 22° C. The resulting solution was stirred at 22° C. for 4 hours. The mixture was concentrated and the residue was purified by ion exchange chromatography, using an SCX column. The desired product was eluted from the column using 2M $NH_3$/MeOH and pure fractions were evaporated to dryness to afford 1-(4-chlorophenyl)-N3,N3-dimethylpropane-1,3-diamine (0.032 g, 92%) as a colourless oil.

1H NMR (399.902 MHz, CDCl3) δ 1.72-1.85 (2H, m), 2.19-2.32 (2H, m), 2.21 (6H, s), 3.99 (1H, t), 7.25-7.31 (4H, m).

MS m/e MH+ 213

Intermediate 34: Tert-butyl 4-(1-(4-chlorophenyl)-3-(dimethylamino)propylcarbamoyl)-1-(7H-pyrrolo[2,3-d]pyrimidin-4-yl)piperidin-4-ylcarbamate O-(7-Azabenzotriazol-1-yl)-N,N,N',N'-tetramethyluronium hexafluorophosphate (0.044 g, 0.12 mmol) was added to 4-(tert-butoxycarbonylamino)-1-(7H-pyrrolo[2,3-d]pyrimidin-4-yl)piperidine-4-carboxylic acid (Intermediate 1) (0.040 g, 0.11 mmol) and N,N-diisopropylethylamine (0.023 mL, 0.13 mmol) in NMP (5 mL) at 22° C. The resulting suspension was stirred at 50° C. for 10 minutes. The mixture was cooled to ambient temperature and 1-(4-chlorophenyl)-N3,N3-dimethylpropane-1,3-diamine (Intermediate 33) (0.023 g, 0.11 mmol) was added as a solution in NMP (2 mL). The mixture was stirred at 22° C. for 3 days. The mixture was diluted with methanol and purified by ion exchange chromatography using an SCX column; the desired product was eluted from the column using 30% (2M $NH_3$ in MeOH) in DCM and product-containing fractions were evaporated to dryness. The crude product was purified by flash silica chromatography, elution gradient 2 to 6% (10:1 MeOH/conc. $NH_{3(aq)}$) in DCM. Pure fractions were evaporated to dryness to afford tert-butyl 4-(1-(4-chlorophenyl)-3-(dimethylamino)propylcarbamoyl)-1-(7H-pyrrolo[2,3-d]pyrimidin-4-yl)piperidin-4-ylcarbamate (0.047 g, 76%) as a white solid.

1H NMR (399.902 MHz, DMSO) δ 1.43 (9H, s), 1.82 (2H, m), 1.90-2.04 (5H, m), 2.14 (6H, s), 2.16 (2H, m), 3.54 (2H, m), 4.25 (2H, m), 4.86 (1H, dt), 6.61 (1H, dd), 7.09 (1H, br.s), 7.17 (1H, dd), 7.33 (4H, s (roof effect)), 8.14 (1H, s), 8.45 (1H, d), 11.65 (1H, s).

MS m/e MH+ 556

Intermediate 35: Methyl 3-(4-(tert-butoxycarbonylamino)-1-(7H-pyrrolo[2,3-d]pyrimidin-4-yl)piperidine-4-carboxamido)-3-(4-chlorophenyl)propanoate

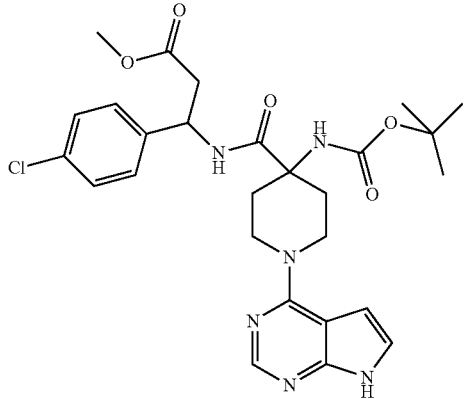 [SMILES: COC(=O)CC(NC(=O)C1(NC(=O)OC(C)(C)C)CCN(c2ncnc3[nH]ccc23)CC1)c1ccc(Cl)cc1]

O-(7-azabenzotriazol-1-yl)-N,N,N',N'-tetramethyluronium hexafluoro-phosphate (84 mg, 0.22 mmol) was added in one portion to 4-(tert-butoxycarbonylamino)-1-(7H-pyrrolo[2,3-d]pyrimidin-4-yl)piperidine-4-carboxylic acid (Intermediate 1) (72.3 mg, 0.20 mmol), 3-amino-3-(4-chlorophenyl)-propionic acid methyl ester hydrochloride (50 mg, 0.20 mmol) and N,N-diisopropylethylamine (0.104 mL, 0.60 mmol) in N-methyl-2-pyrrolidinone (1.5 mL) at 20° C. under argon. The resulting solution was stirred for 5 h. The reaction mixture was purified by preparative HPLC using a Waters X-Bridge reverse-phase column (C-18, 5 microns silica, 19 mm diameter, 100 mm length, flow rate of 40 ml/minute) with decreasingly polar mixtures of water (containing 0.2% ammonium carbonate) and acetonitrile as eluent. The fractions containing the desired compound were evaporated to dryness to afford methyl 3-(4-(tert-butoxycarbonylamino)-1-(7H-pyrrolo[2,3-d]pyrimidin-4-yl)piperidine-4-carboxamido)-3-(4-chlorophenyl)propanoate (71.0 mg, 63.8%) as a white crystalline solid.

1H NMR (500 MHz, DMSO-d6) δ 1.36 (9H, s), 1.94-2.00 (4H, m), 2.79-2.86 (2H, dq), 3.54 (3H, s), 3.52-3.61 (2H, m), 4.19 (2H, t), 5.22 (1H, q), 6.56 (1H, d), 6.9 (1H br s), 7.13 (1H, d), 7.33 (4H, q), 7.98 (1H, d), 8.12 (1H, s), 11.53 (1H, s). m/z (ESI+) (M+H)+=557; HPLC tR=3.18 min.

Intermediate 36: Tert-butyl 4-(1-(4-chlorophenyl)-3-hydroxypropylcarbamoyl)-1-(7H-pyrrolo[2,3-d]pyrimidin-4-yl)piperidin-4-ylcarbamate

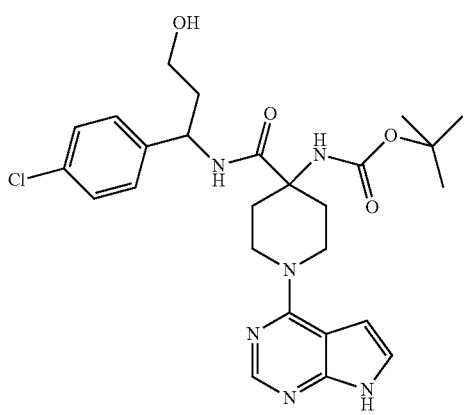 [SMILES: CC(C)(C)OC(=O)NC1(C(=O)NC(CCO)c2ccc(Cl)cc2)CCN(c2ncnc3[nH]ccc23)CC1]

Sodium borohydride (1.019 g, 26.93 mmol) was added in one portion to a stirred suspension of methyl 3-(4-(tert-butoxycarbonylamino)-1-(7H-pyrrolo[2,3-d]pyrimidin-4-yl)piperidine-4-carboxamido)-3-(4-chlorophenyl)propanoate (Intermediate 35) (1.0 g, 1.80 mmol) dissolved in EtOH (400 mL) under argon. The resulting suspension was stirred at 20° C. for 70 hours. A few drops of water were added to quench the excess of hydride and the mixture stirred for 1 hour. The mixture was evaporated to dryness and the residue was partitioned between CH$_2$Cl$_2$ and water saturated with NaCl. The organic phase was dried and concentrated to provide crude product as white crystals. The crude product was purified by flash chromatography on silica gel eluting with 0 to 10% methanol in dichloromethane. The pure fractions were evaporated to dryness to afford tert-butyl 4-(1-(4-chlorophenyl)-3-hydroxypropylcarbamoyl)-1-(7H-pyrrolo[2,3-d]pyrimidin-4-yl)piperidin-4-ylcarbamate (286 mg, 30.1%) as a white solid.

1H NMR (500 MHz, DMSO-d6) δ 1.41 (9H, s), 1.79-1.99 (6H, m), 3.31-3.37 (2H, m), 3.51 (2H, m), 4.21-4.28 (2H, m), 4.55 (1H, s), 4.90 (1H, q), 6.59 (1H, d), 7.06 (1H, s), 7.16 (1H, d), 7.31 (4H, s), 8.01 (1H, d), 8.12 (1H, s), 11.67 (1H, s). m/z (ESI+) (M−H)−=529; HPLC tR=2.93 min.

Intermediate 37: Tert-butyl 4-(1-(4-chlorophenyl)-3-(1,3-dioxoisoindolin-2-yl)propylcarbamoyl)-1-(7H-pyrrolo[2,3-d]pyrimidin-4-yl)piperidin-4-ylcarbamate

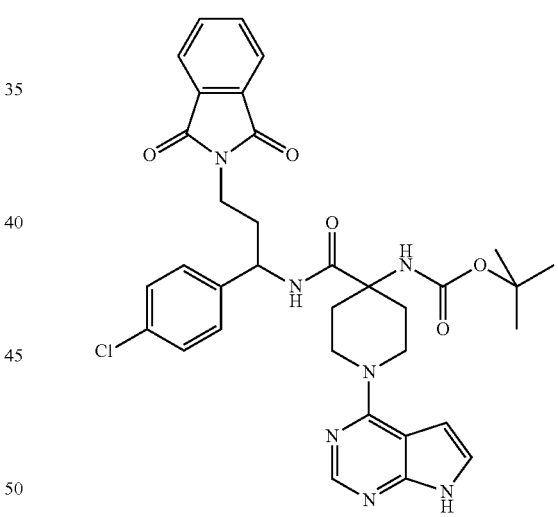

Triphenylphosphine (158 mg) and phthalimide (22.11 mg) were added in one portion to a stirred solution of tert-butyl 4-(1-(4-chlorophenyl)-3-hydroxypropylcarbamoyl)-1-(7H-pyrrolo[2,3-d]pyrimidin-4-yl)piperidin-4-ylcarbamate (Intermediate 36) (53 mg) dissolved in THF (10 mL) and cooled to 0° C. under argon. The resulting solution was stirred at 0° C. for 30 minutes. Diethyl azodicarboxylate (0.093 mL) was added dropwise at 0° C. under argon. The resulting suspension was stirred at 0° C. for 60 minutes and overnight at room temperature. The suspension was quenched with water. The THF was removed in vacuo and the aqueous phase extracted with DCM. The organic phase was dried and concentrated to provide crude product. The crude product was purified by flash chromatography on silica gel eluting with 0 to 10% methanol in DCM. The solvent was evaporated to dryness to afford tert-butyl 4-(1-(4-chlorophenyl)-3-(1,3-dioxoisoindolin-2-yl)propylcarbamoyl)-1-(7H-pyrrolo[2,3-d]pyrimidin-4-yl)piperidin-4-ylcarbamate as a white solid (14.00 mg, 21.23%).

¹H NMR (500 MHz, DMSO-d₆) δ 1.37 (9H, s), 2.01 (4H, m), 2.09 (2H, m), 3.58 (4H, m), 4.23 (2H, m), 4.84 (1H, q), 6.60 (1H, d), 7.00 (1H, m), 7.16 (1H, t), 7.27 (2H, d), 7.33 (2H, d), 7.82 (4H, m), 8.12 (1H, d), 8.13 (1H, s), 11.67 (1H, s).

MS m/e MH⁺ 658.

Intermediate 38: Tert-butyl 4-(3-amino-1-(4-chlorophenyl)propylcarbamoyl)-1-(7H-pyrrolo[2,3-d]pyrimidin-4-yl)piperidin-4-ylcarbamate

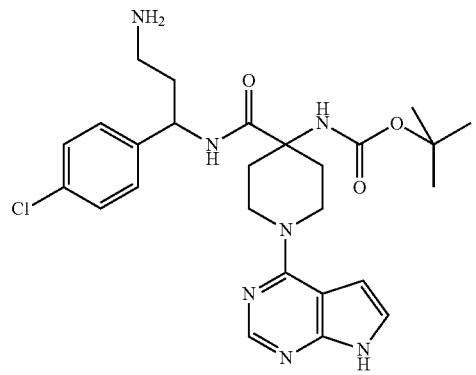 [SMILES: CC(C)(C)OC(=O)NC1(C(=O)NC(CCN)c2ccc(Cl)cc2)CCN(c2ncnc3[nH]ccc23)CC1]

Hydrazine monohydrate (10.32 μL) was added to a stirred suspension of tert-butyl 4-(1-(4-chlorophenyl)-3-(1,3-dioxoisoindolin-2-yl)propylcarbamoyl)-1-(7H-pyrrolo[2,3-d]pyrimidin-4-yl)piperidin-4-ylcarbamate (Intermediate 37) (14 mg) in ethanol (1.0 mL) under argon. The resulting suspension was stirred at room temperature for 3 days. The mixture was filtered and was purified by preparative HPLC using a Waters X-Bridge reverse-phase column (C-18, 5 microns silica, 19 mm diameter, 100 mm length) and decreasingly polar mixtures of water (containing 0.2% ammonium carbonate) and acetonitrile as eluent. Pure fractions were evaporated to dryness to afford tert-butyl 4-(3-amino-1-(4-chlorophenyl)propylcarbamoyl)-1-(7H-pyrrolo[2,3-d]pyrimidin-4-yl)piperidin-4-ylcarbamate as a white powder (5.00 mg, 44.5%).

¹H NMR (500 MHz, CDCl₃+CD₃OD) δ 1.43 (9H, s), 1.93 (2H, s), 2.19 (4H, m), 2.74 (2H, s) 3.57 (4H, m), 4.39 (2H, t), 5.01 (1H, t), 6.53 (1H, d), 7.07 (1H, d), 7.28 (4H, q), 8.19 (1H, s).

MS m/e MH⁺ 528.

Intermediate 39: (R)-methyl 3-(tert-butoxycarbonylamino)-3-(4-chlorophenyl)propanoate

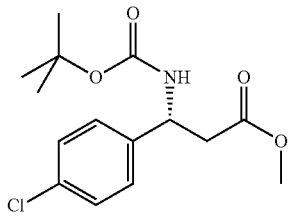 [SMILES: COC(=O)C[C@@H](NC(=O)OC(C)(C)C)c1ccc(Cl)cc1]

Iodomethane (0.987 mL, 15.85 mmol) was added in one portion to boc-(R)-3-amino-3-(4-chloro-phenyl)-propionic acid (950 mg, 3.17 mmol) and potassium carbonate (876 mg, 6.34 mmol) in DMF (15 mL). The resulting suspension was stirred at 80° C. for 24 hours. The reaction mixture was concentrated and diluted with EtOAc (25 mL) with water (25 mL). The organic layer was dried over MgSO₄, filtered and evaporated to afford (R)-methyl 3-(tert-butoxycarbonylamino)-3-(4-chlorophenyl)propanoate (990 mg, 100%) as a orange solid.

¹H NMR (399.9 MHz, DMSO-d6) δ 1.36 (9H, s), 2.67-2.70 (1H, m), 2.71-2.80 (1H, m), 3.57 (3H, s), 4.91 (1H, d), 7.32-7.34 (2H, m), 7.38-7.40 (2H, m), 7.49 (1H, d).

MS m/e MH⁺ 312; HPLC tR=2.57 min.

Intermediate 40: (R)-methyl 3-amino-3-(4-chlorophenyl)propanoate (hydrochloride)

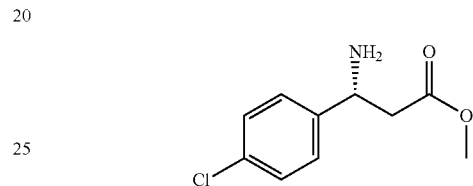

Hydrochloric acid (4.0M in dioxane) (7.89 mL, 31.55 mmol) was added in one portion to (R)-methyl 3-(tert-butoxycarbonylamino)-3-(4-chlorophenyl)propanoate (Intermediate 39) (990 mg, 3.16 mmol) in DCM (20 mL) at 20° C. The resulting solution was stirred at 20° C. for 3 hours. The reaction mixture was evaporated to afford (R)-methyl 3-amino-3-(4-chlorophenyl)propanoate (hydrochloride) (777 mg, 98%) as a yellow solid.

¹H NMR (399.9 MHz, DMSO-d6) δ 2.99-3.05 (1H, m), 3.18-3.23 (1H, m), 3.58 (3H, d), 4.62-4.65 (1H, m), 7.49-7.53 (2H, m), 7.57-7.61 (2H, m), 8.72 (3H, s).

MS m/e MH⁺ 214; HPLC tR=1.71 min.

Intermediate 41: (R)-methyl 3-(4-(tert-butoxycarbonylamino)-1-(7H-pyrrolo[2,3-d]pyrimidin-4-yl)piperidine-4-carboxamido)-3-(4-chlorophenyl)propanoate

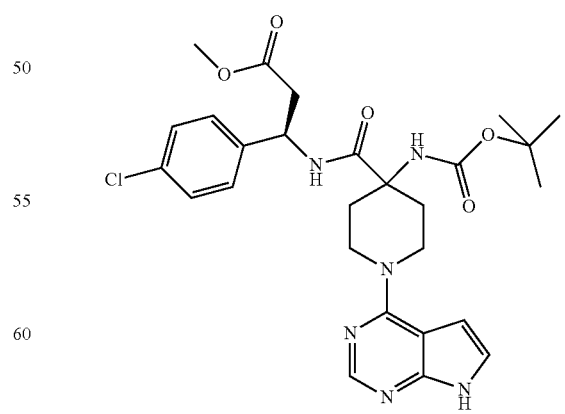

O-(7-azabenzotriazol-1-yl)-N,N,N',N'-tetramethyluronium hexafluoro-phosphate (0.579 g, 1.52 mmol) was added in one portion to 4-(tert-butoxycarbonylamino)-1-(7H-pyrrolo[2,3-d]pyrimidin-4-yl)piperidine-4-carboxylic acid (Intermediate 1) (0.5 g, 1.38 mmol) and DIPEA (0.503 mL, 3.04 mmol) in NMP (5 mL) at 20° C. The resulting solution was stirred at 20° C. for 5 minutes. (R)-methyl 3-amino-3-(4-chlorophenyl)propanoate (hydrochloride) (Intermediate 40) (0.346 g, 1.38 mmol) was then added to the solution and stirred at room temperature for 3 hours. The reaction mixture was diluted with EtOAc (100 mL), and washed sequentially with water (50 mL), water (50 mL), and water (50 mL). The organic layer was dried over MgSO₄, filtered and evaporated to afford crude product. The crude product was purified by flash silica chromatography, elution gradient 0 to 5% MeOH in DCM. Pure fractions were evaporated to dryness to afford (R)-methyl 3-(4-(tert-butoxycarbonylamino)-1-(7H-pyrrolo[2,3-d]pyrimidin-4-yl)piperidine-4-carboxamido)-3-(4-chlorophenyl)propanoate (0.800 g, 100%) as a white solid.

¹H NMR (399.9 MHz, DMSO-d6) δ 1.40 (9H, s), 1.94-1.98 (2H, m), 2.00-2.01 (2H, m), 2.83 (1H, d), 2.85-2.87 (2H, m), 3.55 (3H, s), 3.60 (2H, s), 4.21 (2H, s), 5.23 (1H, d), 6.60-6.61 (1H, m), 7.16-7.18 (1H, m), 7.35 (4H, q), 8.09-8.14 (2H, m), 11.65 (1H, s).

MS m/e MH⁺ 557; HPLC tR=2.29 min.

Intermediate 42: (R)-tert-butyl 4-(1-(4-chlorophenyl)-3-hydroxypropylcarbamoyl)-1-(7H-pyrrolo[2,3-d]pyrimidin-4-yl)piperidin-4-ylcarbamate

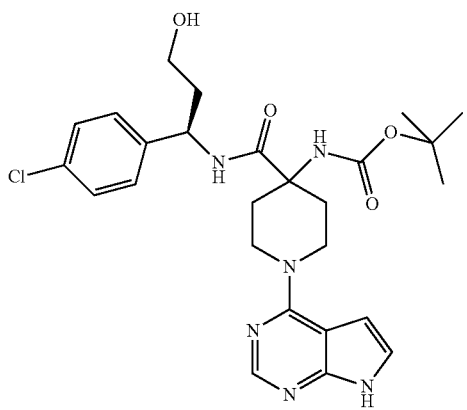 [SMILES: CC(C)(C)OC(=O)NC1(C(=O)N[C@H](CCO)c2ccc(Cl)cc2)CCN(c2ncnc3[nH]ccc23)CC1]

LiAlH₄ (1.398 mL, 1.40 mmol) was added dropwise to (R)-methyl 3-(4-(tert-butoxycarbonylamino)-1-(7H-pyrrolo[2,3-d]pyrimidin-4-yl)piperidine-4-carboxamido)-3-(4-chlorophenyl)propanoate (Intermediate 41) (779 mg, 1.40 mmol) in THF (40 mL) cooled to 0° C. under nitrogen. The resulting solution was stirred at 20° C. for 3 hours. The reaction mixture was quenched with water (1 mL) and neutralised with 2M HCl. The reaction mixture was evaporated to dryness and redissolved in DCM (100 mL) and washed with water (100 mL). The organic layer was dried over MgSO₄, filtered and evaporated to afford crude product. The crude product was purified by flash silica chromatography, elution gradient 0 to 10% MeOH in DCM. The pure fractions were combined and evaporated to give (R)-tert-butyl 4-(1-(4-chlorophenyl)-3-hydroxypropylcarbamoyl)-1-(7H-pyrrolo[2,3-d]pyrimidin-4-yl)piperidin-4-ylcarbamate (160 mg, 21.63%) as a solid.

¹H NMR (399.9 MHz, DMSO-d6) δ 1.37-1.41 (9H, s), 1.86-1.92 (2H, m), 1.94 (2H, d), 2.00 (2H, d), 3.38 (2H, s), 3.53-3.55 (2H, m), 4.25 (2H, t), 4.52 (1H, s), 4.91 (1H, d), 6.60-6.62 (1H, m), 7.01 (1H, s), 7.16-7.18 (1H, m), 7.33 (4H, m), 7.98-8.00 (1H, m), 8.14 (1H, s), 11.67 (1H, s).

MS m/e MH⁺ 529; HPLC tR=2.01 min.

Intermediate 43: 1-(tert-butoxycarbonyl)-4-cyanopiperidine-4-carboxylic acid

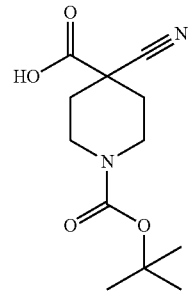 [SMILES: CC(C)(C)OC(=O)N1CCC(C#N)(C(=O)O)CC1]

An aqueous solution of lithium hydroxide (2M, 39.0 mL, 77.92 mmol) was added to a stirred solution of 1-tert-butyl 4-ethyl 4-cyanopiperidine-1,4-dicarboxylate (Intermediate 7) (5.5 g, 19.48 mmol), in THF (78 mL) at 25° C. The resulting mixture was stirred at 25° C. for 3 hours and monitored by TLC. The reaction mixture was diluted with diethyl ether (150 mL), and washed with water (100 mL). The aqueous layers were combined and then acidified with citric acid (1N, 200 mL). The product was extracted into DCM. The organic layer was dried over magnesium sulfate, filtered and evaporated to afford 1-(tert-butoxycarbonyl)-4-cyanopiperidine-4-carboxylic acid (4.50 g, 91%). This material was used in the next steps without further purification.

¹H NMR (400 MHz, CDCl3) δ 1.40 (9H, s), 1.87-1.97 (2H, m), 2.04 (2H, d), 3.08 (2H, t), 4.05 (2H, s), 8.23 (1H, s).

Intermediate 44: (R)—N-(1-(4-chlorophenyl)ethyl)-4-cyanopiperidine-4-carboxamide

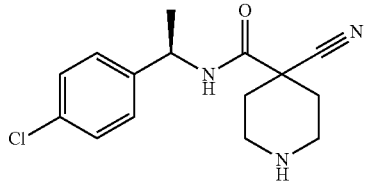 [SMILES: C[C@@H](NC(=O)C1(C#N)CCNCC1)c1ccc(Cl)cc1]

O-(7-azabenzotriazol-1-yl)-N,N,N',N'-tetramethyluronium hexafluorophosphate (1.255 g, 3.30 mmol) was added in one portion to 1-(tert-butoxycarbonyl)-4-cyanopiperidine-4-carboxylic acid (Intermediate 43) (0.763 g, 3 mmol), (R)-1-(4-chlorophenyl)ethanamine (0.462 mL, 3.00 mmol) and DIPEA (1.572 mL, 9.00 mmol) in DMA (20 mL) at 25° C. under nitrogen. The resulting solution was stirred at 60° C. for 4 hours. The reaction mixture was evaporated to dryness and redissolved in DCM (150 mL), and washed sequentially with 1M aqueous citric acid (50 mL), water (50 mL), and saturated sodium hydrogen carbonate (100 mL). The organic layer was dried over magnesium sulfate, filtered and evaporated to afford crude product. The crude product thus obtained was concentrated, then purified by flash silica chromatography, elution gradient 0 to 100% EtOAc in isohexane. Pure fractions were evaporated to afford (R)-tert-butyl 4-(1-(4-chlorophenyl)ethylcarbamoyl)-4-cyanopiperidine-1-carboxylate (1.100 g, 94%) as a colourless gum which solidified on drying under high vacuum. This material was then redissolved in DCM (20.00 mL), and trifluoroacetic acid (2.311 mL, 30.00 mmol) was added. The solution was stirred at room temperature for 3 hours, after which the crude product was purified by ion exchange chromatography, using an SCX column. The desired product was eluted from the column using 7N ammonia/MeOH and pure fractions were evaporated to dryness to afford (R)—N-(1-(4-chlorophenyl)ethyl)-4-cyanopiperidine-4-carboxamide (0.720 g, 82%) as a colourless gum. This material was used directly in the next step without further purification.

MS m/e MH+ 292.

Intermediate 45: (R)—N-(1-(4-chlorophenyl)ethyl)-4-cyano-1-(7H-pyrrolo[2,3-d]pyrimidin-4-yl)piperidine-4-carboxamide

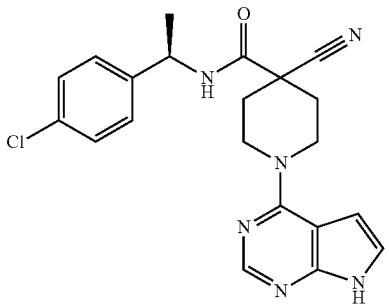 [SMILES: C[C@@H](NC(=O)C1(C#N)CCN(c2ncnc3[nH]ccc23)CC1)c1ccc(Cl)cc1]

DIPEA (1.101 mL, 6.17 mmol) was added to (R)—N-(1-(4-chlorophenyl)ethyl)-4-cyanopiperidine-4-carboxamide (Intermediate 44) (720 mg, 2.47 mmol) and 6-chloro-7-deazapurine (379 mg, 2.47 mmol) in DMA (50 mL) at 25° C. The resulting solution was stirred at 90° C. for 3 hours. The crude product was purified by ion exchange chromatography, using an SCX column. The desired product was eluted from the column using 7N ammonia/MeOH and pure fractions were evaporated to dryness to afford (R)—N-(1-(4-chlorophenyl)ethyl)-4-cyano-1-(7H-pyrrolo[2,3-d]pyrimidin-4-yl)piperidine-4-carboxamide (46.2%) as an orange solid. This was used in the next step without further purification.

$^1$H NMR (400 MHz, DMSO) δ 1.38 (3H, d), 1.94-2.09 (3H, m), 2.19 (3H, t), 4.72 (2H, d), 4.92 (1H, dd), 6.61-6.72 (1H, m), 7.23 (1H, dd), 7.30-7.41 (4H, m), 8.18 (1H, s), 8.77 (1H, d), 11.77 (1H, s).

MS m/e MH+ 409.

Intermediate 46: (S)-4-(1-amino-3-hydroxypropyl)benzonitrile

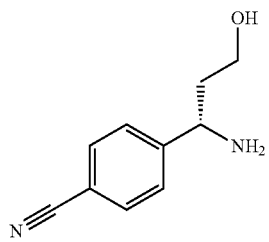 [SMILES: N#Cc1ccc([C@@H](N)CCO)cc1]

Sodium borohydride (1.039 mL, 29.48 mmol) was added portionwise to (S)-methyl 3-amino-3-(4-cyanophenyl)propanoate (2.23 g, 10.92 mmol) in methanol (20 mL) at 0° C. over a period of 5 minutes. The resulting solution was stirred at 20° C. for 24 hours. The reaction mixture was quenched with saturated NaHCO$_3$ (50 mL), extracted with EtOAc (3×100 mL), the organic layer was washed with saturated brine (75 mL), dried over MgSO$_4$, filtered and evaporated to afford crude product. The crude product was purified by flash silica chromatography, elution gradient 0 to 8% MeOH with ammonia in DCM. Pure fractions were evaporated to dryness to afford (S)-4-(1-amino-3-hydroxypropyl)benzonitrile (0.368 g, 19.13%) as a colourless oil.

$^1$H NMR (400.13 MHz, CDCl$_3$) δ 1.84-1.93 (2H, m), 3.77-3.80 (2H, m), 4.22-4.25 (1H, m), 7.43 (2H, m), 7.63-7.66 (2H, m).

MS m/e MH+ 177.

Intermediate 47: (S)-3-amino-3-(4-chlorophenyl)propan-1-ol

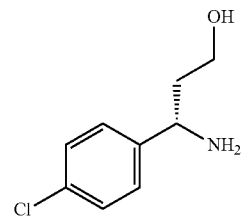 [SMILES: N[C@@H](CCO)c1ccc(Cl)cc1]

Borane-tetrahydrofuran complex (376 mL, 375.69 mmol) was added dropwise to a stirred suspension of (S)-3-amino-3-(4-chlorophenyl)propanoic acid (10 g, 50.09 mmol) in THF (500 mL) at 0° C. over a period of 45 minutes under nitrogen. The resulting suspension was stirred at 0° C. for 30 minutes then at 22° C. for 5 hours. The reaction mixture was added portionwise to methanol (500 mL). The solution was stirred at room temperature for three days. The mixture was concentrated, redissolved in methanol (250 mL) and reconcentrated (this process was repeated three times). The residue was dissolved in DCM (75 mL) and washed with 1N NaOH (50 mL). The aqueous layer was extracted with DCM (3×100 mL) and the extracts combined with the organic layer. The combined organics were washed with saturated brine (50 mL), dried over MgSO$_4$ and concentrated to afford crude product. The crude product was purified by flash silica chromatography, elution gradient 2 to 6% MeOH/ammonia in DCM. Pure fractions were evaporated to dryness to afford (S)-3-amino-3-(4-chlorophenyl)propan-1-ol (5.76 g, 61.9%) as a white solid.

$^1$H NMR (400.13 MHz, CDCl3) δ 1.84-1.93 (2H, m), 3.76-3.81 (2H, m), 4.13 (1H, t), 7.23-7.25 (2H, m), 7.30-7.34 (2H, m).

MS m/e MH+ 186.

Intermediate 48: (S)-tert-butyl 4-(tert-butoxycarbonylamino)-4-(1-(4-chlorophenyl)-3-hydroxypropylcarbamoyl)piperidine-1-carboxylate

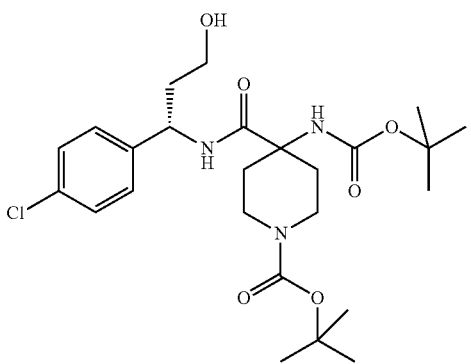 [SMILES: CC(C)(C)OC(=O)NC1(C(=O)N[C@@H](CCO)c2ccc(Cl)cc2)CCN(C(=O)OC(C)(C)C)CC1]

(S)-3-amino-3-(4-chlorophenyl)propan-1-ol (Intermediate 47) (1.09 g, 5.87 mmol) was added in one portion to 1-(tert-butoxycarbonyl)-4-(tert-butoxycarbonylamino)piperidine-4-carboxylic acid (Intermediate 70) (2.022 g, 5.87 mmol) and DIPEA (3.08 mL, 17.61 mmol) in DMA (20 mL). O-(7-azabenzotriazol-1-yl)-N,N,N',N'-tetramethyluronium hexafluorophosphate (2.456 g, 6.46 mmol) was added and the resulting solution was stirred at 20° C. for 24 hours. The reaction mixture was evaporated to dryness then diluted with EtOAc (300 mL), and washed sequentially with water (50 mL) and saturated brine (50 mL). The organic layer was dried over MgSO$_4$, filtered and evaporated then triturated with diethyl ether to afford crude (S)-tert-butyl 4-(tert-butoxycarbonylamino)-4-(1-(4-chlorophenyl)-3-hydroxypropylcarbamoyl)piperidine-1-carboxylate (4.66 g, 155%) as a white solid.

1H NMR (400.13 MHz, DMSO-d6) δ 1.39 (18H, s), 1.71-1.92 (6H, m), 3.06 (2H, s), 3.36 (2H, t), 3.54-3.65 (2H, m), 4.52 (1H, t), 4.89 (1H, q), 6.89 (1H, s), 7.29-7.34 (4H, m).

MS m/e M+Na$^+$ 534.

Intermediate 49: (S)-4-amino-N-(1-(4-chlorophenyl)-3-hydroxypropyl)piperidine-4-carboxamide

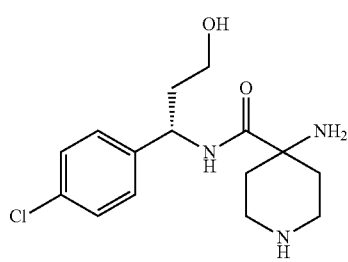 [SMILES: NC1(C(=O)N[C@@H](CCO)c2ccc(Cl)cc2)CCNCC1]

Hydrogen chloride 4M in dioxane (11.72 mL, 46.87 mmol) was added to (S)-tert-butyl 4-(tert-butoxycarbonylamino)-4-(1-(4-chlorophenyl)-3-hydroxypropylcarbamoyl)piperidine-1-carboxylate (Intermediate 48) (3 g, 5.86 mmol) in dioxane (30 mL). The resulting solution was stirred at 20° C. for 2 hours. The reaction mixture was dissolved in methanol and purified by ion exchange chromatography, using an SCX column. The desired product was eluted from the column using 3.5N ammonia/MeOH and pure fractions were evaporated to dryness to afford (S)-4-amino-N-(1-(4-chlorophenyl)-3-hydroxypropyl)piperidine-4-carboxamide (1.970 g, 108%) as a colourless gum.

$^1$H NMR (400.13 MHz, DMSO-d$_6$) δ 1.20-1.28 (2H, m), 1.75-1.91 (4H, m), 2.67-2.83 (2H, m), 3.30 (2H, m), 4.87 (1H, s), 7.30-7.37 (4H, m).

MS m/e MH$^+$ 312.

Intermediate 50: 5-bromo-4-chloro-7H-pyrrolo[2,3-d]pyrimidine

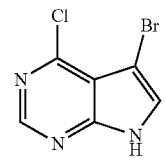

N-Bromosuccinimide (6.84 g, 38.42 mmol) was added portionwise to 4-chloro-7H-pyrrolo[2,3-d]pyrimidine (5 g, 32.56 mmol) in DCM, dry (125 mL) at 20° C. under nitrogen. The resulting suspension was stirred at 20° C. for 1 hour. The reaction mixture was evaporated and the resulting brown solid was triturated with water to give a purple solid which was collected by filtration. The crude solid was triturated with hot MeOH to give a solid which was collected by filtration. The hot trituration was repeated to give 5-bromo-4-chloro-7H-pyrrolo[2,3-d]pyrimidine (5.23 g, 69.1%) as a cream solid.

$^1$H NMR (400.13 MHz, DMSO-d6) δ 7.94 (1H, s), 8.63 (1H, s), 12.95 (1H, s)

MS m/e MH$^+$ 234.

Intermediate 51: (S)-3-amino-3-(4-bromophenyl)propan-1-ol

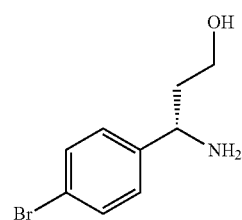 [SMILES: N[C@@H](CCO)c1ccc(Br)cc1]

Borane-tetrahydrofuran complex (71.7 mL, 71.70 mmol) was added dropwise to a stirred suspension of (S)-3-amino-3-(4-bromophenyl)propanoic acid (3.5 g, 14.34 mmol) in THF (80 mL) at 0° C. over a period of 30 minutes under nitrogen. The resulting suspension was stirred at 0° C. for 30 minutes then at 22° C. for 5 hours. The reaction mixture was added portionwise to methanol (250 mL). The solution was stirred at room temperature for 24 hours. The mixture was concentrated, redissolved in methanol (250 mL) and reconcentrated (this process was repeated three times). The residue was dissolved in DCM (75 mL) and washed with 1N NaOH (50 mL). The aqueous layer was extracted with DCM (3×100 mL) and the extracts combined with the organic layer. The combined organics were washed with saturated brine (50 mL), dried over MgSO$_4$ and concentrated to afford crude product. The crude product was purified by flash silica chromatography, elution gradient 2 to 6% MeOH/ammonia in DCM. Pure fractions were evaporated to dryness to afford (S)-3-amino-3-(4-bromophenyl)propan-1-ol (2.160 g, 65.5%) as a colourless gum.

$^1$H NMR (400.13 MHz, CDCl$_3$) δ 1.82-1.90 (2H, m), 3.76-3.82 (2H, m), 4.12 (1H, t), 7.17-7.20 (2H, m), 7.45-7.49 (2H, m).

MS m/e MH$^+$ 230.

Intermediate 52: Ethyl 4-(4-chlorophenyl)-4-(methoxyimino)butanoate

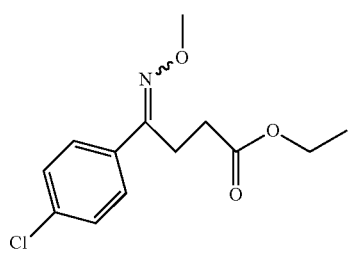 [SMILES: CCOC(=O)CCC(=NOC)c1ccc(Cl)cc1]

4-(4-Chlorophenyl)-4-oxobutanoic acid (10 g, 47.03 mmol), methoxylamine hydrochloride (4.91 g, 58.79 mmol) and sodium carbonate (5.98 g, 56.44 mmol) in ethanol (150 mL) were stirred for 4 hrs at 80° C. The mixture was then cooled to room temperature before being filtered. The filtrate was concentrated by evaporation and purified by flash silica chromatography (eluent 20-50% EtOAc/iso-hexane). Pure fractions were evaporated to dryness to afford ethyl 4-(4-chlorophenyl)-4-(methoxyimino)butanoate (12.33 g, 97%) as an orange transparent liquid.

$^1$H NMR (400.13 MHz, DMSO) 1.13-1.17 (3H, t), 2.26-2.50 (2H, t), 2.50-2.52 (1H, qu), 2.94-2.98 (2H, t), 3.94 (3H, s), 4.00-4.05 (2H, q), 7.47-7.49 (2H, d), 7.66-7.69 (2H, d).

Intermediate 53: 4-(4-chlorophenyl)-4-(methoxyimino)butanoic acid

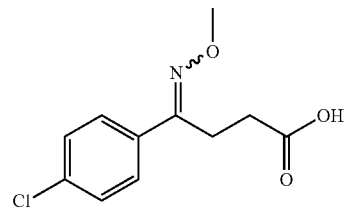 [SMILES: CON=C(CCC(=O)O)c1ccc(Cl)cc1]

Lithium hydroxide monohydrate (9.59 g, 228.57 mmol) was added to ethyl 4-(4-chlorophenyl)-4-(methoxyimino) butanoate (Intermediate 52) (12.33 g, 45.71 mmol) in water (25.4 mL), THF (102 mL) and ethanol (102 mL). The resulting solution was stirred at 20° C. for 1 day. The reaction mixture was diluted with EtOAc (200 mL) and washed with water (200 mL). The aqueous was adjusted to pH5 with 1M citric acid solution then extracted with EtOAc (3×150 mL). The organic extracts were washed with saturated brine (25 mL) then dried over MgSO$_4$, filtered and evaporated to afford desired product 4-(4-chlorophenyl)-4-(methoxyimino)butanoic acid (7.63 g, 69.1%) as a light yellow solid.

$^1$H NMR (400.13 MHz) 2.39-2.43 (2H, t), 2.91-2.95 (2H, t), 3.94 (3H, s), 7.47-7.49 (2H, d), 7.67-7.69 (2H, d), 12.21 (1H, broad).

MS m/e MH$^+$ 242.

Intermediate 54: 4-amino-4-(4-chlorophenyl)butan-1-ol

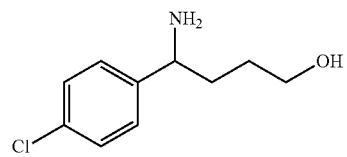 [SMILES: NC(CCCO)c1ccc(Cl)cc1]

4-(4-Chlorophenyl)-4-(methoxyimino)butanoic acid (Intermediate 53) (6.43 g, 26.61 mmol) in tetrahydrofuran (30 mL) was cooled, under an atmosphere of nitrogen, in an ice-methanol bath. Borane-tetrahydrofuran complex (1.0M in THF) (93 mL, 93.12 mmol) was added dropwise over a period of 20 minutes. The resulting solution was allowed to warm to room temperature, stirred for 1 hour then heated at reflux for a further 6 hours. After cooling in ice-water the mixture was treated with water (20 mL) dropwise with stirring over 10 minutes. The mixture was again allowed to warm to room temperature and stirred for 2 hours before evaporating the bulk of the solvent. The residue was then cooled in ice-water and 50% NaOH (aq.) (20 mL) added dropwise with stirring. The resulting mixture was stirred and heated at 90° C. for 4 hours then cooled to room temperature and extracted three times with Et$_2$O. The combined extracts were washed with water followed by brine, dried over MgSO$_4$ and evaporated to dryness. The crude product was then purified by flash silica chromatography (eluent 0-10% 7N ammonia in MeOH/DCM) and pure fractions evaporated to afford 4-amino-4-(4-chlorophenyl)butan-1-ol (3.88 g, 73.0%) as a colourless, transparent gum.

$^1$H NMR (400.13 MHz) 1.25-1.47 (2H, dm), 1.51-1.61 (2H, m), 3.34-3.38 (2H, t), 3.76-3.79 (1H, t), 7.33-7.38 (4H, m).

Intermediate 55: Tert-butyl 1-(4-chlorophenyl)-4-hydroxybutylcarbamate

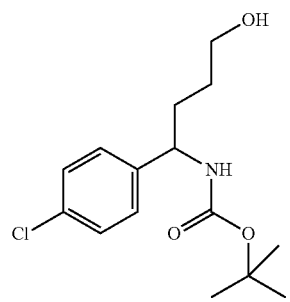 [SMILES: CC(C)(C)OC(=O)NC(CCCO)c1ccc(Cl)cc1]

Di-tert-butyl dicarbonate (1.588 mL, 6.91 mmol) was added in one portion to 4-amino-4-(4-chlorophenyl)butan-1-ol (Intermediate 54) (1.38 g, 6.91 mmol) in DCM (20 mL) at 25° C. under nitrogen. The resulting solution was stirred at room temperature for 24 hours. The resulting mixture was evaporated to dryness and the crude oil was triturated with isohexane to give a solid which was collected by filtration and dried under vacuum to give tert-butyl 1-(4-chlorophenyl)-4-hydroxybutylcarbamate (1.800 g, 87%) as a white solid.

$^1$H NMR (400.13 MHz, CDCl3) δ 1.40 (9H, s), 1.48-1.66 (2H, m), 1.78-1.83 (2H, m), 3.63-3.68 (2H, m), 4.61 (1H, s), 4.84 (1H, s), 7.21 (2H, m), 7.29-7.31 (2H, m).

Intermediate 56: 4-(tert-butoxycarbonylamino)-4-(4-chlorophenyl)butyl methanesulfonate

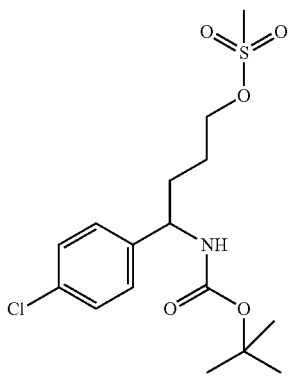 [SMILES: CC(C)(C)OC(=O)NC(CCCOS(C)(=O)=O)c1ccc(Cl)cc1]

Methanesulfonyl chloride (0.511 mL, 6.60 mmol) was added dropwise to tert-butyl 1-(4-chlorophenyl)-4-hydroxybutylcarbamate (Intermediate 55) (1.80 g, 6.00 mmol) and triethylamine (1.004 mL, 7.20 mmol) in DCM (30.0 mL) at 25° C. over a period of 15 minutes under nitrogen. The resulting solution was stirred at room temperature for 30 minutes. The resulting mixture was evaporated to dryness and the residue was suspended in DCM, filtered and the filtrate purified by flash silica chromatography, elution gradient 20 to 100% EtOAc in isohexane. Pure fractions were evaporated to dryness to afford 4-(tert-butoxycarbonylamino)-4-(4-chlorophenyl)butyl methanesulfonate (2.270 g, 100%) as a white solid.

$^1$H NMR (400.13 MHz, CDCl3) δ 1.41 (9H, s), 1.67-1.87 (4H, m), 2.99 (3H, s), 4.23 (2H, t), 4.62 (1H, s), 4.75 (1H, s), 7.20 (2H, d), 7.30-7.33 (2H, d).

MS m/e M+Na$^+$ 400.

Intermediate 57: 1-(4-chlorophenyl)-N4,N4-dimethylbutane-1,4-diamine

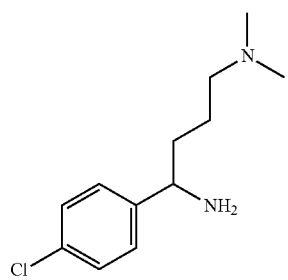

Dimethylamine (84 mg, 1.85 mmol) and 4-(tert-butoxycarbonylamino)-4-(4-chlorophenyl)butyl methanesulfonate (Intermediate 56) (700 mg, 1.85 mmol) were dissolved in THF (10 mL) and sealed into a microwave tube. The reaction was heated to 120° C. for 40 minutes in the microwave reactor and cooled to room temperature. The reaction mixture was concentrated and then dissolved in DCM (10.00 mL) and TFA (2 mL). The reaction was stirred at 20° C. for 2 hours. The crude product was purified by ion exchange chromatography, using an SCX column. The desired product was eluted from the column using 3.5N ammonia/MeOH and pure fractions were evaporated to dryness to afford 1-(4-chlorophenyl)-N4,N4-dimethylbutane-1,4-diamine (366 mg, 87%) as a yellow gum.

$^1$H NMR (400.13 MHz, CDCl3) δ 0.70-0.79 (1H, m), 0.82-0.91 (1H, m), 0.93-1.09 (2H, m), 1.21 (6H, s), 1.64 (2H, t), 3.23 (1H, t), 6.58-6.66 (4H, m). a) MS m/e MH$^+$ 227.

Intermediate 58: (S)-tert-butyl 1-(4-chlorophenyl)-3-hydroxypropylcarbamate

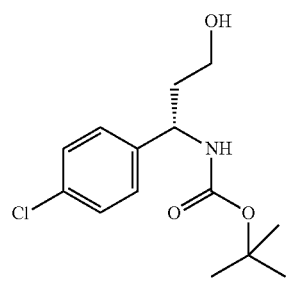 [SMILES: CC(C)(C)OC(=O)N[C@@H](CCO)c1ccc(Cl)cc1]

Di-tert-butyl dicarbonate (8.04 mL, 35.01 mmol) was added in one portion to (S)-3-amino-3-(4-chlorophenyl)propan-1-ol (Intermediate 47) (6.5 g, 35.01 mmol) in DCM (200 mL) at 25° C. under nitrogen. The resulting solution was stirred at room temperature for 24 hours. The resulting mixture was evaporated to dryness and the crude oil was triturated with isohexane to give a solid which was collected by filtration and dried under vacuum to give (S)-tert-butyl 1-(4-chlorophenyl)-3-hydroxypropylcarbamate (9.20 g, 92%) as a white solid.

$^1$H NMR (399.9 MHz, CDCl3) δ 1.43 (9H, s), 1.78-1.84 (1H, m), 2.05 (1H, d), 2.74 (1H, s), 3.67-3.71 (2H, m), 4.88 (1H, s), 5.04 (1H, d), 7.21-7.24 (2H, m), 7.30-7.33 (2H, m). MS m/e M+Na$^+$ 308.

Intermediate 59: (S)-3-(tert-butoxycarbonylamino)-3-(4-chlorophenyl)propyl methanesulfonate

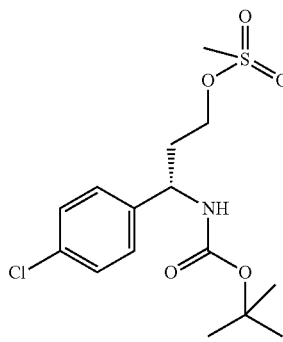

Methanesulfonyl chloride (2.74 mL, 35.41 mmol) was added dropwise to (S)-tert-butyl 1-(4-chlorophenyl)-3-hydroxypropylcarbamate (Intermediate 58) (9.2 g, 32.19 mmol) and triethylamine (5.38 mL, 38.63 mmol) in DCM (161 mL) at 25° C. over a period of 15 minutes under nitrogen. The resulting solution was stirred at room temperature for 30 minutes. The resulting mixture was evaporated to dryness and the residue was purified by flash silica chromatography, elution gradient 40 to 100% EtOAc in isohexane. Pure fractions were evaporated to dryness to afford (S)-3-(tert-butoxycarbonylamino)-3-(4-chlorophenyl)propyl methanesulfonate (10.03 g, 86%) as a white solid.

NMR (399.9 MHz, CDCl3) δ 1.36-1.48 (9H, m), 2.20 (2H, s), 3.01 (3H, s), 4.19-4.29 (2H, m), 4.81 (2H, s), 7.21-7.23 (2H, d), 7.32-7.35 (2H, d).

MS m/e M+Na$^+$ 386.

Intermediate 60: (S)-1-(4-chlorophenyl)-N3,N3-diethylpropane-1,3-diamine

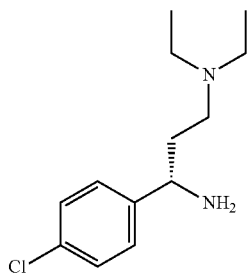 [SMILES: CCN(CC)CC[C@H](N)c1ccc(Cl)cc1]

Diethylamine (0.426 mL, 4.12 mmol) and (S)-3-(tert-butoxycarbonylamino)-3-(4-chlorophenyl)propyl methanesulfonate (Intermediate 59) (500 mg, 1.37 mmol) were dissolved in THF (10 mL) and sealed into a microwave tube. The reaction was heated to 120° C. for 50 minutes in the microwave reactor and cooled to room temperature. The reaction mixture was concentrated and diluted with DCM (5 mL). TFA (1 mL) was added and the reaction was stirred at 20° C. for 1 hour. The crude product was purified by ion exchange chromatography, using an SCX column. The desired product was eluted from the column using 3.5N ammonia/MeOH and pure fractions were evaporated to dryness to afford (S)-1-(4-chlorophenyl)-N3,N3-diethylpropane-1,3-diamine (119 mg, 36.0%) as a yellow oil.

$^1$H NMR (400.13 MHz, CDCl3) δ 1.00 (6H, t), 1.75-1.82 (2H, m), 2.40-2.54 (6H, m), 3.97 (1H, t), 7.27-7.31 (4H, m).
MS m/e MH$^+$ 241.

Intermediate 61: 5-bromo-4-chloro-7-tosyl-7H-pyrrolo[2,3-d]pyrimidine

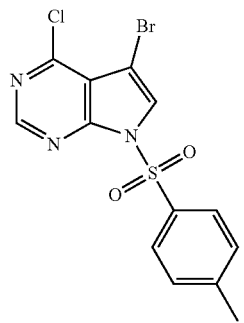 [SMILES: Cc1ccc(S(=O)(=O)n2cc(Br)c3c(Cl)ncnc32)cc1]

5-Bromo-4-chloro-7H-pyrrolo[2,3-d]pyrimidine (Intermediate 50) (2 g, 8.60 mmol) and p-toluenesulfonyl chloride (1.640 g, 8.60 mmol) was taken up in acetone (12 mL) and stirred under nitrogen and cooled to between −5° C. and 5° C. To this solution was added 2.0M NaOH solution (5.50 mL, 10.99 mmol) while maintaining the internal temperature at less than 5° C. The reaction was allowed to warm to room temperature and stirred for 1 hour. The white solid was filtered off and washed well with acetone to afford 5-bromo-4-chloro-7-tosyl-7H-pyrrolo[2,3-d]pyrimidine (3.28 g, 99%) as a pale cream solid.

$^1$H NMR (400.13 MHz, DMSO-d6) δ 2.38 (3H, s), 7.48-7.50 (2H, m), 8.06-8.08 (2H, m), 8.41 (1H, s), 8.84 (1H, s).

MS m/e MH$^+$ 387.

Intermediate 62: Methyl 1-(5-bromo-7-tosyl-7H-pyrrolo[2,3-d]pyrimidin-4-yl)-4-(tert-butoxycarbonylamino)piperidine-4-carboxylate

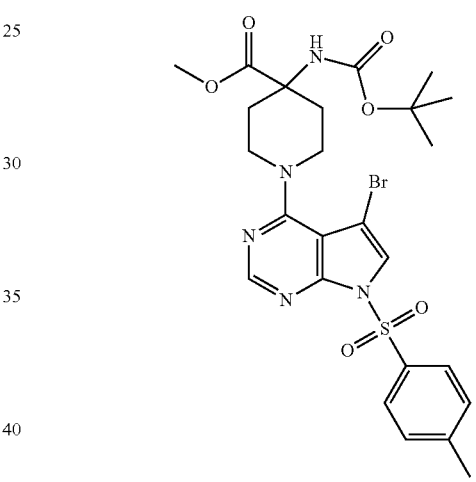

Triethylamine (3.55 mL, 25.45 mmol) was added to 5-bromo-4-chloro-7-tosyl-7H-pyrrolo[2,3-d]pyrimidine (Intermediate 61) (3.28 g, 8.48 mmol) and methyl 4-(tert-butoxycarbonylamino)piperidine-4-carboxylate (WO2008075109) (3.07 g, 11.88 mmol) in DMA (50 mL) at 20° C. The resulting suspension was stirred at 70° C. for 2 hours. The reaction mixture was concentrated and diluted with EtOAc (200 mL), and washed sequentially with water (75 mL) and saturated brine (75 mL). The organic layer was dried over MgSO$_4$, filtered and evaporated to afford crude product. The crude product was purified by flash silica chromatography, elution gradient 30 to 70% EtOAc in isohexane. Pure fractions were evaporated to dryness to afford methyl 1-(5-bromo-7-tosyl-7H-pyrrolo[2,3-d]pyrimidin-4-yl)-4-(tert-butoxycarbonylamino)piperidine-4-carboxylate (3.60 g, 69.7%) as a white solid.

$^1$H NMR (400.13 MHz, DMSO-d$_6$) δ 1.38 (9H, s), 2.03 (2H, s), 2.38 (3H, s), 3.33-3.37 (2H, m), 3.59 (3H, s), 3.84 (2H, d), 7.41 (1H, s), 7.46 (2H, d), 8.00 (1H, s), 8.03 (2H, d), 8.40 (1H, s).

MS m/e MH$^+$ 610.

Intermediate 63: Methyl 4-(tert-butoxycarbonylamino)-1-(5-cyclopropyl-7-tosyl-7H-pyrrolo[2,3-d]pyrimidin-4-yl)piperidine-4-carboxylate

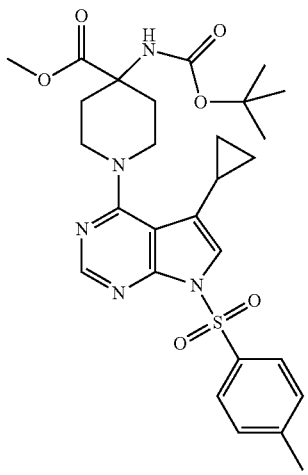

Methyl 1-(5-bromo-7-tosyl-7H-pyrrolo[2,3-d]pyrimidin-4-yl)-4-(tert-butoxycarbonylamino)piperidine-4-carboxylate (Intermediate 62) (1.1 g, 1.81 mmol), potassium phosphate tribasic (1.343 g, 6.33 mmol), tricyclohexyl phosphine (0.101 g, 0.36 mmol) and cyclopropylboronic acid (0.438 g, 4.34 mmol) were taken up in toluene (10 mL) and water (0.400 mL). The mixture was purged with nitrogen for 30 minutes then palladium(II) acetate (0.041 g, 0.18 mmol) was added. The mixture was heated to 75° C. for 6 hours and then allowed to cool and stir at room temperature overnight. The reaction mixture was diluted with EtOAc (75 mL), and washed sequentially with water (50 mL) and saturated brine (50 mL). The organic layer was dried over MgSO₄, filtered and evaporated to afford crude product. The crude product was purified by flash silica chromatography, elution gradient 10 to 30% EtOAc in isohexane. Pure fractions were evaporated to dryness to afford methyl 4-(tert-butoxycarbonylamino)-1-(5-cyclopropyl-7-tosyl-7H-pyrrolo[2,3-d]pyrimidin-4-yl)piperidine-4-carboxylate (0.447 g, 43.4%) as a cream solid.

¹H NMR (400.13 MHz, CDCl₃) δ 0.72-0.76 (2H, m), 0.99-1.04 (2H, m), 1.43 (9H, s), 1.90-1.94 (1H, m), 2.04-2.10 (2H, m), 2.17-2.25 (2H, m), 2.38 (3H, s), 3.34-3.41 (2H, m), 3.74 (3H, s), 3.98-4.03 (2H, m), 4.76 (1H, s), 7.12 (1H, s), 7.28 (2H, m), 8.03-8.05 (2H, m), 8.46 (1H, s).

MS m/e MH⁺ 570.

Intermediate 64: 4-(tert-butoxycarbonylamino)-1-(5-cyclopropyl-7H-pyrrolo[2,3-d]pyrimidin-4-yl)piperidine-4-carboxylic acid

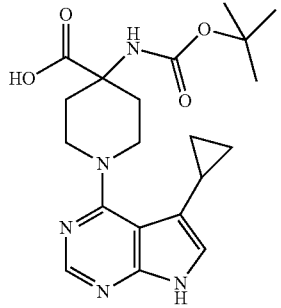 [SMILES: CC(C)(C)OC(=O)NC1(C(=O)O)CCN(c2ncnc3[nH]cc(C4CC4)c23)CC1]

2M sodium hydroxide solution (5.00 mL) was added to methyl 4-(tert-butoxycarbonylamino)-1-(5-cyclopropyl-7-tosyl-7H-pyrrolo[2,3-d]pyrimidin-4-yl)piperidine-4-carboxylate (Intermediate 63) (780 mg, 1.37 mmol) in THF (10 mL) at 20° C. The resulting solution was stirred at 40° C. for 24 hours. The reaction mixture was diluted with EtOAc (50 mL) and the aqueous layer was collected and acidified to pH4 with 2M HCl solution. The aqueous layer was extracted with DCM (2×50 mL) and the organic layers combined and washed with saturated brine (50 mL). The organic layer was dried over MgSO₄, filtered and evaporated to afford crude product 4-(tert-butoxycarbonylamino)-1-(5-cyclopropyl-7H-pyrrolo[2,3-d]pyrimidin-4-yl)piperidine-4-carboxylic acid (375 mg, 68.2%) as a cream solid.

¹H NMR (400.13 MHz, DMSO-d₆) δ 0.66-0.73 (2H, m), 0.88-1.00 (2H, m), 1.40 (9H, s), 1.94-2.09 (5H, m), 3.41-3.53 (2H, m), 3.92-4.01 (2H, m), 6.92 (1H, d), 7.18-7.22 (1H, m), 8.21 (1H, s), 11.51 (1H, s), 12.29 (1H, s).

MS m/e MH⁺ 402.

Intermediate 65: (S)-tert-butyl 4-(1-(4-chlorophenyl)-3-hydroxypropylcarbamoyl)-1-(5-cyclopropyl-7H-pyrrolo[2,3-d]pyrimidin-4-yl)piperidin-4-ylcarbamate

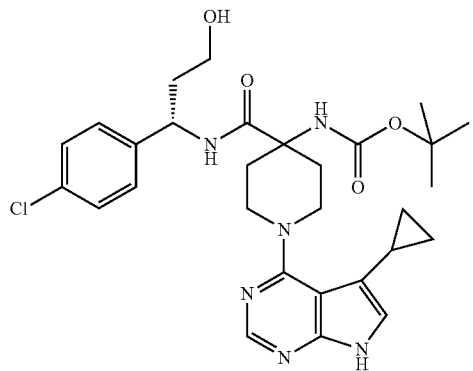 [SMILES: CC(C)(C)OC(=O)NC1(C(=O)N[C@@H](CCO)c2ccc(Cl)cc2)CCN(c2ncnc3[nH]cc(C4CC4)c23)CC1]

(S)-3-amino-3-(4-chlorophenyl)propan-1-ol (173 mg, 0.93 mmol) was added in one portion to 4-(tert-butoxycarbonylamino)-1-(5-cyclopropyl-7H-pyrrolo[2,3-d]pyrimidin-4-yl)piperidine-4-carboxylic acid (Intermediate 64) (375 mg, 0.93 mmol) and DIPEA (0.489 mL, 2.80 mmol) in DMA (5 mL). O-(7-azabenzotriazol-1-yl)-N,N,N',N'-tetramethyluronium hexafluorophosphate (391 mg, 1.03 mmol) was added and the resulting solution was stirred at 20° C. for 24 hours. The reaction mixture was evaporated to dryness then diluted with EtOAc (75 mL), and washed sequentially with water (50 mL) and saturated brine (50 mL). The organic layer was dried over MgSO₄, filtered and evaporated to afford crude product. The crude product was purified by flash silica chromatography, elution gradient 2 to 6% MeOH with ammonia in DCM. Fractions were evaporated to afford (S)-tert-butyl 4-(1-(4-chlorophenyl)-3-hydroxypropylcarbamoyl)-1-(5-cyclopropyl-7H-pyrrolo[2,3-d]pyrimidin-4-yl)piperidin-4-ylcarbamate (420 mg, 79%) as a yellow gum.

¹H NMR (400.13 MHz, DMSO-d₆) δ 0.66-0.70 (2H, m), 0.86-0.91 (2H, m), 1.40 (9H, s), 1.81-2.06 (7H, m), 3.33-3.40 (4H, m), 3.90-3.94 (2H, m), 4.53 (1H, t), 4.91-4.93 (1H, m), 6.92 (1H, s), 7.30-7.38 (4H, m), 7.96 (1H, d), 8.20 (1H, s), 11.49 (1H, s).

MS m/e MH⁺ 569.

Intermediate 66: Tert-butyl 1-(4-chlorophenyl)-3-(methylamino)propylcarbamate

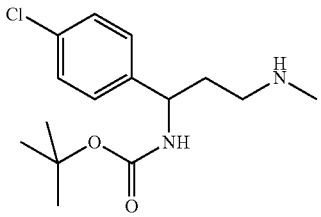 [SMILES: CNCCC(NC(=O)OC(C)(C)C)c1ccc(Cl)cc1]

Methylamine gas was bubbled into a solution of 3-(tert-butoxycarbonylamino)-3-(4-chlorophenyl)propyl methanesulfonate (Intermediate 31) (70 mg, 0.19 mmol) in THF (5 mL) at 22° C. over a period of 5 minutes. The mixture was sealed into a microwave tube. The reaction was heated to 125° C. for 30 minutes in the microwave reactor and cooled to ambient temperature. The mixture was evaporated and the residue was purified by flash silica chromatography, elution gradient 4 to 8% (10:1 MeOH/conc. $NH_{3(aq)}$) in DCM. Pure fractions were evaporated to dryness to afford tert-butyl 1-(4-chlorophenyl)-3-(methylamino)propylcarbamate (52 mg, 90%) as a colourless oil.

$^1$H NMR (399.902 MHz, CDCl3) δ 1.41 (9H, s), 1.80 (1H, br.m), 1.93 (1H, br.m), 2.40 (3H, s), 2.59 (2H, m), 4.73 (1H, br.s), 5.94 (1H, br.s), 7.21 (2H, d), 7.29 (2H, d).

MS m/e MH$^+$ 299.5.

Intermediate 67: 1-(4-chlorophenyl)-N3-methylpropane-1,3-diamine

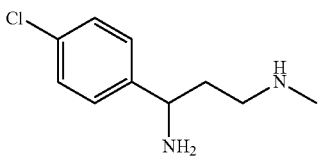

Hydrogen chloride (4M in 1,4-dioxane, 0.50 mL, 2.00 mmol) was added to tert-butyl 1-(4-chlorophenyl)-3-(methylamino)propylcarbamate (Intermediate 66) (50 mg, 0.17 mmol) in a mixture of DCM (5 mL) and methanol (2 mL) at 22° C. The resulting solution was stirred at 22° C. for 4 hours. The mixture was concentrated and the residue was purified by ion exchange chromatography, using an SCX column. The desired product was eluted from the column using 2M NH$_3$/MeOH and pure fractions were evaporated to dryness to afford 1-(4-chlorophenyl)-N3-methylpropane-1,3-diamine (30 mg, 90%) as a colourless oil.

$^1$H NMR (399.902 MHz, CDCl3) δ 1.81 (2H, dt), 2.40 (3H, s), 2.58 (2H, m), 4.01 (1H, t), 7.25-7.31 (4H, m).

MS m/e MH$^+$ 199.3.

Intermediate 68: Tert-butyl 4-(1-(4-chlorophenyl)-3-(methylamino)propylcarbamoyl)-1-(7H-pyrrolo[2,3-d]pyrimidin-4-yl)piperidin-4-ylcarbamate

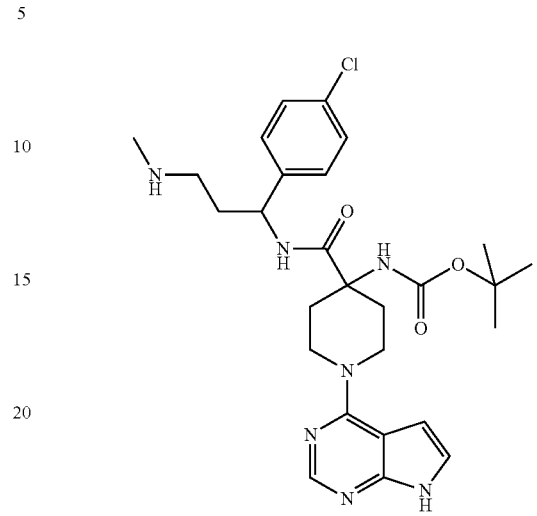

O-(7-azabenzotriazol-1-yl)-N,N,N',N'-tetramethyluronium hexafluorophosphate (44 mg, 0.12 mmol) was added to 4-(tert-butoxycarbonylamino)-1-(7H-pyrrolo[2,3-d]pyrimidin-4-yl)piperidine-4-carboxylic acid (Intermediate 1) (40 mg, 0.11 mmol) and N,N-diisopropylethylamine (0.023 mL, 0.13 mmol) in NMP (5 mL) at 22° C. The resulting suspension was stirred at 50° C. for 10 minutes. The mixture was cooled to ambient temperature and 1-(4-chlorophenyl)-N3-methylpropane-1,3-diamine (Intermediate 67) (22 mg, 0.11 mmol) was added as a solution in NMP (2 mL) and the mixture stirred at 22° C. for 3 days. The reaction mixture was diluted with EtOAc (50 mL) and washed with water (50 mL). The aqueous layer was passed through an SCX column. The column was eluted with water and methanol to remove impurities followed by 30% (2M NH$_3$ in methanol) in DCM to elute the product. The appropriate fractions were evaporated to dryness to afford tert-butyl 4-(1-(4-chlorophenyl)-3-(methylamino)propylcarbamoyl)-1-(7H-pyrrolo[2,3-d]pyrimidin-4-yl)piperidin-4-ylcarbamate (10.00 mg, 17%) as a white solid.

MS m/e MH$^+$ 542.5.

Intermediate 69: 1-tert-butyl 4-methyl 4-(tert-butoxycarbonylamino)piperidine-1,4-dicarboxylate

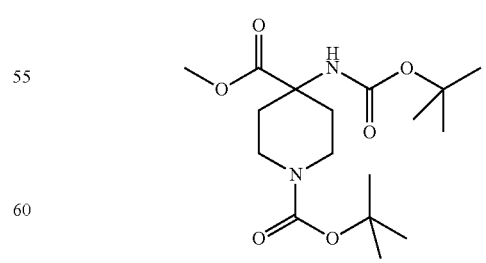

Methyl 4-(tert-butoxycarbonylamino)piperidine-4-carboxylate (WO2008075109) (10 g, 38.71 mmol) was dissolved in DCM (194 mL). To this was added di-tert-butyl dicarbonate (10.67 mL, 46.46 mmol) portionwise. After the addition the reaction was stirred at 25° C. for 1 hour. The crude product was washed with saturated sodium bicarbonate (3×50 mL) and the organic layers dried over MgSO₄ before being evaporated to dryness to afford 1-tert-butyl 4-methyl 4-(tert-butoxycarbonylamino)piperidine-1,4-dicarboxylate (13.6 g, 98%) as a white solid.

¹H NMR (400.13 MHz, DMSO) δ 1.39 (9H, s), 1.40 (9H, s), 1.70-1.77 (2H, td), 1.88-1.92 (2H, d), 3.05 (2H, broad), 3.61 (3H, s), 3.62-3.65 (2H, m), 7.33 (broad, exchange).

Intermediate 70: 1-(tert-butoxycarbonyl)-4-(tert-butoxycarbonylamino)piperidine-4-carboxylic acid

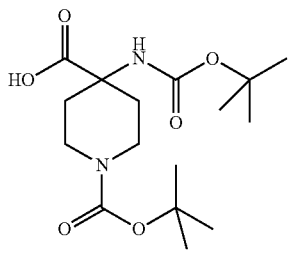 [SMILES: CC(C)(C)OC(=O)NC1(C(=O)O)CCN(C(=O)OC(C)(C)C)CC1]

Lithium hydroxide monohydrate (8.13 g, 193.62 mmol) was added to 1-tert-butyl 4-methyl 4-(tert-butoxycarbonylamino)piperidine-1,4-dicarboxylate (Intermediate 69) (13.88 g, 38.72 mmol) in water (21.51 mL), THF (86 mL) and methanol (86 mL). The resulting solution was stirred at 20° C. for 1 day. The reaction mixture was diluted with EtOAc (75 mL) and washed with water (75 mL). The aqueous was adjusted to pH5 with 1M citric acid solution, then extracted with EtOAc (3×200 mL). The organic extracts were washed with saturated brine (50 mL), then dried over MgSO₄, filtered and evaporated to afford desired product 1-(tert-butoxycarbonyl)-4-(tert-butoxycarbonylamino)piperidine-4-carboxylic acid (10.36 g, 78%) as a fine white solid.

¹H NMR (400.13 MHz, DMSO) δ 1.39 (9H, s), 1.40 (9H, s), 1.68-1.76 (2H, td), 1.89-1.92 (2H, d), 3.03 (2H, broad), 3.62-3.65 (2H, d), 7.16 (exchange), 12.36 (exchange).

Intermediate 71: Tert-butyl 4-(tert-butoxycarbonylamino)-4-(1-(4-chlorophenyl)-4-hydroxybutylcarbamoyl)piperidine-1-carboxylate

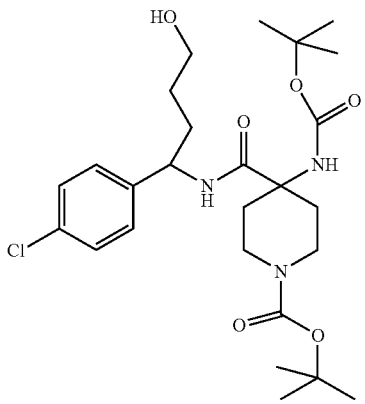 [SMILES: CC(C)(C)OC(=O)NC1(C(=O)NC(CCCO)c2ccc(Cl)cc2)CCN(C(=O)OC(C)(C)C)CC1]

O-(7-azabenzotriazol-1-yl)-N,N,N',N'-tetramethyluronium hexafluorophosphate (5.24 g, 13.77 mmol) was added in one portion to 1-(tert-butoxycarbonyl)-4-(tert-butoxycarbonylamino)piperidine-4-carboxylic acid (Intermediate 70) (4.31 g, 12.5 mmol), 4-amino-4-(4-chlorophenyl)butan-1-ol (Intermediate 16) (2.5 g, 12.5 mmol) and DIPEA (6.56 mL, 37.6 mmol) in DMA (62.6 mL) under nitrogen. The resulting solution was stirred at 60° C. for 3 hours and evaporated to dryness. The crude reaction mixture was dissolved in 100 mL EtOAc and then basified with saturated NaHCO₃ (150 mL) and the organic fraction dried over MgSO₄, filtered and evaporated to dryness. The organic fraction was purified by flash silica chromatography (eluent 0-10% 7N ammonia in MeOH/DCM). Pure fractions were then evaporated to afford tert-butyl 4-(tert-butoxycarbonylamino)-4-(1-(4-chlorophenyl)-4-hydroxybutylcarbamoyl) piperidine-1-carboxylate (5.06 g, 77%) as an off-white solid.

¹H NMR (400.13 MHz, DMSO) δ 1.39 (18H, s), 1.42-1.50 (2H, sex), 1.67-1.73 (2H, q), 1.74-1.82 (2H, m), 1.87 (2H, broad), 3.07 (2H, broad), 3.34-3.41 (2H, m), 3.53-3.61 (2H, t), 4.71-4.76 (1H, q), 6.79 (3× change, broad), 7.29-7.34 (4H, m), 7.80-7.82 (exchange, d).

MS m/e MH⁺=527; HPLC t_R=2.48 min.

Intermediate 72: 4-amino-N-(1-(4-chlorophenyl)-4-hydroxybutyl)piperidine-4-carboxamide

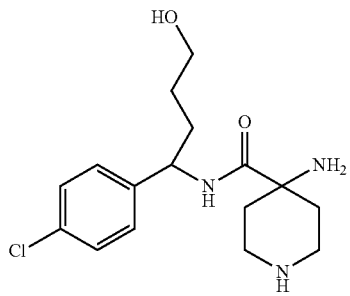 [SMILES: NC1(C(=O)NC(CCCO)c2ccc(Cl)cc2)CCNCC1]

Tert-butyl4-(tert-butoxycarbonylamino)-4-(1-(4-chlorophenyl)-4-hydroxybutylcarbamoyl)piperidine-1-carboxylate (Intermediate 71) (1.98 g, 3.76 mmol) was stirred in THF (18.82 mL) and 4M hydrogen chloride (14.11 mL, 56.46 mmol) in dioxane was added with stirring. The resulting solution was stirred at ambient temperature overnight. The crude mixture was purified by SCX chromatography (eluent 20% 7N ammonia/MeOH in DCM). Pure fractions were evaporated to dryness to afford 4-amino-(1.04 g, 85%), as a colourless, transparent gum.

¹H NMR (400.13 MHz) δ 1.16-1.27 (2H, dd), 1.29-1.51 (2H, sepd), 1.70-1.76 (2H, q), 1.75-1.89 (2H, m), 2.65-2.72 (2H, m), 2.74-2.83 (2H, dq), 3.37-3.39 (2H, m), 4.39 (exchange, broad) 4.70-4.76 (1H, q), 7.32-7.35 (2H, d), 7.36-7.39 (2H, d), 8.25-8.27 (exchange, d)

MS m/e MH⁺=326; HPLC t_R=1.70 min.

Intermediate 73: Tert-butyl 2-amino-1-(4-chlorophenyl)ethylcarbamate

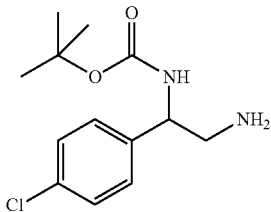 [SMILES: CC(C)(C)OC(=O)NC(CN)c1ccc(Cl)cc1]

A solution of 2-(tert-butoxycarbonylamino)-2-(4-chlorophenyl)ethyl methanesulfonate (Intermediate 23) (535 mg, 1.53 mmol) in DMF (8 mL) was treated with sodium azide (199 mg, 3.06 mmol) and the mixture was heated at 80° C. for 1 hour. The mixture was cooled and allowed to stir at room temperature overnight. The solution was partitioned between ethyl acetate and water. The organic layer was washed twice with water then dried with magnesium sulfate, filtered and concentrated until the final volume was approximately 5 mL. Ethanol (20 mL) and 10% palladium on carbon (75 mg, 0.07 mmol) were added. The resulting suspension was stirred under an atmosphere of hydrogen at ambient pressure and temperature for 1 hour. The mixture was filtered and the filtrate was concentrated under reduced pressure to give tert-butyl 2-amino-1-(4-chlorophenyl)ethylcarbamate as a gum (410 mg, 99%).

MS m/e MH$^+$=271

Intermediate 74: Tert-butyl 1-(4-chlorophenyl)-2-(methylsulfonamido)ethylcarbamate

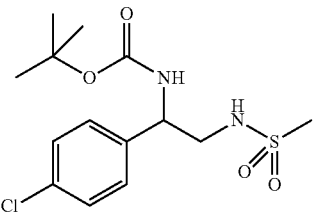 [SMILES: CC(C)(C)OC(=O)NC(CNS(C)(=O)=O)c1ccc(Cl)cc1]

A solution of tert-butyl 2-amino-1-(4-chlorophenyl)ethylcarbamate (Intermediate 73) (220 mg, 0.81 mmol) and N-ethyldiisopropylamine (0.281 mL, 1.63 mmol) in THF (5 mL) was treated with methanesulfonyl chloride (0.075 mL, 0.98 mmol). The resulting solution was stirred at ambient temperature for 2 hours. The mixture was partitioned between DCM and sodium bicarbonate solution. The organic layer was concentrated and the residue was purified by flash column chromatography on silica using gradient elution (10% ethyl acetate/DCM to 30% ethyl acetate/DCM). The desired product, tert-butyl 1-(4-chlorophenyl)-2-(methylsulfonamido)ethylcarbamate, was thus isolated as a colourless solid (154 mg, 54.3%).

$^1$H NMR (399.9 MHz, CDCl$_3$) δ 1.43 (9H, s), 2.92 (3H, s), 3.38-3.52 (2H, m), 4.68-4.84 (2H, m), 5.20-5.28 (1H, m), 7.23 (2H, d), 7.35 (2H, d)

MS m/e (M−H)−=347

Intermediate 75: N-(2-amino-2-(4-chlorophenyl)ethyl)methanesulfonamide

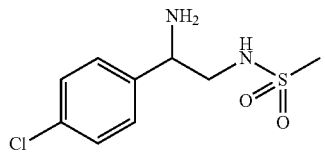

tert-butyl 1-(4-chlorophenyl)-2-(methylsulfonamido)ethylcarbamate (Intermediate 74) (151 mg, 0.43 mmol) was treated with trifluoroacetic acid (2 mL). The solution was stirred for 1 hour at room temperature. The mixture was concentrated under reduced pressure. The crude product was purified by ion exchange chromatography, using an SCX column. The residue was loaded onto the column in methanol and washed with methanol. The desired product was eluted from the column using 2M ammonia in methanol and pure fractions were evaporated to dryness to afford N-(2-amino-2-(4-chlorophenyl)ethyl)methanesulfonamide (93 mg, 86%) as a colourless crystalline solid.

$^1$H NMR (399.9 MHz, CDCl$_3$) δ 2.89 (3H, s), 3.17 (1H, dd), 3.33 (1H, dd), 4.12 (1H, dd), 4.74 (1H, br, s), 7.29 (2H, d), 7.34 (2H, d)

MS m/e (M−H)−=247

Intermediate 76: Tert-butyl 4-(1-(4-chlorophenyl)-2-(methylsulfonamido)ethylcarbamoyl)-1-(7H-pyrrolo[2,3-d]pyrimidin-4-yl)piperidin-4-ylcarbamate

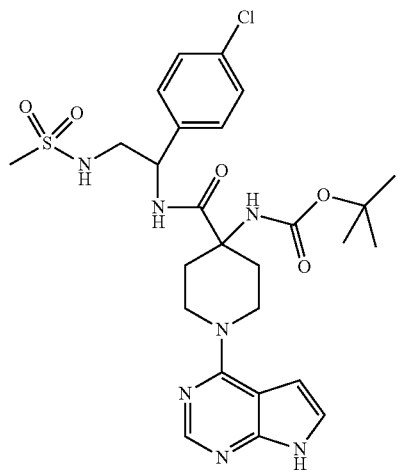 [SMILES: CC(C)(C)OC(=O)NC1(C(=O)NC(CNS(C)(=O)=O)c2ccc(Cl)cc2)CCN(c2ncnc3[nH]ccc23)CC1]

O-(7-Azabenzotriazol-1-yl)-N,N,N',N'-tetramethyluronium hexafluorophosphate (88 mg, 0.23 mmol) was added in one portion to a stirred solution of 4-(tert-butoxycarbonylamino)-1-(7H-pyrrolo[2,3-d]pyrimidin-4-yl)piperidine-4-carboxylic acid (Intermediate 1) (79 mg, 0.22 mmol) and N-ethyldiisopropylamine (0.046 mL, 0.26 mmol) in NMP (3 mL). The mixture was treated with N-(2-amino-2-(4-chlorophenyl)ethyl)methanesulfonamide (Intermediate 75) (60 mg, 0.24 mmol). The solution was stirred for 65 hours at room temperature. The mixture was partitioned between ethyl acetate and water. The organic layer was washed twice with water. The organic solution was concentrated under reduced pressure. The residue was purified by flash column chromatography on silica using gradient elution (1% methanol/DCM to 15% methanol/DCM). Product containing fractions were combined to give tert-butyl 4-(1-(4-chlorophenyl)-2-(methylsulfonamido)ethylcarbamoyl)-1-(7H-pyrrolo[2,3-d]pyrimidin-4-yl)piperidin-4-ylcarbamate (103 mg, 79%) as colourless solid.

$^1$H NMR (399.9 MHz, DMSO-$d_6$) δ 1.41 (9H, s), 2.00 (4H, br, s), 2.81 (3H, s), 3.52-3.69 (2H, m), 4.18-4.27 (2H, m), 4.96 (1H, q), 6.60 (1H, s), 6.97 (1H, br, s), 7.10-7.22 (2H, m), 7.37 (4H, s), 8.01 (1H, d), 8.14 (1H, s), 11.65 (1H, s)

MS m/e MH$^+$=592

Intermediate 77: 2-(tert-butoxycarbonylamino)-2-(4-chlorophenyl)ethyl ethanethioate

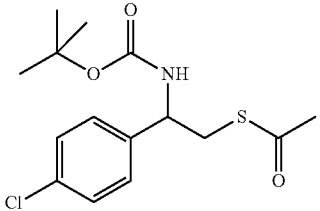 [SMILES: CC(=O)SCC(NC(=O)OC(C)(C)C)c1ccc(Cl)cc1]

A solution of 2-(tert-butoxycarbonylamino)-2-(4-chlorophenyl)ethyl methanesulfonate (Intermediate 23) (600 mg, 1.72 mmol) in DMF (10 mL) was treated with potassium thioacetate (392 mg, 3.43 mmol) and the mixture was heated at 50° C. for 1 hour. The mixture was cooled and partitioned between ethyl acetate and water. The organic layer was washed twice with water then dried with magnesium sulfate, filtered and concentrated to dryness. The residue was purified by flash column chromatography on silica using gradient elution (10% ethyl acetate/isohexane to 20% ethyl acetate/isohexane). The desired product, 2-(tert-butoxycarbonylamino)-2-(4-chlorophenyl)ethyl ethanethioate (509 mg, 90%), was thus isolated as a cream crystalline solid.

$^1$H NMR (399.9 MHz, CDCl3) δ 1.40 (9H, s), 2.35 (3H, s), 3.15-3.28 (2H, m), 4.78 (1H, br, s), 5.07 (1H, br, s), 7.24 (2H, d), 7.31 (2H, d)

MS m/e (M–H—CH$_3$CO)—=286

Intermediate 78: Tert-butyl 1-(4-chlorophenyl)-2-(chlorosulfonyl)ethylcarbamate

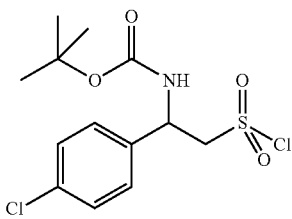 [SMILES: CC(C)(C)OC(=O)NC(CS(=O)(=O)Cl)c1ccc(Cl)cc1]

N-Chlorosuccinimide (819 mg, 6.14 mmol) was added to a solution of 2M hydrochloric acid (0.8 mL) in acetonitrile (10 mL). The reaction flask was cooled with an ice bath to 10° C. and 2-(tert-butoxycarbonylamino)-2-(4-chlorophenyl)ethyl ethanethioate (Intermediate 77) (506 mg, 1.53 mmol) was added portionwise. The mixture warmed during the addition and was stirred for 10 minutes at room temperature. The mixture was partitioned between ethyl acetate and water. The organic layer was washed with brine, dried with magnesium sulfate, filtered and concentrated to dryness. tert-butyl chlorophenyl)-2-(chlorosulfonyl)ethylcarbamate (602 mg, quant.) was thus obtained as a colourless solid.

$^1$H NMR (399.9 MHz, CDCl$_3$) δ 1.44 (9H, s), 2.77 (1H, s), 4.06 (1H, dd), 4.36 (1H, br, s), 5.15-5.23 (1H, m), 5.29-5.37 (1H, m), 7.29 (2H, d), 7.38 (2H, d)

Intermediate 79: Tert-butyl 1-(4-chlorophenyl)-2-sulfamoylethylcarbamate

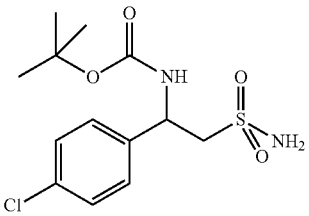 [SMILES: CC(C)(C)OC(=O)NC(CS(N)(=O)=O)c1ccc(Cl)cc1]

Ammonia (1.5 mL, 31.50 mmol) was added to a suspension of tert-butyl 1-(4-chlorophenyl)-2-(chlorosulfonyl)ethylcarbamate (Intermediate 78) (0.542 g, 1.53 mmol) in acetonitrile (10 mL). The mixture was stirred for 16 hours at room temperature. The mixture was partitioned between ethyl acetate and water and the organic layer was washed with brine. The organic solution was dried with magnesium sulfate, filtered, and concentrated under reduced pressure. The residue was purified by flash column chromatography on silica using gradient elution (10% ethyl acetate/DCM to 30% ethyl acetate/DCM). The desired product, tert-butyl 1-(4-chlorophenyl)-2-sulfamoylethylcarbamate (0.351 g, 68.5%), was thus isolated as a colourless solid.

$^1$H NMR (399.9 MHz, DMSO-$d_6$) δ 1.36 (9H, s), 3.21-3.28 (1H, m), 3.47-3.56 (1H, m), 5.02 (1H, br, s), 6.88 (2H, s), 7.35 (2H, d), 7.41 (2H, d), 7.49-7.60 (1H, m)

MS m/e (M–H–)–=333

Intermediate 80: 2-amino-2-(4-chlorophenyl)ethanesulfonamide

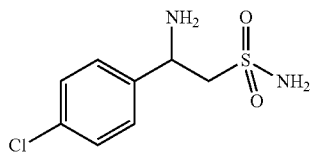 [SMILES: NC(CS(N)(=O)=O)c1ccc(Cl)cc1]

Tert-butyl 1-(4-chlorophenyl)-2-sulfamoylethylcarbamate (Intermediate 79) (325 mg, 0.97 mmol) was treated with trifluoroacetic acid (8 mL). The resulting solution was stirred for 15 minutes at room temperature. The mixture was concentrated under reduced pressure and the residue was purified by ion exchange chromatography, using an SCX column. The column was washed with methanol and the desired product was eluted using ammonia in methanol (2M) and pure fractions were evaporated to dryness to afford 2-amino-2-(4-chlorophenyl)ethanesulfonamide (221 mg, 97%) as a near colourless solid.

¹H NMR (399.9 MHz, DMSO-d6) δ 3.13-3.25 (2H, m), 4.39 (1H, dd), 7.35-7.48 (4H, m)
MS m/e (M–H–)–=233

Intermediate 81: Tert-butyl 4-(1-(4-chlorophenyl)-2-sulfamoylethylcarbamoyl)-1-(7H-pyrrolo[2,3-d]pyrimidin-4-yl)piperidin-4-ylcarbamate

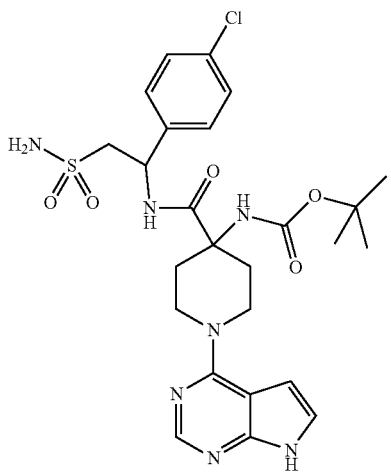 [SMILES: CC(C)(C)OC(=O)NC1(C(=O)NC(CS(N)(=O)=O)c2ccc(Cl)cc2)CCN(c2ncnc3[nH]ccc23)CC1]

O-(7-Azabenzotriazol-1-yl)-N,N,N',N'-tetramethyluronium hexafluorophosphate (128 mg, 0.34 mmol) was added in one portion to a stirred solution of 4-(tert-butoxycarbonylamino)-1-(7H-pyrrolo[2,3-d]pyrimidin-4-yl)piperidine-4-carboxylic acid (Intermediate 1) (115 mg, 0.32 mmol) and N-ethyldiisopropylamine (0.066 mL, 0.38 mmol) in NMP (2.5 mL). The mixture was treated with 2-amino-2-(4-chlorophenyl)ethanesulfonamide (Intermediate 80) (75 mg, 0.32 mmol). The solution was stirred for 1 hour at room temperature. The mixture was treated with water (5 mL) and the resulting colourless precipitate was isolated by filtration, washed with water and then acetonitrile to give tert-butyl 4-(1-(4-chlorophenyl)-2-sulfamoylethylcarbamoyl)-1-(7H-pyrrolo[2,3-d]pyrimidin-4-yl)piperidin-4-ylcarbamate (157 mg, 85%) as colourless solid.
¹H NMR (399.9 MHz, DMSO-d6) δ 1.40 (9H, s), 1.90-2.10 (4H, m), 3.35-3.39 (1H, m), 3.51-3.59 (1H, m), 3.62-3.71 (2H, m), 4.12-4.26 (2H, m), 5.30-5.39 (1H, m), 6.59 (1H, s), 6.82 (2H, s), 7.09-7.18 (2H, m), 7.30-7.43 (4H, m), 8.13 (1H, s), 8.19 (1H, d), 11.65 (1H, s)
MS m/e MH+=578

Intermediate 82: Tert-butyl 2-acetamido-1-(4-chlorophenyl)ethylcarbamate

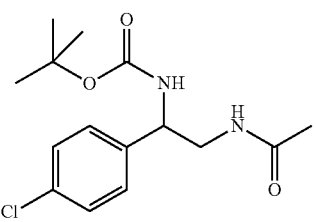 [SMILES: CC(=O)NCC(NC(=O)OC(C)(C)C)c1ccc(Cl)cc1]

A solution of tert-butyl 2-amino-1-(4-chlorophenyl)ethylcarbamate (Intermediate 73) (0.208 g, 0.77 mmol) and N-ethyldiisopropylamine (0.266 mL, 1.54 mmol) in THF (5 mL) was treated with acetic anhydride (0.102 mL, 1.08 mmol). The resulting solution was stirred at ambient temperature for 2 hours. The mixture was partitioned between DCM and sodium bicarbonate solution. The organic layer was concentrated and the residue was purified by flash column chromatography on silica using gradient elution (10% ethyl acetate/DCM to 40% ethyl acetate/DCM). The desired product, tert-butyl 2-acetamido-1-(4-chlorophenyl)ethylcarbamate (0.151 g, 62.7%), was thus isolated as a colourless solid.
¹H NMR (399.9 MHz, CDCl₃) δ 1.41 (9H, s), 1.98 (3H, s), 3.46-3.67 (2H, m), 4.74 (1H, br, s), 4.97-5.56 (1H, m), 5.89 (1H, br, s), 7.22 (2H, d), 7.32 (2H, d)
MS m/e MH+=313

Intermediate 83: N-(2-amino-2-(4-chlorophenyl)ethyl)acetamide

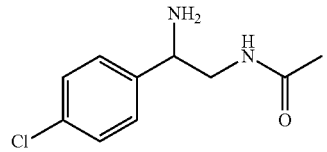

Tert-butyl 2-acetamido-1-(4-chlorophenyl)ethylcarbamate (Intermediate 82) (148 mg, 0.47 mmol) was treated with trifluoroacetic acid (2 mL). The solution was stirred for 1 hours at room temperature. The mixture was concentrated under reduced pressure. The crude product was purified by ion exchange chromatography, using an SCX column. The residue was loaded onto the column in methanol and washed with methanol. The desired product was eluted from the column using 2M ammonia in methanol and pure fractions were evaporated to dryness to afford N-(2-amino-2-(4-chlorophenyl)ethyl)acetamide (98 mg, 97%) as a pale yellow crystalline solid.
¹H NMR (399.9 MHz, CDCl₃) δ 1.61 (2H, br, s), 1.97 (3H, s), 3.28-3.37 (1H, m), 3.44-3.52 (1H, m), 4.05-4.11 (1H, m), 5.78 (1H, br, s), 7.28-7.36 (4H, m)
MS m/e MH+=213

Intermediate 84: Tert-butyl 4-(2-acetamido-1-(4-chlorophenyl)ethylcarbamoyl)-1-(7H-pyrrolo[2,3-d]pyrimidin-4-yl)piperidin-4-ylcarbamate

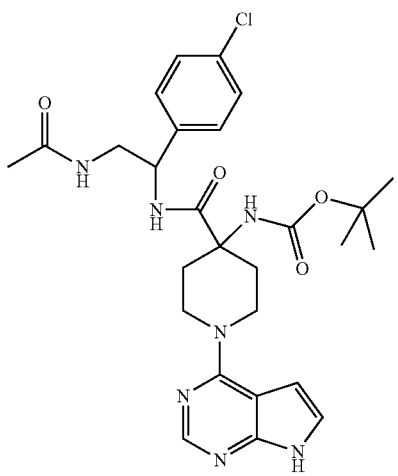 [SMILES: CC(=O)NCC(NC(=O)C1(NC(=O)OC(C)(C)C)CCN(c2ncnc3[nH]ccc23)CC1)c1ccc(Cl)cc1]

O-(7-Azabenzotriazol-1-yl)-N,N,N',N'-tetramethyluronium hexafluorophosphate (89 mg, 0.23 mmol) was added in one portion to a stirred solution of 4-(tert-butoxycarbonylamino)-1-(7H-pyrrolo[2,3-d]pyrimidin-4-yl)piperidine-4-carboxylic acid (Intermediate 1) (80 mg, 0.22 mmol) and N-ethyldiisopropylamine (0.046 mL, 0.27 mmol) in NMP (3 mL). The mixture was treated with N-(2-amino-2-(4-chlorophenyl)ethyl)acetamide (Intermediate 83) (52 mg, 0.24 mmol). The solution was stirred for 65 hours at room temperature. The mixture was partitioned between ethyl acetate and water. The organic layer was washed twice with water. The organic solution was concentrated under reduced pressure. The residue was purified by flash column chromatography on silica using gradient elution (1% methanol/DCM to 15% methanol/DCM). Product containing fractions were combined to give tert-butyl 4-(2-acetamido-1-(4-chlorophenyl)ethylcarbamoyl)-1-(7H-pyrrolo[2,3-d]pyrimidin-4-yl)piperidin-4-ylcarbamate (100 mg, 81%) as colourless solid.

$^1$H NMR (399.9 MHz, DMSO-$d_6$) δ 1.42 (9H, s), 1.78 (3H, s), 1.98 (4H, br, s), 3.36-3.43 (1H, m), 3.50-3.68 (2H, m), 4.18-4.28 (2H, m), 4.85-4.93 (1H, m), 6.58-6.61 (1H, m), 7.14-7.23 (2H, m), 7.30-7.37 (4H, m), 7.84 (1H, br, s), 8.12-8.17 (2H, m), 11.65 (1H, br, s)

MS m/e MH$^+$=556

Intermediate 85: 2-methyl-1-trityl-1H-imidazole

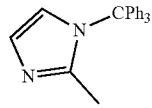

Triethylamine (11.54 mL, 82.82 mmol) was added dropwise to 2-methyl-1H-imidazole (4.0 g, 48.72 mmol) and chlorotriphenylmethane (14.94 g, 53.59 mmol) in acetonitrile (120 mL) at room temperature over a period of 20 minutes under nitrogen. The resulting suspension was stirred at room temperature for 18 hours. Water (120 mL) and i-hexane (12 mL) were added and the slurry stirred for 30 minutes before filtering. The filtered solid was washed with water (3×15 mL) and dried under vacuum to afford 2-methyl-1-trityl-1H-imidazole (15.41 g, 97%) as a cream solid which was used without further purification.

1H NMR (399.902 MHz, CDCl3) δ 1.65 (3H, s), 6.70 (1H, d), 6.90 (1H, d), 7.11-7.16 (6H, m), 7.29-7.35 (9H, m);

m/z (ESI+) (M+H)+=325; HPLC tR=2.88 min.

Intermediate 86: 1-(4-chlorophenyl)-2-(1-trityl-1H-imidazol-2-yl)ethanol

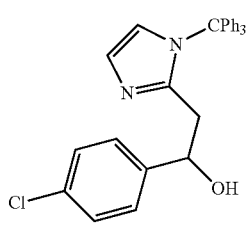

Butyllithium (1.6M in hexanes) (4.24 mL, 6.78 mmol) was added dropwise to 2-methyl-1-trityl-1H-imidazole (Intermediate 85) (2.0 g, 6.16 mmol) in THF (30 mL) cooled to −78° C. over a period of 20 minutes under nitrogen. The resulting dark red solution was stirred at −78° C. for 30 minutes then a solution of 4-Chlorobenzaldehyde (0.867 g, 6.16 mmol) in THF (10 mL) added dropwise. The reaction was allowed to warm slowly to 0° C. then quenched with saturated NH4Cl (50 mL) and extracted with TBME (2×). The combined extracts were washed with brine, dried over MgSO4, concentrated by evaporation then purified by flash silica chromatography, elution gradient 20 to 30% EtOAc in isohexane. Pure fractions were evaporated to dryness to afford 1-(4-chlorophenyl)-2-(1-trityl-1H-imidazol-2-yl)ethanol (1.810 g, 63.1%) as a colourless solid.

1H NMR (399.902 MHz, DMSO) δ 2.05 (2H, d), 4.59-4.63 (1H, m), 5.99 (1H, d), 6.66 (1H, d), 6.96-7.02 (9H, m), 7.26 (2H, d), 7.37-7.40 (9H, m);

m/z (ESI+) (M+H)+=465; HPLC tR=3.54 min.

Intermediate 87: 2-(1-(4-chlorophenyl)-2-(1-trityl-1H-imidazol-2-yl)ethyl)isoindoline-1,3-dione

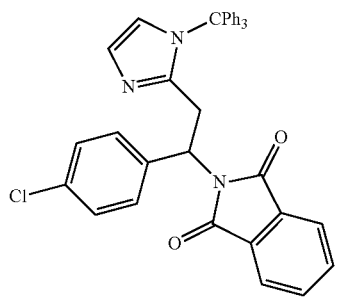

Di-tert-butyl azodicarboxylate (0.808 g, 3.51 mmol) was added portionwise to 1-(4-chlorophenyl)-2-(1-trityl-1H-imidazol-2-yl)ethanol (Intermediate 86) (1.36 g, 2.92 mmol), phthalimide (0.473 g, 3.22 mmol) and triphenylphosphine (0.921 g, 3.51 mmol) in THF (25 mL) at room temperature over a period of 15 minutes. The resulting solution was stirred at room temperature for 60 minutes then concentrated by evaporation and purified by flash silica chromatography, elution gradient 20 to 40% EtOAc in isohexane. Pure fractions were evaporated to dryness to afford 2-(1-(4-chlorophenyl)-2-(1-trityl-1H-imidazol-2-yl)ethyl)isoindoline-1,3-dione (1.78 g, 102%) as a colourless foam.

m/z (ESI+) (M+H)+=594; HPLC tR=2.80 min.

Intermediate 88: 1-(4-chlorophenyl)-2-(1-trityl-1H-imidazol-2-yl)ethanamine

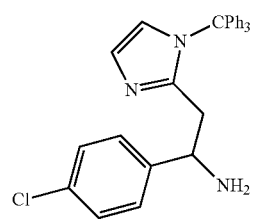

2-(1-(4-chlorophenyl)-2-(1-trityl-1H-imidazol-2-yl)ethyl)isoindoline-1,3-dione (Intermediate 87) (1.78 g, 3.00 mmol) and hydrazine hydrate (0.204 mL, 4.19 mmol) in methanol (30 mL) were refluxed for 3 hours. The resulting clear solution was left to cool to room temperature overnight then filtered. The filtrate was applied to a 20 g SCX cartridge and eluted with methanol followed by 2N NH₃(MeOH). Product-containing fractions were combined and concentrated by evaporation then purified by flash silica chromatography, elution gradient 2 to 5% MeOH in DCM. Pure fractions were evaporated to dryness to afford 1-(4-chlorophenyl)-2-(1-trityl-1H-imidazol-2-yl)ethanamine (0.942 g, 67.8%) as a colourless solid.

1H NMR (399.902 MHz, CDCl3) δ 2.16 (2H, d), 4.01 (1H, t), 6.74 (1H, d), 6.90 (2H, d), 6.99 (1H, d), 7.08-7.13 (7H, m), 7.29-7.32 (10H, m);

m/z (ESI+) (M+H)+=464; HPLC tR=3.13 min.

Intermediate 89: Tert-butyl 4-(1-(4-chlorophenyl)-2-(1-trityl-1H-imidazol-2-yl)ethylcarbamoyl)-1-(7H-pyrrolo[2,3-d]pyrimidin-4-yl)piperidin-4-ylcarbamate

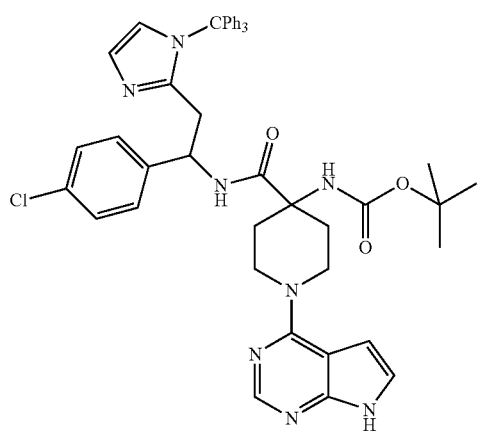

O-(7-Azabenzotriazol-1-yl)-N,N,N',N'-tetramethyluronium hexafluorophosphate (166 mg, 0.44 mmol) was added portionwise to 4-(tert-butoxycarbonylamino)-1-(7H-pyrrolo [2,3-d]pyrimidin-4-yl)piperidine-4-carboxylic acid (Intermediate 1) (150 mg, 0.42 mmol), 1-(4-chlorophenyl)-2-(1-trityl-1H-imidazol-2-yl)ethanamine (Intermediate 88) (193 mg, 0.42 mmol) and N-ethyldiisopropylamine (0.087 mL, 0.50 mmol) in DMF (2.0 mL) at room temperature. The resulting solution was stirred at room temperature for 3 hours then quenched in water (10 mL) to give a pale yellow ppt. The precipitate was collected by filtration, washed with water and dried under vacuum to afford tert-butyl 4-(1-(4-chlorophenyl)-2-(1-trityl-1H-imidazol-2-yl)ethylcarbamoyl)-1-(7H-pyrrolo[2,3-d]pyrimidin-4-yl)piperidin-4-ylcarbamate (320 mg, 95%) as a cream solid, which was used without further purification.

1H NMR (399.902 MHz, CDCl3) δ 1.40 (9H, s), 2.05-2.29 (6H, m), 3.56-3.61 (2H, m), 4.35-4.42 (2H, m), 5.33 (1H, s), 6.50 (1H, d), 6.78 (1H, m), 6.93 (2H, d), 6.97-7.01 (7H, m), 7.13 (2H, d), 7.26-7.35 (10H, m), 8.27 (1H, s), 9.25 (1H, br s), 10.22 (1H, br s).

m/z (ESI+) (M+H)+=807; HPLC tR=2.28 min.

Intermediate 90: 1-(4-chlorophenyl)-2-(1H-pyrazol-1-yl)ethanone

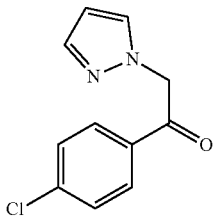 [SMILES: O=C(Cn1cccn1)c1ccc(Cl)cc1]

A solution of pyrazole (3.40 g, 49.98 mmol) and 2-bromo-4'-chloroacetophenone (11.44 g, 49 mmol) dissolved in DME (70 mL) was stirred at room temperature under argon for 5 days. Diethyl ether was added and the precipitate was filtered, washed with diethyl ether and dried in vacuo overnight to give the crude product, 8.842 g of pure white crystals. Concentrated aqueous ammonia (30%; 36 ml) was added to a suspension of 8.76 g of the crude product in 7 ml of water. The reaction was stirred for 40 min after which the yellow crystals were filtered, washed with a little water and dried in vacuo to afford 1-(4-chlorophenyl)-2-(1H-pyrazol-1-yl)ethanone (5.04 g, 22.84 mmol, 46.6%) as a pale yellow solid. Reextraction of the washings gave further product. This was purified by flash chromatography on silica gel eluting with 0 to 10% ethyl acetate in dichloromethane. The solvent was evaporated to dryness to afford 1-(4-chlorophenyl)-2-(1H-pyrazol-1-yl)ethanone (2.78 g, 12.60 mmol, 25.7%) as a colorless crystalline solid.

m/z (ESI+) (M+H)+=221.

1H NMR (500 MHz, DMSO-d6) δ 5.83 (2H, s), 6.61 (1H, dd), 7.48 (1H, d), 7.66 (2H, d), 7.73 (1H, d), 8.04 (2H, d)

Intermediate 91: (Z) and (E)-1-(4-chlorophenyl)-2-(1H-pyrazol-1-yl)ethanone O-methyl Oxime

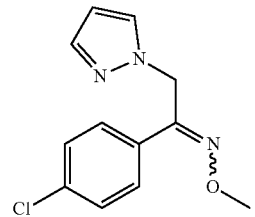 [SMILES: CON=C(Cn1cccn1)c1ccc(Cl)cc1]

Methoxylamine hydrochloride (0.668 g, 8.00 mmol), was added to a stirred solution of 1-(4-chlorophenyl)-2-(1H-pyrazol-1-yl)ethanone (Intermediate 90) (1.103 g, 5 mmol), at room temperature under argon. The resulting solution was stirred at room temperature overnight. The pyridine was evaporated in vacuo and the residual solid was triturated with a saturated aqueous solution of sodium hydrogencarbonate (50-100 ml). The solid was filtered, washed with water and dried to afford (Z) and (E)-1-(4-chlorophenyl)-2-(1H-pyrazol-1-yl)ethanone O-methyl oxime (1.080 g, 87%) as a dark yellow solid.

m/z (ESI+) (M+H)+=250.

1H NMR (500 MHz, DMSO-d6) δ 3.99 (3H, s), 5.44 (2H, s), 6.19 (1H, dd), 7.36 (1H, d), 7.42 (2H, d), 7.65 (2H, d), 7.71 (1H, d)

Intermediate 92: 1-(4-chlorophenyl)-2-(1H-pyrazol-1-yl)ethanamine

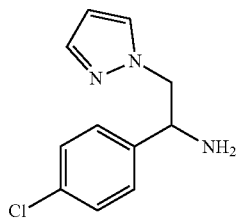 [SMILES: NC(Cn1cccn1)c1ccc(Cl)cc1]

Borane tetrahydrofuran complex (15.00 mL, 15.00 mmol) was added to a stirred solution of (Z) and (E)-1-(4-chlorophenyl)-2-(1H-pyrazol-1-yl)ethanone O-methyl oxime (Intermediate 91) (0.749 g, 3 mmol) dissolved in THF (30 mL) at room temperature under argon. The resulting solution was stirred under reflux for 3 hours. The mixture was cooled in an ice/water bath and water (25 ml) was carefully added followed by 20% NaOH (25 ml). The resulting biphasic mixture was refluxed overnight with vigorous magnetic stirring and allowed to cool. Diethyl ether was added and the layers were separated. The organic layer was further extracted with diethyl ether dried over MgSO$_4$, filtered and evaporated to give the crude product (741 mg, 55%). This was used directly in the following reaction.

1H NMR (500 MHz, CDCl3) δ 4.23 (1H, dd), 4.42 (1H, dd), 4.61 (1H, dd), 6.54 (1H, dd), 7.14 (2H, d), 7.34 (2H, d), 7.60 (1H, d), 7.88 (1H, d)

Intermediate 93: Tert-butyl 4-(1-(4-chlorophenyl)-2-(1H-pyrazol-1-yl)ethylcarbamoyl)-1-(7H-pyrrolo[2,3-d]pyrimidin-4-yl)piperidin-4-ylcarbamate

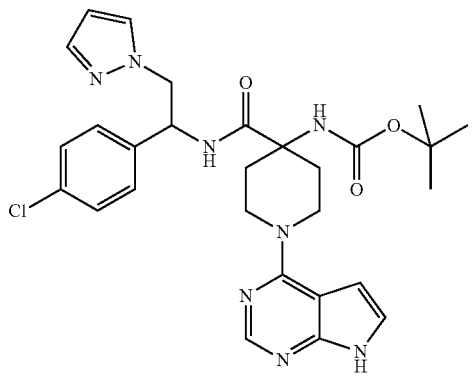 [SMILES: CC(C)(C)OC(=O)NC1(C(=O)NC(Cn2cccn2)c2ccc(Cl)cc2)CCN(c2ncnc3[nH]ccc23)CC1]

HATU (0.209 g, 0.55 mmol) was added in one portion to 4-(tert-butoxycarbonylamino)-1-(7H-pyrrolo[2,3-d]pyrimidin-4-yl)piperidine-4-carboxylic acid (Intermediate 1) (0.181 g, 0.50 mmol), 1-(4-chlorophenyl)-2-(1H-pyrazol-1-yl)ethanamine (Intermediate 92) (0.202 g, 0.5 mmol) and N,N-diisopropylethylamine (0.174 mL, 1.00 mmol) in N-methyl-2-pyrrolidinone (3.0 mL) at room temperature under argon. The resulting solution was stirred overnight. The reaction mixture was purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford tert-butyl 4-(1-(4-chlorophenyl)-2-(1H-pyrazol-1-yl)ethylcarbamoyl)-1-(7H-pyrrolo[2,3-d]pyrimidin-4-yl)piperidin-4-ylcarbamate (0.216 g, 76%) as a white crystalline solid.

m/z (ESI+) (M+H)+=565.

1H NMR (500 MHz, DMSO-d6) δ 1.40 (9H, s), 1.72 (1H, m), 1.87 (2H, m), 2.00 (1H, m), 3.53 (1H, m), 3.52 (1H, m), 3.94 (1H, m), 4.13 (1H, m), 4.38 (1H, dd), 4.74 (1H, dd), 5.30 (1H, dt), 6.14 (1H, dd), 6.57 (1H, d), 7.16 (1H, d), 7.25 (1H, s), 7.29 (4H, s), 7.43 (1H, d), 7.53 (1H, s), 8.12 (1H, s), 8.35 (1H, d), 11.67 (1H, s)

Intermediate 94: (Z)-1-(4-Chlorophenol)-2-(thiazol-2-yl)ethanamine

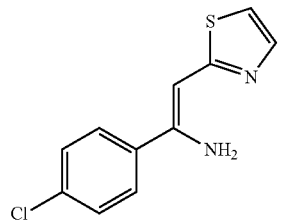 [SMILES: N/C(=C\c1nccs1)c1ccc(Cl)cc1]

A 2.5M solution of N-butyllithium (8.00 mL, 20.00 mmol) in hexanes, was added dropwise to 2-methylthiazole (1.983 g, 20 mmol) dissolved in THF (35.00 mL) over a period of 5 minutes under argon at −70° C. The resulting pale yellow slurry was stirred at −70° C. for 2.5 hour. 4-chlorobenzonitrile (2.75 g, 20.00 mmol) in THF (35.00 mL) was added dropwise to the suspension, which was stirred at −70° C. for 90 minutes after the end of the addition. The reaction mixture was allowed to warm to room temperature under stirring and darkened. The crude was concentrated to dryness and diluted with ethyl acetate then washed with water, dried over magnesium sulphate and concentrated. The crude product was purified by flash chromatography on silica gel eluting with 10 to 100% ethyl acetate in dichloromethane. The solvent was evaporated to dryness to afford (Z)-1-(4-chlorophenyl)-2-(thiazol-2-yl) ethenamine (1.466 g, 31.0%) as a pale yellow solid.

m/z (ESI+) (M+H)+=237

1H NMR (500 MHz, CDCl3) δ 5.72 (1H, s), 6.54 (2H, m), 6.99 (1H, d), 7.38 (d, 2H), 7.55 (2H, d), 7.68 (1H, d)

Intermediate 95: 1-(4-Chlorophenyl)-2-(thiazol-2-yl)ethanamine

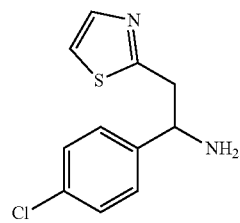 [SMILES: NC(Cc1nccs1)c1ccc(Cl)cc1]

A 2N solution of hydrochloric acid in MeOH at room temperature, was added dropwise to (Z)-1-(4-chlorophenyl)-2-(thiazol-2-yl)ethenamine (Intermediate 94) (1.45 g, 6.13 mmol) and traces of bromocresol green dissolved in MeOH (45 mL) until the solution turned from dark blue to orange. Sodium cyanoborohydride (0.481 g, 7.66 mmol) was added in one portion to the stirred solution and orange color was maintained by adding dropwise the 2N solution of hydrochloric acid in methanol at room temperature. After 1 h stirring, solvent was removed under vacuum. the crude was taken up into water, pH was adjusted around 2 by adding a few drops of the 2N solution of hydrochloric acid in methanol. The aqueous phase was washed with diethyl ether twice then pH was adjusted to 14 by adding a 6N aqueous solution of sodium hydroxide and the basic aqueous phase was extracted with diethyl ether twice. The organic phases were washed with brine dried over magnesium sulphate and concentrated to afford 1-(4-chlorophenyl)-2-(thiazol-2-yl)ethanamine (1.310 g, 90%) as a colorless oil.

1H NMR (500 MHz, DMSO-d6) δ 2.10 (2H, m), 3.22 (1H, dd), 3.26 (1H, dd), 4.22 (1H, t), 7.32 (2H, d), 7.37 (2H, d), 7.51 (1H, d), 7.66 (1H, d)

Intermediate 96: Tert-butyl 4-(1-(4-chlorophenyl)-2-(thiazol-2-yl)ethylcarbamoyl)-1-(7H-pyrrolo[2,3-d]pyrimidin-4-yl)piperidin-4-ylcarbamate

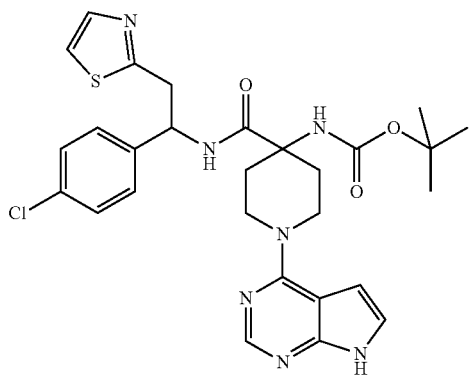 [SMILES: CC(C)(C)OC(=O)NC1(C(=O)NC(Cc2nccs2)c2ccc(Cl)cc2)CCN(c2ncnc3[nH]ccc23)CC1]

HATU (0.418 g, 1.10 mmol) was added in one portion to 4-(tert-butoxycarbonylamino)-1-(7H-pyrrolo[2,3-d]pyrimidin-4-yl)piperidine-4-carboxylic acid (Intermediate 1) (0.361 g, 1.0 mmol), 1-(4-chlorophenyl)-2-(thiazol-2-yl)ethanamine (Intermediate 95) (0.318 g, 1.00 mmol) and N,N-diisopropylethylamine (0.348 mL, 2.00 mmol) in N-methyl-2-pyrrolidinone (5.0 mL) at room temperature under argon. The resulting solution was stirred overnight. Et₂O was added to precipitate the rude product, which was filtered, washed plentifully with Et₂O and dried in vacuo to give tert-butyl 4-(1-(4-chlorophenyl)-2-(thiazol-2-yl)ethylcarbamoyl)-1-(7H-pyrrolo[2,3-d]pyrimidin-4-yl)piperidin-4-ylcarbamate (0.550 g, 94%).

1H NMR (500 MHz, DMSO-d6) δ 1.23 (9H, s), 1.74 (1H, m), 1.89 (2H, m), 2.00 (1H, m), 3.10 (2H, dd), 3.52 (1H, m), 3.58 (1H, m), 4.00 (1H, m), 4.19 (1H, m), 5.29 (1H, dt), 6.57 (1H, d), 7.17 (1H, d), 7.30 (2H, d), 7.37 (2H, d), 7.54 (1H, d), 7.69 (1H, d), 8.13 (1H, s), 8.33 (1H, d), 8.47 (1H, d), 11.68 (1H, s)

m/z (ESI+) (M+H)+=582

Intermediate 97: Lithium 3-(4-(tert-butoxycarbonylamino)-1-(7H-pyrrolo[2,3-d]pyrimidin-4-yl)piperidine-4-carboxamido)-3-(4-chlorophenyl)propanoate

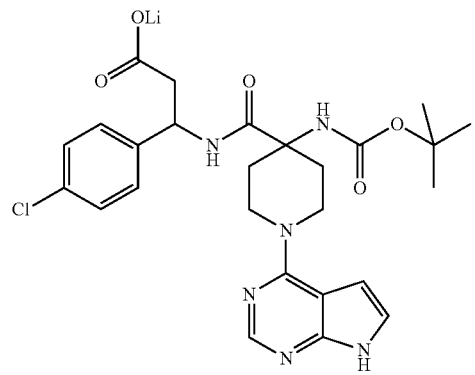

Lithium hydroxide (1.436 mL, 2.87 mmol) 2N in water was added to a stirred suspension of methyl 3-(4-(tert-butoxycarbonylamino)-1-(7H-pyrrolo[2,3-d]pyrimidin-4-yl)piperidine-4-carboxamido)-3-(4-chlorophenyl)propanoate (Intermediate 35) (400 mg, 0.72 mmol) in THF (40 mL) at room temperature. The resulting suspension quickly went into solution and was then stirred at RT overnight. The following morning a white precipitate had formed. This was filtered and dried in vacuo to give lithium 3-(4-(tert-butoxycarbonylamino)-1-(7H-pyrrolo[2,3-d]pyrimidin-4-yl)piperidine-4-carboxamido)-3-(4-chlorophenyl)propanoate (396 mg, 100%).

1H NMR (500 MHz, DMSO-d6) δ 1.41 (9H, s), 1.89 (2H, m), 2.06 (2H, m), 2.27 (2H, m), 3.30 (2H, m partially hidden by H2O), 4.33 (2H, m), 4.83 (1H, m), 6.57 (1H, s), 7.14 (1H, s), 7.22 (2H, d), 7.32 (2H, d), 7.58 (1H, m), 8.10 (1H, s), 10.02 (1H, s);

m/z (ESI–) (M–Li)–=541

Intermediate 98: Tert-butyl 4-(1-(4-chlorophenyl)-3-(dimethylamino)-3-oxopropylcarbamoyl)-1-(7H-pyrrolo[2,3-d]pyrimidin-4-yl)piperidin-4-ylcarbamate

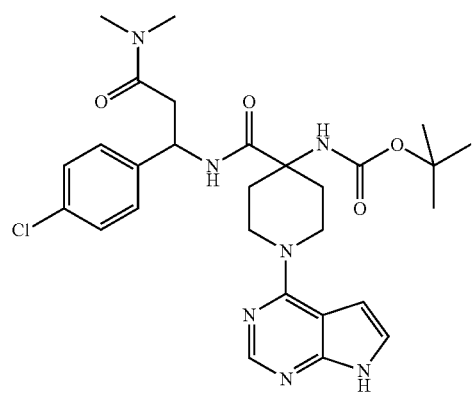 [SMILES: CN(C)C(=O)CC(NC(=O)C1(NC(=O)OC(C)(C)C)CCN(c2ncnc3[nH]ccc23)CC1)c1ccc(Cl)cc1]

HATU (152 mg, 0.40 mmol) was added in one portion to lithium 3-(4-(tert-butoxycarbonylamino)-1-(7H-pyrrolo[2,3-d]pyrimidin-4-yl)piperidine-4-carboxamido)-3-(4-chlorophenyl)propanoate (Intermediate 97) (200 mg, 0.36 mmol), dimethylamine hydrochloride (48.0 mg, 0.59 mmol) and N,N-diisopropylethylamine (0.190 mL, 1.09 mmol) in N-methyl-2-pyrrolidinone (3.0 mL) at room temperature under argon. The resulting solution was stirred overnight. Diethyl ether added to precipitate the crude product which formed as a gum. This was rinsed with Et$_2$O and dried to give the crude gum (770 mg) which was used in subsequent reactions without further purification.

Intermediate 99: Tert-butyl 1-(4-chlorophenyl)-3-methoxypropylcarbamate

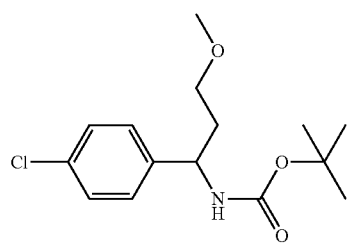 [SMILES: COCCC(NC(=O)OC(C)(C)C)c1ccc(Cl)cc1]

Sodium hydride (35.0 mg, 0.87 mmol) was added to tert-butyl 1-(4-chlorophenyl)-3-hydroxypropylcarbamate (Intermediate 30) (200 mg, 0.70 mmol) in THF (10 mL) at 0° C. under nitrogen. The mixture was stirred at 0° C. for 15 minutes. Methyl iodide (0.044 mL, 0.70 mmol) was added dropwise, and the resulting suspension was stirred at 22° C. for 4 hours. The reaction was quenched with KHSO$_4$ solution (1M, 0.5 mL) and water (15 mL). The mixture was extracted with diethyl ether (3×20 mL); the combined extracts were washed with saturated brine (20 mL), dried over MgSO$_4$, filtered and evaporated to give crude product. The crude product was purified by flash silica chromatography, elution gradient 20 to 60% EtOAc in isohexane. Pure fractions were evaporated to dryness to afford tert-butyl 1-(4-chlorophenyl)-3-methoxypropylcarbamate (80 mg, 38.1%) as a white solid.

1H NMR (399.902 MHz, CDCl3) δ 1.40 (9H, s), 1.91 (1H, s), 2.01 (1H, s), 3.30 (3H, s), 3.32 (2H, m), 4.79 (1H, br.s), 5.45 (1H, br.s), 7.20 (2H, d), 7.29 (2H, d);

m/z (ESI+) (M+H)+=300, 302 (M+H+), 244.3, 246.3 (M+H+-C4H8); HPLC tR=2.58 min.

Intermediate 100: 1-(4-chlorophenyl)-3-methoxypropan-1-amine

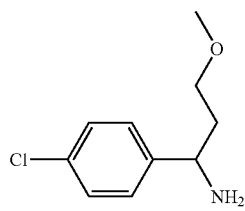

Hydrogen chloride (4M in 1,4-dioxane, 0.667 mL, 2.67 mmol) was added to tert-butyl 1-(4-chlorophenyl)-3-methoxypropylcarbamate (Intermediate 99) (80 mg, 0.27 mmol) in a mixture of DCM (5 mL) and methanol (2 mL) at 22° C. The resulting solution was stirred at 22° C. for 5 hours. The mixture was concentrated and the residue was purified by ion exchange chromatography, using an SCX column. The desired product was eluted from the column using 2M NH$_3$/MeOH and pure fractions were evaporated to dryness to afford 1-(4-chlorophenyl)-3-methoxypropan-1-amine (47.0 mg, 88%) as a colourless oil.

1H NMR (399.902 MHz, CDCl3) δ 1.80-1.96 (2H, m), 3.31 (3H, s), 3.32 (1H, m), 3.43 (1H, m), 4.09 (1H, t), 7.27-7.31 (4H, m);

m/z (ESI+) (M+H)+=200.2, 202.3 (M+H+); HPLC tR=1.70 min.

Intermediate 101: Tert-butyl 4-(1-(4-chlorophenyl)-3-methoxypropylcarbamoyl)-1-(7H-pyrrolo[2,3-d]pyrimidin-4-yl)piperidin-4-ylcarbamate

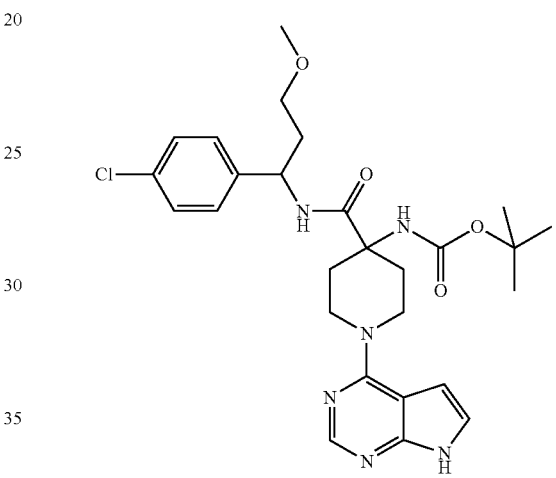

O-(7-Azabenzotriazol-1-yl)-N,N,N',N'-tetramethyluronium hexafluorophosphate (55.2 mg, 0.15 mmol) was added to 4-(tert-butoxycarbonylamino)-1-(7H-pyrrolo[2,3-d]pyrimidin-4-yl)piperidine-4-carboxylic acid (Intermediate 1) (50 mg, 0.14 mmol) and N-ethyldiisopropylamine (0.029 mL, 0.17 mmol) in NMP (5 mL). The resulting solution was stirred at 50° C. for 10 minutes then cooled to ambient temperature. 1-(4-Chlorophenyl)-3-methoxypropan-1-amine (Intermediate 100) (27.6 mg, 0.14 mmol) was added as a solution in NMP (2 mL). The resulting mixture was stirred at 22° C. for 16 hours. The reaction mixture was diluted with EtOAc (75 mL) and washed sequentially with water (6×75 mL), and saturated brine (50 mL). The organic layer was dried over MgSO$_4$, filtered and evaporated to afford crude product. The crude product was purified by flash silica chromatography, elution gradient 1 to 4% (10:1 MeOH/conc. NH$_3$ (aq)) in DCM. Pure fractions were evaporated to dryness to afford tert-butyl 4-(1-(4-chlorophenyl)-3-methoxypropylcarbamoyl)-1-(7H-pyrrolo[2,3-d]pyrimidin-4-yl)piperidin-4-ylcarbamate (52.0 mg, 69.2%) as a white solid.

1H NMR (399.902 MHz, DMSO) δ 1.42 (9H, s), 1.90 (2H, t), 1.92-2.05 (4H, m), 3.22 (3H, s), 3.29 (2H, t), 3.55 (2H, m), 4.24 (2H, m), 4.89 (1H, dt), 6.60 (1H, dd), 7.05 (1H, br.), 7.16 (1H, dd), 7.33 (4H, m), 7.99 (1H, d), 8.13 (1H, s), 11.65 (1H, s);

m/z (ESI+) (M+H)+=543.4, 545.3; HPLC tR=2.31 min.

Intermediate 102: S-3-(tert-butoxycarbonylamino)-3-(4-chlorophenyl)propyl ethanethioate

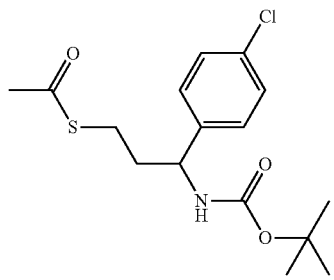 [SMILES: CC(=O)SCCC(NC(=O)OC(C)(C)C)c1ccc(Cl)cc1]

Potassium thioacetate (43.9 mg, 0.38 mmol) was added to 3-(tert-butoxycarbonylamino)-3-(4-chlorophenyl)propyl methanesulfonate (Intermediate 31) (70 mg, 0.19 mmol) in DMF (5 mL) at 22° C. The resulting solution was stirred at 50° C. for 2 hours. The reaction mixture was diluted with EtOAc (50 mL) and washed sequentially with 20% saturated brine (4×50 mL) and saturated brine (25 mL). The organic layer was dried over MgSO$_4$, filtered and evaporated to afford crude product. The crude product was purified by flash silica chromatography, elution solvent 15% EtOAc in isohexane. Pure fractions were evaporated to dryness to afford S-3-(tert-butoxycarbonylamino)-3-(4-chlorophenyl) propyl ethanethioate (61.0 mg, 92%) as a white solid.

1H NMR (399.902 MHz, CDCl3) δ 1.41 (9H, s), 1.98 (2H, dt), 2.32 (3H, s), 2.83 (2H, m), 4.67 (1H, br.s), 4.88 (1H, br.s), 7.20 (2H, d), 7.30 (2H, d);

m/z (ESI+) (M+H+-C4H8)=288.3, 290.3; HPLC tR=2.80 min.

Intermediate 103: Tert-butyl 1-(4-chlorophenyl)-3-sulfamoylpropylcarbamate

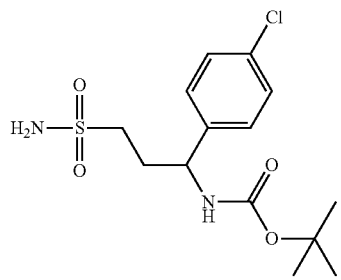 [SMILES: CC(C)(C)OC(=O)NC(CCS(N)(=O)=O)c1ccc(Cl)cc1]

N-Chlorosuccinimide (90 mg, 0.67 mmol) was added to a mixture of acetonitrile (3 mL) and 2M hydrochloric acid (0.1 mL) cooled to 10° C. S-3-(tert-Butoxycarbonylamino)-3-(4-chlorophenyl)propyl ethanethioate (Intermediate 102) (58 mg, 0.17 mmol) was added dropwise as a solution in acetonitrile (2 mL) and the resulting solution was stirred at 22° C. for 1 hour. Concentrated aqueous ammonia solution (3 mL, 63.00 mmol) was added dropwise and the mixture stirred for 3 days. The mixture was evaporated and the residue was partitioned between DCM (30 mL) and water. The aqueous layer was extracted with DCM (30 mL) and the extracts combined with the organic layer. The combined organics were filtered through a phase-separating paper and evaporated. The residue was purified by flash silica chromatography, elution gradient 30 to 80% EtOAc in isohexane. Product-containing fractions were evaporated to dryness to afford tert-butyl 1-(4-chlorophenyl)-3-sulfamoylpropylcarbamate (40.0 mg, 68.0%) as a white solid.

1H NMR (399.902 MHz, CDCl3) δ 1.42 (9H, s), 2.75-2.91 (2H, m), 3.11-3.17 (2H, m), 4.74 (1H, br.s), 4.93 (1H, t), 7.23 (2H, d), 7.34 (2H, d);

m/z (ESI+) (M+H+-C4H8)=293.2, 295.2; HPLC tR=2.11 min.

Intermediate 104: 3-amino-3-(4-chlorophenyl)propane-1-sulfonamide

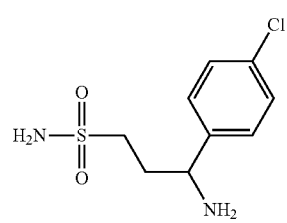 [SMILES: NC(CCS(N)(=O)=O)c1ccc(Cl)cc1]

Hydrogen chloride (4M in dioxan, 1.0 mL, 4.00 mmol) was added to tert-butyl 1-(4-chlorophenyl)-3-sulfamoylpropylcarbamate (Intermediate 103) (38 mg, 0.11 mmol) in a mixture of DCM (5 mL) and methanol (2 mL) at 22° C. The resulting solution was stirred at 22° C. for 24 hours. The mixture was evaporated to dryness and the residue was purified by ion exchange chromatography, using an SCX column. The desired product was eluted from the column using 30% (2M NH$_3$ in MeOH) in DCM and pure fractions were evaporated to dryness to afford 3-amino-3-(4-chlorophenyl)propane-1-sulfonamide (20.00 mg, 73.8%) as a colourless gum.

m/z (ESI+) (M+H)+=249.2, 251.2; HPLC tR=1.32 min.

Intermediate 105: Tert-butyl 4-(1-(4-chlorophenyl)-3-sulfamoylpropylcarbamoyl)-1-(7H-pyrrolo[2,3-d]pyrimidin-4-yl)piperidin-4-ylcarbamate

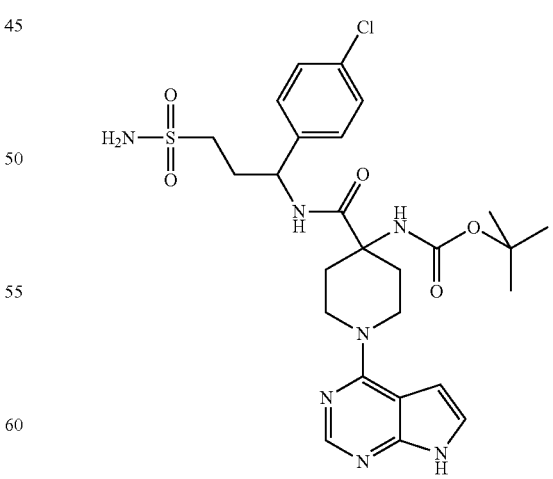

O-(7-Azabenzotriazol-1-yl)-N,N,N',N'-tetramethyluronium hexafluorophosphate (30.9 mg, 0.08 mmol) was added to 4-(tert-butoxycarbonylamino)-1-(7H-pyrrolo[2,3-d]pyrimidin-4-yl)piperidine-4-carboxylic acid (Intermediate 1)

(28 mg, 0.08 mmol) and N,N-diisopropylethylamine (0.016 mL, 0.09 mmol) in NMP (5 mL) at 22° C. The resulting suspension was stirred at 50° C. for 10 minutes. The mixture was cooled to ambient temperature and 3-amino-3-(4-chlorophenyl)propane-1-sulfonamide (Intermediate 104) (19.27 mg, 0.08 mmol) was added as a solution in NMP (2 mL). The mixture was stirred at 22° C. for 3 days. The mixture was diluted with methanol and loaded onto an SCX column. The crude product was purified by ion exchange chromatography; the desired product was eluted from the column using 2M NH$_3$/MeOH and pure fractions were evaporated to dryness. The crude product was purified by flash silica chromatography, elution gradient 2 to 6% (10:1 MeOH/conc. NH$_3$ (aq)) in DCM. Pure fractions were evaporated to dryness to afford tert-butyl 4-(1-(4-chlorophenyl)-3-sulfamoylpropylcarbamoyl)-1-(7H-pyrrolo[2,3-d]pyrimidin-4-yl)piperidin-4-ylcarbamate (16.00 mg, 34.9%) as a white solid.

m/z (ESI+) (M+H)+=592.4, 594.3; HPLC tR=1.99 min.

Intermediate 106: Tert-butyl
3-amino-1-(4-chlorophenyl)-3-oxopropylcarbamate

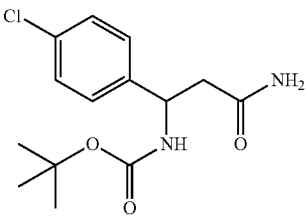 [SMILES: CC(C)(C)OC(=O)NC(CC(N)=O)c1ccc(Cl)cc1]

O-(7-Azabenzotriazol-1-yl)-N,N,N',N'-tetramethyluronium hexafluoro-phosphate (466 mg, 1.23 mmol) was added in one portion to tert-butyl-3-amino-3-(4-chlorophenyl) propanoic acid (245 mg, 0.82 mmol), ammonium chloride (131 mg, 2.45 mmol) and N,N-diisopropylethylamine (0.811 mL, 4.90 mmol) in DMF (4 mL) at 20° C. under nitrogen. The resulting suspension was stirred at 20° C. for 18 hours. The reaction mixture was evaporated to dryness and redissolved in EtOAc (25 mL), and washed sequentially with water (25 mL) and saturated brine (25 mL). The organic layer was dried over MgSO$_4$, filtered and evaporated to afford tert-butyl 3-amino-1-(4-chlorophenyl)-3-oxopropylcarbamate (200 mg, 82%) as a white solid. m/z (ESI−) (M−H)−=297; HPLC tR=1.91 min.

Intermediate 107:
3-amino-3-(4-chlorophenyl)propanamide

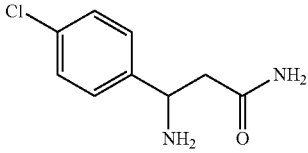 [SMILES: NC(=O)CC(N)c1ccc(Cl)cc1]

HCl (4M) in 1,4 dioxane (1.674 mL, 6.69 mmol) was added to tert-butyl 3-amino-1-(4-chlorophenyl)-3-oxopropylcarbamate (Intermediate 106) (200 mg, 0.67 mmol) in DCM (20 mL) at 20° C. The resulting solution was stirred at 20° C. for 4 hours. The reaction mixture was evaporated and was purified by ion exchange chromatography, using an SCX column. The desired product was eluted from the column using 7M NH$_3$/MeOH and pure fractions were evaporated to dryness to afford 3-amino-3-(4-chlorophenyl) propanamide (46.0 mg, 34.6%) as a white solid.

1H NMR (399.9 MHz, DMSO-d6) δ 0.99 (2H, t), 2.33-2.37 (2H, m), 3.38 (2H, s), 4.24 (1H, t), 7.35-7.42 (4H, m), m/z (ESI+) (M+H)+=199; HPLC tR=1.14 min.

Intermediate 108: Tert-butyl 4-(3-amino-1-(4-chlorophenyl)-3-oxopropylcarbamoyl)-1-(7H-pyrrolo[2,3-d]pyrimidin-4-yl)piperidin-4-ylcarbamate

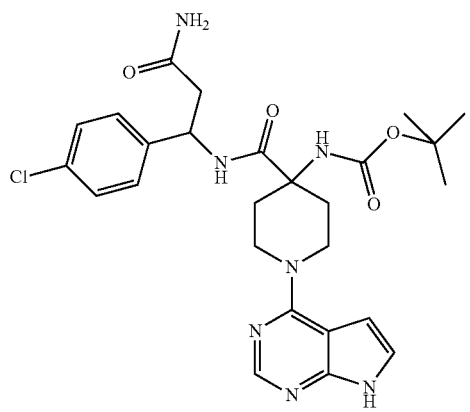 [SMILES: CC(C)(C)OC(=O)NC1(C(=O)NC(CC(N)=O)c2ccc(Cl)cc2)CCN(c2ncnc3[nH]ccc23)CC1]

O-(7-Azabenzotriazol-1-yl)-n,n,n',n'-tetramethyluronium hexafluoro-phosphate (129 mg, 0.34 mmol) was added in one portion to 4-(tert-butoxycarbonylamino)-1-(7H-pyrrolo[2,3-d]pyrimidin-4-yl)piperidine-4-carboxylic acid (Intermediate 1) (82 mg, 0.23 mmol) and N,N-diisopropylethylamine (0.112 mL, 0.68 mmol) in DMF (4 mL) at 20° C. under nitrogen. The resulting solution was stirred at 20° C. for 5 minutes. 3-amino-3-(4-chlorophenyl)propanamide (Intermediate 107) (45 mg, 0.23 mmol) was then added to the reaction and stirred for 3 hours. The reaction mixture was concentrated and diluted with EtOAc (20 mL) and washed with water (20 mL). The organic layer was dried over MgSO$_4$, filtered and evaporated to afford tert-butyl 4-(3-amino-1-(4-chlorophenyl)-3-oxopropylcarbamoyl)-1-(7H-pyrrolo[2,3-d]pyrimidin-4-yl)piperidin-4-ylcarbamate (99 mg, 100%).

m/z (ESI+) (M+H)+=542; HPLC tR=1.88 min.

Intermediate 109: Tert-butyl N-[1-(4-chlorophenyl)-3-(phenoxycarbonylamino)-propyl]carbamate

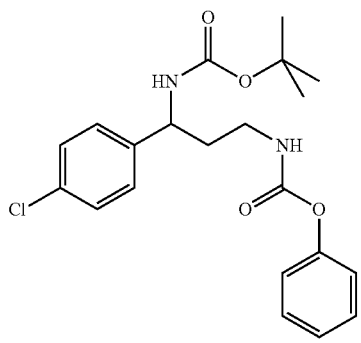 [SMILES: CC(C)(C)OC(=O)NC(CCNC(=O)Oc1ccccc1)c1ccc(Cl)cc1]

Phenyl chloroformate (0.132 mL, 1.05 mmol) was added dropwise to tert-butyl 3-amino-1-(4-chlorophenyl)propylcarbamate (Intermediate 25) (300 mg, 1.05 mmol) and sodium bicarbonate (133 mg, 1.58 mmol) in dioxane (10 mL) at 20° C. under nitrogen. The resulting solution was stirred at 20° C. for 2 hours. The reaction mixture was concentrated and diluted with EtOAc (20 mL) and washed with water (20 mL). The organic layer was dried over MgSO₄, filtered and evaporated to afford tert-butyl N-[1-(4-chlorophenyl)-3-(phenoxycarbonylamino)-propyl]carbamate (427 mg, 100%) as a gum.

m/z (ESI+) (M+H)+=405; HPLC tR=2.85 min.

Intermediate 110: Tert-butyl 1-(4-chlorophenyl)-3-ureidopropylcarbamate

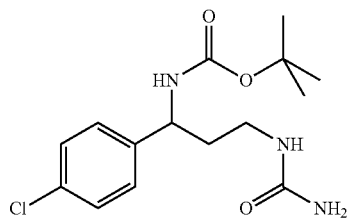 [SMILES: CC(C)(C)OC(=O)NC(CCNC(N)=O)c1ccc(Cl)cc1]

Ammonium chloride (113 mg, 2.11 mmol) was added in one portion to tert-butyl N-[1-(4-chlorophenyl)-3-(phenoxycarbonylamino)propyl]carbamate (Intermediate 109) (427 mg, 1.05 mmol) and triethylamine (0.882 mL, 6.33 mmol) in DMF (3 mL). The resulting solution was stirred at 0.352 molar for 24 hours. The reaction mixture was concentrated and diluted with EtOAc (20 mL) and washed with water (20 mL). The organic layer was dried over MgSO₄, filtered and evaporated to afford tert-butyl 1-(4-chlorophenyl)-3-ureidopropylcarbamate (346 mg, 100%), m/z (ESI+) (M+H)+=328; HPLC tR=1.91 min.

Intermediate 111: 1-(3-amino-3-(4-chlorophenyl)propyl)urea

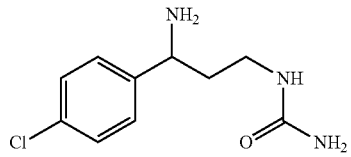 [SMILES: NC(=O)NCCC(N)c1ccc(Cl)cc1]

Tert-butyl 1-(4-chlorophenyl)-3-ureidopropylcarbamate (Intermediate 110) (346 mg, 1.06 mmol) was dissolved in TFA (3 mL) and stirred at 20° C. for 2 hours. The reaction was vacuumed to dryness and was purified by ion exchange chromatography, using an SCX column. The desired product was eluted from the column using 0.35M NH₃/MeOH and pure fractions were evaporated to dryness to afford 1-(3-amino-3-(4-chlorophenyl)propyl)urea (151 mg, 62.8%) as a yellow gum.

1H NMR (399.9 MHz, DMSO-d6) δ 1.61 (2H, q), 2.98 (2H, m), 3.82 (1H, t), 4.05 (2H, s), 5.38 (2H, s), 5.94 (1H, s), 7.37 (4H, m), m/z (ESI+) (M+H)+=228; HPLC tR=1.25 min.

Intermediate 112: Tert-butyl 4-(1-(4-chlorophenyl)-3-ureidopropylcarbamoyl)-1-(7H-pyrrolo[2,3-d]pyrimidin-4-yl)piperidin-4-ylcarbamate

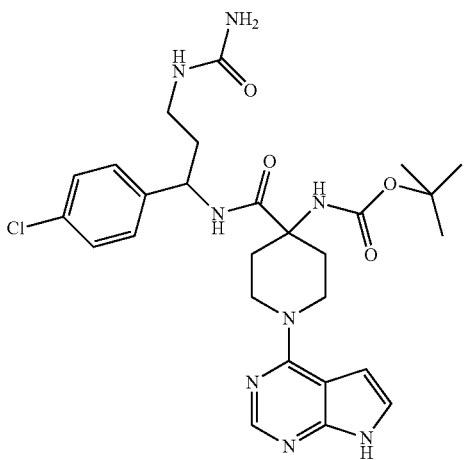 [SMILES: CC(C)(C)OC(=O)NC1(C(=O)NC(CCNC(N)=O)c2ccc(Cl)cc2)CCN(c2ncnc3[nH]ccc23)CC1]

O-(7-Azabenzotriazol-1-yl)-n,n,n',n'-tetramethyluronium hexafluoro-phosphate (378 mg, 0.99 mmol) was added in one portion to 4-(tert-butoxycarbonylamino)-1-(7H-pyrrolo[2,3-d]pyrimidin-4-yl)piperidine-4-carboxylic acid (Intermediate 1) (240 mg, 0.66 mmol) and N,N-diisopropylethylamine (0.329 mL, 1.99 mmol) in NMP (2 mL) at 20° C. under nitrogen. The resulting solution was stirred at 20° C. for 5 minutes. 1-(3-amino-3-(4-chlorophenyl)propyl)urea (Intermediate 111) (151 mg, 0.66 mmol) in NMP (2 mL) was then added to the reaction and stirred for 18 hours. The reaction mixture was diluted with EtOAc (20 mL) and washed with water (20 mL). The organic layer was dried over MgSO₄, filtered and evaporated to afford tert-butyl 4-(1-(4-chlorophenyl)-3-ureidopropylcarbamoyl)-1-(7H-pyrrolo[2,3-d]pyrimidin-4-yl)piperidin-4-ylcarbamate (379 mg, 100%) as a white solid. m/z (ESI+) (M+H)+=571; HPLC tR=1.88 min.

Intermediate 113: 3-amino-3-(4-chlorophenyl)propanenitrile

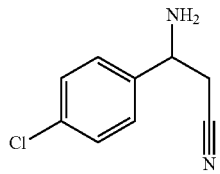 [SMILES: N#CCC(N)c1ccc(Cl)cc1]

HCl (4M) in 1,4-dioxane (0.668 mL, 2.67 mmol) was added in one portion to tert-butyl 1-(4-chlorophenyl)-2-cyanoethylcarbamate (Intermediate 24) (150 mg, 0.53 mmol) in DCM (4 mL) at 20° C. The resulting solution was stirred at 20° C. for 18 hours. The reaction mixture was evaporated to afford 3-amino-3-(4-chlorophenyl)propanenitrile (HCl salt) (115 mg, 99%) as a white solid.

Intermediate 114: (4-chlorophenyl)-2-cyanoethylcarbamoyl)-1-(7H-pyrrolo[2,3-d]pyrimidin-4-yl)piperidin-4-ylcarbamate

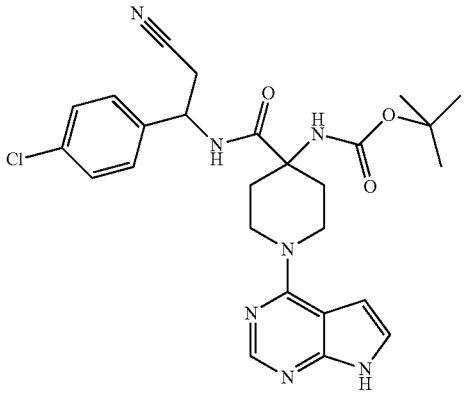 [SMILES: CC(C)(C)OC(=O)NC1(C(=O)NC(CC#N)c2ccc(Cl)cc2)CCN(c2ncnc3[nH]ccc23)CC1]

O-(7-Azabenzotriazol-1-yl)-N,N,N',N'-tetramethyluronium hexafluoro-phosphate (306 mg, 0.81 mmol) was added in one portion to 4-(tert-butoxycarbonylamino)-1-(7H-pyrrolo[2,3-d]pyrimidin-4-yl)piperidine-4-carboxylic acid (194 mg, 0.54 mmol) and N,N-diisopropylethylamine (0.533 mL, 3.22 mmol) in NMP (3 mL) at 20° C. under nitrogen. The resulting solution was stirred at 20° C. for 5 minutes. 3-amino-3-(4-chlorophenyl)-propanenitrile (Intermediate 113) (97 mg, 0.54 mmol) in NMP (3 mL) was then added to the reaction and stirred for 1 hour. The reaction mixture was concentrated and diluted with EtOAc (50 mL) and washed with water (50 mL). The organic layer was dried over MgSO$_4$, filtered and evaporated to afford (4-chlorophenyl)-2-cyanoethylcarbamoyl)-1-(7H-pyrrolo[2,3-d]pyrimidin-4-yl)piperidin-4-ylcarbamate (0.281 g, 100%).

m/z (ESI+) (M+H)+=524; HPLC tR=2.19 min.

Intermediate 115: Tert-butyl 1-(4-chlorophenyl)-3-(methylsulfonamido)propylcarbamate

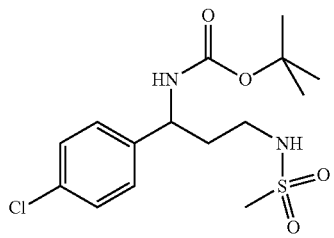 [SMILES: CC(C)(C)OC(=O)NC(CCNS(C)(=O)=O)c1ccc(Cl)cc1]

Methanesulfonyl chloride (0.082 mL, 1.05 mmol) was added dropwise to tert-butyl 3-amino-1-(4-chlorophenyl)propylcarbamate (Intermediate 25) (300 mg, 1.05 mmol) and N,N-diisopropylethylamine (0.367 mL, 2.11 mmol) in DCM (4 mL) at 20° C. The resulting solution was stirred at 20° C. for 18 hours. The reaction mixture was concentrated and diluted with Et2O (25 mL) and washed with water (25 mL). The organic layer was dried over MgSO$_4$, filtered and evaporated to afford crude product. The crude product was purified by flash silica chromatography, elution gradient 0 to 20% EtOAc in DCM. Pure fractions were evaporated to dryness to afford tert-butyl 1-(4-chlorophenyl)-3-(methylsulfonamido)propylcarbamate (275 mg, 71.9%) as a white solid.

1H NMR (399.9 MHz, DMSO-d6) δ 1.37 (9H, s), 1.76 (1H, m), 1.82-1.88 (1H, m), 2.87 (3H, s), 2.89-2.91 (2H, m), 4.58 (1H, d), 7.00 (1H, t), 7.32 (2H, d), 7.39 (2H, d), 7.48 (1H, d), m/z (ESI+) (M+H)+=361; HPLC tR=2.25 min.

Intermediate 116: N-(3-amino-3-(4-chlorophenyl)propyl)methanesulfonamide

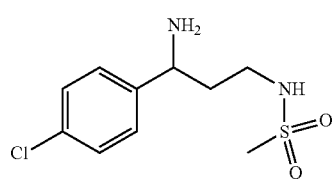 [SMILES: CS(=O)(=O)NCCC(N)c1ccc(Cl)cc1]

TFA (4 mL) was added to tert-butyl 1-(4-chlorophenyl)-3-(methylsulfonamido)propylcarbamate (Intermediate 115) (275 mg, 0.76 mmol) and stirred at 20° C. for 2 hours. The reaction was vacuumed to dryness. The crude product was purified by ion exchange chromatography, using an SCX column. The desired product was eluted from the column using 7M NH$_3$/MeOH and pure fractions were evaporated to dryness to afford N-(3-amino-3-(4-chlorophenyl)propyl)methanesulfonamide (113 mg, 56.7%) as a colourless gum.

1H NMR (399.9 MHz, DMSO-d6) δ 1.69-1.72 (2H, m), 2.87 (3H, s), 2.94-2.98 (2H, m), 3.18-3.19 (1H, m), 3.87 (1H, t), 7.35-7.40 (4H, m), m/z (ESI+) (M+H)+=262; HPLC tR=1.43 min.

Intermediate 117: Tert-butyl 4-(1-(4-chlorophenyl)-3-(methylsulfonamido)propylcarbamoyl)-1-(7H-pyrrolo[2,3-d]pyrimidin-4-yl)piperidin-4-ylcarbamate

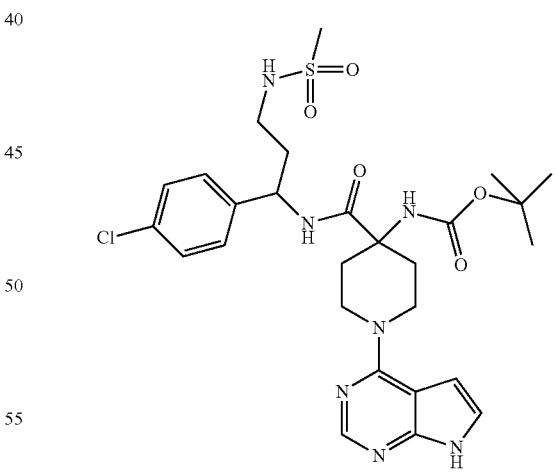

O-(7-Azabenzotriazol-1-yl)-N,N,N',N'-tetramethyluronium hexafluoro-phosphate (245 mg, 0.65 mmol) was added in one portion to 4-(tert-butoxycarbonylamino)-1-(7H-pyrrolo[2,3-d]pyrimidin-4-yl)piperidine-4-carboxylic acid (Intermediate 1) (155 mg, 0.43 mmol) and N,N-diisopropylethylamine (0.213 mL, 1.29 mmol) in NMP (2 mL) at 20° C. under nitrogen. The resulting solution was stirred at 20° C. for 5 minutes. N-(3-amino-3-(4-chlorophenyl)propyl)methanesulfonamide (Intermediate 116) (113 mg, 0.43 mmol) in NMP (2 mL) was then added to the reaction and stirred for 18 hours. The reaction mixture was concentrated and diluted with EtOAc (20 mL) and washed with water (20 mL). The organic layer was dried over $MgSO_4$, filtered and evaporated to afford tert-butyl 4-(1-(4-chlorophenyl)-3-(methylsulfonamido)propylcarbamoyl)-1-(7H-pyrrolo[2,3-d]pyrimidin-4-yl)piperidin-4-ylcarbamate (261 mg, 100%).

m/z (ESI+) (M+H)+=606; HPLC tR=2.09 min.

The biological effects of the compounds of Formula (I) may be tested as set out below.

In Vitro MDA-MB-468 Human Breast Adenocarcinoma GSK-3 Phosphorylation Assay

This assay determines the ability of test compounds to inhibit phosphorylation of Serine-9 residue in Glycogen Synthase Kinase-3beta (GSK-3β) as a surrogate marker of cellular PKB (Akt) activity, as assessed using Acumen Explorer Fluorescent Plate-Reader technology. A MDA-MB-468 human breast adenocarcinoma cell line (LGC Promochem, Teddington, Middlesex, UK, Catalogue No. HTB-132) was routinely maintained in Dulbecco's modified Eagle's growth medium (DMEM; Invitrogen Limited, Paisley, UK Catalogue No. 11966-025) containing 10% heat-inactivated foetal calf serum (FCS; Sigma, Poole, Dorset, UK, Catalogue No. F0392) and 1% L-glutamine (Gibco, Catalogue No. 25030-024) at 37° C. with 5% $CO_2$ up to a confluency of 70-90%.

For the phosphorylation assay, the cells were detached from the culture flask using Trypsin-EDTA (Invitrogen Limited, Catalogue No. 25300-062) and seeded into the wells of a black transparent-bottom Corning Costar Polystyrene 96 well plate (Fisher Scientific UK, Loughborough, Leicestershire, UK; Catalogue No. 3904 and DPS-130-020K) at a density of 5000 cells per well in 100 μl of complete growth media. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and dosed directly to required concentration into test wells using non-contact (acoustic dispensing of multiple 2.5 nl droplets directly into assay wells) ECHO dosing technology (Labcyte Inc. Sunnyvale, Calif., USA). Each plate contained control wells without test compound.

20 μl of fixing buffer (Phosphate Buffered Saline (PBS) containing 10% formaldehyde; Sigma; Catalogue No. F1635) was then added to each well to give a final well concentration 1.6%. Plates were then incubated for 30 minutes at room temperature prior to the fixative being removed. Each well was washed once with 250 μl of PBS and then 50 μl PBS added to each well. PBS was then aspirated and cells permeabilised and blocked by incubating each well with 50 μl of permeabilisation/blocking buffer (PBS containing 0.5% Tween 20 (Sigma; Catalogue No. P5927) and 5% Marvel Milk Powder (Andrews Pharmacy Ltd, Macclesfield, Cheshire, UK; Catalogue No. APC100199)) for 1 hour at room temperature prior to staining.

Following removal of Perm/Block buffer, 50 μl of primary anti-phospho-GSK-3β antibody (Cell Signalling Technology (New England Biolabs (Uk) Ltd.), Hitchin, Hertfordshire, UK; Catalogue No. 9336 diluted 1:400 in Blocking buffer (PBS containing 5% Marvel and 0.05% Tween/Polysorbate 20) was added to each well and incubated overnight at 4° C.

Each well was washed three times in 250 μl of wash buffer (PBS containing 0.05% polysorbate 20), and cells incubated for 1 hour at room temperature with 50 μl of secondary fluorescently-labelled anti-rabbit Alexa Fluor 488 antibody (Molecular Probes, Invitrogen Limited, Catalogue No. A11008) diluted 1:750 in blocking buffer. Plates were washed at three times in 250 μl of wash buffer and stored containing 50 μl of PBS at 4° C. until required.

Plates were analysed using an Acumen Explorer Plate-reader to quantify level of fluorescent signal that represents quantity of phosphorylated-GSK-3β. Active compounds caused a decrease in phospho-GSK-3β phosphorylation relative to the maximum (undosed) control for each assay, which is measured by the number of phosphorylated objects per well, and enabled potency of PKB (Akt) inhibitors to be determined.

$IC_{50}$ calculation—$IC_{50}$ is the concentration of compound required to give 50% effect over the range of activity affected by the compound, between maximum (no compound) and minimum (excess level of compound) response control data. $IC_{50}$ values were determined by fitting background corrected, dose response assay data to a 4 parameter logistic curve fit equation model with the minimum response set to zero. This was done using an in-house developed algorithm within the Origin graphing software package (OriginLab Corporation, Northampton, Mass., USA).

Examples of the invention were tested in the above assay and their mean $IC_{50}$ values calculated. These values are shown in Table G.

In Vitro AKT1 Kinase Assay

This assay detects inhibitors of AKT1 (PKBα) kinase activity using Caliper LabChip LC3000. The Caliper off-chip incubation mobility shift assay uses a microfluidic chip to measure the conversion of a fluorescent labelled peptide to a phosphorylated product by a respective kinase. The complete enzyme reaction is carried out in microtitre plates and then quenched. The resulting stopped solutions are serially 'sipped' through a capillary onto the chip, where the peptide substrate and phosphorylated product are separated by electrophoresis. They are then detected via laser-induced fluorescence. Substrate and product are separated into two peaks by the application of a high electric field and directly detected using fluorescence. The signature of the fluorescent signal reveals the extent of the reaction.

For Echo dosing the solvent was 100% DMSO. A master plate was prepared with 40 ul of 10 mM stock from our Primary Liquid Store in quadrant 1 of a Labcyte 384 well plate. A 1 in 100 dilution was made from quadrant 1 into quadrant 2 by removing 0.4 ul and adding it to 39.6 ul of DMSO. Subsequent 1 in 100 dilutions were made into quadrant 3 from quadrant 2 and quadrant 4 from quadrant 3.

Multiple 2.5 nl droplets were dispensed from each quadrant of the master plate using ECHO dosing technology (Labcyte Inc. Sunnyvale, Calif., USA) to generate the dose range that was required in the test. The dose range most commonly used was as follows: 100 uM, 30 uM, 10 uM, 3 uM, 1 uM, 0.3 uM, 0.1 uM, 0.03 uM, 0.01 uM, 0.003 uM, 0.001 uM, 0.0001 uM. Each well was backfilled with Dimethyl Sulphoxide (DMSO) to a total volume of 120 nl, such that when the enzyme and substrate mix was added the final DMSO concentration was 1%. DMSO was added to max control wells as 120 nl, minimum control wells were treated with 120 nl of compound at a concentration that inhibited the enzyme activity 100%.

Following addition of compound or control to the assay plate, 6 μl peptide mix containing 3 μM substrate (5-FAM-GRPRTSSFAEG-CONH2; CRB) and 40 μM ATP in Kinase base buffer (100 mM Hepes pH 7.5, 0.015% Brij-35) and 6 μl enzyme mix containing 8 nM AKT1/PKBα active enzyme (Upstate Biotechnology, Cat No. 14-276), 8 mM DTT and 20 mM $MgCl_2$ in kinase base buffer was added. All buffers were made up with 18MΩ water. The plates were sealed and incubated at room temperature for 50 minutes. The reaction was stopped by the addition of 10 μl stop buffer (100 mM Hepes pH 7.5, 0.015% Brij-35 solution, 0.1% coating reagent #3, 40 mM EDTA, 5% DMSO) to each well (N.B. plates can be frozen after stopping and read later). The plates were then analysed using the Caliper LabChip LC3000 Drug Discovery System (Caliper Life Sciences, 1 Wellfield, Preston Brook, Runcorn, WA7 3AZ) using the following separation conditions; −1.8 PSI, −500 upstream voltage, −1700 downstream voltage, sample sip time of 0.2 sec, post sample sip time of 30 sec and a final delay of 120 sec. Integration of the substrate and product peaks was carried out using Caliper LabChip software and IC50 curves were calculated using Origin™ software (OriginLab Corporation, Northampton, Mass., USA). Examples of the invention were tested in the in vitro AKT1 enzyme assay and the mean $IC_{50}$ values obtained are presented in Table G.

TABLE G

| Example Number | Cellular PKB Mean $IC_{50}$ (μM) | In vitro PKBα Mean $IC_{50}$ (μM) |
| --- | --- | --- |
| 1 | 0.2 | 0.0076 |
| 2 | 0.13 | 0.0038 |
| 3 | 0.14 | 0.0067 |
| 3A, 3B | 0.11, >3.10 | 0.0026, 0.27 |
| 4 | 0.23 | 0.005 |
| 5 | 0.27 | 0.0097 |
| 6 | 0.02 | 0.0012 |
| 7 | 0.14 | 0.0061 |
| 7A, 7B | 0.10, >3.10 | 0.0045, 0.24 |
| 8 | 0.3 | 0.0071 |
| 9 | 0.09 | 0.0032 |
| 10 | 0.25 | 0.0042 |
| 11 | 0.1 | 0.002 |
| 11A, 11B | 0.11, 0.48 | 0.0028, 0.021 |
| 12 | 0.1 | 0.0027 |
| 13 | 0.09 | 0.0042 |
| 14 | 0.94 | 0.003 |
| 15 | >3.10 | 0.093 |
| 16 | 4.6 | 0.28 |
| 17 | 0.24 | 0.012 |
| 18 | 1.4 | 0.016 |
| 19 | 0.26 | 0.011 |
| 20 | 0.98 | 0.02* |
| 21 | >3.10 | 0.059* |
| 22 | 0.17 | 0.0075 |
| 23 | 0.08 | 0.0013 |
| 24 | 0.06 | 0.0022 |
| 25 | 0.13 | 0.0029 |
| 26 | 0.09 | 0.0056 |
| 27 | 0.37 | 0.016* |
| 28 | 0.47 | 0.0045 |
| 29 | 1.6 | 0.041 |
| 30 | 1.1 | 0.03 |
| 31 | 1.1 | 0.024 |
| 32 | 0.42 | 0.012 |
| 33 | 0.24 | 0.014 |
| 34 | 0.35 | 0.0092 |
| 35 | 0.28 | 0.004 |
| 36 | 0.38 | 0.014 |
| 37 | 0.55 | 0.019 |
| 38 | 0.36 | 0.0054 |
| 39 | 1.9 | 0.05 |
| 40 | 1.9 | 0.032 |
| 41 | 0.54 | 0.016 |
| 42 | 4.3 | 0.032 |
| 43 | 0.87 | 0.031 |
| 44 | 1.8 | 0.0089 |
| 45 | 0.77 | 0.23 |
| 46 | 6.7 | 0.15 |
| 47 | 0.21 | 0.0036 |
| 48 | 0.16 | 0.0056 |
| 49 | 0.081 | 0.005 |
| 49A, 49B | 0.077, 1.2 | 0.0033, 0.048 |
| 50 | 0.19 | 0.0043 |
| 51 | 0.31 | 0.01 |
| 52 | 0.078 | 0.0037 |
| 53 | >2.4 | 0.0063 |
| 54 | 0.18 | 0.0034 |
| 55 | 0.043 | 0.0039 |
| 56 | 1 | 0.016 |
| 57 | 0.49 | 0.012 |
| 58 | 2.9 | 0.031 |
| 59 | 0.84 | 0.0063 |
| 60 | 0.47 | 0.023 |
| 61 | 0.85 | 0.023 |
| 62 | 0.56 | 0.028 |
| 63 | 0.68 | 0.042 |
| 64 | 0.3 | 0.0095 |
| 65 | 0.87 | 0.0064 |
| 66 | 0.99 | 0.0066* |
| 67 | 0.89 | 0.0077* |
| 68 | 0.34 | 0.012 |
| 69 | 0.41 | 0.0069 |

*tested once only hERG Analysis

Cell Culture

The hERG-expressing Chinese hamster ovary K1 (CHO) cells described by (Persson, Carlsson, Duker, & Jacobson, 2005) were grown to semi-confluence at 37° C. in a humidified environment (5% $CO_2$) in F-12 Ham medium containing L-glutamine, 10% foetal calf serum (FCS) and 0.6 mg/ml hygromycin (all Sigma-Aldrich). Prior to use, the monolayer was washed using a pre-warmed (37° C.) 3 ml aliquot of Versene 1:5,000 (Invitrogen). After aspiration of this solution the flask was incubated at 37° C. in an incubator with a further 2 ml of Versene 1:5,000 for a period of 6 minutes. Cells were then detached from the bottom of the flask by gentle tapping and 10 ml of Dulbecco's Phosphate-Buffered Saline containing calcium (0.9 mM) and magnesium (0.5 mM) (PBS; Invitrogen) was then added to the flask and aspirated into a 15 ml centrifuge tube prior to centrifugation (50 g, for 4 mins). The resulting supernatant was discarded and the pellet gently re-suspended in 3 ml of PBS. A 0.5 ml aliquot of cell suspension was removed and the number of viable cells (based on trypan blue exclusion) was determined in an automated reader (Cedex; Innovatis) so that the cell re-suspension volume could be adjusted with PBS to give the desired final cell concentration. It is the cell concentration at this point in the assay that is quoted when referring to this parameter. CHO-Kv1.5 cells, which were used to adjust the voltage offset on IonWorks™ HT, were maintained and prepared for use in the same way.

Electrophysiology

The principles and operation of this device have been described by (Schroeder, Neagle, Trezise, & Worley, 2003). Briefly, the technology is based on a 384-well plate (Patch-Plate™) in which a recording is attempted in each well by using suction to position and hold a cell on a small hole separating two isolated fluid chambers. Once sealing has taken place, the solution on the underside of the Patch-Plate™ is changed to one containing amphotericin B. This permeablises the patch of cell membrane covering the hole in each well and, in effect, allows a perforated, whole-cell patch clamp recording to be made.

A β-test IonWorks™ HT from Essen Instrument was used. There is no capability to warm solutions in this device hence it was operated at room temperature (~21° C.), as follows.

The reservoir in the "Buffer" position was loaded with 4 ml of PBS and that in the "Cells" position with the CHO-hERG cell suspension described above. A 96-well plate (V-bottom, Greiner Bio-one) containing the compounds to be tested (at 3-fold above their final test concentration) was placed in the "Plate 1" position and a PatchPlate™ was clamped into the PatchPlate™ station. Each compound plate was laid-out in 12 columns to enable ten, 8-point concentration-effect curves to be constructed; the remaining two columns on the plate were taken up with vehicle (final concentration 0.33% DMSO), to define the assay baseline, and a supra-maximal blocking concentration of cisapride (final concentration 10 µM) to define the 100% inhibition level. The fluidics-head (F-Head) of IonWorks™ HT then added 3.5 µl of PBS to each well of the PatchPlate™ and its underside was perfused with "internal" solution that had the following composition (in mM): K-Gluconate 100, KCl 40, $MgCl_2$ 3.2, EGTA 3 and HEPES 5 (all Sigma-Aldrich; pH 7.25-7.30 using 10 M KOH). After priming and de-bubbling, the electronics-head (E-head) then moved round the PatchPlate™ performing a hole test (i.e. applying a voltage pulse to determine whether the hole in each well was open). The F-head then dispensed 3.5 µl of the cell suspension described above into each well of the PatchPlate™ and the cells were given 200 seconds to reach and seal to the hole in each well. Following this, the E-head moved round the PatchPlate™ to determine the seal resistance obtained in each well. Next, the solution on the underside of the PatchPlate™ was changed to "access" solution that had the following composition (in mM): KCl 140, EGTA 1, $MgCl_2$ 1 and HEPES 20 (pH 7.25-7.30 using 10 M KOH) plus 100 µg/ml of amphotericin B (Sigma-Aldrich). After allowing 9 minutes for patch perforation to take place, the E-head moved round the PatchPlate™ 48 wells at a time to obtain pre-compound hERG current measurements. The F-head then added 3.5 µl of solution from each well of the compound plate to 4 wells on the PatchPlate™ (the final DMSO concentration was 0.33% in every well). This was achieved by moving from the most dilute to the most concentrated well of the compound plate to minimise the impact of any compound carry-over. After approximately 3.5 mins incubation, the E-head then moved around all 384-wells of the PatchPlate™ to obtain post-compound hERG current measurements. In this way, non-cumulative concentration-effect curves could be produced where, providing the acceptance criteria were achieved in a sufficient percentage of wells (see below), the effect of each concentration of test compound was based on recording from between 1 and 4 cells.

The pre- and post-compound hERG current was evoked by a single voltage pulse consisting of a 20 s period holding at −70 mV, a 160 ms step to −60 mV (to obtain an estimate of leak), a 100 ms step back to −70 mV, a 1 s step to +40 mV, a 2 s step to −30 mV and finally a 500 ms step to −70 mV. In between the pre- and post-compound voltage pulses there was no clamping of the membrane potential. Currents were leak-subtracted based on the estimate of current evoked during the +10 mV step at the start of the voltage pulse protocol. Any voltage offsets in IonWorks™ HT were adjusted in one of two ways. When determining compound potency, a depolarising voltage ramp was applied to CHO-Kv1.5 cells and the voltage noted at which there was an inflection point in the current trace (i.e. the point at which channel activation was seen with a ramp protocol). The voltage at which this occurred had previously been determined using the same voltage command in conventional electrophysiology and found to be −15 mV (data not shown); thus an offset potential could be entered into the IonWorks™ HT software using this value as a reference point. When determining the basic electrophysiological properties of hERG, any offset was adjusted by determining the hERG tail current reversal potential in IonWorks™ HT, comparing it with that found in conventional electrophysiology (−82 mV) and then making the necessary offset adjustment in the IonWorks™ HT software. The current signal was sampled at 2.5 kHz.

Pre- and post-scan hERG current magnitude was measured automatically from the leak subtracted traces by the IonWorks™ HT software by taking a 40 ms average of the current during the initial holding period at −70 mV (baseline current) and subtracting this from the peak of the tail current response. The acceptance criteria for the currents evoked in each well were: pre-scan seal resistance >60 MΩ, pre-scan hERG tail current amplitude >150 pA; post-scan seal resistance >60 MΩ. The degree of inhibition of the hERG current was assessed by dividing the post-scan hERG current by the respective pre-scan hERG current for each well.

REFERENCES

Persson, F., Carlsson, L., Duker, G., & Jacobson, I. (2005). Blocking characteristics of hERG, hNav1.5, and hKv-LQT1/hminK after administration of the novel anti-arrhythmic compound AZD7009. *J Cardiovasc. Electrophysiol.*, 16, 329-341.

Schroeder, K., Neagle, B., Trezise, D. J., & Worley, J. (2003). Ionworks HT: a new high-throughput electrophysiology measurement platform. *J Biomol Screen.*, 8, 50-64.

Results of hERG Analysis

Example 9, (S)-4-amino-N-(1-(4-chlorophenyl)-3-hydroxypropyl)-1-(7H-pyrrolo[2,3-d]pyrimidin-4-yl)piperidine-4-carboxamide, was tested up to 100 µM according to the procedure described above and a mean hERG $IC_{50}$ value of 177 µM was derived by extrapolation of the curve.

In Vivo Experiments

Pharmacodynamic Analysis of PKB Substrate Proteins GSK3β and PRAS40 in Response to (S)-4-amino-N-(1-(4-chlorophenyl)-3-hydroxypropyl)-1-(7H-pyrrolo[2,3-d]pyrimidin-4-yl)piperidine-4-carboxamide $2.5 \times 10^6$ U87-MG cells (ATCC number HTB-14™)+50% matrigel were injected s.c. (subcutaneously) into the flank of nude mice. When tumours reached a volume of about 0.5 $cm^3$ an acute dose of 150 or 300 mg/kg of (S)-4-amino-N-(1-(4-chlorophenyl)-3-hydroxypropyl)-1-(7H-pyrrolo[2,3-d]pyrimidin-4-yl)piperidine-4-carboxamide (E9) was given p.o. (oral gavage). Animals were euthanised at the specified timepoint and tumours dissected out and snap frozen in liquid nitrogen.

Ex-vivo tumour lysates were prepared in 10% triton-X-100 Tris Lysis buffer containing protease and phosphatase inhibitors using 'FastPrep 24' methodology (MP Biomedicals matrix #6910-500). Protein concentrations were estimated against a BSA standard curve using Pierce BCA kit (#23225). pGSK3β was measured by western blotting and pPRAS40 by solid phase sandwich ELISA (Biosource KHO0421).

For western blotting, equivalent amounts of protein were resolved by 4-12% gradient Bis-Tris polyacrylamide pre-cast gels (Invitrogen NP0323), transferred to Hybond C Extra nitrocellulose membranes (Invitrogen LC2001) and incubated with primary antiserum (pGSK3β ser9, Cell Signaling Technology #9336; total GSK3β, BD Transduction Labs #610202) and subsequently with either horseradish peroxidase conjugated anti-rabbit IgG (Cell Signaling Technology #7074) or anti-mouse IgG (Cell Signalling Technology #7076). Immunoreactive proteins were detected by enhanced chemiluminescence (#34076 Pierce Supersignal Dura) and bands quantified with a ChemiGenius II (Syngene). Plotted values show the percentage inhibition of pGSK3β compared to vehicle controls, following normalisation for total pGSK3β.

For ELISA (Enzyme linked Immuno Sorbent Assay), equivalent amounts of protein were added to a 96 well plate pre-coated with a 'capture' pPRAS40 specific monoclonal antibody. A 'detection' antibody specific for pPRAS40(Thr 246) is then added followed by an HRP labelled anti-rabbit IgG antibody. The assay is then quantified using stabilised TMB (tetramethylbenzidine) at 450 nm on a plate reader. Colour intensity is proportional to the concentration of pPRAS40 (Thr 246). The results are shown in FIG. 1.

MCF-7 Anti-Tumour Study Using (S)-4-amino-N-(1-(4-chlorophenyl)-3-hydroxypropyl)-1-(7H-pyrrolo[2,3-d]pyrimidin-4-yl)piperidine-4-carboxamide (E9)

Figure 2:
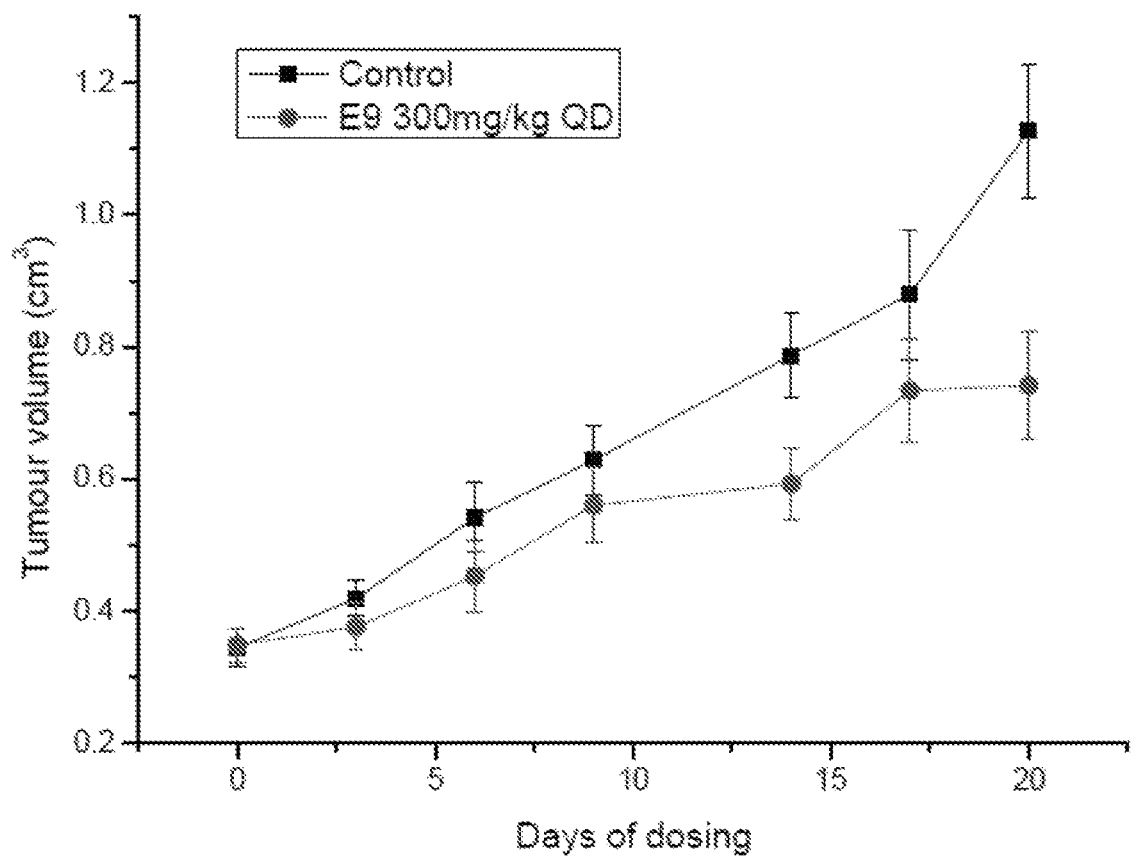

Severe Combined Immuno-Deficient (SCID) mice were obtained from Charles River Laboratories. The mice were housed and maintained in specific, pathogen-free conditions. For in vivo implant, cells were harvested from T225 tissue culture flasks by a 2- to 5-minute treatment with 3× trypsin (Invitrogen) in EDTA solution followed by suspension in basic medium and three washes in phosphate buffered saline (Invitrogen). Only single-cell suspensions of greater than 90% viability, as determined by trypan blue exclusion, were used for injection. MCF-7 breast tumor cells (ATCC number HTB-22™) ($5 \times 10^6$ cells+50% Matrigel™) were injected subcutaneously in the left flank of the animal in a volume of 0.1 mL. Prior to implantation of the MCF-7 cells, SCID mice were anaesthetized and implanted with a 0.5 mg/21 day duration estrogen pellet. When mean tumor size reached ~0.3 cm³, the mice were randomized into control and treatment groups. The treatment group received 300 mg/kg E9 solubilized in a vehicle consisting of 10% (v/v) DMSO, 25% (w/v) Kleptose™ in water, by oral gavage. The control group received the vehicle alone, once daily by oral gavage. Tumor volumes (measured by caliper) were recorded at intervals for the duration of the study. Mice were sacrificed by $CO_2$ euthanasia. The tumor volume was calculated (taking length to be the longest diameter across the tumor and width to be the corresponding perpendicular diameter using the formula: (length×width)×√(length×width)×(π/6). Growth inhibition from the start of treatment was assessed by comparison of the differences in tumor volume between control and treated groups. Because the variance in mean tumor volume data increases proportionally with volume (and is therefore disproportionate between groups), data were log-transformed to remove any size dependency before statistical evaluation. Statistical significance was evaluated using a one-tailed, two-sample t test. The results are shown in FIG. 2.

Human Dose Prediction

Human dose prediction for clinical studies requires an estimate of human pharmacokinetic (PK) parameters important for defining the elimination $T_{1/2}$ and the shape and magnitude of the plasma concentration vs time profile at a particular dose. These estimated parameters include Clearance, Volume of Distribution at Steady State (Vss), absorption rate constant (Ka), bioavailability (F) and dosing frequency. Human dose predictions also require some pharmacological evidence as to how exposure relates to efficacy (McGinnity, Collington, Austin & Riley, Current Drug Metabolism 2007 8 463-479).

For (S)-4-amino-N-(1-(4-chlorophenyl)-3-hydroxypropyl)-1-(7H-pyrrolo[2,3-d]pyrimidin-4-yl)piperidine-4-carboxamide (E9), human clearance was estimated from intrinsic clearance (Clint) data determined in human hepatocytes corrected to in vivo clearance by incorporation of the well-stirred model (Riley, McGinnity & Austin, Drug Metabolism & Disposition 2005 33(9) 1304-1311). Minor differences were observed in the plasma protein binding of the compound across rat, dog and human; consequently, observed rat and dog Vss values were corrected by the factor Fu, human/Fu (rat or dog) (where Fu=fraction unbound in plasma). Human Vss was estimated to be 3.3 L/kg using this approach. Fraction absorbed (Fabs) in humans was taken as the average across rat and dog. This Fabs parameter was then adjusted to bioavailability (F) by correction for hepatic extraction. The absorption rate (Ka) was set to ensure that Tmax was 1 h for E9, a relatively conservative value given that observed pre-clinically, and should equally result in a conservative Cmax value for use in calculation of margins with respect to safety studies. The clinical dosing frequency desired was assumed to be twice daily (BID).

Having defined the shape and magnitude of the human plasma concentration vs time curve, the final step was to adjust the dose so that plasma concentrations are attained that are likely to achieve efficacy. In mouse PD studies, inhibition of pGSK (a surrogate end-point for anti-tumour activity) has been observed when free plasma concentrations exceed 1-fold $IC_{50}$ for each compound as measured in the cell assay of AKT inhibitory activity, corrected for binding due to Foetal Calf Serum present in the assay. Consequently, the human PK model assumed that free exposure to E9 must exceed the free PKB $IC_{50}$ to ensure clinical efficacy.

Putting all of this data together, (S)-4-amino-N-(1-(4-chlorophenyl)-3-hydroxypropyl)-1-(7H-pyrrolo[2,3-d]pyrimidin-4-yl)piperidine-4-carboxamide (E9) is predicted to require a human dose of about 7 mg/kg BID to achieve efficacy, with a half-life estimated to be around 6 hours.

LIST OF FIGURES

FIG. 1: GSK3β and PRAS40 phosphorylation levels in samples taken from U87-MG tumours grown in nude mice following an acute dose of 150 or 300 mg/kg (S)-4-amino-N-(1-(4-chlorophenyl)-3-hydroxypropyl)-1-(7H-pyrrolo[2,3-d]pyrimidin-4-yl)piperidine-4-carboxamide (E9), n=5 per timepoint.

FIG. 2: Results of MCF-7 antitumour study in SCID mice using a once daily (QD) dose of 300 mg/kg (S)-4-amino-N-(1-(4-chlorophenyl)-3-hydroxypropyl)-1-(7H-pyrrolo[2,3-d]pyrimidin-4-yl)piperidine-4-carboxamide (E9).

The invention claimed is:

1. A method of treating breast cancer, comprising: administering to a person in need thereof a therapeutically effective amount of a compound of Formula (I), or a pharmaceutically acceptable salt thereof:

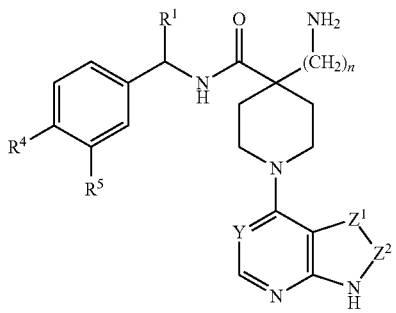

(I)

wherein:

Y represents N;

$Z^1$-$Z^2$ represents a group selected from $C(R^6)$=CH; where
- $R^6$ represents hydrogen, fluoro, chloro, bromo, cyano, methyl, ethyl, difluoromethyl, trifluoromethyl or cyclopropyl;

n is 0, 1 or 2;

$R^1$ represents $C_{1-4}$alkyl, $C_{2-4}$alkenyl, $C_{2-4}$alkynyl, $C_{1-4}$alkoxy, $C_{1-4}$alkoxy$C_{1-4}$alkyl, fluoro$C_{1-4}$alkyl, amino$C_{1-4}$alkyl, hydroxy$C_{1-4}$alkyl, cyano, cyano$C_{1-4}$alkyl, $C_{3-6}$cycloalkyl, —$(CH_2)_p$NHCOCH$_3$, —$(CH_2)_p$NHSO$_2$CH$_3$, —$(CH_2)_p$NHCONH$_2$, —$(CH_2)_p$NHCONR$^2$R$^3$, —$(CH_2)_p$NR$^2$R$^3$, —$(CH_2)_p$SO$_2$NH$_2$, —$(CH_2)_p$SO$_2$NR$^2$R$^3$, —$(CH_2)_p$CONH$_2$, —$(CH_2)_p$CONR$^2$R$^3$ or —$(CH_2)_p$—R$^7$; where
p is 0, 1, 2 or 3;

$R^2$ represents hydrogen or $C_{1-3}$alkyl;

$R^3$ represents $C_{1-3}$alkyl; and $R^7$ represents phenyl;

$R^7$ represents a 5 or 6 membered monocyclic heteroaryl ring which comprises 1, 2 or 3 heteroatoms selected from O, N or S; or $R^7$ represents a monocyclic 4, 5, or 6 membered heterocyclic ring which comprises 1, 2 or 3 heteroatoms selected from O, N or S;

wherein $R^7$ is optionally substituted by 1 or 2 substituents selected from $C_{1-4}$alkyl, trifluoromethyl, $C_{1-4}$alkoxy, fluoro, chloro, bromo, and cyano;

$R^4$ represents hydrogen, fluoro, chloro, bromo, cyano or trifluoromethyl; and $R^5$ represents hydrogen, fluoro, chloro or bromo.

2. The method according to claim 1, wherein the compound of Formula (I) has the configuration shown in Formula (IA):

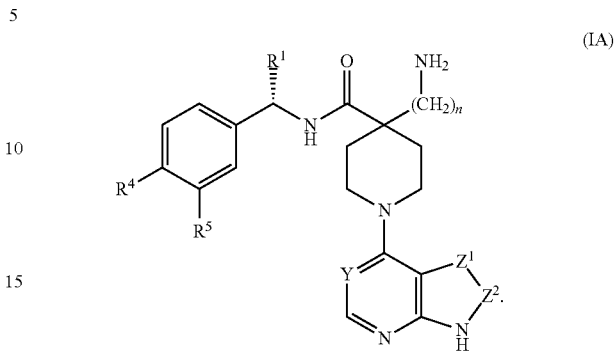

(IA)

3. The method according to claim 1, wherein $Z^1$-$Z^2$ represents CH=CH.

4. The method according to claim 1, wherein $R^1$ represents methoxy$C_{1-4}$alkyl, fluoro$C_{1-4}$alkyl, amino$C_{1-4}$alkyl, hydroxy$C_{1-4}$alkyl, cyano$C_{1-4}$alkyl, $C_{3-6}$cycloalkyl, —$(CH_2)_p$ NHCOCH$_3$, —$(CH_2)_p$NHSO$_2$CH$_3$, —$(CH_2)_p$NHCONH$_2$, —$(CH_2)_p$NHCONR$^2$R$^3$, —$(CH_2)_p$NR$^2$R$^3$, —$(CH_2)_p$ SO$_2$NH$_2$, —$(CH_2)_p$CONH$_2$, —$(CH_2)_p$CONR$^2$R$^3$ or —$(CH_2)_p$—R$^7$.

5. The method according to claim 4 wherein $R^1$ represents —$(CH_2)_p$—P$^7$, p represents 1, 2 or 3, $R^7$ is selected from phenyl, piperidinyl, piperazinyl, pyrrolidinyl, morpholinyl, imidazolyl, isoxazolyl, pyrazolyl and thiazolyl and $R^7$ is optionally substituted by a single methyl group.

6. The method according to claim 1, wherein $R^1$ represents hydroxyethyl.

7. The method according to claim 1, wherein $R^4$ represents chloro or bromo.

8. The method according to claim 1, wherein $R^5$ represents hydrogen.

9. The method according to claim 1, wherein n is 0 or 1.

10. A method of treating breast cancer, comprising administering to a person in need thereof a therapeutically effective amount of a pharmaceutical composition comprising: a compound according to claim 1, or a pharmaceutically-acceptable salt thereof, together with a pharmaceutically acceptable diluent or carrier.

* * * * *